(12) United States Patent
Pan et al.

(10) Patent No.: US 12,280,066 B2
(45) Date of Patent: *Apr. 22, 2025

(54) METHODS AND COMPOSITIONS RELATED TO GLUCOCORTICOID RECEPTOR ANTAGONISTS AND BREAST CANCER

(71) Applicant: The University of Chicago, Chicago, IL (US)

(72) Inventors: Deng Pan, Chicago, IL (US); Masha Kocherginsky, Chicago, IL (US); Suzanne D. Conzen, Park Ridge, IL (US)

(73) Assignee: The University of Chicago, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/541,675

(22) Filed: Dec. 15, 2023

(65) Prior Publication Data

US 2024/0148754 A1 May 9, 2024

Related U.S. Application Data

(63) Continuation of application No. 17/577,882, filed on Jan. 18, 2022, now Pat. No. 11,883,417, which is a continuation of application No. 16/596,342, filed on Oct. 8, 2019, now Pat. No. 11,234,990, which is a continuation of application No. 15/448,827, filed on Mar. 3, 2017, now Pat. No. 10,441,596, which is a continuation of application No. 14/296,127, filed on Jun. 4, 2014, now Pat. No. 9,623,032, which is a continuation of application No. 14/172,051, filed on Feb. 4, 2014, now Pat. No. 9,149,485, which is a continuation of application No. 13/071,363, filed on Mar. 24, 2011, now Pat. No. 8,710,035.

(60) Provisional application No. 61/317,182, filed on Mar. 24, 2010.

(51) Int. Cl.
| | | |
|---|---|---|
| A61K 31/575 | (2006.01) | |
| A61J 1/00 | (2023.01) | |
| A61K 31/282 | (2006.01) | |
| A61K 31/337 | (2006.01) | |
| A61K 31/357 | (2006.01) | |
| A61K 31/4745 | (2006.01) | |
| A61K 31/567 | (2006.01) | |
| A61K 31/58 | (2006.01) | |
| A61K 31/7068 | (2006.01) | |
| A61K 33/243 | (2019.01) | |
| A61K 39/395 | (2006.01) | |
| A61K 45/06 | (2006.01) | |
| A61N 5/00 | (2006.01) | |

(52) U.S. Cl.
CPC ............ *A61K 31/575* (2013.01); *A61J 1/00* (2013.01); *A61K 31/282* (2013.01); *A61K 31/337* (2013.01); *A61K 31/357* (2013.01); *A61K 31/4745* (2013.01); *A61K 31/567* (2013.01); *A61K 31/58* (2013.01); *A61K 31/7068* (2013.01); *A61K 33/243* (2019.01); *A61K 39/3955* (2013.01); *A61K 45/06* (2013.01); *A61N 5/00* (2013.01)

(58) Field of Classification Search
CPC .... A61K 31/575; A61K 45/06; A61K 33/243; A61K 31/282; A61K 31/337; A61K 31/357; A61K 31/4745; A61K 31/7068; A61K 39/3955; A61K 31/567; A61K 31/58; A61N 5/00; A61J 1/00
See application file for complete search history.

(56) References Cited

U.S. PATENT DOCUMENTS

| | | |
|---|---|---|
| 8,003,689 B2 | 8/2011 | Veverka |
| 8,658,128 B2 | 2/2014 | Altschul et al. |
| 8,710,035 B2 | 4/2014 | Pan et al. |
| 9,114,147 B2 | 8/2015 | Altschul et al. |
| 9,149,485 B2 | 10/2015 | Pan et al. |
| 9,623,032 B2 | 4/2017 | Pan et al. |
| 10,071,130 B2 | 9/2018 | Conzen |
| 10,441,596 B2 | 10/2019 | Pan et al. |
| 11,234,990 B2 | 2/2022 | Pan et al. |
| 2002/0115613 A1 | 8/2002 | Kumar |
| 2005/0124533 A1 | 6/2005 | Schatzberg et al. |
| 2006/0063748 A1 | 3/2006 | Belanoff |
| 2008/0287419 A1 | 11/2008 | Bruncko et al. |
| 2010/0135956 A1 | 6/2010 | Gant et al. |
| 2014/0186367 A1 | 7/2014 | Pan |
| 2014/0315866 A1 | 10/2014 | Pan et al. |
| 2017/0182066 A1 | 6/2017 | Pan et al. |

FOREIGN PATENT DOCUMENTS

WO 2009064738 A2 5/2009

OTHER PUBLICATIONS

"Data Sheet: Glucocorticoid Receptor mouse monoclonal antibody NCL-GCR", Novocastra Laboratories Ltd., Available Online at: http://www.ebiotrade.com/buyf/Novocastra/data/hrerp/gcr.pdf, Accessed from internet at Jun. 7, 2011,.

(Continued)

*Primary Examiner* — Shirley V Gembeh
(74) *Attorney, Agent, or Firm* — Kilpatrick Townsend & Stockton LLP

(57) ABSTRACT

Embodiments of the invention are directed to methods of determining the prognosis of a breast cancer patient by evaluating the activity of the glucocorticoid receptor in tumor cells. Other embodiment include methods of treating breast cancer cells, particularly, chemo-resistant cells, with a glucocorticoid receptor antagonist and an anticancer agent or compound.

12 Claims, 12 Drawing Sheets

Specification includes a Sequence Listing.

(56) References Cited

OTHER PUBLICATIONS

U.S. Appl. No. 14/172,051, Non-Final Office Action, Mailed On Mar. 10, 2015, 9 pages.
U.S. Appl. No. 14/172,051, Notice of Allowance, Mailed On Jun. 24, 2015, 11 pages.
U.S. Appl. No. 14/172,051, Notice of Allowance, Mailed On Apr. 30, 2015, 5 pages.
U.S. Appl. No. 14/296,127, Final Office Action, Mailed On Jul. 5, 2016, 9 pages.
U.S. Appl. No. 14/296,127, Non-Final Office Action, Mailed On Dec. 17, 2015, 10 pages.
U.S. Appl. No. 14/296,127, Non-Final Office Action, Mailed On Sep. 14, 2016, 7 pages.
U.S. Appl. No. 14/296,127, Notice of Allowance, Mailed On Dec. 8, 2016, 9 pages.
U.S. Appl. No. 14/296,127, "Restriction Requirement", Oct. 8, 2015, 11 pages.
U.S. Appl. No. 14/451,207, Notice of Withdrawal from Issue under 37 CFR 1.313 (b), Feb. 4, 2016, 2 pages.
U.S. Appl. No. 17/577,882, Non-Final Office Action, Mailed On Jul. 14, 2023, 12 pages.
U.S. Appl. No. 17/577,882, Notice of Allowance, Mailed On Oct. 23, 2023, 5 pages.
U.S. Appl. No. 61/317,182, "U.S. Provisional Application No.", Mar. 24, 2010, 72 pages.
Belanoff et al., "Selective Glucocorticoid Receptor {Type II} Antagonists Prevent Weight Gain Caused by Olanzapine in Rats", European Journal of Pharmacology, vol. 655, No. 1-3, Mar. 25, 2011, pp. 117-120.
Belova et al., "Glucocorticoid Receptor Expression in Breast Cancer Associates with Older Patient Age", Breast Cancer Research and Treatment, vol. 116, No. 3, Aug. 2009, pp. 441-447.
Cho et al., "Role of Activation function Domain-1, DNA Binding, and Coactivator GRIP1 in the Expression of Partial Agonist Activity of Glucocorticoid Receptor-Antagonist Complexes", Biochemistry, vol. 44, No. 9, Mar. 8, 2005, pp. 3547-3561.
Clark, "Glucocorticoid Receptor Antagonists", Current Topics in Medicinal Chemistry, vol. 8, No. 9, Jun. 1, 2008, pp. 813-838.
Colleoni et al., "Response to Primary Chemotherapy in Breast Cancer Patients with Tumors Not Expressing Estrogen and Progesterone Receptors", Annals of Oncology, vol. 11, No. 8, Aug. 1, 2000, pp. 1057-1059.
Dennis, "Off by a Whisker", Nature, vol. 442, Aug. 7, 2006, pp. 739-741.
Desmedt et al., "Strong Time Dependence of the 76-Gene Prognostic Signature for Node-Negative Breast Cancer Patients in the TRANSBIG Multicenter Independent Validation Series", Clinical Cancer Research, vol. 13, No. 11, Jun. 1, 2007, pp. 3207-3214.
Gaddy et al., "Mifepristone Induces Growth Arrest, Caspase Activation, and Apoptosis of Estrogen Receptor-Expressing, Antiestrogen-Resistant Breast Cancer Cells", Clinical Cancer Research, vol. 10, No. 15, Aug. 1, 2004, pp. 5215-5225.
Grover et al., "The Initiation of Breast and Prostate Cancer", Carcinogenesis, vol. 23, No. 7, Jul. 1, 2002, pp. 1095-1102.
Gura, "Systems for Identifying New Drugs are Often Faulty", Science, Cancer Models, vol. 278, No. 5340, Nov. 7, 1997, pp. 1041-1042.
Hein et al., "Click Chemistry, A powerful Tool for Pharmaceutical Sciences", Pharmaceutical Research, vol. 25, No. 10, Oct. 2008, pp. 2216-2230.
Henderson et al., "Estrogens as a Cause of Human Cancer: the Richard and Hinda Rosenthal Foundation Award Lecture", Cancer Research, vol. 48, No. 2, Jan. 15, 1988, pp. 246-253.
Huang et al., "Reversal Effect of Mifepristone on Adriamycin Resistance in Human Breast Cancer Cell Line MCF-7/ADM in Vitro and in Vivo", Journal of Central South University, Medical Sciences, vol. 35,No. 6, Jun. 2010, pp. 576-583.
Keen et al., "The Biology of Breast Carcinoma", Cancer, vol. 97, No. 3, Feb. 1, 2003, pp. 825-833.

Kriaucionis et al., "The Nuclear DNA Base 5-Hydroxymethylcytosine is Present in Brain and Enriched in Purkinje Neurons", Science, vol. 324, No. 5929, May 15, 2009, 5 pages.
Loi et al., "Definition of Clinically Distinct Molecular Subtypes in Estrogen Receptor-Positive Breast Carcinomas Through Genomic Grade", Journal of Clinical Oncology, vol. 25, No. 10, Apr. 1, 2007, pp. 1239-1246.
Loi et al., "Predicting Prognosis Using Molecular Profiling in Estrogen Receptor-Positive Breast Cancer Treated With Tamoxifen", BMC Genomics, vol. 9, No. 239, May 22, 2008, pp. 1-12.
Lucci et al., "Modification of Ceramide Metabolism Increases Cancer Cell Sensitivity to Cytotoxics", International Journal of Oncology, vol. 15, No. 3, Sep. 1999, pp. 541-546.
Ma et al., "IL-21 Activates Both Innate and Adaptive Immunity to Generate Potent Antitumor Responses that Require Perforin but Are Independent of IFN-Gamma", Journal of Immunology, vol. 171, No. 2, Jul. 15, 2003, pp. 608-615.
Melhem et al., "Administration of Glucocorticoids to Ovarian Cancer Patients is Associated with Expression of the Anti-apoptotic Genes SGK1 and MKP1/DUSP1 in Ovarian Tissues", Clinical Cancer Research, vol. 15, No. 9, May 1, 2009, pp. 3196-3204.
Mikosz et al., "Glucocorticoid Receptor-Mediated Protection from Apoptosis is Associated with Induction of the Serine/Threonine Survival Kinase Gene, sgk-1", The Journal of Biological Chemistry, vol. 276, No. 20, May 18, 2001, pp. 16649-16654.
Minn et al., "Genes that Mediate Breast Cancer Metastasis to Lung", Nature, vol. 436, No. 7050, Jul. 28, 2005, pp. 518-524.
Moran et al., "The Glucocorticoid Receptor Mediates a Survival Signal in Human Mammary Epithelial Cells", Cancer Research, vol. 60, No. 4, Feb. 15, 2000, pp. 867-872.
Moses et al., "The Growing Applications of Click Chemistry", Chemical Society Reviews, vol. 36, No. 8, May 2007, pp. 1249-1262.
Neckers et al., "Heat-Shock Protein 90 Inhibitors As Novel Cancer Chemotherapeutic Agents", Breast Disease, Available Online at: https://content.iospress.com/articles/breast-disease/bd000102 vol. 15, No. 1, Jun. 1, 2002, pp. 1-2.
Pan et al., "Activation of the Glucocorticoid Receptor is Associated with Poor Prognosis in Estrogen Receptor-Negative Breast Cancer", Cancer Research, vol. 71, No. 20, Oct. 15, 2011, pp. 6360-6370.
Pan et al., "Identification of Glucocorticoid Receptor (GR) Signatures in Primary Human Breast Cancer: Association with Relapse-Free Survival Time", Poster Presented by S.D. Conzen as a Short Talk, presented at Nuclear Receptors: Signaling, Gene Regulation and Cancer, Keystone Symposia on Molecular and Cellular Biology, Keystone Resort, Keystone, Colorado, Mar. 25, 2010, 1 page.
Pang et al., "Dexamethasone Decreases Xenograft Response to Paclitaxel Through Inhibition of Tumor Cell Apoptosis", Cancer Biology & Therapy, vol. 5, No. 8, Aug. 2006, pp. 933-940.
Peeters et al., "Differential Effects of the New Glucocorticoid Receptor Antagonist ORG 34517 and RU486 (Mifepristone) on Glucocorticoid Receptor Nuclear Translocation in the AtT20 Cell Line", Annals of the New York Academy of Sciences, vol. 1148, No. 1, Dec. 2008, pp. 536-541.
Pike et al., "Estrogens, Progestogens, Normal Breast Cell Proliferation, and Breast Cancer Risk", Epidemiologic Reviews, vol. 15, No. 1, Jan. 1, 1993, pp. 17-30.
Reagan-Shaw et al., "Dose Translation from Animal to Human Studies Revisited", The Faseb Journal, vol. 22, Mar. 2007, pp. 659-661.
Robinson et al., "Octahydrophenanthrene-2,7-diol Analogues as Dissociated Glucocorticoid Receptor Agonists: Discovery and Lead Exploration", Journal of Medicinal Chemistry, vol. 52, No. 6, Mar. 26, 2009, pp. 1731-1743.
Sims et al., "The Removal of Multiplicative, Systematic Bias Allows Integration of Breast Cancer Gene Expression Datasets—Improving Meta-Analysis and Prediction of Prognosis", BMC Medical Genomics, vol. 1, No. 42, Sep. 21, 2008, pp. 1-14.
Smith et al., "Expression of Glucocorticoid and Progesterone Nuclear Receptor Genes in Archival Breast Cancer Tissue", Breast Cancer Research, vol. 5, No. 1, 2003, pp. R9-R12.

(56) References Cited

OTHER PUBLICATIONS

Smith et al., "Progesterone, Glucocorticoid, but Not Estrogen Receptor mRNA is Altered in Breast Cancer Stroma", Cancer Letters, vol. 255, No. 1, Sep. 18, 2007, pp. 77-84.

Sorlie et al., "Gene Expression Patterns of Breast Carcinomas Distinguish Tumor Subclasses with Clinical Implications", Proceedings of the National Academy of Sciences of the United States of America, vol. 98, No. 19, Sep. 11, 2001, p. 10869-10874.

Sotiriou et al., "Gene Expression Profiling in Breast Cancer: Understanding the Molecular Basis of Histologic Grade to Improve Prognosis", Journal of the National Cancer Institute, vol. 98, No. 4, Feb. 15, 2006, pp. 262-272.

Srinivas et al., "Proteomics for Cancer Biomarker Discovery", Clinical Chemistry, vol. 48, No. 8, Aug. 2002, pp. 1160-1169.

Sui et al., "Estrogen Receptor a Mediates Breast Cancer Cell Resistance to Paclitaxel Through Inhibition of Apoptotic Cell Death", Cancer Research, vol. 67, No. 11, Jun. 1, 2007, pp. 5337-5344.

Wang et al., "Gene-Expression Profiles to Predict Distant Metastasis of Lymph-Node-Negative Primary Breast Cancer", The Lancet, vol. 365, No. 9460, Feb. 19, 2005, pp. 671-679.

Wu et al., "Glucocorticoid Receptor Activation Signals Through Forkhead Transcription Factor 3a in Breast Cancer Cells", Molecular Endocrinology, vol. 20, No. 10, Oct. 1, 2006, pp. 2304-2314.

Wu et al., "Microarray Analysis Reveals Glucocorticoid-Regulated Survival Genes that are Associated with Inhibition of Apoptosis in Breast Epithelial Cells", Cancer Research, vol. 64, No. 5, Mar. 1, 2004, pp. 1757-1764.

Wu et al., "Prevalent Expression of the Immunostimulatory MHC Class I Chain-Related Molecule Is Counteracted by Shedding in Prostate Cancer", Journal of Clinical Investigation, vol. 114, No. 4, Aug. 16, 2004, pp. 560-568.

Primary human breast ductal epithelium, DCIS (60%) invasive human cancers (~30-40%) exhibit significant glucocorticoid receptor expression

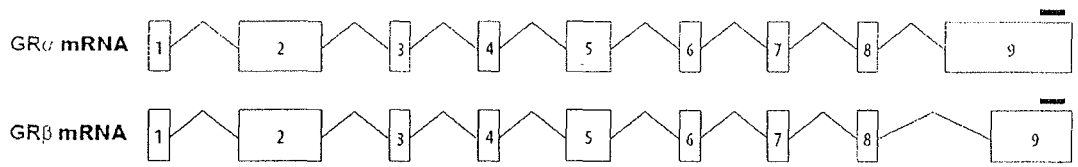

```
Query = GR alpha
Length=6784

18665 = GR beta

ALIGNMENTS

Query   1     GGCGCCGCCTCCACCCGCTCCCCGCTCGGTCCCGCTCGCTCGCCCAGGCCGGGCTGCCCT   60
18665   1     GGCGCCGCCTCCACCCGCTCCCCGCTCGGTCCCGCTCGCTCGCCCAGGCCGGGCTGCCCT   60

Query   61    TTCGCGTGTCCGCGCTCTCTTCCCTCCGCCGCCGCCTCCTCCATTTTGCGAGCTCGTGTC   120
18665   61    TTCGCGTGTCCGCGCTCTCTTCCCTCCGCCGCCGCCTCCTCCATTTTGCGAGCTCGTGTC   120

Query   121   TGTGACGGGAGCCCGAGTCACCGCCTGCCCGTCGGGGACGGATTCTGTGGGTGGAAGGAG   180
18665   121   TGTGACGGGAGCCCGAGTCACCGCCTGCCCGTCGGGGACGGATTCTGTGGGTGGAAGGAG   180

Query   181   ACGCCGCAGCCGGAGCGGCCGAAGCAGCTGGGACCGGGACGGGGCACGCGCGCCCGGAAC   240
18665   181   ACGCCGCAGCCGGAGCGGCCGAAGCAGCTGGGACCGGGACGGGGCACGCGCGCCCGGAAC   240

Query   241   CTCGACCCGCGGAGCCCGGCGCGGGGCGGAGGGCTGGCTTGTCAGCTGGGCAATGGGAGA   300
18665   241   CTCGACCCGCGGAGCCCGGCGCGGGGCGGAGGGCTGGCTTGTCAGCTGGGCAATGGGAGA   300

Query   301   CTTTCTTAAATAGGGGCTCTCCCCCCACCCATGGAGAAAGGGGCGGCTGTTTACTTCCtt   360
18665   301   CTTTCTTAAATAGGGGCTCTCCCCCCACCCATGGAGAAAGGGGCGGCTGTTTACTTCCTT   360

Query   361   ttttAGaaaaaaaaaaaTATATTTCCCTCCTGCTCCTTCTGCGTTCACAAGCTAAGTTGT   420
18665   361   TTTTTAGAAAAAAAAAATATATTTCCCTCCTGCTCCTTCTGCGTTCACAAGCTAAGTTGT   420

Query   421   TTATCTCGGCTGCGGCGGGAACTGCGGACGGTGGCGGGCGAGCGGCTCCTCTGCCAGAGT   480
18665   421   TTATCTCGGCTGCGGCGGGAACTGCGGACGGTGGCGGGCGAGCGGCTCCTCTGCCAGAGT   480

Query   481   TGATATTCACTGATGGACTCCAAAGAATCATTAACTCCTGGTAGAGAAGAAAACCCCAGC   540
18665   481   TGATATTCACTGATGGACTCCAAAGAATCATTAACTCCTGGTAGAGAAGAAAACCCCAGC   540

Query   541   AGTGTGCTTGCTCAGGAGAGGGAGATGTGATGGACTTCTATAAACCCTAAGAGGAGGA   600
18665   541   AGTGTGCTTGCTCAGGAGAGGGAGATGTGATGGACTTCTATAAACCCTAAGAGGAGGA   600

Query   601   GCTACTGTGAAGGTTTCTGCGTCTTCACCCTCACTGGCTGTCGCTTCTCAATCAGACTCC   660
18665   601   GCTACTGTGAAGGTTTCTGCGTCTTCACCCTCACTGGCTGTCGCTTCTCAATCAGACTCC   660

Query   661   AAGCAGCGAAGACTTTTGGTTGATTTTCCAAAAGGCTCAGTAAGCAATGCGCAGCAGCCA   720
18665   661   AAGCAGCGAAGACTTTTGGTTGATTTTCCAAAAGGCTCAGTAAGCAATGCGCAGCAGCCA   720

Query   721   GATCTGTCCAAAGCAGTTTCACTCTCAATGGGACTGTATATGGGAGAGACAGAAACAAAA   780
18665   721   GATCTGTCCAAAGCAGTTTCACTCTCAATGGGACTGTATATGGGAGAGACAGAAACAAAA   780

Query   781   GTGATGGGAAATGACCTGGGATTCCCACAGCAGGGCAAATCAGCCTTTCCTCGGGGGAA   840
18665   781   GTGATGGGAAATGACCTGGGATTCCCACAGCAGGGCAAATCAGCCTTTCCTCGGGGGAA   840

Query   841   ACAGACTTAAAGCTTTTGGAAGAAAGCATTGCAAACCTCAATAGGTCGACCAGTGTTCCA   900
18665   841   ACAGACTTAAAGCTTTTGGAAGAAAGCATTGCAAACCTCAATAGGTCGACCAGTGTTCCA   900
```

FIG. 7A

```
Query    901   GAGAACCCCAAGAGTTCAGCATCCACTGCTGTGTCTGCTGCCCCCACAGAGAAGGAGTTT   960
18665    901   GAGAACCCCAAGAGTTCAGCATCCACTGCTGTGTCTGCTGCCCCCACAGAGAAGGAGTTT   960

Query    961   CCAAAAACTCACTCTGATGTATCTTCAGAACAGCAACATTTGAAGGGCCAGACTGGCACC   1020
18665    961   CCAAAAACTCACTCTGATGTATCTTCAGAACAGCAACATTTGAAGGGCCAGACTGGCACC   1020

Query    1021  AACGGTGGCAATGTGAAATTGTATACCACAGACCAAAGCACCTTTGACATTTTGCAGGAT   1080
18665    1021  AACGGTGGCAATGTGAAATTGTATACCACAGACCAAAGCACCTTTGACATTTTGCAGGAT   1080

Query    1081  TTGGAGTTTTCTTCTGGGTCCCCAGGTAAAGAGACGAATGAGAGTCCTTGGAGATCAGAC   1140
18665    1081  TTGGAGTTTTCTTCTGGGTCCCCAGGTAAAGAGACGAATGAGAGTCCTTGGAGATCAGAC   1140

Query    1141  CTGTTGATAGATGAAAACTGTTTGCTTTCTCCTCTGGCGGGAGAAGACGATTCATTCCTT   1200
18665    1141  CTGTTGATAGATGAAAACTGTTTGCTTTCTCCTCTGGCGGGAGAAGACGATTCATTCCTT   1200

Query    1201  TTGGAAGGAAACTCGAATGAGGACTGCAAGCCTCTCATTTTACCGGACACTAAACCCAAA   1260
18665    1201  TTGGAAGGAAACTCGAATGAGGACTGCAAGCCTCTCATTTTACCGGACACTAAACCCAAA   1260

Query    1261  ATTAAGGATAATGGAGATCTGGTTTTGTCAAGCCCCAGTAATGTAACACTGCCCCAAGTG   1320
18665    1261  ATTAAGGATAATGGAGATCTGGTTTTGTCAAGCCCCAGTAATGTAACACTGCCCCAAGTG   1320

Query    1321  AAAACAGAAAAGAAGATTTCATCGAACTCTGCACCCCTGGGGTAATTAAGCAAGAGAAA   1380
18665    1321  AAAACAGAAAAGAAGATTTCATCGAACTCTGCACCCCTGGGGTAATTAAGCAAGAGAAA   1380

Query    1381  CTGGGCACAGTTTACTGTCAGGCAAGCTTTCCTGGAGCAAATATAATTGGTAATAAAATG   1440
18665    1381  CTGGGCACAGTTTACTGTCAGGCAAGCTTTCCTGGAGCAAATATAATTGGTAATAAAATG   1440

Query    1441  TCTGCCATTTCTGTTCATGGTGTGAGTACCTCTGGAGGACAGATGTACCACTATGACATG   1500
18665    1441  TCTGCCATTTCTGTTCATGGTGTGAGTACCTCTGGAGGACAGATGTACCACTATGACATG   1500

Query    1501  AATACAGCATCCCTTTCTCAACAGCAGGATCAGAAGCCTATTTTTAATGTCATTCCACCA   1560
18665    1501  AATACAGCATCCCTTTCTCAACAGCAGGATCAGAAGCCTATTTTTAATGTCATTCCACCA   1560

Query    1561  ATTCCCGTTGGTTCCGAAAATTGGAATAGGTGCCAAGGATCTGGAGATGACAACTTGACT   1620
18665    1561  ATTCCCGTTGGTTCCGAAAATTGGAATAGGTGCCAAGGATCTGGAGATGACAACTTGACT   1620

Query    1621  TCTCTGGGGACTCTGAACTTCCCTGGTCGAACAGTTTTTTCTAATGGCTATTCAAGCCCC   1680
18665    1621  TCTCTGGGGACTCTGAACTTCCCTGGTCGAACAGTTTTTTCTAATGGCTATTCAAGCCCC   1680

Query    1681  AGCATGAGACCAGATGTAAGCTCTCCTCCATCCAGCTCCTCAACAGCAACAACAGGACCA   1740
18665    1681  AGCATGAGACCAGATGTAAGCTCTCCTCCATCCAGCTCCTCAACAGCAACAACAGGACCA   1740

Query    1741  CCTCCCAAACTCTGCCTGGTGTGCTCTGATGAAGCTTCAGGATGTCATTATGGAGTCTTA   1800
18665    1741  CCTCCCAAACTCTGCCTGGTGTGCTCTGATGAAGCTTCAGGATGTCATTATGGAGTCTTA   1800

Query    1801  ACTTGTGGAAGCTGTAAAGTTTTCTTCAAAAGAGCAGTGGAAGGACAGCACAATTACCTA   1860
18665    1801  ACTTGTGGAAGCTGTAAAGTTTTCTTCAAAAGAGCAGTGGAAGGACAGCACAATTACCTA   1860

Query    1861  TGTGCTGGAAGGAATGATTGCATCATCGATAAAATTCGAAGAAAAACTGCCCAGCATGC   1920
18665    1861  TGTGCTGGAAGGAATGATTGCATCATCGATAAAATTCGAAGAAAAACTGCCCAGCATGC   1920

Query    1921  CGCTATCGAAAATGTCTTCAGGCTGGAATGAACCTGGAAGCTCGaaaaacaaagaaaaaa   1980
18665    1921  CGCTATCGAAAATGTCTTCAGGCTGGAATGAACCTGGAAGCTCGAAAAACAAAGAAAAAA   1980

Query    1981  ataaaaGGAATTCAGCAGGCCACTACAGGAGTCTCACAAGAAACCTCTGAAAATCCTGGT   2040
18665    1981  ATAAAAGGAATTCAGCAGGCCACTACAGGAGTCTCACAAGAAACCTCTGAAAATCCTGGT   2040

Query    2041  AACAAAACAATAGTTCCTGCAACGTTACCACAACTCACCCCTACCCTGGTGTCACTGTTG   2100
18665    2041  AACAAAACAATAGTTCCTGCAACGTTACCACAACTCACCCCTACCCTGGTGTCACTGTTG   2100

Query    2101  GAGGTTATTGAACCTGAAGTGTTATATGCAGGATATGATAGCTCTGTTCCAGACTCAACT   2160
18665    2101  GAGGTTATTGAACCTGAAGTGTTATATGCAGGATATGATAGCTCTGTTCCAGACTCAACT   2160
```

FIG. 7B

```
Query  2161  TGGAGGATCATGACTACGCTCAACATGTTAGGAGGGCGGCAAGTGATTGCAGCAGTGAAA  2220
18665  2161  TGGAGGATCATGACTACGCTCAACATGTTAGGAGGGCGGCAAGTGATTGCAGCAGTGAAA  2220

Query  2221  TGGGCAAAGGCAATACCAGGTTTCAGGAACTTACACCTGGATGACCAAATGACCCTACTG  2280
18665  2221  TGGGCAAAGGCAATACCAGGTTTCAGGAACTTACACCTGGATGACCAAATGACCCTACTG  2280

Query  2281  CAGTACTCCTGGATGTTTCTTATGGCATTTGCTCTGGGGTGGAGATCATATAGACAATCA  2340
18665  2281  CAGTACTCCTGGATGTTTCTTATGGCATTTGCTCTGGGGTGGAGATCATATAGACAATCA  2340

Query  2341  AGTGCAAACCTGCTGTGTTTTGCTCCTGATCTGATTATTAATGAGCAGAGAATGACTCTA  2400
18665  2341  AGTGCAAACCTGCTGTGTTTTGCTCCTGATCTGATTATTAATGAGCAGAGAATGACTCTA  2400

Query  2401  CCCTGCATGTACGACCAATGTAAACACATGCTGTATGTTTCCTCTGAGTTACACAGGCTT  2460
18665  2401  CCCTGCATGTACGACCAATGTAAACACATGCTGTATGTTTCCTCTGAGTTACACAGGCTT  2460

Query  2461  CAGGTATCTTATGAAGAGTATCTCTGTATGAAAACCTTACTGCTTCTCTCTTCAGTTCCT  2520
18665  2461  CAGGTATCTTATGAAGAGTATCTCTGTATGAAAACCTTACTGCTTCTCTCTTCAGTTCCT  2520

Query  2521  AAGGACGGTCTGAAGAGCCAAGAGCTATTTGATGAAATTAGAATGACCTACATCAAAGAG  2580
18665  2521  AAGGACGGTCTGAAGAGCCAAGAGCTATTTGATGAAATTAGAATGACCTACATCAAAGAG  2580

Query  2581  CTAGGAAAAGCCATTGTCAAGAGGGAAGGAAACTCCAGCCAGAACTGGCAGCGGTTTTAT  2640
18665  2581  CTAGGAAAAGCCATTGTCAAGAGGGAAGGAAACTCCAGCCAGAACTGGCAGCGGTTTTAT  2640

Query  2641  CAACTGACAAAACTCTTGGATTCTATGCATGAAGTGGTTGAAATCTCCTTAACTATTGC  2700
18665  2641  CAACTGACAAAACTCTTGGATTCTATGCATGAA                            2673

Query  2701  TTCCAAACATTTTTGGATAAGACCATGAGTATTGAATTCCCCGAGATGTTAGCTGAAATC  2760
Query  2761  ATCACCAATCAGATACCAAAATATTCAAATGGAAATATCAAAAAACTTCTGTTTCATCAA  2820
Query  2821  AAGTGACTGCCTTAATAAGAATGGTTGCCTTAAAGAAAGTCGAATTAATAGCTTTTATTG  2880
Query  2881  TATAAACTATCAGTTTGTCCTGTAGAGgttttgttgttttattttttattgttttcatct  2940
Query  2941  gttgttttgttttAAATACGCACTACATGTGGTTTATAGAGGGCCAAGACTTGGCAACAG  3000
Query  3001  AAGCAGTTGAGTCGTCATCACTTTTCAGTGATGGGAGAGTAGATGGTGAAATTTATTAGT  3060
Query  3061  TAATATATCCCAGAAATTAGAAACCTTAATATGTGGACGTAATCTCCACAGTCAAAGAAG  3120
Query  3121  GATGGCACCTAAACCACCAGTGCCCAAAGTCTGTGTGATGAACTTTCTCTTCATACtttt  3180
Query  3181  tttCACAGTTGGCTGGATGAAATTTTCTAGACTTTCTGTTGGTGTATccccccccTGTAT  3240
Query  3241  AGTTAGGATAGCATTTTTGATTTATGCATGGAAACCTGaaaaaaaGTTTACAAGTGTATA  3300
Query  3301  TCAGAAAAGGGAAGTTGTGCCTTTTATAGCTATTACTGTCTGGTTTTAACAATTTCCTTT  3360
Query  3361  ATATTTAGTGAACTACGCTTGCTCATTTTTTCTTACATAATTTTTTATTCAAGTTATTGT  3420
Query  3421  ACAGCTGTTTAAGATGGGCAGCTAGTTCGTAGCTTTCCCAAATAAACTCTAAACATTAAT  3480
Query  3481  CAATCATCTGTGTGAAAATGGGTTGGTGCTTCTAACCTGATGGCACTTAGCTATCAGAAG  3540
Query  3541  ACCACAAAAATTGACTCAAATCTCCAGTATTCTTGTCaaaaaaaaaaaaaaaaaGCTCA  3600
Query  3601  TATTTTGTATATATCTGCTTCAGTGGAGAATTATATAGGTTGTGCAAATTAACAGTCCTA  3660
Query  3661  ACTGGTATAGAGCACCTAGTCCAGTGACCTGCTGGGTAAACTGTGGATGATGGTTGCAAA  3720
Query  3721  AGACTAATTTAAAAAATAACTACCAAGAGGCCCTGTCTGTACCTAACGCCCTATTTTTGC  3780
```

FIG. 7C

```
Query  3781  AATGGCTATATGGCAAGAAAGCTGGTAAACTATTTGTCTTTCAGGACCTTTTGAAGTAGT  3840
Query  3841  TTGTATAACTTCTTAAAAGTTGTGATTCCAGATAACCAGCTGTAACACAGCTGAGAGACT  3900
Query  3901  TTTAATCAGACAAAGTAATTCCTCTCACTAAACTTTACCCAAAAACTAAATCTCTAATAT  3960
Query  3961  GGCAAAAATGGCTAGACACCCATTTTCACATTCCCATCTGTCACCAATTGGTTAATCTTT  4020
Query  4021  CCTGATGGTACAGGAAAGCTCAGCTACTGATTTTTGTGATTTAGAACTGTATGTCAGACA  4080
Query  4081  TCCATGTTTGTAAAACTACACATCCCTAATGTGTGCCATAGAGTTTAACACAAGTCCTGT  4140
Query  4141  GAATTTCTTCACTGTTGAAAATTATTTTAAACAAAATAGAAGCTGTAGTAGCCCTTTCTG  4200
Query  4201  TGTGCACCTTACCAACTTTCTGTAAACTCAAAACTTAACATATTTACTAAGCCACAAGAA  4260
Query  4261  ATTTGATTTCTATTCAAGGTGGCCAAATTATTTGTGTAATAGAAAACTGAAAATCTAATA  4320
Query  4321  TTAAAAATATGGAACTTCTAatatattttatatttagttatagtttcagatatatatca  4380
Query  4381  tatTGGTATTCACTAATCTGGGAAGGGAAGGGCTACTGCAGCTTTACATGCAATTTATTA  4440
Query  4441  AAATGATTGTAAAATAGCTTGTATAGTGTAAAATAAGAATGATTTTTAGATGAGATTGTT  4500
Query  4501  TTATCATGACATGTTATATATTTTTTGTAGGGGTCAAAGAAATGCTGATGGATAACCTAT  4560
Query  4561  ATGATTTATAGTTTGTACATGCATTCATACAGGCAGCGATGGTCTCAGAAACCAAACAGT  4620
Query  4621  TTGCTCTAGGGGAAGAGGGAGATGGAGACTGGTCCTGTGTGCAGTGAAGGTTGCTGAGGC  4680
Query  4681  TCTGACCCAGTGAGATTACAGAGGAAGTTATCCTCTGCCTCCCATTCTGACCACCCTTCT  4740
Query  4741  CATTCCAACAGTGAGTCTGTCAGCGCAGGTTTAGTTTACTCAATCTCCCCTTGCACTAAA  4800
Query  4801  GTATGTAAAGTATGTAAACAGGAGACAGGAAGGTGGTGCTTACATCCTTAAAGGCACCAT  4860
Query  4861  CTAATAGCGGGTTACTTTCACATACAGCCCTCCCCCAGCAGTTGAATGACAACAGAAGCT  4920
Query  4921  TCAGAAGTTTGGCAATAGTTTGCATAGAGGTACCAGCAATATGTAAATAGTGCAGAATCT  4980
Query  4981  CATAGGTTGCCAATAATACACTAATTCCTTTCTATCCTACAACAAGAGTTTATTTCCAAA  5040
Query  5041  TAAAATGAGGACAtgttttgttttctttgaatgcttttgaatgttatttgttattttc  5100
Query  5101  agtattttggagaaattatttAATaaaaaaaCAATCATTTGCTTTTTGAATGCTCTCTAA  5160
Query  5161  AAGGGAATGTAATATTTTAAGATGGTGTGTAACCCGGCTGGATAAATTTTTGGTGCCTAA  5220
Query  5221  GAAAACTGCTTGAATATTCTTATCAATGACAGTGTTAAGTTTCAAAAAGAGCTTCTAAAA  5280
Query  5281  CGTAGATTATCATTCCTTTATAGAATGTTATGTGGTTAAAACCAGAAAGCACATCTCACA  5340
18665  2674                           AATGTTATGTGGTTAAAACCAGAAAGCACATCTCACA  2710
Query  5341  CATTAATCTGATTTTCATCCCAACAATCTTGGCGCTCAAAAAATAGAACTCAATGAGAAA  5400
18665  2711  CATTAATCTGATTTTCATCCCAACAATCTTGGCGCTCAAAAAATAGAACTCAATGAGAAA  2770
Query  5401  AAGAAGATTATGTGCACTTCGTTGTCAATAATAAGTCAACTGATGCTCATCGACAACTAT  5460
18665  2771  AAGAAGATTATGTGCACTTCGTTGTCAATAATAAGTCAACTGATGCTCATCGACAACTAT  2830
Query  5461  AGGAGGCTTTTCATTAAATGGGAAAAGAAGCTGTGCCCTTTTAGGATACGTGGGGGAAAA  5520
18665  2831  AGGAGGCTTTTCATTAAATGGGAAAAGAAGCTGTGCCCTTTTAGGATACGTGGGGGAAAA  2890
Query  5521  GAAAGTCATCTTAATTATGTTTAATTGTGGATTTAAGTGCTATATGGTGGTGCTGTTTGA  5580
```

FIG. 7D

```
18665  2891  GAAAGTCATCTTAATTATGTTTAATTGTGGATTTAAGTGCTATATGGTGGTGCTGTTTGA  2950

Query  5581  AAGCAGATTTATTTCCTATGTATGTGTTATCTGGCCATCCCAACCCAAACTGTTGAAGTT  5640
18665  2951  AAGCAGATTTATTTCCTATGTATGTGTTATCTGGCCATCCCAACCCAAACTGTTGAAGTT  3010

Query  5641  TGTAGTAACTTCAGTGAGAGTTGGTTACTCACAACAAATCCTGAAAAGTATTTTTAGTGT  5700
18665  3011  TGTAGTAACTTCAGTGAGAGTTGGTTACTCACAACAAATCCTGAAAAGTATTTTTAGTGT  3070

Query  5701  TTGTAGGTATTCTGTGGGATACTATACAAGCAGAACTGAGGCACTTAGGACATAACACTT  5760
18665  3071  TTGTAGGTATTCTGTGGGATACTATACAAGCAGAACTGAGGCACTTAGGACATAACACTT  3130

Query  5761  TTGGGGTATATATATCCAAATGCCTAAAACTATGGGAGGAAACCTTGGCCACCCCAAAAG  5820
18665  3131  TTGGGGTATATATATCCAAATGCCTAAAACTATGGGAGGAAACCTTGGCCACCCCAAAAG  3190

Query  5821  GAAAACTAACATGATTTGTGTCTATGAAGTGCTGGATAATTAGCATGGGATGAGCTCTGG  5880
18665  3191  GAAAACTAACATGATTTGTGTCTATGAAGTGCTGGATAATTAGCATGGGATGAGCTCTGG  3250

Query  5881  GCATGCCATGAAGGAAAGCCACGCTCCCTTCAGAATTCAGAGGCAGGGAGCAATTCCAGT  5940
18665  3251  GCATGCCATGAAGGAAAGCCACGCTCCCTTCAGAATTCAGAGGCAGGGAGCAATTCCAGT  3310

Query  5941  TTCACCTAAGTCTCATAATTTTAGTTCCCTTTTAAAAACCCTGAAAACTACATCACCATG  6000
18665  3311  TTCACCTAAGTCTCATAATTTTAGTTCCCTTTTAAAAACCCTGAAAACTACATCACCATG  3370

Query  6001  GAATGAAAATATTGTTATACAATACATTGATCTGTCAAACTTCCAGAACCATGGTAGCC  6060
18665  3371  GAATGAAAATATTGTTATACAATACATTGATCTGTCAAACTTCCAGAACCATGGTAGCC  3430

Query  6061  TTCAGTGAGATTTCCATCTTGGCTGGTCACTCCCTGACTGTAGCTGTAGGTGAAtgtgtt  6120
18665  3431  TTCAGTGAGATTTCCATCTTGGCTGGTCACTCCCTGACTGTAGCTGTAGGTGAATGTGTT  3490

Query  6121  tttgtgtgtgtgtgtCTGGTTTTAGTGTCAGAAGGGAAATAAAAGTGTAAGGAGGACACT  6180
18665  3491  TTTGTGTGTGTGTGTCTGGTTTTAGTGTCAGAAGGGAAATAAAAGTGTAAGGAGGACACT  3550

Query  6181  TTAAACCCTTTGGGTGGAGTTTCGTAATTTCCCAGACTATTTTCAAGCAACCTGGTCCAC  6240
18665  3551  TTAAACCCTTTGGGTGGAGTTTCGTAATTTCCCAGACTATTTTCAAGCAACCTGGTCCAC  3610

Query  6241  CCAGGATTAGTGACCAGGTTTTCAGGAAAGGATTTGCTTCTCTAGAAAATGTCTGAAA  6300
18665  3611  CCAGGATTAGTGACCAGGTTTTCAGGAAAGGATTTGCTTCTCTCTAGAAAATGTCTGAAA  3670

Query  6301  GGATTTTATTTTCTGATGAAAGGCTGTATGAAAATACCCTCCTCAAATAACTTGCTTAAC  6360
18665  3671  GGATTTTATTTTCTGATGAAAGGCTGTATGAAAATACCCTCCTCAAATAACTTGCTTAAC  3730

Query  6361  TACATATAGATTCAAGTGTGTCAATATTCTATTTTGTATATTAAATGCTATATAATGGGG  6420
18665  3731  TACATATAGATTCAAGTGTGTCAATATTCTATTTTGTATATTAAATGCTATATAATGGGG  3790

Query  6421  ACAAATCTATATTATACTGTGTATGGCATTATTAAGAAGCTTTTTCATTATTTTTTATCA  6480
18665  3791  ACAAATCTATATTATACTGTGTATGGCATTATTAAGAAGCTTTTTCATTATTTTTTATCA  3850

Query  6481  CAGTAATTTTAAAATGTGTAAAAATTAAAACCAGTGACTCCTGTTTAAAAATAAAAGTTG  6540
18665  3851  CAGTAATTTTAAAATGTGTAAAAATTAAAACCAGTGACTCCTGTTTAAAAATAAAAGTTG  3910

Query  6541  TAGTTTTTTATTCATGCTGAATAATAATCTGTAGTTaaaaaaaaaGTGTCTTTTTACCTA  6600
18665  3911  TAGTTTTTTATTCATGCTGAATAATAATCTGTAGTTAAAAAAAAAGTGTCTTTTTACCTA  3970

Query  6601  CGCAGTGAAATGTCAGACTGTAAAACCTTGTGTGGAAATGTTTAACTTTTATTTTTTCAT  6660
18665  3971  CGCAGTGAAATGTCAGACTGTAAAACCTTGTGTGGAAATGTTTAACTTTTATTTTTTCAT  4030

Query  6661  TTAAATTTGCTGTTCTGGTATTACCAAACCACACATTTGTACCGAATTGGCAGTAAATGT  6720
18665  4031  TTAAATTTGCTGTTCTGGTATTACCAAACCACACATTTGTACCGAATTGGCAGTAAATGT  4090

Query  6721  TAGCCATTTACAGCAATGCCAAATATGGAGAAACATCATAATaaaaaaaTCTGCTTTTTC  6780
18665  4091  TAGCCATTTACAGCAATGCCAAATATGGAGAAACATCATAATAAAAAAATCTGCTTTTTC  4150

Query  6781  ATTA  6784
```

FIG. 7E 18665 4151 ATTA 4154

FIG. 7F

METHODS AND COMPOSITIONS RELATED TO GLUCOCORTICOID RECEPTOR ANTAGONISTS AND BREAST CANCER

CROSS-REFERENCES TO RELATED APPLICATIONS

This application is a Continuation of U.S. application Ser. No. 17/577,882, filed Jan. 18, 2022, which is a Continuation of U.S. application Ser. No. 16/596,342, filed Oct. 8, 2019 (now U.S. Pat. No. 11,234,990, issued Feb. 1, 2022), which is a Continuation of U.S. application Ser. No. 15/448,827, filed Mar. 3, 2017 (now U.S. Pat. No. 10,441,596, issued Oct. 15, 2019), which is a Continuation of U.S. application Ser. No. 14/296,127, filed Jun. 4, 2014 (now U.S. Pat. No. 9,623,032, issued Apr. 18, 2017), which is a Continuation of U.S. application Ser. No. 14/172,051, filed Feb. 4, 2014 (now U.S. Pat. No. 9,149,485, issued Oct. 6, 2015), which is a Continuation of U.S. application Ser. No. 13/071,363, filed Mar. 24, 2011 (now U.S. Pat. No. 8,710,035, issued Apr. 29, 2014), which claims priority to U.S. Provisional Application No. 61/317,182, filed on Mar. 24, 2010, the disclosures of which are hereby incorporated by reference in their entireties.

This invention was made with government support under CA089208 awarded by the National Institutes of Health. The government has certain rights in the invention.

REFERENCE TO A "SEQUENCE LISTING," A TABLE, OR A COMPUTER PROGRAM LISTING APPENDIX SUBMITTED ON AN XML FILE

The Sequence Listing written in file "096487-1417565-000180US", created on Dec. 12, 2023, is 209,468 bytes in size and, is hereby incorporated by reference in its entirety for all purposes.

BACKGROUND OF THE INVENTION

I. Field of the Invention

Embodiments of this invention are directed generally to biology and medicine. In certain aspects methods involve determining the prognosis for a breast cancer patient. In other embodiments, there are methods and compositions for treating a breast cancer patient with a glucocorticoid antagonist.

II. Background

There are over 1 million cases of breast cancer per year on a global basis, of which around 0.5 million are in the US, 40,000 are in the UK and nearly 2,000 in Ireland. It is the leading cause of cancer deaths among women (Keen and Davidson, 2003). Although the overall incidence of the disease is increasing within the western world, wider screening and improved treatments have led to a gradual decline in the fatality rate of about 1% per year since 1991. Inheritance of susceptibility genes, such as BRCA1 and BRCA2, account for only 5% of breast cancer cases and the factors responsible for the other 95% remain obscure (Grover and Martin, 2002). In the absence of a strategy to reduce causative agents of breast cancer, early detection remains the best approach to reducing the mortality rate of this disease. It is widely held that breast cancer initiates as the pre-malignant stage of atypical ductal hyperplasia (ADH), progresses into the pre-invasive stage of ductal carcinoma in situ (DCIS), and culminates in the potentially lethal stage of invasive ductal carcinoma (IDC). This linear model of breast cancer progression has been the rationale for the use of detection methods such as mammography in the hope of diagnosing and treating breast cancer at earlier clinical stages (Ma et al., 2003).

As more molecular information is being collated, diseases such as breast cancer are being sub-divided according to genetic signatures linked to patient outcome, providing valuable information for the clinician. Emerging novel technologies in molecular medicine have already demonstrated their power in discriminating between disease sub-types that are not recognizable by traditional pathological criteria (Sorlie et al., 2001) and in identifying specific genetic events involved in cancer progression (Srinivas et al., 2002).

Endocrine therapy is a popular mode of treatment for all stages of breast cancer. A majority of breast cancers belong to the type in which growth is stimulated by the female sex hormones, estrogens and progesterone. Therefore some of the therapies are based on depriving the tumor of the hormone-induced growth stimulus. Some of the current modes of endocrine treatments include blockade of the estrogen receptor with an antiestrogen, e.g. tamoxifen; hormonal ablation by surgery (oophorectomy, adrenalectomy or hypophysectomy), radiotherapy or medically by administration of a luteinizing hormone-releasing hormone analogue (LH-RHa), e.g., goserelin; suppression of estrogen synthesis with aromatase inhibitors, e.g., anastrozole; pharmacological doses of estrogens and progestagens, e.g., megestrol acetate.

Despite recent advances, the challenge of cancer treatment, including breast cancer therapy remains. Progress is limited with respect to the development of specific treatment regimens to clinically distinct tumor types, and to personalize tumor treatment in order to maximize outcome and efficiency. Moreover, a number of patients exhibit chemotherapy resistance.

Mere classification of breast cancers into a few subgroups characterized by low to absent gene expression of the estrogen receptor (ER) alone may not reflect the cellular and molecular heterogeneity of breast cancer, and may not allow the design of treatment strategies maximizing patient response. Once a patient is diagnosed with cancer, such as breast or ovarian cancer, or an individual wants predisposition analysis, there is a strong need for methods that allow the physician to predict the expected course of disease, including the likelihood of cancer recurrence, long-term survival of the patient, and the like, and accordingly select an appropriate treatment option that is effective.

SUMMARY OF THE INVENTION

Embodiments concern methods, compositions, and apparatuses related to assessing, prognosing, and/or treating breast cancer patients. It concerns using information related to glucocorticoid receptor (GR) activity and/or expression in conjunction with information related to estrogen receptor (ER) activity or expression to identify patients with the least favorable prognosis based on current standards of care for breast cancer. Patients with relatively low levels of estrogen receptor expression and relatively high levels of glucocorticoid expression fall into a group of breast cancer patients with the least favorable prognosis (i.e., mortality rate).

Accordingly, methods concern evaluating a patient with breast cancer. Embodiments include evaluating a biological sample from a patient; evaluating breast cancer cells from a patient; evaluating a biological sample from a breast cancer patient; assessing a breast cancer patient; testing a breast cancer sample or biopsy; testing a breast tumor; prognosing a breast cancer patient; treating a breast cancer patient, particularly a patient with a particular profile related to ER and GR; determining a treatment for a breast cancer patient; altering a treatment plan for a breast cancer patient; reporting prognosis of a breast cancer patient; determining a prognosis score for a breast cancer patient; generating a prognosis score for a breast cancer patient; assessing the risk of mortality of a breast cancer patient generally or within a certain time frame, such as 150 months from end of cancer treatment; generating an ER and GR expression profile for a breast cancer patient; comparing a patient's ER and GR expression profile to a standardized profile; and/or, determining a breast cancer patient has a poor prognosis based on the patient's ER and GR status.

Embodiments also cover apparatuses, kits, and computer readable medium and systems for assessing the level or activity of ER and/or GR in a patient's breast cancer sample and determining a prognosis; and/or treating the patient accordingly. It is specifically contemplated that a breast cancer patient is a human. Accordingly, in human patients, ER refers to an estrogen receptor in a human and GR refers to a glucocorticoid receptor in a human.

Some embodiments include generating an expression profile for glucocorticoid receptor, which means obtaining the level of expression of GR directly or indirectly by measuring or assaying activity or expression. Methods include directly measuring or assaying the level of expression or activity refers to measuring or assaying a sample to determine the level of GR expression (protein or transcript) in the cell. Indirectly obtaining the level of expression includes measuring or assaying expression or activity of a gene or protein that correlates with GR expression or activity. In some embodiments, the level of GR expression can be indirectly obtained by measuring or assaying expression of a GR-responsive gene, which refers to a gene whose expression is affected in a dose-dependent manner by GR expression or activity. Expression refers to either protein expression or RNA (transcript) expression. Methods may involve either type of expression and a variety of assays are well known to those of skill in the art. For example, quantitative PCR may be performed to obtain RNA expression levels. The Affymetrix chip used in the Examples also provides information regarding RNA expression levels. Alternatively, reagents to detect protein expression levels may be employed in embodiments. Methods may involve probes, primers, and/or antibodies that are specific to GR or ER in order to assess expression levels.

In some embodiments, the activity level of GR is measured by assaying the level of GR expression. In additional embodiments, GR expression is GR transcript expression. In other embodiments, GR expression is GR protein expression. As discussed above, in some embodiments, the activity level of GR is measured by assaying the expression level of one or more GR-responsive genes. A GR-responsive gene may be one or more of the following: MCL1, SAP30, DUSP1, SGK1, SMARCA2, PTGDS, TNFRSF9, SFN, LAPTM5, GPSM2, SORT1, DPT, NRP1, ACSL5, BIRC3, NNMT, IGFBP6, PLXNC1, SLC46A3, C14orf139, PIAS1, IDH2, SERPINF1, ERBB2, PECAM1, LBH, ST3 GAL5, IL1R1, BIN1, WIPF1, TFPI, FN1, FAM134A, NRIP1, RAC2, SPP1, PHF15, BTN3A2, SESN1, MAP3K5, DPYSL2, SEMA4D, STOM, or MAOA.

In some embodiments, there is a step of assaying or measuring the activity level of glucocorticoid receptor (GR) in a biological sample from the patient containing breast cancer cells. As discussed above, the activity level of GR can be obtained directly or indirectly. It is specifically contemplated that levels of glucocorticoid activity or expression refers to activity or expression of GR α, GR β, or both. Unless specifically stated otherwise, the terms "glucocorticoid receptor" or "GR" refer to both forms. Embodiments discussed with respect to glucocorticoid receptor or GR may also be implemented solely with GRα or solely with GRβ.

Methods may also include obtaining a level of estrogen receptor (ER) expression in breast cancer cells from the patient. The level can be obtained by obtaining the results of an assay that measured the level of ER expression. In some embodiments, the level is obtained by measuring or assaying the level of ER expression.

In some embodiments, the level of estrogen receptor expression in breast cancer cells from patient is obtained by measuring the level of estrogen receptor expression from the biological sample from the patient. In other embodiments, the level is obtained by receiving qualitative and/or quantitative data regarding the level.

In some embodiments, methods include identifying the patient as having or not having a risk factor for cancer recurrence based on the levels of ER and GR expression. Methods may involve categorizing the patient as ER+ or ER− based the level of estrogen receptor expression and a predetermined threshold value for ER expression. The term "ER+" refers to a classification of ER expression that indicates the patient expresses estrogen receptor in breast cancer cells at or above a certain level. The term "ER−" refers to a classification of ER expression that indicates the patient expresses estrogen receptor at a relatively low level in breast cancer cells, meaning at or below a certain level. In embodiments of the invention, that certain level or a predetermined threshold value is at, below, or above 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percentile, or any range derivable therein.

Methods may involve measuring the activity level of glucocorticoid receptor in a biological sample from the patient containing breast cancer cells and measuring the expression level of estrogen receptor in the biological sample.

In certain embodiments, the predetermined threshold value for ER expression identifies a patient as ER+ if the patient's ER expression level is in the $25^{th}$ percentile or greater compared to a normalized sample. This means the patient may be designated as having a level of ER expression that is at or above 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percentile, or any range derivable therein. It is contemplated that in some cases, a patient may be designated as ER+ if the patient's ER expression level is at or above 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or any range derivable therein. The patient may also be referred to as having a normal or high ER expression level. The higher the percentile, the higher the relative expression level.

In embodiments, methods may also involve categorizing the patient as GR+ or GR− based on a predetermined threshold value for GR activity. In some cases, a predetermined threshold value for GR activity is dependent on whether the patient is categorized as ER+ or ER−. Embodiments may involve a predetermined threshold value for GR activity that identifies a patient as GR+ if the patient is ER− and GR activity level is in the $65^{th}$ percentile or greater compared to a normalized sample. It is contemplated that in some cases, a patient may be designated as GR+ if the patient's GR expression level is at or above 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or any range derivable therein. The threshold value may or may not be dependent on ER expression levels or status. In some embodiments, the threshold value depends on whether the patient is ER− or not. The higher the percentile, the higher the relative expression level.

Methods may involve the use of a normalized sample or control that is based on one or more breast cancer samples that are not from the patient being tested.

In some embodiments, methods involve calculating a prognosis score for the patient based on the levels of ER and/or GR expression. Methods may alternatively or additionally involve reporting a prognosis score or report the levels of ER and/or GR expression. The score or report may contain or reflect raw data regarding expression levels or it may reflect a categorization of the expression levels obtained. A score could indicate the risk factor for mortality, recurrennce, and/or both. The score could be a number within a numeric scale in which one end of the scale is most favorable and the other end is the least favorable with respect to a prognosis for breast cancer.

In certain embodiments, methods may involve identifying the patient as having a poor prognosis if the patient is determined to have a glucocorticoid receptor activity level at or above a certain threshold level and a level of estrogen receptor that is at or below a second threshold level. In each case, the threshold levels are specific for each of GR and ER. In certain embodiments, it is contemplated that a GR level in the 65th percentile or above based on breast cancer patients whose are in the $35^{th}$ percentile or below is indicative of a poor prognosis. In some embodiments, patients with a poor prognosis include a population of breast cancer patients that numbers approximately 10% or less.

Methods also include identifying the patient as having a poor prognosis if the patient is determined to have i) an activity level of glucocorticoid receptor that is higher than the activity level of glucocorticoid receptor in normalized control sample and ii) a expression level of estrogen receptor expression that is lower than the expression level of estrogen receptor in a normalized control sample. Consequently, methods of the invention include prognosing a breast cancer patient. In some cases, a patient is identified as having a relatively good prognosis.

Other embodiments include methods of treating a patient for breast cancer comprising: treating the patient for breast cancer after a biological sample from the patient containing breast cancer cells is analyzed for i) the activity level of glucocorticoid receptor and ii) the expression level of estrogen receptor. A patient may be treated with a different treatment protocol than the patient would have been treated with if the patient's biological sample had not been analyzed. In some embodiments, the patient is categorized as ER− and GR+ based on the activity level of the glucocorticoid receptor and the expression level of estrogen receptor. In some cases, the patient is treated with a more aggressive therapy than the patient would have been treated with if the patient had not been categorized as ER− and GR+. The term "more aggressive" refers to a treatment regimen that may include more drugs or drugs with more severe side effects and/or it may include an increased dosage or increased frequency of drugs. It may also include radiation or a combination of therapies. In some cases, the therapy includes one or more chemotherapeutics and/or biologics. In some embodiments, the patient is treated with a therapy comprising an anti-angiogenic agent. In additional embodiments, the therapy further comprises a chemotherapeutic agent in addition to the anti-angiogenic agent. Embodiments also include administering a glucocorticoid receptor antagonist and/or tyrosine kinase inhibitor.

Embodiments may also include where the patient is treated with more than one type of cancer therapy. This may be after the patient is determined to have a particular prognosis or after the status of the patient's GR and ER expression profile is known. In some embodiments, certain treatments are provided to an ER−/GR+ breast cancer patient who might have otherwise been treated with a less aggressive treatment for breast cancer. In some embodiments, a patient is treated with at least two of the following: radiation, chemotherapy, or a biologic. In particular embodiments, the patient may be treated with a kinase inhibitor and/or anti-angiogenic agent.

Methods may also involve obtaining a biological sample comprising breast cancer cells from the patient and categorizing the patient as i) GR+ or GR− based on the level of glucocorticoid activity assayed in the sample and compared to a predetermined threshold value for GR activity; and ii) ER+ or ER− based on the level of estrogen receptor expression assayed in the sample and compared to a predetermined threshold value for ER expression.

Any method may also include treating the patient for breast cancer, which may include directly administering or providing a cancer therapy. In some embodiments, a practitioner or doctor may prescribe a cancer therapy that the patient administers to herself.

To achieve these methods, a doctor, medical practitioner, or their staff may retrieve a biological sample from a patient for evaluation. The sample may be a biopsy, such as a breast tissue or tumor biopsy. The sample may be analyzed by the practitioner or their staff, or it may be sent to an outside or independent laboratory. The medical practitioner may be cognizant of whether the test is providing information regarding the patient's level of GR and/or ER expression or activity, or the medical practitioner may be aware only that the test indicates directly or indirectly that the test reflects that the patient has a particular prognosis or can be given a particular prognosis score. Furthermore, the practitioner may know the patient's ER or GR status, such as ER+ or ER−, or GR+ or GR−. Alternatively, she may be aware only that the test or assay indicates the patient has a poor prognosis, or the worst prognosis.

Embodiments also concern kits to determine glucocorticoid receptor status in breast cancer cells comprising: (a) one or more reagents for determining expression levels of NR3C1 in a biological sample; and (b) an algorithm and software encoding the algorithm for calculating a risk factor index from the expression of NR3C1 in a sample and the estrogen receptor status of the breast cancer cells to determine a prognosis or a prognosis score. Kits may also include one or more reagents for determining expression levels of ESR1 in the biological sample to provide estrogen receptor status.

Other embodiments include a computer readable medium having software modules for performing a method comprising the acts of: (a) comparing glucocorticoid receptor data obtained from a patient's breast cancer sample with a reference; and (b) providing an assessment of glucocorticoid receptor status to a physician for use in determining an appropriate therapeutic regimen for a patient. In further embodiments, the computer readable medium further comprises a software module for assessing estrogen receptor status of the patient's breast cancer sample.

Computer systems are also included. In some embodiments, they have a processor, memory, external data storage, input/output mechanisms, a display, for assessing glucocorticoid receptor activity, comprising: (a) a database; (b) logic mechanisms in the computer generating for the database a GR-responsive gene expression reference; and (c) a comparing mechanism in the computer for comparing the GR-responsive gene expression reference to expression data from a patient sample using a comparison model to determine a GR gene expression profile of the sample.

Other embodiments include an internet accessible portal for providing biological information constructed and arranged to execute a computer-implemented method for providing: (a) a comparison of gene expression data of one or more GR-responsive genes in a patient sample with a calculated reporter index; and (b) providing an assessment of GR activity or expression to a physician for use in determining an appropriate therapeutic regime for a patient.

In addition to compiling, collecting and or processing data related to GR status, methods, media and systems may also include the same embodiments with respect to data related to ER status. Such aspects may be instead of or in addition to the aspects related to GR status or data.

Embodiments also include methods of killing breast cancer cells comprising administering to a breast cancer patient an effective amount of a combination of anti-cancer compounds, wherein the anticancer compounds comprise a glucocorticoid receptor antagonist and a chemotherapeutic.

In other embodiments, there are methods for treating breast cancer in a patient comprising administering to the patient an effective amount of glucocorticoid receptor antagonist and a chemotherapeutic.

In further embodiments, methods are provided for treating chemotherapy-insensitive breast cancer cells comprising administering to a breast cancer patient an effective amount of a glucocorticoid receptor antagonist followed by chemotherapy.

Other methods include methods for treating breast cancer in a patient comprising: a) administering radiation or at least a first chemotherapeutic to the patient; b) subsequently administering an effective amount of a glucocorticoid receptor antagonist to the patient; and, c) administering radiation again or at least a second chemotherapeutic to the patient after the glucocorticoid receptor antagonist is administered to the patient.

In some embodiments, there are methods for treating breast cancer in a patient comprising: a) administering an effective amount of a glucocorticoid receptor antagonist to the patient, wherein the patient expresses detectable levels of GR prior to administration of the GR antagonist; b) then administering an effective amount of radiation or at least one chemotherapeutic.

It is contemplated that in methods described herein, breast cancer cells may undergo apoptosis following treatment set forth herein. Moreover, in some embodiments, the combination of a glucocorticoid receptor antagonist and an anti-cancer agent or compound induces more apoptosis than treatment with just the anticancer treatment alone. In other methods, it is specifically contemplated to exclude treatment with a synthetic glucocorticoid, such as dexamethasone.

Glucocorticoid receptor antagonists are known to those of skill in the art. It refers to a compound or substance that that does not provoke a biological response itself upon binding to the glucocorticoid receptor, but blocks or dampens agonist-mediated responses. Examples include, but are not limited to, beclometasone, betamethasone, budesonide, ciclesonide, flunisolide, fluticasone, mifepristone, mometasone, and triamcinolone. In additional embodiments, the glucocorticoid receptor antagonist has undetectable level or a lower level of activity as a progesterone receptor antagonist. In certain embodiments, the glucocorticoid receptor antagonist has greater than 10-fold, 50-fold, 100-fold, 200-fold, 300-fold, 400-fold, 500-fold, 1000-fold lower binding activity (or any range derivable therein) for another hormone receptor compared to its binding activity for glucocorticoid receptor. In specific embodiments the hormone receptor is estrogen receptor or progesterone receptor.

In some embodiments, a patient had been previously treated with an anti-cancer therapy, such as radiation, chemotherapy, or immunotherapy (or a combination or multiple therapies thereof). In certain embodiments, a first anti-cancer therapy prior to therapy with glucocorticoid receptor antagonist was last administered more than two weeks prior to the glucocorticoid receptor antagonist or its combination with a second anti-cancer therapy. In certain embodiments, this first anti-cancer therapy that does not include a glucocorticoid receptor antagonist was last administered to the breast cancer patient at least 7, 8, 9, 10, 11, 12, 13, 14 days, and/or 1, 2, 3, 4, or 5 weeks, and/or 1, 2, 3, 4, 5, 6, 7, 8, 9, 10, 11, or 12 months prior to treatment with a glucocorticoid receptor antagonist. Treatment methods may be applied to breast cancer or breast cancer cells that are chemo-resistant or breast cancer cells that are not chemo-sensitive. Moreover, treatment may be applied to breast cancer or to breast cancer cells that were previously administered a first apoptosis inducing agent, but were resistant to apoptosis.

In some embodiments, the breast cancer cells are determined to be resistant to apoptosis. In additional embodiments, the breast cancer or the breast cancer cells are determined not to be chemo-sensitive or are determined to be chemo-resistant. This determination may be based on the results of a genetic test or based on information obtained from an assessment of a tumor or the breast cancer after treatment with a first anti-cancer therapy. In specific embodiments, the first anti-cancer therapy is a chemotherapeutic, Herceptin®, radiation, a combination of chemotherapeutics, or a combination of one or more chemotherapeutic agents and Herceptin®.

In additional embodiments, the breast cancer cells express a detectable level of glucocorticoid receptor or its transcript. In some embodiments, the patient is determined to have breast cancer cells that express a detectable level of glucocorticoid receptor or its transcript. This may be determined directly or indirectly.

It is contemplated that breast cancer cells may be treated with a glucocorticoid receptor antagonist regardless of estrogen receptor status. Therefore, breast cancer cells may be estrogen receptor-negative (ER−) or estrogen receptor-positive (ER+), accordingly to a standardized and industry accepted test for ER status. In certain embodiments, the breast cancer cells do not express any detectable levels of ER; in other embodiments, ER expression is detectable in the breast cancer cells.

It is contemplated that breast cancer cells may be treated with a glucocorticoid receptor antagonist depending on or regardless of progesterone receptor status. Therefore, breast cancer cells may be progesterone receptor-negative (PR−) or progesterone receptor-positive (PR+), accordingly to a standardized and industry accepted test for ER status. In certain embodiments, the breast cancer cells do not express any detectable levels of PR; in other embodiments, PR expression is detectable in the breast cancer cells.

Methods involve treating breast cancer, particularly a chemo-resistant breast cancer, with a combination of therapies that includes a glucocorticoid receptor antagonist and an anticancer therapy that induces apoptosis (together they may be referred to as a combination of anti-cancer agents or compounds), such as a chemotherapeutic. In some embodiments, the chemotherapeutic is capecitabine, carboplatin, cyclophosphamide (Cytoxan), daunorubicin, docetaxel (Taxotere), doxorubicin (Adriamycin), epirubicin (Ellence), fluorouracil (also called 5-fluorouracil or 5-FU), gemcitabine, eribulin, ixabepilone, methotrexate, mitomycin C, mitoxantrone, paclitaxel (Taxol), thiotepa, vincristine, or vinorelbin, or a combination of these agents. In other embodiments, therapy with a glucocorticoid receptor antagonist is combined Herceptin®, radiation, chemotherapeutic(s) and radiation, a combination of chemotherapeutics, or a combination of one or more chemotherapeutic agents and Herceptin®.

It is contemplated that in some embodiments of the combination therapy the glucocorticoid receptor antagonist is administered within 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof within administration of at least one or the combination of the anti-cancer agents or compounds. In specific embodiments, the glucocorticoid receptor antagonist is administered within 2 hours, 12 hours or 24 hours of administration of a anticancer agent or compound (or a combination of such agents or compounds).

It is specifically contemplated that treatment may continue or be repeated. In some embodiments, once treated with the combination of a glucocorticoid receptor antagonist and at least one anticancer agent or compound, all or part of the treatment may be repeated alone or in combination with a different anticancer agent or compound.

In certain embodiments, the glucocorticoid receptor antagonist is administered prior to as the other agent or therapy included in the combination therapy. In certain embodiments, the glucocorticoid receptor antagonist is administered 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof prior to administration of at least one or the combination of the anti-cancer agents or compounds. It is specifically contemplated that in some embodiments, the glucocorticoid receptor antagonist is given prior to administration of the anticancer agent or compound but that the glucocorticoid receptor antagonist is also given concurrently with or after administration of the initial or a subsequent dose of the anticancer agent or compound. As discussed throughout, the anticancer agent or compound may be in a combination of such agents or compounds. In certain embodiments, the glucocorticoid receptor antagonist is administered up to three days prior to administering the anticancer agent or compound.

Additionally or alternatively, the glucocorticoid receptor antagonist is administered after administration of the other agent or therapy included in the combination therapy. In certain embodiments, the glucocorticoid receptor antagonist is administered 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof after administration of at least one or the combination of the anti-cancer agents or compounds. It is specifically contemplated that in some embodiments, the glucocorticoid receptor antagonist is given after to administration of the anticancer agent or compound; such administration may be repeated. As discussed throughout, the anticancer agent or compound may be in a combination of such agents or compounds. In certain embodiments, the glucocorticoid receptor antagonist is administered up to three days after administering the anticancer agent or compound.

In certain embodiments, the breast cancer is an unresectable breast cancer. In further embodiments, the breast cancer is inflammatory breast cancer.

It is specifically contemplated that in some methods, dexamethasone has not been administered to the patient within 24 hours of administration of the glucocorticoid receptor antagonist.

Compositions are contemplated to include a glucocorticoid receptor antagonist and any other anticancer compound discussed herein, such a Herceptin or one or more chemotherapeutic compounds. In some embodiments, the composition is in a pharmaceutically acceptable formulation.

Use of the one or more compositions may be employed based on methods described herein. Other embodiments are discussed throughout this application. Any embodiment discussed with respect to one aspect of the invention applies to other aspects of the invention as well and vice versa. The embodiments in the Example section are understood to be embodiments o that are applicable to all aspects of the technology described herein.

"Cancer prognosis" generally refers to a forecast or prediction of the probable course or outcome of the cancer. As used herein, cancer prognosis includes the forecast or prediction of any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, and/or duration of response in a patient or a group of patients susceptible to or diagnosed with a cancer.

In certain aspects, prognosis is an estimation of the likelihood of metastasis free survival of said patient over a predetermined period of time, e.g., over a period of 5 years.

In further aspects, prognosis is an estimation of the likelihood of death of disease of said patient over a predetermined period of time, e.g., over a period of 5 years.

The term "recurrence" refers to the detection of breast cancer in form of metastatic spread of tumor cells, local recurrence, contralateral recurrence or recurrence of breast cancer at any site of the body of the patient after breast cancer had been substantially undetectable or responsive to treatments.

As used herein, "prognostic for cancer" means providing a forecast or prediction of the probable course or outcome of the cancer. In some embodiments, "prognostic for cancer" comprises providing the forecast or prediction of (prognostic for) any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, and/or duration of response in a patient or a group of patients susceptible to or diagnosed with a cancer.

By "gene" is meant any polynucleotide sequence or portion thereof with a functional role in encoding or transcribing a protein or regulating other gene expression. The gene may consist of all the nucleic acids responsible for encoding a functional protein or only a portion of the nucleic acids responsible for encoding or expressing a protein. The polynucleotide sequence may contain a genetic abnormality within exons, introns, initiation or termination regions, promoter sequences, other regulatory sequences or unique adjacent regions to the gene.

As used herein, "treatment" or "therapy" is an approach for obtaining beneficial or desired clinical results. This includes: reduce the number of cancer cells; reduce the tumor size; inhibit (i.e., slow to some extent and/or stop) cancer cell infiltration into peripheral organs; inhibit (i.e., slow to some extent and/or stop) tumor metastasis; inhibit, to some extent, tumor growth; and/or relieve to some extent one or more of the symptoms associated with the disorder, shrinking the size of the tumor, decreasing symptoms resulting from the disease, increasing the quality of life of those suffering from the disease, decreasing the dose of other medications required to treat the disease, delaying the progression of the disease, and/or prolonging survival of patients.

The term "therapeutically effective amount" refers to an amount of the drug that may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The terms "overexpress", "overexpression", "overexpressed", "up-regulate", or "up-regulated" interchangeably refer to a biomarker that is transcribed or translated at a detectably greater level, usually in a cancer cell, in comparison to a non-cancer cell or cancer cell that is not associated with the worst or poorest prognosis. The term includes overexpression due to transcription, post transcriptional processing, translation, post-translational processing, cellular localization, and/or RNA and protein stability, as compared to a non-cancer cell or cancer cell that is not associated with the worst or poorest prognosis. Overexpression can be detected using conventional techniques for detecting mRNA (i.e., RT-PCR, PCR, hybridization) or proteins (i.e., ELISA, immunohistochemical techniques, mass spectroscopy). Overexpression can be 10%, 20%, 30%, 40%, 50%, 60%, 70%, 80%, 90% or more in comparison to a normal cell or cancer cell that is not associated with the worst or poorest prognosis. In certain instances, overexpression is 1-fold, 2-fold, 3-fold, 4-fold 5, 6, 7, 8, 9, 10, or 15-fold or more higher levels of transcription or translation in comparison to a non-cancer cell or cancer cell that is not associated with the worst or poorest prognosis.

"Biological sample" includes sections of tissues such as biopsy and autopsy samples, and frozen sections taken for histologic purposes. Such samples include breast cancer tissues, cultured cells, e.g., primary cultures, explants, and transformed cells. A biological sample is typically obtained from a mammal, such as a primate, e.g., human.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., breast), the size and type of the tumor, among other factors. Representative biopsy techniques include, but are not limited to, excisional biopsy, incisional biopsy, needle biopsy, and surgical biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy", or a "fine-needle aspiration biopsy" which generally obtains a suspension of cells from within a target tissue. Biopsy techniques are discussed, for example, in Harrison's Principles of Internal Medicine, 2005. Obtaining a biopsy includes both direct and indirect methods, including obtaining the biopsy from the patient or obtaining the biopsy sample after it is removed from the patient.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 7A-7F. Schematic of glucocorticoid receptor (GR) isoforms.

DETAILED DESCRIPTION OF THE INVENTION

Figure 1:
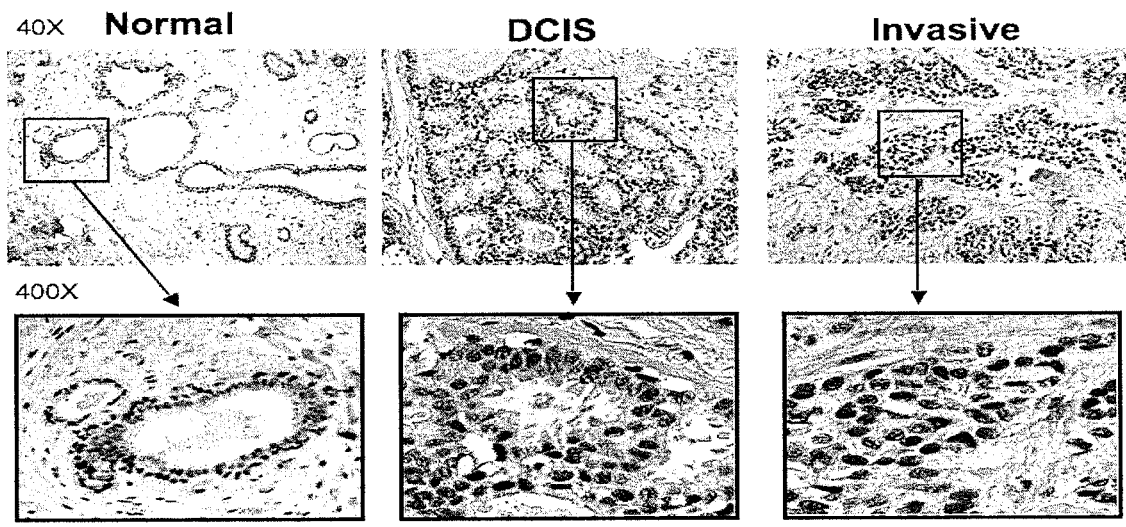
FIG. 1. Primary human breast ductal epithelium, DCIS (60%) in vasive human cancers (30-40%) exhibit significant glucocorticoid receptor expression.
Figure 2:
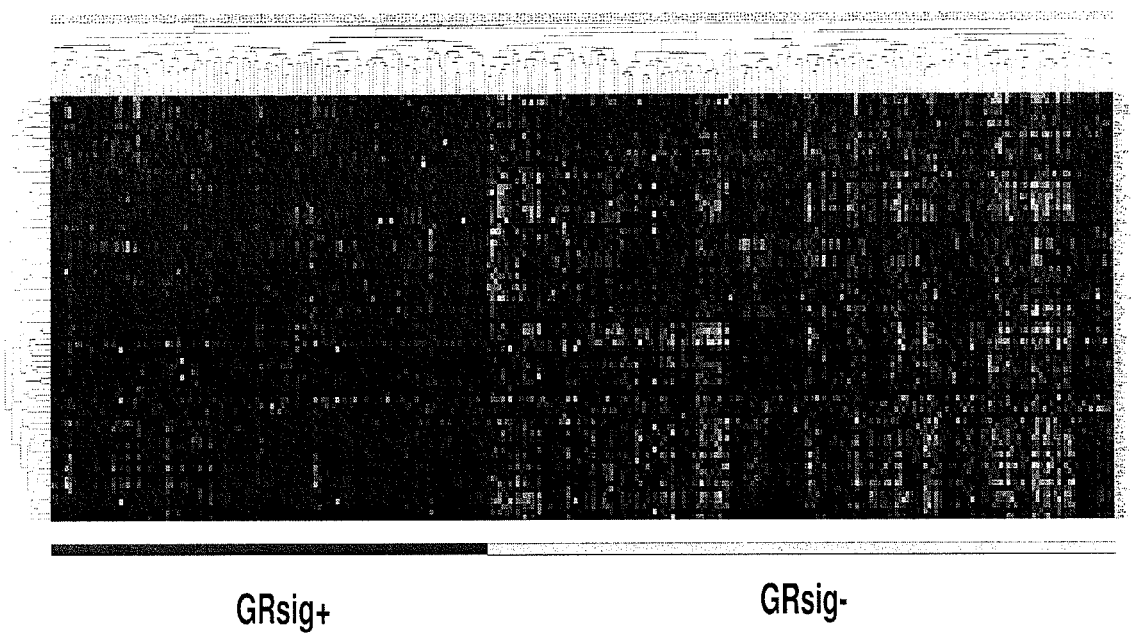
FIG. 2. Unsupervised cluster analysis identifies GR target gene signature (Sig+) vs Sig− tumors (n=68 genes) A GR-regulated gene expression set from MCF10A-Myc (ER−/GR+) cells treated+/−Dex from 30 m-24 h was used to perform a two dimensional unsupervised clustering analysis on the NKI-295 early breast cancer gene expression data set (n=2034 starting genes). GR-regulated genes (n=68) that separate these tumors into two groups (GRsig+=Red and GRsig−=Green) are shown in rows while each column represents a patient. Several EMT genes (e.g. Snail) and known anti-apoptotic genes are included.
Figure 3:
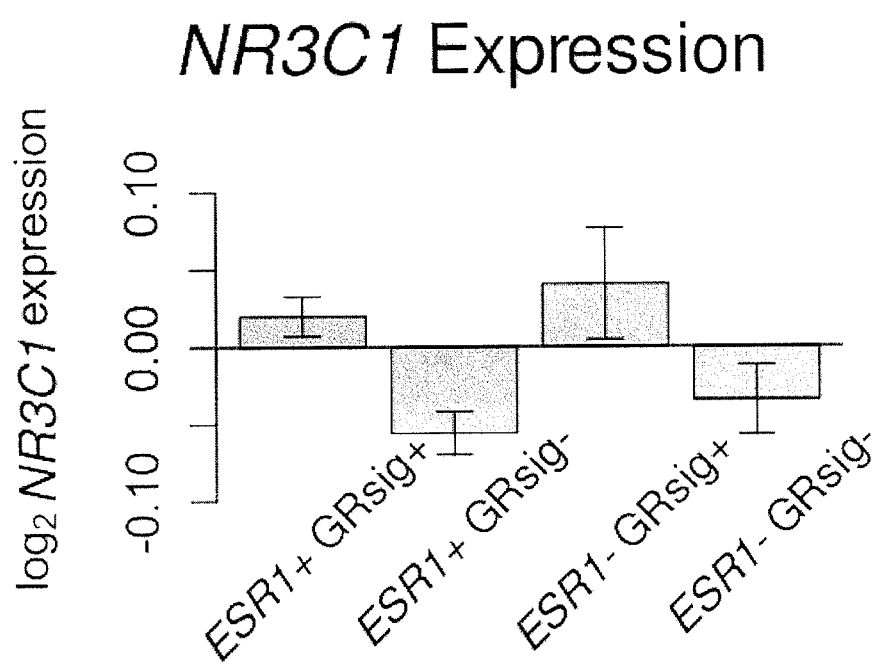
FIG. 3. NR3C1 expression correlates with GR signature gene expression. The GRsig+vs. GRsig− tumor designations correlate with higher NR3C1 vs. lower expression, respectively. For ESR1+ tumors (orange) the P<0.00001 and for ESR1− tumors (green) p=0.7 (t test). Error bars are +/−SD.
Figure 4:
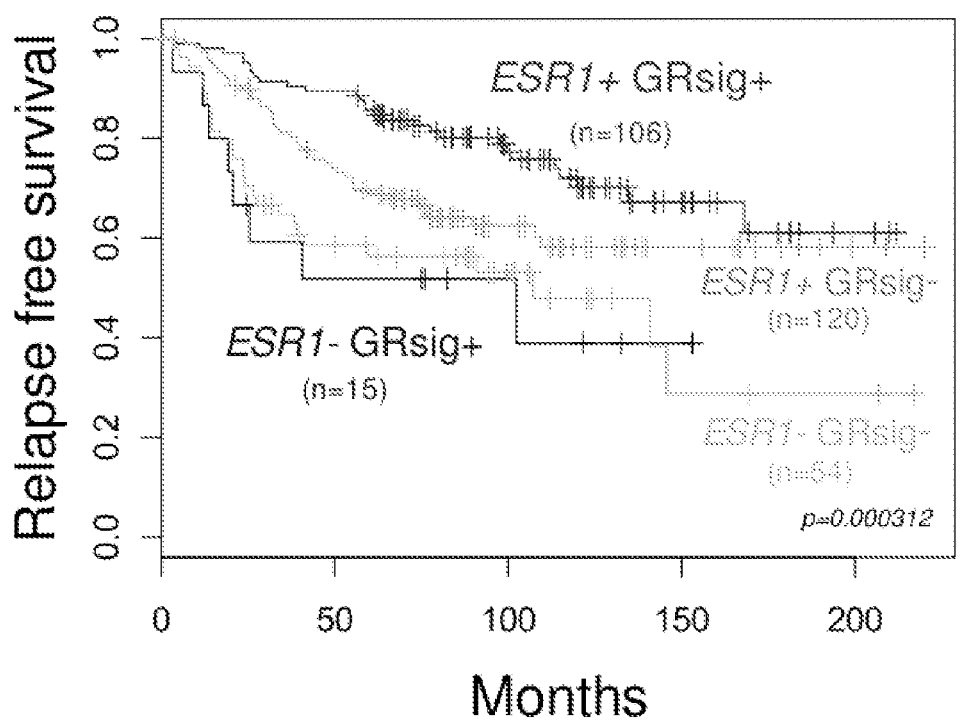
FIG. 4. RFS of GR gene expression signature. The GR signature predicts a differential prognosis for ESR1+ patients and ESR1− pts with respect to GR-signature expression. ESR1−/GR+ signature patients have the worst prognosis.
Figure 5:
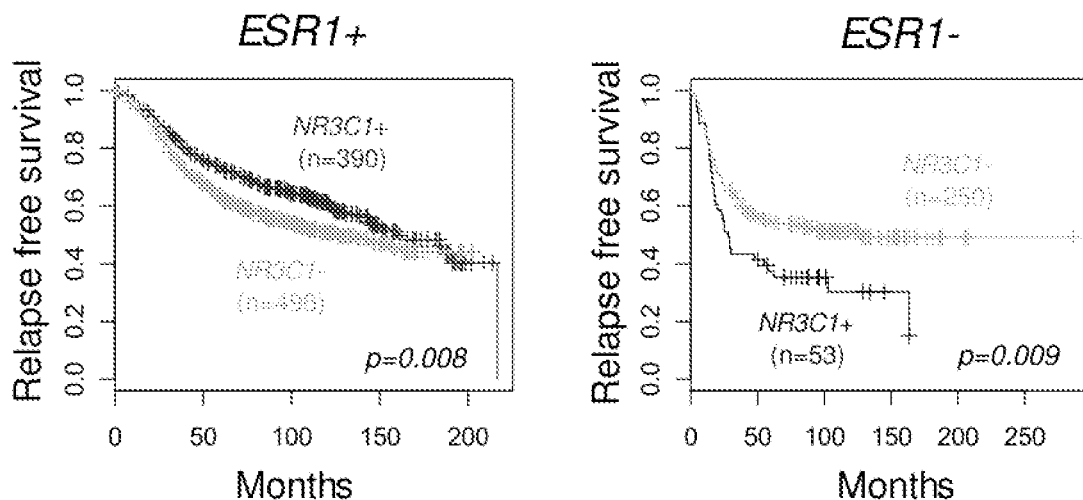
FIG. 5. Meta-analysis of NR3C1 expression and RFS.
Figure 6:
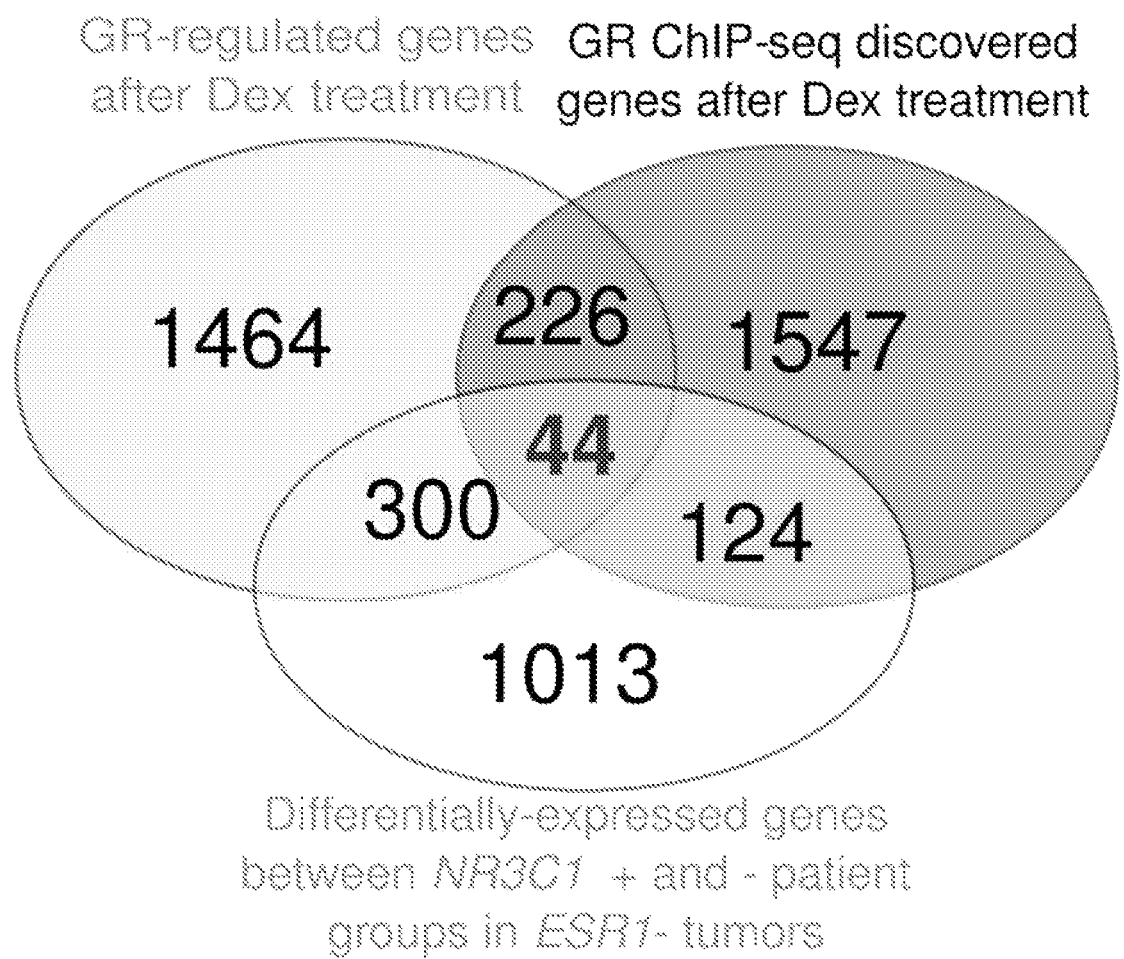
FIG. 6. Common genes differentially expressed in ESR1− and NR3C1+/− tumors, ChIP-seq and gene expression in Dex-treated MCF10A-Myc cells.

Glucocorticoid receptor (GR) activation initiates a potent cell survival signal in ER-breast cancer models. However, GR activity has not been previously examined in primary human breast cancers. Because anti-apoptotic signaling is believed to be an important determinant of breast cancer viability and relapse, the inventors contemplate that early stage primary human breast cancer demonstrates a correlation between high GR (NR3C1) and GR-mediated gene expression and cancer recurrence.

The Dutch NKI 295 data set was examined and the inventors determined that a gene expression signature of 68 GR-regulated genes (based on in vitro data) could cluster patients into different groups with differential outcome. In addition, it was found that GR-mediated gene expression correlated with NR3C1 expression levels. The inventors examined NR3C1 tumor expression in a much larger meta-dataset and again found that ER−/GR (NR3C1)+ patients did the worst. Moreover, key cell survival genes identified as GR gene targets from ChIP-seq experiments were differentially expressed.

I. Hormone Receptor Status of Breast Cancer

Intracellular receptors (IRs) form a class of structurally-related genetic regulators scientists have named "ligand dependent transcription factors" (R. M. Evans, Science, 240:889, 1988). Steroid receptors are a recognized subset of the IRs, including androgen receptor (AR), progesterone receptor (PR), estrogen receptor (ER), glucocorticoid receptor (GR), and mineralocorticoid receptor (MR). Regulation of a gene by such factors requires both the IR itself and a corresponding ligand, which has the ability to selectively bind to the IR in a way that affects gene transcription.

Naturally occurring as well as synthetic steroidal glucocorticoids (e.g., cortisol, cortisone, prednisolone, dexamethasone) have been widely used for over fifty years for the treatment of acute and chronic inflammatory and immune disorders. In particular, glucocorticoids have been prescribed for the treatment of rheumatoid arthritis, osteoarthritis, rheumatic fever, asthma, allergic rhinitis, systemic lupus erythematosus, chronic obstructive pulmonary disease, Crohn's disease, inflammatory bowel disease, and ulcerative colitis. However, the use of glucocorticoids is often associated with severe and sometimes irreversible side effects such as bone loss/osteoporosis, hyperglycemia, diabetes mellitus, hypertension, glaucoma, muscle atrophy, Cushing's syndrome, and psychosis.

Glucocorticoids exert their pharmacological effects by regulating gene transcription after the formation of a complex with the glucocorticoid receptor (GR). GR-glucocorticoid complex affects gene transcription by translocating to the nucleus after binding of the glucocorticoid where it acts as a dimer in binding to DNA glucocorticoid hormone response elements (GREs) in the promoter regions of particular genes. The GR-glucocorticoid/GRE complex then, in turn, activates (transactivation) or inhibits transcription of proximally located genes. Conversely, the GR-glucocorticoid complex may negatively regulate gene transcription by a process that does not involve binding to DNA. In this process, termed transrepression, following binding of the glucocorticoid, the complexed GR enters the nucleus where it acts as a monomer to directly interact (via protein-protein interaction) with other transcription factors, repressing their ability to induce gene transcription and thus protein expression.

Estrogen, mediated through the estrogen receptor (ER), plays a major role in regulating the growth and differentiation of normal breast epithelium (Pike et al. Epidemiologic Reviews (1993) 15(1):17-35; Henderson et al. Cancer Res. (1988) 48:246-253). It stimulates cell proliferation and regulates the expression of other genes, including the progesterone receptor (PgR). PgR then mediates the mitogenic effect of progesterone, further stimulating proliferation (Pike et al., 1993; Henderson et al., 1988). The molecular differences between estrogen receptor ("ER") negative and ER positive tumors are significant in light of clinical observations which indicate that the nature and biological behavior of ER positive and ER negative tumors are distinct even in the absence of hormonal therapy. For example, ER negative cancers tend to recur sooner and show a different rate of recurrence in distant organ sites compared to ER positive tumors. Clinical observations and molecular profiling data suggest that tumors not expressing both ER and PgR represent a different clinical entity in terms of chemotherapy responsiveness. (Colleoni et al., Annals of Oncology 11(8): 1057 (2000)). Thus, ER negative and ER positive breast cancers are two distinct disease entities rather than phenotypic variations of the same disease.

Relatively increased expression of these genes in primary ER-negative human breast tumors is associated with high GR expression and with an earlier relapse in ER-negative breast cancer patients (described herein). Activation of the glucocorticoid receptor (GR) in epithelial cells has been shown to initiate an anti-apoptotic (i.e., cell survival) signaling pathway that prevents breast (Wu et al, 2004) and ovarian cancer (Melhem et al, 2009) cell death in vitro and in vivo (Pang et al, 2006). Blocking or antagonizing GR activation with a GR antagonist such as mifepristone reverses cell survival signaling pathways initiated by the GR (Moran et al., 2000). Other GR antagonists (e.g., dexamethasone oxetanone) also reverse GR-mediated cell survival and potentiate apoptosis in response to cell stressors such as growth factor withdrawal (Mikosz et al, 2001). The mechanism(s) whereby GR activation protects from cell death includes the transcriptional upregulation of genes encoding anti-apoptotic proteins such as SGK1, MKP1, MCL1, and BIRC3. However, experiments with a glucocorticoid receptor antagonist, RU486, in conjunction with dexamethasone did not increase the number of apoptotic cells induced by paclitaxel, compared to paclitaxel alone (Wu et al., 2004).

II. Biomarkers and Evaluating Levels of Biomarkers

Biomarkers for prognosing human breast cancer patients have been identified. They include estrogen receptor (ER) in combination with the activity of the glucocorticoid receptor (GR) activity. It is contemplated that these biomarkers may be evaluated based on their gene products. In some embodiments, the gene product is the RNA transcript. In other embodiments, the gene product is the protein expressed by the RNA transcript. In still another embodiment is the evaluation of surrogate genes or gene targets of ER, GR, or ER and GR.

In certain aspects a meta-analysis of expression or activity can be performed. In statistics, a meta-analysis combines the results of several studies that address a set of related research hypotheses. This is normally done by identification of a common measure of effect size, which is modeled using a form of meta-regression. Generally, three types of models can be distinguished in the literature on meta-analysis: simple regression, fixed effects meta-regression and random effects meta-regression. Resulting overall averages when controlling for study characteristics can be considered meta-effect sizes, which are more powerful estimates of the true effect size than those derived in a single study under a given single set of assumptions and conditions. A meta-gene expression value, in this context, is to be understood as being the median of the normalized expression of a marker gene or activity. Normalization of the expression of a marker gene is preferably achieved by dividing the expression level of the individual marker gene to be normalized by the respective individual median expression of this marker genes, wherein said median expression is preferably calculated from multiple measurements of the respective gene in a sufficiently large cohort of test individuals. The test cohort preferably comprises at least 3, 10, 100, 200, 1000 individuals or more including all values and ranges thereof. Dataset-specific bias can be removed or minimized allowing multiple datasets to be combined for meta-analyses (See Sims et al. BMC Medical Genomics (1:42), 1-14, 2008, which is incorporated herein by reference in its entirety).

The calculation of a meta-gene expression value is performed by: (i) determining the gene expression value of at least two, preferably more genes (ii) "normalizing" the gene expression value of each individual gene by dividing the expression value with a coefficient which is approximately the median expression value of the respective gene in a representative breast cancer cohort (iii) calculating the median of the group of normalized gene expression values.

A gene shall be understood to be specifically expressed in a certain cell type if the expression level of said gene in said cell type is at least 2-fold, 5-fold, 10-fold, 100-fold, 1000-fold, or 10000-fold higher than in a reference cell type, or in a mixture of reference cell types. Reference cell types include non-cancerous breast tissue cells or a heterogenous population of breast cancers.

In certain algorithms a suitable threshold level is first determined for a marker gene. The suitable threshold level can be determined from measurements of the marker gene expression in multiple individuals from a test cohort. The median expression of the marker gene in said multiple expression measurements is taken as the suitable threshold value.

Comparison of multiple marker genes with a threshold level can be performed as follows:

1. The individual marker genes are compared to their respective threshold levels.
2. The number of marker genes, the expression level of which is above their respective threshold level, is determined.
3. If a marker genes is expressed above its respective threshold level, then the expression level of the marker gene is taken to be "above the threshold level".

"A sufficiently large number", in this context, means preferably 30%, 50%, 80%, 90%, or 95% of the marker genes used.

In certain aspects, the determination of expression levels is on a gene chip, such as an Affymetrix™ gene chip.

In another aspect, the determination of expression levels is done by kinetic real time PCR.

In certain aspects, the methods can relate to a system for performing such methods, the system comprising (a) apparatus or device for storing data on the ER or nodal status of the patient; (b) apparatus or device for determining the expression level of at least one marker gene or activity; (c) apparatus or device for comparing the expression level of the first marker gene or activity with a predetermined first threshold value; (d) apparatus or device for determining the expression level of at least one second marker gene or activity; and (e) computing apparatus or device programmed to provide a unfavorable or poor prognosis if the data indicates a negative ER status and an increased or decreased expression level of said first marker gene or activity (e.g., GR expression or activity) with the predetermined first threshold value and, alternatively, the expression level of said second marker gene is above or below a predetermined second threshold level.

The person skilled in the art readily appreciates that an unfavorable or poor prognosis can be given if the expression level of the first marker gene with the predetermined first threshold value indicates a tumor that is likely to recur or not respond well to standard therapies.

The expression patterns can also be compared by using one or more ratios between the expression levels of different breast cancer biomarkers. Other suitable measures or indicators can also be employed for assessing the relationship or difference between different expression patterns.

The GR nucleic acid and protein sequences are provided in GenBank accession number AY436590. The ER nucleic acid and protein sequences are provided in GenBank accession number NG_008493. The content of all of these GenBank Accession numbers is specifically incorporated herein by reference as of the filing date of this application.

The following biomarkers are provided for implementation with embodiments discussed herein. All of them designate nucleic acid sequences for the particular gene identifier. Nucleic acid sequences related to these gene designation can be found in the Genbank sequence databases. Additional biomarkers include the MCL1, SAP30, DUSP1, SGK1, SMARCA2, PTGDS, TNFRSF9, SFN, LAPTM5, GPSM2, SORT1, DPT, NRP1, ACSL5, BIRC3, NNMT, IGFBP6, PLXNC1, SLC46A3, C14orf139, PIAS1, IDH2, SERPINF1, ERBB2, PECAM1, LBH, ST3GAL5, IL1R1, BIN1, WIPF1, TFPI, FN1, FAM134A, NRIP1, RAC2, SPP1, PHF15, BTN3A2, SESN1, MAP3K5, DPYSL2, SEMA4D, STOM, and MAOA genes.

One or more of the biomarkers can be used to prognose a human patient with breast cancer. The expression pattern of these biomarkers in breast cancer cells may be used to evaluate a patient to determine whether they are likely to respond to standard chemotherapy, likely not to respond to standard chemotherapy, or likely to relapse after standard chemotherapy.

The expression levels of breast cancer biomarkers can be compared to reference expression levels using various methods. These reference levels can be determined using expression levels of a reference based on all breast cancer patients or all breast cancer patients determined to be ER+ and/or ER−. Alternatively, it can be based on an internal reference such as a gene that is expressed in all cells. In some embodiments, the reference is a gene expressed in breast cancer cells at a higher level than any biomarker. Any comparison can be performed using the fold change or the absolute difference between the expression levels to be compared. One or more breast cancer biomarkers can be used in the comparison. It is contemplated that 1, 2, 3, 4, 5, 6, 7, 8, and/or 9 biomarkers may be compared to each other and/or to a reference that is internal or external. A person of ordinary skill in the art would know how to do such comparisons.

Comparisons or results from comparisons may reveal or be expressed as x-fold increase or decrease in expression relative to a standard or relative to another biomarker or relative to the same biomarker but in a different class of prognosis. In some embodiments, patients with a poor prognosis have a relatively high level of expression (overexpression) or relatively low level of expression (underexpression) when compared to patients with a better or favorable prognosis, or vice versa.

Fold increases or decreases may be, be at least, or be at most 1-, 2-, 3-, 4-, 5-, 6-, 7-, 8-, 9-, 10-, 11-, 12-, 13-, 14-, 15-, 16-, 17-, 18-, 19-, 20-, 25-, 30-, 35-, 40-, 45-, 50-, 55-, 60-, 65-, 70-, 75-, 80-, 85-, 90-, 95-, 100- or more, or any range derivable therein. Alternatively, differences in expression may be expressed as a percent decrease or increase, such as at least or at most 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900, 1000% difference, or any range derivable therein.

Other ways to express relative expression levels are by normalized or relative numbers such as 0.001, 0.002, 0.003, 0.004, 0.005, 0.006, 0.007, 0.008, 0.009, 0.01, 0.02, 0.03. 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, or any range derivable therein.

Algorithms, such as the weighted voting programs, can be used to facilitate the evaluation of biomarker levels. In addition, other clinical evidence can be combined with the biomarker-based test to reduce the risk of false evaluations.

Other cytogenetic evaluations may be considered in some embodiments of the invention.

Any biological sample from the patient that contains breast cancer cells may be used to evaluate the expression pattern of any biomarker discussed herein. In some embodiments, a biological sample from a breast tumor is used. Evaluation of the sample may involve, though it need not involve, panning (enriching) for cancer cells or isolating the cancer cells.

A. Nucleic Acids

Screening methods based on differentially expressed gene products are well known in the art. In accordance with one aspect of the present invention, the differential expression patterns of breast cancer biomarkers can be determined by measuring the levels of RNA transcripts of these genes, or genes whose expression is modulated by the these genes, in the patient's breast cancer cells. Suitable methods for this purpose include, but are not limited to, RT-PCR, Northern Blot, in situ hybridization, Southern Blot, slot-blotting, nuclease protection assay and oligonucleotide arrays.

In certain aspects, RNA isolated from breast cancer cells can be amplified to cDNA or cRNA before detection and/or quantitation. The isolated RNA can be either total RNA or mRNA. The RNA amplification can be specific or non-specific. Suitable amplification methods include, but are not limited to, reverse transcriptase PCR, isothermal amplification, ligase chain reaction, and Qbeta replicase. The amplified nucleic acid products can be detected and/or quantitated through hybridization to labeled probes. In some embodiments, detection may involve fluorescence resonance energy transfer (FRET) or some other kind of quantum dots.

Amplification primers or hybridization probes for a breast cancer biomarker can be prepared from the gene sequence or obtained through commercial sources, such as Affymatrix. In certain embodiments the gene sequence is identical or complementary to at least 8 contiguous nucleotides of the coding sequence.

Sequences suitable for making probes/primers for the detection of their corresponding breast cancer biomarkers include those that are identical or complementary to all or part of genes or SEQ ID NOs described herein. These sequences are all nucleic acid sequences of breast cancer biomarkers.

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

In one embodiment, each probe/primer comprises at least 15 nucleotides. For instance, each probe can comprise at least or at most 20, 25, 50, 75, 100, 125, 150, 175, 200, 225, 250, 275, 300, 325, 350, 400 or more nucleotides (or any range derivable therein). They may have these lengths and have a sequence that is identical or complementary to a gene or SEQ ID NO described herein. Preferably, each probe/primer has relatively high sequence complexity and does not have any ambiguous residue (undetermined "n" residues).

The probes/primers preferably can hybridize to the target gene, including its RNA transcripts, under stringent or highly stringent conditions. In some embodiments, because each of the biomarkers has more than one human sequence, it is contemplated that probes and primers may be designed for use with each on of these sequences. For example, inosine is a nucleotide frequently used in probes or primers to hybridize to more than one sequence. It is contemplated that probes or primers may have inosine or other design implementations that accommodate recognition of more than one human sequence for a particular biomarker.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

In another embodiment, the probes/primers for a gene are selected from regions which significantly diverge from the sequences of other genes. Such regions can be determined by checking the probe/primer sequences against a human genome sequence database, such as the Entrez database at the NCBI. One algorithm suitable for this purpose is the BLAST algorithm. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence to increase the cumulative alignment score. Cumulative scores are calculated using, for nucleotide sequences, the parameters M (reward score for a pair of matching residues; always >0) and N (penalty score for mismatching residues; always <0). The BLAST algorithm parameters W, T, and X determine the sensitivity and speed of the alignment. These parameters can be adjusted for different purposes, as appreciated by one of ordinary skill in the art.

In one embodiment, quantitative RT-PCR (such as TaqMan, ABI) is used for detecting and comparing the levels of RNA transcripts in breast cancer samples. Quantitative RT-PCR involves reverse transcription (RT) of RNA to cDNA followed by relative quantitative PCR (RT-PCR). The concentration of the target DNA in the linear portion of the PCR process is proportional to the starting concentration of the target before the PCR was begun. By determining the concentration of the PCR products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived may be determined for the respective tissues or cells. This direct proportionality between the concentration of the PCR products and the relative mRNA abundances is true in the linear range portion of the PCR reaction. The final concentration of the target DNA in the plateau portion of the curve is determined by the availability of reagents in the reaction mix and is independent of the original concentration of target DNA. Therefore, the sampling and quantifying of the amplified PCR products preferably are carried out when the PCR reactions are in the linear portion of their curves. In addition, relative concentrations of the amplifiable cDNAs preferably are normalized to some independent standard, which may be based on either internally existing RNA species or externally introduced RNA species. The abundance of a particular mRNA species may also be determined relative to the average abundance of all mRNA species in the sample.

In one embodiment, the PCR amplification utilizes one or more internal PCR standards. The internal standard may be an abundant housekeeping gene in the cell or it can specifically be GAPDH, GUSB and β-2 microglobulin. These standards may be used to normalize expression levels so that the expression levels of different gene products can be compared directly. A person of ordinary skill in the art would know how to use an internal standard to normalize expression levels.

A problem inherent in clinical samples is that they are of variable quantity and/or quality. This problem can be overcome if the RT-PCR is performed as a relative quantitative RT-PCR with an internal standard in which the internal standard is an amplifiable cDNA fragment that is similar or larger than the target cDNA fragment and in which the abundance of the mRNA encoding the internal standard is roughly 5-100 fold higher than the mRNA encoding the target. This assay measures relative abundance, not absolute abundance of the respective mRNA species.

In another embodiment, the relative quantitative RT-PCR uses an external standard protocol. Under this protocol, the PCR products are sampled in the linear portion of their amplification curves. The number of PCR cycles that are optimal for sampling can be empirically determined for each target cDNA fragment. In addition, the reverse transcriptase products of each RNA population isolated from the various samples can be normalized for equal concentrations of amplifiable cDNAs.

Nucleic acid arrays can also be used to detect and compare the differential expression patterns of breast cancer biomarkers in breast cancer cells. The probes suitable for detecting the corresponding breast cancer biomarkers can be stably attached to known discrete regions on a solid substrate. As used herein, a probe is "stably attached" to a discrete region if the probe maintains its position relative to the discrete region during the hybridization and the subsequent washes. Construction of nucleic acid arrays is well known in the art. Suitable substrates for making polynucleotide arrays include, but are not limited to, membranes, films, plastics and quartz wafers.

A nucleic acid array of the present invention can comprise at least 1, 2, 3, 4, 5, 6, 7, 8, 9, 10, 15, 20, 25, 30, 35, 40, 45, 50, 60, 70, 80, 90, 100, 150, 200, 250 or more different polynucleotide probes, which may hybridize to different and/or the same biomarkers. Multiple probes for the same gene can be used on a single nucleic acid array. Probes for other disease genes can also be included in the nucleic acid array. The probe density on the array can be in any range. In some embodiments, the density may be 50, 100, 200, 300, 400, 500 or more probes/cm$^2$.

Specifically contemplated by the present inventors are chip-based nucleic acid technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see also, Pease et al., 1994; and Fodor et al, 1991). It is contemplated that this technology may be used in conjunction with evaluating the expression level of one or more breast cancer biomarkers with respect to diagnostic, prognostic, and treatment methods of the invention.

The present invention may involve the use of arrays or data generated from an array. Data may be readily available. Moreover, an array may be prepared in order to generate data that may then be used in correlation studies.

An array generally refers to ordered macroarrays or microarrays of nucleic acid molecules (probes) that are fully or nearly complementary or identical to a plurality of mRNA molecules or cDNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass and silicon. Such arrays may vary in a number of different ways, including average probe length, sequence or types of probes, nature of bond between the probe and the array surface, e.g. covalent or non-covalent, and the like. The labeling and screening methods of the present invention and the arrays are not limited in its utility with respect to any parameter except that the probes detect expression levels; consequently, methods and compositions may be used with a variety of different types of genes.

Representative methods and apparatus for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 5,492,806; 5,525,464; 5,503,980; 5,510,270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610,287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000; the disclosures of which are all herein incorporated by reference.

It is contemplated that the arrays can be high density arrays, such that they contain 100 or more different probes. It is contemplated that they may contain 1000, 16,000, 65,000, 250,000 or 1,000,000 or more different probes. The probes can be directed to targets in one or more different organisms. The oligonucleotide probes range from 5 to 50, 5 to 45, 10 to 40, or 15 to 40 nucleotides in length in some embodiments. In certain embodiments, the oligonucleotide probes are 20 to 25 nucleotides in length.

The location and sequence of each different probe sequence in the array are generally known. Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The surface area of the array can be about or less than about 1, 1.6, 2, 3, 4, 5, 6, 7, 8, 9, or 10 $cm^2$.

Moreover, a person of ordinary skill in the art could readily analyze data generated using an array. Such protocols include information found in WO 9743450; WO 03023058; WO 03022421; WO 03029485; WO 03067217; WO 03066906; WO 03076928; WO 03093810; WO 03100448A1, all of which are specifically incorporated by reference.

In one embodiment, nuclease protection assays are used to quantify RNAs derived from the breast cancer samples. There are many different versions of nuclease protection assays known to those practiced in the art. The common characteristic that these nuclease protection assays have is that they involve hybridization of an antisense nucleic acid with the RNA to be quantified. The resulting hybrid double-stranded molecule is then digested with a nuclease that digests single-stranded nucleic acids more efficiently than double-stranded molecules. The amount of antisense nucleic acid that survives digestion is a measure of the amount of the target RNA species to be quantified. An example of a nuclease protection assay that is commercially available is the RNase protection assay manufactured by Ambion, Inc. (Austin, Tex.).

B. Proteins and Polypeptides

In other embodiments, the differential expression patterns of breast cancer biomarkers can be determined by measuring the levels of polypeptides encoded by these genes in breast cancer cells. Methods suitable for this purpose include, but are not limited to, immunoassays such as ELISA, RIA, FACS, dot blot, Western Blot, immunohistochemistry, and antibody-based radioimaging. Protocols for carrying out these immunoassays are well known in the art. Other methods such as 2-dimensional SDS-polyacrylamide gel electrophoresis can also be used. These procedures may be used to recognize any of the polypeptides encoded by the breast cancer biomarker genes described herein.

One example of a method suitable for detecting the levels of target proteins in peripheral blood samples is ELISA. In an exemplifying ELISA, antibodies capable of binding to the target proteins encoded by one or more breast cancer biomarker genes are immobilized onto a selected surface exhibiting protein affinity, such as wells in a polystyrene or polyvinylchloride microtiter plate. Then, breast cancer cell samples to be tested are added to the wells. After binding and washing to remove non-specifically bound immunocomplexes, the bound antigen(s) can be detected. Detection can be achieved by the addition of a second antibody which is specific for the target proteins and is linked to a detectable label. Detection may also be achieved by the addition of a second antibody, followed by the addition of a third antibody that has binding affinity for the second antibody, with the third antibody being linked to a detectable label. Before being added to the microtiter plate, cells in the peripheral blood samples can be lysed using various methods known in the art. Proper extraction procedures can be used to separate the target proteins from potentially interfering substances.

In another ELISA embodiment, the breast cancer cell samples containing the target proteins are immobilized onto the well surface and then contacted with the antibodies of the invention. After binding and washing to remove non-specifically bound immunocomplexes, the bound antigen is detected. Where the initial antibodies are linked to a detectable label, the immunocomplexes can be detected directly. The immunocomplexes can also be detected using a second antibody that has binding affinity for the first antibody, with the second antibody being linked to a detectable label.

Another typical ELISA involves the use of antibody competition in the detection. In this ELISA, the target proteins are immobilized on the well surface. The labeled antibodies are added to the well, allowed to bind to the target proteins, and detected by means of their labels. The amount of the target proteins in an unknown sample is then determined by mixing the sample with the labeled antibodies before or during incubation with coated wells. The presence of the target proteins in the unknown sample acts to reduce the amount of antibody available for binding to the well and thus reduces the ultimate signal.

Different ELISA formats can have certain features in common, such as coating, incubating or binding, washing to remove non-specifically bound species, and detecting the bound immunocomplexes. For instance, in coating a plate with either antigen or antibody, the wells of the plate can be incubated with a solution of the antigen or antibody, either overnight or for a specified period of hours. The wells of the plate are then washed to remove incompletely adsorbed material. Any remaining available surfaces of the wells are then "coated" with a nonspecific protein that is antigenically neutral with regard to the test samples. Examples of these nonspecific proteins include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means can also be used. After binding of a protein or antibody to the well, coating with a non-reactive material to reduce background, and washing to remove unbound material, the immobilizing surface is contacted with the control and/or clinical or biological sample to be tested under conditions effective to allow immunocomplex (antigen/antibody) formation. These conditions may include, for example, diluting the antigens and antibodies with solutions such as BSA, bovine gamma globulin (BGG) and phosphate buffered saline (PBS)/Tween and incubating the antibodies and antigens at room temperature for about 1 to 4 hours or at 49° C. overnight. Detection of the immunocomplex then requires a labeled secondary binding ligand or antibody, or a secondary binding ligand or antibody in conjunction with a labeled tertiary antibody or third binding ligand.

After all of the incubation steps in an ELISA, the contacted surface can be washed so as to remove non-complexed material. For instance, the surface may be washed with a solution such as PBS/Tween, or borate buffer. Following the formation of specific immunocomplexes between the test sample and the originally bound material, and subsequent washing, the occurrence of the amount of immunocomplexes can be determined.

To provide a detecting means, the second or third antibody can have an associated label to allow detection. In one embodiment, the label is an enzyme that generates color development upon incubating with an appropriate chromogenic substrate. Thus, for example, one may contact and incubate the first or second immunocomplex with a urease, glucose oxidase, alkaline phosphatase or hydrogen peroxidase-conjugated antibody for a period of time and under conditions that favor the development of further immunocomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl)-benzhiazoline-6-sulfonic acid (ABTS) and hydrogen peroxide, in the case of peroxidase as the enzyme label. Quantitation can be achieved by measuring the degree of color generation, e.g., using a spectrophotometer.

Another suitable method is RIA (radioimmunoassay). An example of MA is based on the competition between radiolabeled-polypeptides and unlabeled polypeptides for binding to a limited quantity of antibodies. Suitable radiolabels include, but are not limited to, $I^{125}$. In one embodiment, a fixed concentration of $I^{125}$-labeled polypeptide is incubated with a series of dilution of an antibody specific to the polypeptide. When the unlabeled polypeptide is added to the system, the amount of the $I^{125}$-polypeptide that binds to the antibody is decreased. A standard curve can therefore be constructed to represent the amount of antibody-bound $I^{125}$-polypeptide as a function of the concentration of the unlabeled polypeptide. From this standard curve, the concentration of the polypeptide in unknown samples can be determined. Various protocols for conducting RIA to measure the levels of polypeptides in breast cancer cell samples are well known in the art.

Suitable antibodies for this invention include, but are not limited to, polyclonal antibodies, monoclonal antibodies, chimeric antibodies, humanized antibodies, single chain antibodies, Fab fragments, and fragments produced by a Fab expression library.

Antibodies can be labeled with one or more detectable moieties to allow for detection of antibody-antigen complexes. The detectable moieties can include compositions detectable by spectroscopic, enzymatic, photochemical, biochemical, bioelectronic, immunochemical, electrical, optical or chemical means. The detectable moieties include, but are not limited to, radioisotopes, chemiluminescent compounds, labeled binding proteins, heavy metal atoms, spectroscopic markers such as fluorescent markers and dyes, magnetic labels, linked enzymes, mass spectrometry tags, spin labels, electron transfer donors and acceptors, and the like.

Protein array technology is discussed in detail in Pandey and Mann (2000) and MacBeath and Schreiber (2000), each of which is herein specifically incorporated by reference. These arrays typically contain thousands of different proteins or antibodies spotted onto glass slides or immobilized in tiny wells and allow one to examine the biochemical activities and binding profiles of a large number of proteins at once. To examine protein interactions with such an array, a labeled protein is incubated with each of the target proteins immobilized on the slide, and then one determines which of the many proteins the labeled molecule binds. In certain embodiments such technology can be used to quantitate a number of proteins in a sample, such as a breast cancer biomarker proteins.

The basic construction of protein chips has some similarities to DNA chips, such as the use of a glass or plastic surface dotted with an array of molecules. These molecules can be DNA or antibodies that are designed to capture proteins. Defined quantities of proteins are immobilized on each spot, while retaining some activity of the protein. With fluorescent markers or other methods of detection revealing the spots that have captured these proteins, protein microarrays are being used as powerful tools in high-throughput proteomics and drug discovery.

The earliest and best-known protein chip is the ProteinChip by Ciphergen Biosystems Inc. (Fremont, Calif.). The ProteinChip is based on the surface-enhanced laser desorption and ionization (SELDI) process. Known proteins are analyzed using functional assays that are on the chip. For example, chip surfaces can contain enzymes, receptor proteins, or antibodies that enable researchers to conduct protein-protein interaction studies, ligand binding studies, or immunoassays. With state-of-the-art ion optic and laser optic technologies, the ProteinChip system detects proteins ranging from small peptides of less than 1000 Da up to proteins of 300 kDa and calculates the mass based on time-of-flight (TOF).

The ProteinChip biomarker system is the first protein biochip-based system that enables biomarker pattern recognition analysis to be done. This system allows researchers to address important clinical questions by investigating the proteome from a range of crude clinical samples (i.e., laser capture microdissected cells, biopsies, tissue, urine, and serum). The system also utilizes biomarker pattern software that automates pattern recognition-based statistical analysis methods to correlate protein expression patterns from clinical samples with disease phenotypes.

In other aspects, the levels of polypeptides in samples can be determined by detecting the biological activities associated with the polypeptides. If a biological function/activity of a polypeptide is known, suitable in vitro bioassays can be designed to evaluate the biological function/activity, thereby determining the amount of the polypeptide in the sample.

III. Breast Cancer Therapy

Certain embodiments are directed to methods of treating breast cancer based on GR status of the breast cancer tissue. In some embodiments, the hormone receptor status is determined based on the expression of a hormone receptor such as the estrogen receptor (ER) in combination with the glucocorticoid receptor (GR).

In certain aspects, the hormone receptor status is high for GR and may also be low for one or more other hormone receptors such as the estrogen receptor. An individual having an elevated GR and low ER is likely to have a poor prognosis. In the event of a poor prognosis the physician may pursue a more aggressive therapy for those patients. In some embodiments, the method comprises identifying a breast cancer patient based on a hormone receptor status of patients having tumor tissue with elevated levels of GR expression.

In certain aspects, there may be provided methods for treating a subject determined to have cancer and with a predetermined expression profile of one or more biomarkers disclosed herein.

In a further aspect, biomarkers and related systems that can establish a prognosis of cancer patients in this invention can be used to identify patients who may get benefit of conventional single or combined modality therapy. In the same way, the invention can identify those patients who do not get much benefit from such conventional single or combined modality therapy and can offer them alternative treatment(s).

In certain aspects of the present invention, conventional cancer therapy may be applied to a subject wherein the subject is identified or reported as having a good prognosis based on the assessment of the biomarkers as disclosed. On the other hand, at least an alternative cancer therapy may be prescribed, as used alone or in combination with conventional cancer therapy, if a poor prognosis is determined by the disclosed methods, systems, or kits.

Embodiments concern a glucocorticoid receptor antagonist. In some embodiments, the glucocorticoid receptor antagonist is a selective glucocorticoid receptor antagonist, as set forth in Clark, 2008, which is hereby incorporated by reference. In other embodiments, the glucocorticoid receptor antagonist is a non-selective glucocorticoid receptor antagonist, such as mifepristone. In certain embodiments, the glucocorticoid receptor antagonist is steroidal. In other embodiments, the glucocorticoid receptor antagonist is non-steroidal. A glucocorticoid receptor antagonist includes those in the following classes of chemical compounds: octahydrophenanthrenes, spirocyclic dihydropyridines, triphenylmethanes and diaryl ethers, chromenes, dibenzyl anilines, dihydroisoquinolines, pyrimidinediones, azadecalins, and aryl pyrazolo azadecalins, and which are described in more detail in Clark, 2008, which is hereby incorporated by reference. Some embodiments of steroidal antagonists from Clark, 2008 are: RU-486, RU-43044, 11-monoaryl and 11,21 bisaryl steroids (including 11(3-substituted steroids), 10β-substituted steroids, 11β-aryl conjugates of mifepristone, and phosphorous-containing mifepristone analogs. Further embodiments of nonsteroidal antagonists from Clark, 2008 are: octahydrophenanthrenes, spirocyclic dihydropyridines, triphenylmethanes and diaryl ethers, chromenes, dibenzyl anilines, dihyrdroquinolines, pyrimidinediones, azadecalins, aryl pyrazolo azadecalins (including 8a-benzyl isoquinolones, N-substituted derivatives, bridgehead alcohol and ethers, bridgehead amines). Additional specific examples include, but are not limited to the following specific antagonists: beclometasone, betamethasone, budesonide, ciclesonide, flunisolide, fluticasone, mifepristone, mometasone, and triamcinolone. Other examples include those described and/or depicted in U.S. Patent Application Publication 2010/0135956, which is hereby incorporated by reference. Even further examples include ORG-34517 (Merck), RU-43044, dexamethasone mesylate (Dex-Mes), dexamethasone oxetanone (Dex-Ox), deoxycorticosterone (DOC) (Peeters et al., 2008, which is hereby incorporated by reference in its entirety and Cho et al. 2005, which is hereby incorporated by reference in its entirety). In additional embodiments the glucocorticoid receptor antagonist may be CORT 0113083 or CORT 00112716, which are described in Belanoff et al. (2011), which is hereby incorporated by reference. It is specifically contemplated that one or more of the antagonists discussed herein or in the incorporated references may be excluded in embodiments of the invention. It is also contemplated that in some embodiments, more than one glucocorticoid receptor antagonist is employed, while in other embodiments, only one is employed as part of the therapeutic method (though it may be administered multiple times). It is contemplated that the second one may be administered concurrently with the first one or they may be administered at different times.

Conventional cancer therapies include one or more selected from the group of chemical or radiation based treatments and surgery. Chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, navelbine, farnesyl-protein transferase inhibitors, transplatinum, 5-fluorouracil, vincristin, vinblastin and methotrexate, or any analog or derivative variant of the foregoing.

Suitable therapeutic agents include, for example, vinca alkaloids, agents that disrupt microtubule formation (such as colchicines and its derivatives), anti-angiogenic agents, therapeutic antibodies, EGFR targeting agents, tyrosine kinase targeting agent (such as tyrosine kinase inhibitors), serine kinase targeting agents, transitional metal complexes, proteasome inhibitors, antimetabolites (such as nucleoside analogs), alkylating agents, platinum-based agents, anthracycline antibiotics, topoisomerase inhibitors, macrolides, therapeutic antibodies, retinoids (such as all-trans retinoic acids or a derivatives thereof); geldanamycin or a derivative thereof (such as 17-AAG), and other standard chemotherapeutic agents well recognized in the art.

Certain chemotherapeutics are well known for use against breast cancer. These breast cancer chemotherapeutics are capecitabine, carboplatin, cyclophosphamide (Cytoxan), daunorubicin, docetaxel (Taxotere), doxorubicin (Adriamycin), epirubicin (Ellence), fluorouracil (also called 5-fluorouracil or 5-FU), gemcitabine, eribulin, ixabepilone, methotrexate, mitomycin C, mitoxantrone, paclitaxel (Taxol), thiotepa, vincristine, vinorelbine.

In some embodiments, the chemotherapeutic agent is any of (and in some embodiments selected from the group consisting of) adriamycin, colchicine, cyclophosphamide, actinomycin, bleomycin, daunorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof (e.g., paclitaxel and derivatives thereof, taxotere and derivatives thereof, and the like), topetecan, vinblastine, vincristine, tamoxifen, piposulfan, nab-5404, nab-5800, nab-5801, Irinotecan, HKP, Ortataxel, gemcitabine, Herceptin®, vinorelbine, Doxil®, capecitabine, Gleevec®, Alimta®, Avastin®, Velcade®, Tarceva®, Neulasta®, Lapatinib, STI-571, ZD1839, Iressa® (gefitinib), SH268, genistein, CEP2563, SU6668, SU11248, EMD121974, and Sorafenib.

In some embodiments, the chemotherapeutic agent is a composition comprising nanoparticles comprising a thiocolchicine derivative and a carrier protein (such as albumin).

In further embodiments a combination of chemotherapeutic agents is administered to breast cancer cells. The chemotherapeutic agents may be administered serially (within minutes, hours, or days of each other) or in parallel; they also may be administered to the patient in a pre-mixed single composition. The composition may or may not contain a glucocorticoid receptor antagonist. Combinations of breast cancer therapeutics include, but are not limited to the following: AT (Adriamycin and Taxotere), AC±T: (Adriamycin and Cytoxan, with or without Taxol or Taxotere), CMF (Cytoxan, methotrexate, and fluorouracil), CEF (Cytoxan, Ellence, and fluorouracil), FAC (fluorouracil, Adriamycin, and Cytoxan), CAF (Cytoxan, Adriamycin, and fluorouracil) (the FAC and CAF regimens use the same medicines but use different doses and frequencies), TAC (Taxotere, Adriamycin, and Cytoxan), and GET (Gemzar, Ellence, and Taxol). In some embodiments trastuzumab (Herceptin®) is administered to a breast cancer patient with a glucocorticoid receptor antagonist, which may be with or without a chemotherapeutic or a combination of chemotherapeutics.

Various combinations with a glucocorticoid receptor antagonist and an anticancer agent or compound (or a combination of such agents and/or compounds) may be employed, for example glucocorticoid receptor antagonist is "A" and the anticancer agent or compound (or a combination of such agents and/or compounds) given as part of an anticancer therapy regime, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the therapeutic compounds or agents to a patient will follow general protocols for the administration of such compounds, taking into account the toxicity, if any, of the therapy. It is expected that the treatment cycles would be repeated as necessary. It also is contemplated that various standard therapies, as well as surgical intervention, may be applied in combination with the described therapy.

The term "a serine/threonine kinase inhibitor", as used herein, relates to a compound which inhibits serine/threonine kinases. An example of a target of a serine/threonine kinase inhibitor includes, but is not limited to, dsRNA-dependent protein kinase (PKR). Examples of indirect targets of a serine/threonine kinase inhibitor include, but are not limited to, MCP-1, NF-kappaB, eIF2alpha, COX2, RANTES, IL8, CYP2A5, IGF-1, CYP2B1, CYP2B2, CYP2H1, ALAS-1, HIF-1, erythropoietin and/or CYP1A1. An example of a serine/theronin kinase inhibitor includes, but is not limited to, Sorafenib and 2-aminopurine, also known as 1H-purin-2-amine(9CI). Sorafenib is marketed as NEXAVAR.

The term "an angiogenesis inhibitor", as used herein, relates to a compound which targets, decreases or inhibits the production of new blood vessels. Targets of an angiogenesis inhibitor include, but are not limited to, methionine aminopeptidase-2 (MetAP-2), macrophage inflammatory protein-1 (MIP-1a), CCL5, TGF-.beta., lipoxygenase, cyclooxygenase, and topoisomerase. Indirect targets of an angiogenesis inhibitor include, but are not limited to, p21, p53, CDK2 and collagen synthesis. Examples of an angiogenesis inhibitor include, but are not limited to, Fumagillin, which is known as 2,4,6,8-decatetraenedioic acid, mono[3R, 4S,5S,6R)-5-methoxy-4-[(2R,3R)-2-methyl-3-(3-methyl-2-butenyl)oxi-ranyl]-1-oxaspiro[2.5]oct-6-yl]ester, (2E,4E, 6E,8E)-(9CI); Shikonin, which is also known as 1,4-naphthalenedione, 5,8-dihydroxy-2-[(1R)-1-hydroxy-4-methyl-3-pentenyl]-(9CI); Tranilast, which is also known as benzoic acid, 2-[[3-(3,4-dimethoxyphenyl)-1-oxo-2-propenyl]amino]-(9CI); ursolic acid; suramin; thalidomide and lenalidomide, and marketed as REVLIMID.

Radiation therapy that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Laser therapy is the use of high-intensity light to destroy tumor cells. Laser therapy affects the cells only in the treated area. Laser therapy may be used to destroy cancerous tissue and relieve a blockage in the esophagus when the cancer cannot be removed by surgery. The relief of a blockage can help to reduce symptoms, especially swallowing problems.

Photodynamic therapy (PDT), a type of laser therapy, involves the use of drugs that are absorbed by cancer cells; when exposed to a special light, the drugs become active and destroy the cancer cells. PDT may be used to relieve symptoms of esophageal cancer such as difficulty swallowing.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well. A patient may be administered a single compound or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg (or any range derivable therein). A patient may be administered a single compound or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500 mg/kg/day (or any range derivable therein).

Alternative cancer therapy include any cancer therapy other than surgery, chemotherapy and radiation therapy in the present invention, such as immunotherapy, gene therapy, hormonal therapy or a combination thereof. Subjects identified with poor prognosis using the present methods may not have favorable response to conventional treatment(s) alone and may be prescribed or administered one or more alternative cancer therapy per se or in combination with one or more conventional treatments.

For example, the alternative cancer therapy may be a targeted therapy. The targeted therapy may be an anti-EGFR treatment. In one embodiment of the method of the invention, the anti-EGFR agent used is a tyrosine kinase inhibitor. Examples of suitable tyrosine kinase inhibitors are the quinazoline derivatives described in WO 96/33980, in particular gefitinib (Iressa). Other examples include quinazoline derivatives described in WO 96/30347, in particular erlotinib (Tarceva), dual EGFR/HER2 tyrosine kinase inhibitors, such as lapatinib, or pan-Erb inhibitors. In a preferred embodiment of the method or use of the invention, the anti-EGFR agent is an antibody capable of binding to EGFR, i.e. an anti-EGFR antibody.

In a further embodiment, the anti-EGFR antibody is an intact antibody, i.e. a full-length antibody rather than a fragment. An anti-EGFR antibody used in the method of the present invention may have any suitable affinity and/or avidity for one or more epitopes contained at least partially in EGFR. Preferably, the antibody used binds to human EGFR with an equilibrium dissociation constant ($K_D$) of $10^{-8}$ M or less, more preferably $10^{-10}$ M or less.

Particularly antibodies for use in the present invention include zalutumumab (2F8), cetuximab (Erbitux), nimotuzumab (h-R3), panitumumab (ABX-EGF), and matuzumab (EMD72000), or a variant antibody of any of these, or an antibody which is able to compete with any of these, such as an antibody recognizing the same epitope as any of these. Competition may be determined by any suitable technique. In one embodiment, competition is determined by an ELISA assay. Often competition is marked by a significantly greater relative inhibition than 5% as determined by ELISA analysis.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Gene therapy is the insertion of polynucleotides, including DNA or RNA, into an individual's cells and tissues to treat a disease. Antisense therapy is also a form of gene therapy in the present invention. A therapeutic polynucleotide may be administered before, after, or at the same time of a first cancer therapy. Delivery of a vector encoding a variety of proteins is encompassed within the invention. For example, cellular expression of the exogenous tumor suppressor oncogenes would exert their function to inhibit excessive cellular proliferation, such as p53, p16 and C-CAM.

Additional agents to be used to improve the therapeutic efficacy of treatment include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

II. Kits

Certain aspects of the present invention also encompass kits for performing the diagnostic and prognostic methods of the invention. Such kits can be prepared from readily available materials and reagents. For example, such kits can comprise any one or more of the following materials: enzymes, reaction tubes, buffers, detergent, primers, probes, antibodies. In a preferred embodiment, these kits allow a practitioner to obtain samples of neoplastic cells in blood, tears, semen, saliva, urine, tissue, serum, stool, sputum, cerebrospinal fluid and supernatant from cell lysate. In another preferred embodiment these kits include the needed apparatus for performing RNA extraction, RT-PCR, and gel electrophoresis. Instructions for performing the assays can also be included in the kits.

In a particular aspect, these kits may comprise a plurality of agents for assessing the differential expression of a plurality of biomarkers, for example, GR and/or ER, wherein the kit is housed in a container. The kits may further comprise instructions for using the kit for assessing expression, means for converting the expression data into expression values and/or means for analyzing the expression values to generate prognosis. The agents in the kit for measuring biomarker expression may comprise a plurality of PCR probes and/or primers for qRT-PCR and/or a plurality of antibody or fragments thereof for assessing expression of the biomarkers. In another embodiment, the agents in the kit for measuring biomarker expression may comprise an array of polynucleotides complementary to the mRNAs of the biomarkers of the invention. Possible means for converting the expression data into expression values and for analyzing the expression values to generate scores that predict survival or prognosis may be also included.

Kits may comprise a container with a label. Suitable containers include, for example, bottles, vials, and test tubes. The containers may be formed from a variety of materials such as glass or plastic. The container may hold a composition which includes a probe that is useful for prognostic or non-prognostic applications, such as described above. The label on the container may indicate that the composition is used for a specific prognostic or non-prognostic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Tumor Biomarker Status

A. Results

The glucocorticoid receptor (GR) is highly expressed in the myoepithelium of the normal human breast and in a subset of both ERalpha-positive and negative human breast cancers. In vitro and in vivo experiments suggest that activation of the GR in ER− pre-malignant breast epithelial and cancer cells triggers cell survival pathways under stress conditions (e.g. chemotherapy) that usually induce apoptosis. The inventors examined the association between NR3C1 gene expression and GR target gene expression in human ER− breast cancers and found that ER− breast cancers with high NR3C1 expression also express GR target genes associated with EMT and anti-apoptotic signaling, and that those ER− patients with high NR3C1 gene expression have a significantly worse outcome than NR3C1-low patients. Interestingly, the high NR3C1 gene expression in the ER+ (ESR1-high) subset of patients suggests a slight better outcome, implying a crosstalk between the ER and the GR that is absent in ER− tumors.

Using a global approach of gene expression studies merged with data from GR ChIP-sequencing in ER− pre-malignant breast cells (MCF10A-Myc), the inventors have identified direct GR target genes are significantly associated with cell survival signaling pathways. Interestingly, a meta-analysis of the high NR3C1-expressing ER− tumors reveals that many genes identified by ChIP-sequencing/gene expression analysis are indeed differentially expressed in high versus low NR3C1-primary breast cancers. These results suggest that GR expression may be a functional biomarker in ER− breast cancer.

TABLE 1

Clinical studies used for meta-analysis

| GEO ID | # of pts | Reference |
|---|---|---|
| GSE9195 | 77 | Loi S, et al |
| GSE7390 | 189 | Desmedt C, et al |
| GSE6532 | 212 | Loi S, et al |
| GSE2603 | 73 | Minn AJ, et al |
| GSE2990 | 183 | Sotiriou C, et al |
| GSE2034 | 280 | Wang YX, et al |
| TOTAL | 1206 | |

Human Primary Breast Cancer Analysis: 1) Data Collection: All the clinical data and raw CEL files (all Affymetrix HU-133A and HU-133+2) were obtained from GEO (see Table 1). Low quality arrays were removed by AffyPLM. Arrays were normalized by using RMA and then centered by mean within each study and pooled together. 2) Determination of ESR1 and NR3C1 positivity: Expression data of tumors with known ER IHC status were analyzed using ROC analysis. The Youden Index of the best ESR1 probe's ROC curve was used as the cut-off point to separate ESR1+ and ESR1− tumors. Due to the lack of tumors with both GR IHC and NR3C1 gene expression information, we were unable to use ROC analysis to determine the NR3C1 cutoff. Therefore, based on published and our unpublished GR IHC data, we used the percentiles of NR3C1 gene expression levels that correspond to the observed proportion of GR+ patients. 3) Clustering: Un-supervised clustering was performed by Cluster using Pearson correlation distance and complete-linkage method. Heat-maps were plotted by Treeview. 4) Statistical analysis: Relapse-free survival (RFS) Kaplan-Meier plot and log-rank test were done by

TABLE 2

Differentially expressed genes with concordant expression by all three methods (33/44 genes)

| Gene expression after Dex-treatment in MCF10A-Myc | Gene expression in NR3C1 + vs. − tumors | GR-binding within distance to TSS after Dex-treatment in MCF10A-Myc | Genes |
|---|---|---|---|
| Up | Up | 10 kb | DUSP1, SGK1, SMARCA2, PTGDS, MCL1 |
| | | 10-100 kb | DPYSL2, STOM, LAPTM5, NNMT, SERPINF1, NRIP1, WIPF1, BIN1, IL1R1, ST3GAL5, SEMA4D, MAP3K5, SMARCA2, DPT, BIRC3, PTGDS, PHF15, MAOA, TFPI, SLC46A3, PIAS1, ACSL5, SESN1, C14orf139, LBH |
| Down | Down | 10 kb | NONE |
| | | 10-100 kb | SFN, SPP1, ERBB2 |
| Overlapping genes with NKI-295 gene signature | | | DUSP1, DPT, NNMT SERPINF1, IL1R1, FN1, DPYSL2 |

B. Materials and Methods

Cell culture and glucocorticoid treatment: MCF10A-Myc cells were cultured in a 1:1 mixture of DMEM and Hams/F12 medium supplemented with 10% fetal bovine serum, hydrocortisone (0.5 µg/ml), EGF (10 ng/ml), insulin (5 ng/ml) and 100 U/ml penicillin/streptomycin were also added. The cells were then starved for three days of all growth factors and treated with dexamethasone (10-6M) and ethanol of the same volume as a control.

Microarray gene expression: MCF10A-Myc Cells: Time course (0.5 h, 2 h, 4 h and 24 h) microarray data were obtained using Affymetrix gene arrays (HG-U133A) (Wu et al., 2006). Genes that were induced or repressed ≥1.5 fold-change were considered to be regulated.

GR ChIP-Seq experiment and analysis for MCF10A-Myc Cells: Cells were collected for the ChIP assay following 1 hour of Dex (10-6M) or EtOH treatment. The ChIP assay was done basically following Millipore's ChIP Assay Kit instructions. The DNA input (1%) was also sequenced using Illumina's Solexa Sequencer. Short-tag reads (36 bp) were mapped to the Human Genome (UCSC, hg18) by using Maq aligner. GR-binding peaks were called by using MACS software. Known SGK1 and GILZ promoter GR binding-regions (GBRs) were used as positive controls to determine the FDR threshold for retrieving significant GBRs.

using R's "survival" package. Microarray SAM analysis was performed by using R's "siggenes" package.

Tumor assessment. pAUC areas were calculated for all the probes on the chip by setting p=0.2 (meaning can separate at least 80% patients) for tumors with known ER status (n=1000). A probe was then selected that has biggest pAUC area, which is the ESR1 probe 205225_at. So, this probe is the best one that can separate ER IHC+ versus−. Using the 205225_at probe, the Youden Index of its ROC curve was calculated, that is the max (sensitivity+specificity-1) as the cut-off value for ESR1+ and −. The range of ESR1 expression after normalization was [−5.223868–3.944120]. The Youden Index, i.e. the cut-off is −1.257434. In the n=1000, training set, n=773>−1.257434 (ESR1+), and n=227<=−1.257434. (ESR1−) or i.e. 77.3% quantile This cut-off was applied to the entire dataset, n=898 (ESR+), n=308 (ESR−). In addition to the method, the ACTUAL Log 2 value cutoff is needed for ESR1 positivity in normalized meta-dataset, as well as the range of ESR1 values encountered following batched mean normalization. If in one study, samples are obtained from different hospitals, they were normalized separately. So, to be precisely accurate, the normalization is done within the samples from the same source.

The ESR1 probe ID from Affymetrix is 205225_at.
The NR3C1 probe ID from Affymetrix is 216321_s_at The range for NR3C1 probe (216321_s_at) is [−3.145456 to 2.158716] for the entire data set. For ESR1+, the range is [−3.009359 2.158716] and for ESR1−, the range is [−3.145456 1.917823] Thus, the cut-off for ESR1+, is 0.172189, 55.98% quantile (or about 44% NR3C1+percentage) and the cut-off for ESR1−, is 0.47332, 82.51% quantile (or about 17.5% NR3C1+percentage). All the cut-off are log 2 values.

The cutoffs used are the best cut-off that can separate patients with a p<0.01. If the p-value is loosened to 0.05, the range can be widened.

For ESR1+ patients, NR3C1+ patients can be from about 35% to 60% (about 44% is the best). For ESR1− patients, NR3C1+ patients can be from about 30% to 15% (about 17.5% is the best)

Example 2

Figure 8:
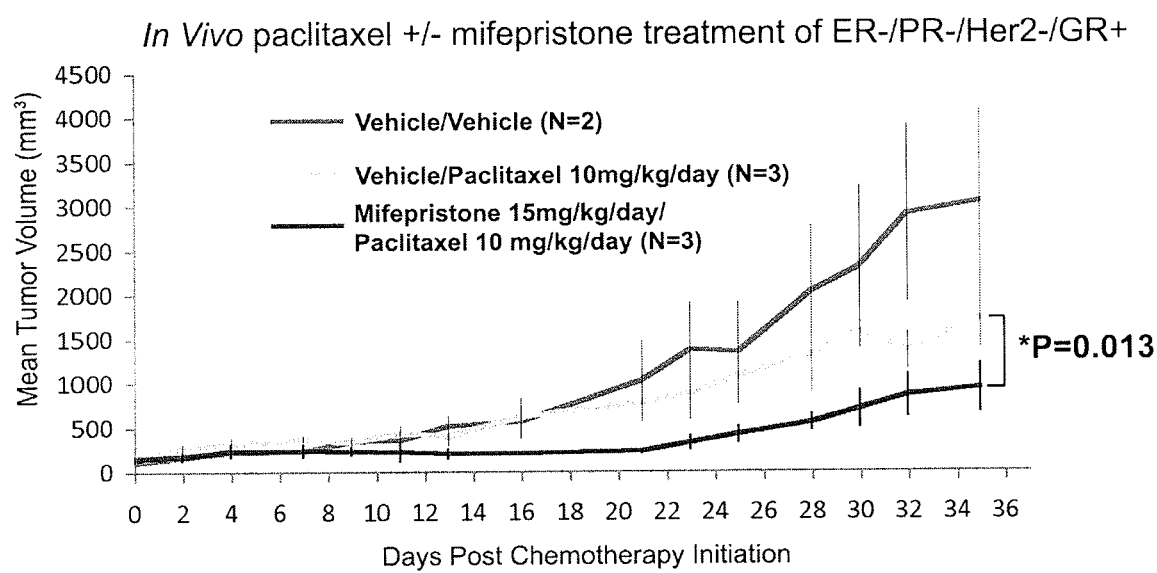
FIG. 8. Administration of mifepristone increases MDA-MB-231 tumor susceptibility to paclitaxel treatment in vivo.

Mifepristone Pretreatment Enhances Paclitaxel Anti-Tumor Effectiveness in Models of Human Breast Cancer Xenografted ER−/PR−/HER2−(GR+) MDA-MB-231 human breast cancer cells ($1 \times 10^7$ cells in 50 μl of PBS) were injected into the mammary fat pad of female Severe Combined Immunodeficient Mice (SCID) mice and allowed to grow until reaching approximately 100 mm$^3$. Mice were then injected intraperitoneally with either both vehicles, paclitaxel (10 mg/kg)+the mifepristone vehicle, or the combination of mifepristone (15 mg/kg) administered two hours prior to paclitaxel (10 mg/kg) for five successive days. The longest (L) and shortest (S) diameters of the tumors were measured bi-weekly with electronic calipers and tumor volume was calculated using the formula for an ellipsoid sphere: volume=S2×L×0.52. Mifepristone pretreatment significantly decreased tumor volume over time (P=0.013) compared to treatment with paclitaxel alone (FIG. 8).

Example 3

Figure 9:
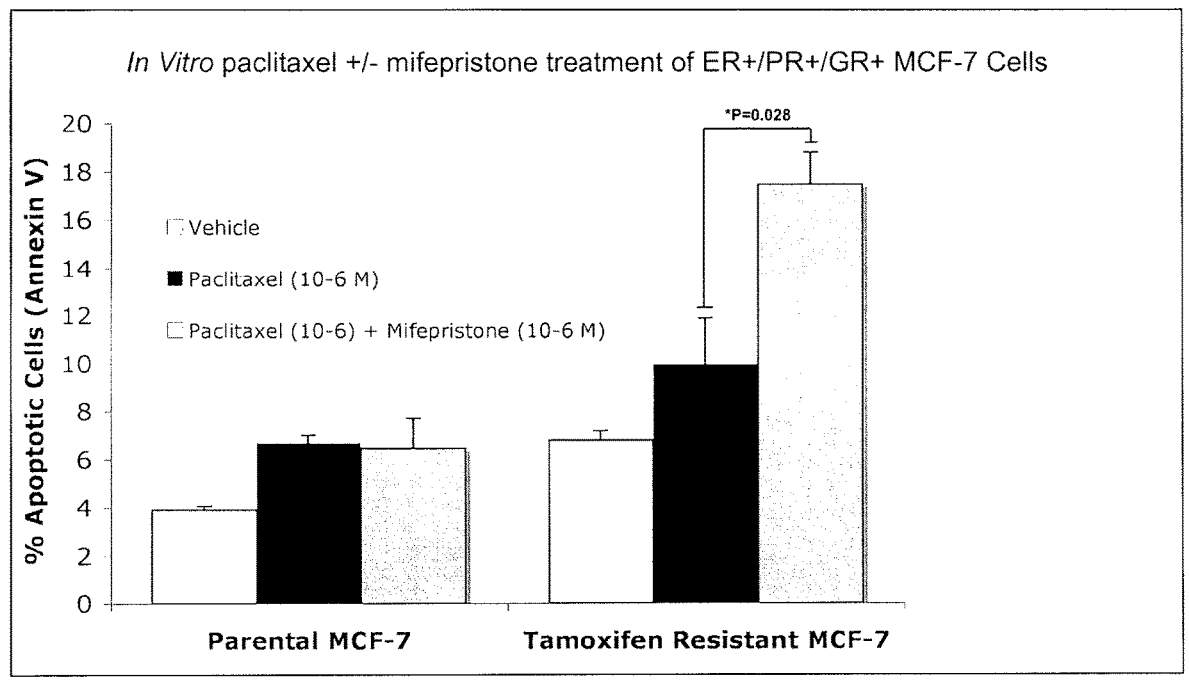
FIG. 9. Mifepristone pretreatment increases tamoxifen-resistant MCF-7 (T-R-MCF-7), but not parental MCF-7 cell susceptibility to paclitaxel in vitro.

Mifepristone Pretreatment Increases Tamoxifen-Resistant MCF-7 (T-R-MCF-7), but not Parental MCF-7 Cell Susceptibility to Paclitaxel In Vitro Parental MCF-7 (ER+/PR+/GR+) and T-R MCF-7 (ER+/PR+/GR+) cells were treated with the appropriate vehicle (ethanol for mifepristone and castor oil/saline for paclitaxel), paclitaxel alone ($10^{-6}$ M), and paclitaxel/mifepristone ($10^{-6}$ M). Apoptosis was measured using FITC conjugated-anti-Annexin V antibody labeling followed FACS analysis to determine the percentage of the total cell population undergoing apoptosis after 20 hours of treatment. Mean+/−SE is shown. Significantly more apoptosis (P=0.028) was observed in the T-R MCF-7 cells when treated with mifepristone/paclitaxel compared to paclitaxel alone (FIG. 9). No difference was seen in the parental MCF-7 cells.

```
Sequence Listing
NR3C1 GenBank AY436590 - 127687 bp, incorporated herein by reference
ESR1 GenBank NG_008493 - 419779 bp, incorporated herein by reference
NR3C1 mRNA
                                                          SEQ ID NO: 1
TTTTTAGAAAAAAAAAATATATTTCCCTCCTGCTCCTTCTGCGTTCACAAGCTAAGTTGTTTATCTCGGC

TGCGGCGGGAACTGCGGACGGTGGCGGGCGAGCGGCTCCTCTGCCAGAGTTGATATTCACTGATGGACTC

CAAAGAATCATTAACTCCTGGTAGAGAAGAAAACCCCAGCAGTGTGCTTGCTCAGGAGAGGGGAGATGTG

ATGGACTTCTATAAAACCCTAAGAGGAGGAGCTACTGTGAAGGTTTCTGCGTCTTCACCCTCACTGGCTG

TCGCTTCTCAATCAGACTCCAAGCAGCGAAGACTTTTGGTTGATTTTCCAAAAGGCTCAGTAAGCAATGC

GCAGCAGCCAGATCTGTCCAAAGCAGTTTCACTCTCAATGGGACTGTATATGGGAGAGACAGAAACAAAA

GTGATGGGAAATGACCTGGGATTCCCACAGCAGGGCCAAATCAGCCTTTCCTCGGGGGAAACAGACTTAA

AGCTTTTGGAAGAAAGCATTGCAAACCTCAATAGGTCGACCAGTGTTCCAGAGAACCCCAAGAGTTCAGC

ATCCACTGCTGTGTCTGCTGCCCCCACAGAGAAGGAGTTTCCAAAAACTCACTCTGATGTATCTTCAGAA

CAGCAACATTTGAAGGGCCAGACTGGCACCAACGGTGGCAATGTGAAATTGTATACCACAGACCAAAGCA

CCTTTGACATTTTGCAGGATTTGGAGTTTTCTTCTGGGTCCCCAGGTAAAGAGACGAATGAGAGTCCTTG

GAGATCAGACCTGTTGATAGATGAAAACTGTTTGCTTTCTCCTCTGGCGGGAGAAGACGATTCATTCCTT

TTGGAAGGAAACTCGAATGAGGACTGCAAGCCTCTCATTTTACCGGACACTAAACCCAAAATTAAGGATA

ATGGAGATCTGGTTTTGTCAAGCCCCAGTAATGTAACACTGCCCCAAGTGAAAACAGAAAAGAAGATTT

CATCGAACTCTGCACCCCTGGGGTAATTAAGCAAGAGAAACTGGGCACAGTTTACTGTCAGGCAAGCTTT

CCTGGAGCAAATATAATTGGTAATAAAATGTCTGCCATTTCTGTTCATGGTGTGAGTACCTCTGGAGGAC

AGATGTACCACTATGACATGAATACAGCATCCCTTTCTCAACAGCAGGATCAGAAGCCTATTTTTAATGT

CATTCCACCAATTCCCGTTGGTTCCGAAAATTGGAATAGGTGCCAAGGATCTGGAGATGACAACTTGACT

TCTCTGGGGACTCTGAACTTCCCTGGTCGAACAGTTTTTTCTAATGGCTATTCAAGCCCCAGCATGAGAC

CAGATGTAAGCTCTCCTCCATCCAGCTCCTCAACAGCAACAACAGGACCACCTCCCAAACTCTGCCTGGT
```

```
GTGCTCTGATGAAGCTTCAGGATGTCATTATGGAGTCTTAACTTGTGGAAGCTGTAAAGTTTTCTTCAAA

AGAGCAGTGGAAGGACAGCACAATTACCTATGTGCTGGAAGGAATGATTGCATCATCGATAAAATTCGAA

GAAAAAACTGCCCAGCATGCCGCTATCGAAAATGTCTTCAGGCTGGAATGAACCTGGAAGCTCGAAAAAC

AAAGAAAAAATAAAAGGAATTCAGCAGGCCACTACAGGAGTCTCACAAGAAACCTCTGAAAATCCTGGT

AACAAAACAATAGTTCCTGCAACGTTACCACAACTCACCCCTACCCTGGTGTCACTGTTGGAGGTTATTG

AACCTGAAGTGTTATATGCAGGATATGATAGCTCTGTTCCAGACTCAACTTGGAGGATCATGACTACGCT

CAACATGTTAGGAGGGCGGCAAGTGATTGCAGCAGTGAAATGGGCAAAGGCAATACCAGGTTTCAGGAAC

TTACACCTGGATGACCAAATGACCCTACTGCAGTACTCCTGGATGTTTCTTATGGCATTTGCTCTGGGGT

GGAGATCATATAGACAATCAAGTGCAAACCTGCTGTGTTTTGCTCCTGATCTGATTATTAATGAGCAGAG

AATGACTCTACCCTGCATGTACGACCAATGTAAACACATGCTGTATGTTTCCTCTGAGTTACACAGGCTT

CAGGTATCTTATGAAGAGTATCTCTGTATGAAAACCTTACTGCTTCTCTCTTCAGTTCCTAAGGACGGTC

TGAAGAGCCAAGAGCTATTTGATGAAATTAGAATGACCTACATCAAAGAGCTAGGAAAAGCCATTGTCAA

GAGGGAAGGAAACTCCAGCCAGAACTGGCAGCGGTTTTATCAACTGACAAAACTCTTGGATTCTATGCAT

GAAGTGGTTGAAAATCTCCTTAACTATTGCTTCCAAACATTTTTGGATAAGACCATGAGTATTGAATTCC

CCGAGATGTTAGCTGAAATCATCACCAATCAGATACCAAAATATTCAAATGGAAATATCAAAAAACTTCT

GTTTCATCAAAAGTGACTGCCTTAATAAGAATGGTTGCCTTAAAGAAAGTCGAATTAATAGCTTTTATTG

TATAAACTATCAGTTTGTCCTGTAGAGGTTTTGTTGTTTTATTTTTATTGTTTTCATCTGTTGTTTTGT

TTTAAATACGCACTACATGTGGTTTATAGAGGGCCAAGACTTGGCAACAGAAGCAGTTGAGTCGTCATCA

CTTTTCAGTGATGGGAGAGTAGATGGTGAAATTTATTAGTTAATATATCCCAGAAATTAGAAACCTTAAT

ATGTGGACGTAATCTCCACAGTCAAAGAAGGATGGCACCTAAACCACCAGTGCCCAAAGTCTGTGTGATG

AACTTTCTCTTCATACTTTTTTTCACAGTTGGCTGGATGAAATTTTCTAGACTTTCTGTTGGTGTATCCC

CCCCCCTGTATAGTTAGGATAGCATTTTTGATTTATGCATGGAAACCTGAAAAAAAGTTTACAAGTGTAT

ATCAGAAAAGGGAAGTTGTGCCTTTTATAGCTATTACTGTCTGGTTTTAACAATTTCCTTTATATTTAGT

GAACTACGCTTGCTCATTTTTTCTTACATAATTTTTTATTCAAGTTATTGTACAGCTGTTTAAGATGGGC

AGCTAGTTCGTAGCTTTCCCAAATAAACTCTAAACATTAATCAATCATCTGTGTGAAAATGGGTTGGTGC

TTCTAACCTGATGGCACTTAGCTATCAGAAGACCACAAAAATTGACTCAAATCTCCAGTATTCTTGTCAA

AAAAAAAAAAAAAAGCTCATATTTTGTATATATCTGCTTCAGTGGAGAATTATATAGGTTGTGCAAAT

TAACAGTCCTAACTGGTATAGAGCACCTAGTCCAGTGACCTGCTGGGTAAACTGTGGATGATGGTTGCAA

AAGACTAATTTAAAAAATAACTACCAAGAGGCCCTGTCTGTACCTAACGCCCTATTTTTGCAATGGCTAT

ATGGCAAGAAAGCTGGTAAACTATTTGTCTTTCAGGACCTTTTGAAGTAGTTTGTATAACTTCTTAAAAG

TTGTGATTCCAGATAACCAGCTGTAACACAGCTGAGAGACTTTTAATCAGACAAAGTAATTCCTCTCACT

AAACTTTACCCAAAAACTAAATCTCTAATATGGCAAAAATGGCTAGACACCCATTTTCACATTCCCATCT

GTCACCAATTGGTTAATCTTTCCTGATGGTACAGGAAAGCTCAGCTACTGATTTTTGTGATTTAGAACTG

TATGTATGTCAGACATCCATGTTTGTAAAACTACACATCCCTAATGTGTGCCATAGAGTTTAACACAAGT

CCTGTGAATTTCTTCACTGTTGAAAATTATTTTAAACAAAATAGAAGCTGTAGTAGCCCTTTCTGTGTGC

ACCTTACCAACTTTCTGTAAACTCAAAACTTAACATATTTACTAAGCCACAAGAAATTTGATTTCTATTC

AAGGTGGCCAAATTATTTGTGTAATAGAAAACTGAAAATCTAATATTAAAAATATGGAACTTCTAATATA

TTTTTATATTTAGTTATAGTTTCAGATATATATCATATTGGTATTCACTAATCTGGGAAGGGAAGGGCTA

CTGCAGCTTTACATGCAATTTATTAAAATGATTGTAAAATAGCTTGTATAGTGTAAAATAAGAATGATTT

TTAGATGAGATTGTTTTATCATGACATGTTATATATTTTTTGTAGGGGTCAAAGAAATGCTGATGGATAA
```

-continued

CCTATATGATTTATAGTTTGTACATGCATTCATACAGGCAGCGATGGTCTCAGAAACCAAACAGTTTGCT

CTAGGGGAAGAGGGAGATGGAGACTGGTCCTGTGTGCAGTGAAGGTTGCTGAGGCTCTGACCCAGTGAGA

TTACAGAGGAAGTTATCCTCTGCCTCCCATTCTGACCACCCTTCTCATTCCAACAGTGAGTCTGTCAGCG

CAGGTTTAGTTTACTCAATCTCCCCTTGCACTAAAGTATGTAAAGTATGTAAACAGGAGACAGGAAGGTG

GTGCTTACATCCTTAAAGGCACCATCTAATAGCGGGTTACTTTCACATACAGCCCTCCCCCAGCAGTTGA

ATGACAACAGAAGCTTCAGAAGTTTGGCAATAGTTTGCATAGAGGTACCAGCAATATGTAAATAGTGCAG

AATCTCATAGGTTGCCAATAATACACTAATTCCTTTCTATCCTACAACAAGAGTTTATTTCCAAATAAAA

TGAGGACATGTTTTTGTTTTCTTTGAATGCTTTTTGAATGTTATTTGTTATTTTCAGTATTTTGGAGAAA

TTATTTAATAAAAAAAACAATCATTTGCTTTTTG

ESR1 mRNA

SEQ ID NO: 2

AGGAGCTGGC GGAGGGCGTT CGTCCTGGGA CTGCACTTGC TCCCGTCGGG TCGCCCGGCT

TCACCGGACC CGCAGGCTCC CGGGGCAGGG CCGGGGCCAG AGCTCGCGTG TCGGCGGGAC

ATGCGCTGCG TCGCCTCTAA CCTCGGGCTG TGCTCTTTTT CCAGGTGGCC CGCCGGTTTC

TGAGCCTTCT GCCCTGCGGG GACACGGTCT GCACCCTGCC CGCGGCCACG GACCATGACC

ATGACCCTCC ACACCAAAGC ATCTGGGATG CCCTACTGC ATCAGATCCA AGGGAACGAG

CTGGAGCCCC TGAACCGTCC GCAGCTCAAG ATCCCCCTGG AGCGGCCCCT GGGCGAGGTG

TACCTGGACA GCAGCAAGCC CGCCGTGTAC AACTACCCCG AGGGCGCCGC CTACGAGTTC

AACGCCGCGG CCGCCGCCAA CGCGCAGGTC TACGGTCAGA CCGGCCTCCC CTACGGCCCC

GGGTCTGAGG CTGCGGCGTT CGGCTCCAAC GGCCTGGGG GTTTCCCCCC ACTCAACAGC

GTGTCTCCGA GCCCGCTGAT GCTACTGCAC CCGCCGCCGC AGCTGTCGCC TTTCCTGCAG

CCCCACGGCC AGCAGGTGCC CTACTACCTG GAGAACGAGC CCAGCGGCTA CACGGTGCGC

GAGGCCGGCC CGCCGGCATT CTACAGGCCA AATTCAGATA ATCGACGCCA GGGTGGCAGA

GAAAGATTGG CCAGTACCAA TGACAAGGGA AGTATGGCTA TGGAATCTGC CAAGGAGACT

CGCTACTGTG CAGTGTGCAA TGACTATGCT TCAGGCTACC ATTATGGAGT CTGGTCCTGT

GAGGGCTGCA AGGCCTTCTT CAAGAGAAGT ATTCAAGGAC ATAACGACTA TATGTGTCCA

GCCACCAACC AGTGCACCAT TGATAAAAAC AGGAGGAAGA GCTGCCAGGC CTGCCGGCTC

CGCAAATGCT ACGAAGTGGG AATGATGAAA GGTGGGATAC GAAAAGACCG AAGAGGAGGG

AGAATGTTGA ACACAAGCG CCAGAGAGAT GATGGGGAGG GCAGGGGTGA AGTGGGGTCT

GCTGGAGACA TGAGAGCTGC CAACCTTTGG CCAAGCCCGC TCATGATCAA ACGCTCTAAG

AAGAACAGCC TGGCCTTGTC CCTGACGGCC GACCAGATGG TCAGTGCCTT GTTGGATGCT

GAGCCCCCCA TACTCTATTC CGAGTATGAT CCTACCAGAC CCTTCAGTGA AGCTTCGATG

ATGGGCTTAC TGACCAACCT GGCAGACAGG GAGCTGGTTC ACATGATCAA CTGGGCGAAG

AGGGTGCCAG GCTTTGTGGA TTTGACCCTC CATGATCAGG TCCACCTTCT AGAATGTGCC

TGGCTAGAGA TCCTGATGAT TGGTCTCGTC TGGCGCTCCA TGGAGCACCC AGGGAAGCTA

CTGTTTGCTC CTAACTTGCT CTTGGACAGG AACCAGGGAA AATGTGTAGA GGGCATGGTG

GAGATCTTCG ACATGCTGCT GGCTACATCA TCTCGGTTCC GCATGATGAA TCTGCAGGGA

GAGGAGTTTG TGTGCCTCAA ATCTATTATT TTGCTTAATT CTGGAGTGTA CACATTTCTG

TCCAGCACCC TGAAGTCTCT GGAAGAGAAG GACCATATCC ACCGAGTCCT GGACAAGATC

ACAGACACTT TGATCCACCT GATGGCCAAG GCAGGCCTGA CCCTGCAGCA GCAGCACCAG

CGGCTGGCCC AGCTCCTCCT CATCCTCTCC CACATCAGGC ACATGAGTAA CAAAGGCATG

GAGCATCTGT ACAGCATGAA GTGCAAGAAC GTGGTGCCCC TCTATGACCT GCTGCTGGAG

-continued

```
ATGCTGGACG CCCACCGCCT ACATGCGCCC ACTAGCCGTG GAGGGGCATC CGTGGAGGAG

ACGGACCAAA GCCACTTGGC CACTGCGGGC TCTACTTCAT CGCATTCCTT GCAAAAGTAT

TACATCACGG GGGAGGCAGA GGGTTTCCCT GCCACGGTCT GAGAGCTCCC TGGCTCCCAC

ACGGTTCAGA TAATCCCTGC TGCATTTTAC CCTCATCATG CACCACTTTA GCCAAATTCT

GTCTCCTGCA TACACTCCGG CATGCATCCA ACACCAATGG CTTTCTAGAT GAGTGGCCAT

TCATTTGCTT GCTCAGTTCT TAGTGGCACA TCTTCTGTCT TCTGTTGGGA ACAGCCAAAG

GGATTCCAAG GCTAAATCTT TGTAACAGCT CTCTTTCCCC CTTGCTATGT TACTAAGCGT

GAGGATTCCC GTAGCTCTTC ACAGCTGAAC TCAGTCTATG GGTTGGGGCT CAGATAACTC

TGTGCATTTA AGCTACTTGT AGAGACCCAG GCCTGGAGAG TAGACATTTT GCCTCTGATA

AGCACTTTTT AAATGGCTCT AAGAATAAGC CACAGCAAAG AATTTAAAGT GGCTCCTTTA

ATTGGTGACT TGGAGAAAGC TAGGTCAAGG GTTTATTATA GCACCCTCTT GTATTCCTAT

GGCAATGCAT CCTTTTATGA AAGTGGTACA CCTTAAAGCT TTTATATGAC TGTAGCAGAG

TATCTGGTGA TTGTCAATTC ATTCCCCCTA TAGGAATACA AGGGGCACAC AGGGAAGGCA

GATCCCCTAG TTGGCAAGAC TATTTTAACT TGATACACTG CAGATTCAGA TGTGCTGAAA

GCTCTGCCTC TGGCTTTCCG GTCATGGGTT CCAGTTAATT CATGCCTCCC ATGGACCTAT

GGAGAGCAGC AAGTTGATCT TAGTTAAGTC TCCCTATATG AGGGATAAGT TCCTGATTTT

TGTTTTTATT TTTGTGTTAC AAAAGAAAGC CCTCCCTCCC TGAACTTGCA GTAAGGTCAG

CTTCAGGACC TGTTCCAGTG GGCACTGTAC TTGGATCTTC CCGGCGTGTG TGTGCCTTAC

ACAGGGGTGA ACTGTTCACT GTGGTGATGC ATGATGAGGG TAAATGGTAG TTGAAAGGAG

CAGGGGCCCT GGTGTTGCAT TTAGCCCTGG GGCATGGAGC TGAACAGTAC TTGTGCAGGA

TTGTTGTGGC TACTAGAGAA CAAGAGGGAA AGTAGGGCAG AAACTGGATA CAGTTCTGAG

GCACAGCCAG ACTTGCTCAG GGTGGCCCTG CCACAGGCTG CAGCTACCTA GGAACATTCC

TTGCAGACCC CGCATTGCCC TTTGGGGGTG CCCTGGGATC CCTGGGGTAG TCCAGCTCTT

CTTCATTTCC CAGCGTGGCC CTGGTTGGAA GAAGCAGCTG TCACAGCTGC TGTAGACAGC

TGTGTTCCTA CAATTGGCCC AGCACCCTGG GGCACGGGAG AAGGGTGGGG ACCGTTGCTG

TCACTACTCA GGCTGACTGG GGCCTGGTCA GATTACGTAT GCCCTTGGTG GTTTAGAGAT

AATCCAAAAT CAGGGTTTGG TTTGGGGAAG AAAATCCTCC CCCTTCCTCC CCCGCCCCGT

TCCCTACCGC CTCCACTCCT GCCAGCTCAT TTCCTTCAAT TTCCTTTGAC CTATAGGCTA

AAAAAGAAAG GCTCATTCCA GCCACAGGGC AGCCTTCCCT GGGCCTTTGC TTCTCTAGCA

CAATTATGGG TTACTTCCTT TTTCTTAACA AAAAGAATG TTTGATTTCC TCTGGGTGAC

CTTATTGTCT GTAATTGAAA CCCTATTGAG AGGTGATGTC TGTGTTAGCC AATGACCCAG

GTGAGCTGCT CGGGCTTCTC TTGGTATGTC TTGTTTGGAA AAGTGGATTT CATTCATTTC

TGATTGTCCA GTTAAGTGAT CACCAAAGGA CTGAGAATCT GGGAGGGCAA AAAAAAAAA

AAAGTTTTTA TGTGCACTTA AATTTGGGGA CAATTTTATG TATCTGTGTT AAGGATATGT

TTAAGAACAT AATTCTTTTG TTGCTGTTTG TTTAAGAAGC ACCTTAGTTT GTTTAAGAAG

CACCTTATAT AGTATAATAT ATATTTTTTT GAAATTACAT TGCTTGTTTA TCAGACAATT

GAATGTAGTA ATTCTGTTCT GGATTTAATT TGACTGGGTT AACATGCAAA AACCAAGGAA

AAATATTTAG TTTTTTTTTT TTTTTTTGTA TACTTTTCAA GCTACCTTGT CATGTATACA

GTCATTTATG CCTAAAGCCT GGTGATTATT CATTTAAATG AAGATCACAT TTCATATCAA

CTTTTGTATC CACAGTAGAC AAAATAGCAC TAATCCAGAT GCCTATTGTT GGATACTGAA
```

-continued

```
TGACAGACAA TCTTATGTAG CAAAGATTAT GCCTGAAAAG GAAAATTATT CAGGGCAGCT

AATTTTGCTT TTACCAAAAT ATCAGTAGTA ATATTTTTGG ACAGTAGCTA ATGGGTCAGT

GGGTTCTTTT TAATGTTTAT ACTTAGATTT TCTTTTAAAA AAATTAAAAT AAAACAAAAA

AAAATTTCTA GGACTAGACG ATGTAATACC AGCTAAAGCC AAACAATTAT ACAGTGGAAG

GTTTTACATT ATTCATCCAA TGTGTTTCTA TTCATGTTAA GATACTACTA CATTTGAAGT

GGGCAGAGAA CATCAGATGA TTGAAATGTT CGCCCAGGGG TCTCCAGCAA CTTTGGAAAT

CTCTTTGTAT TTTTACTTGA AGTGCCACTA ATGGACAGCA GATATTTTCT GGCTGATGTT

GGTATTGGGT GTAGGAACAT GATTTAAAAA AAAACTCTTG CCTCTGCTTT CCCCCACTCT

GAGGCAAGTT AAAATGTAAA AGATGTGATT TATCTGGGGG GCTCAGGTAT GGTGGGGAAG

TGGATTCAGG AATCTGGGGA ATGGCAAATA TATTAAGAAG AGTATTGAAA GTATTTGGAG

GAAAATGGTT AATTCTGGGT GTGCACCAGG GTTCAGTAGA GTCCACTTCT GCCCTGGAGA

CCACAAATCA ACTAGCTCCA TTTACAGCCA TTTCTAAAAT GGCAGCTTCA GTTCTAGAGA

AGAAAGAACA ACATCAGCAG TAAAGTCCAT GGAATAGCTA GTGGTCTGTG TTTCTTTTCG

CCATTGCCTA GCTTGCCGTA ATGATTCTAT AATGCCATCA TGCAGCAATT ATGAGAGGCT

AGGTCATCCA AAGAGAAGAC CCTATCAATG TAGGTTGCAA AATCTAACCC CTAAGGAAGT

GCAGTCTTTG ATTTGATTTC CCTAGTAACC TTGCAGATAT GTTTAACCAA GCCATAGCCC

ATGCCTTTTG AGGGCTGAAC AAATAAGGGA CTTACTGATA ATTTACTTTT GATCACATTA

AGGTGTTCTC ACCTTGAAAT CTTATACACT GAAATGGCCA TTGATTTAGG CCACTGGCTT

AGAGTACTCC TTCCCCTGCA TGACACTGAT TACAAATACT TTCCTATTCA TACTTTCCAA

TTATGAGATG GACTGTGGGT ACTGGGAGTG ATCACTAACA CCATAGTAAT GTCTAATATT

CACAGGCAGA TCTGCTTGGG GAAGCTAGTT ATGTGAAAGG CAAATAGAGT CATACAGTAG

CTCAAAAGGC AACCATAATT CTCTTTGGTG CAGGTCTTGG GAGCGTGATC TAGATTACAC

TGCACCATTC CCAAGTTAAT CCCCTGAAAA CTTACTCTCA ACTGGAGCAA ATGAACTTTG

GTCCCAAATA TCCATCTTTT CAGTAGCGTT AATTATGCTC TGTTTCCAAC TGCATTTCCT

TTCCAATTGA ATTAAAGTGT GGCCTCGTTT TTAGTCATTT AAAATTGTTT TCTAAGTAAT

TGCTGCCTCT ATTATGGCAC TTCAATTTTG CACTGTCTTT TGAGATTCAA GAAAAATTTC

TATTCTTTTT TTTGCATCCA ATTGTGCCTG AACTTTTAAA ATATGTAAAT GCTGCCATGT

TCCAAACCCA TCGTCAGTGT GTGTGTTTAG AGCTGTGCAC CCTAGAAACA ACATATTGTC

CCATGAGCAG GTGCCTGAGA CACAGACCCC TTTGCATTCA CAGAGAGGTC ATTGGTTATA

GAGACTTGAA TTAATAAGTG ACATTATGCC AGTTTCTGTT CTCTCACAGG TGATAAACAA

TGCTTTTTGT GCACTACATA CTCTTCAGTG TAGAGCTCTT GTTTTATGGG AAAAGGCTCA

AATGCCAAAT TGTGTTTGAT GGATTAATAT GCCCTTTTGC CGATGCATAC TATTACTGAT

GTGACTCGGT TTTGTCGCAG CTTTGCTTTG TTTAATGAAA CACACTTGTA AACCTCTTTT

GCACTTTGAA AAAGAATCCA GCGGGATGCT CGAGCACCTG TAAACAATTT TCTCAACCTA
```

SEQ ID NO: 3-46
MCL1, SAP30, DUSP1, SGK1, SMARCA2, PTGDS, TNFRSF9, SFN, LAPTM5, GPSM2, SORT1, DPT, NRP1, ACSL5, BIRC3, NNMT, IGFBP6, PLXNC1, SLC46A3, C14orf139, PIAS1, IDH2, SERPINF1, ERBB2, PECAM1, LBH, ST3GAL5, IL1R1, BIN1, WIPF1, TFPI, FN1, FAM134A, NRIP1, RAC2, SPP1, PHF15, BTN3A2, SESN1, MAP3K5, DPYSL2, SEMA4D, STOM, and MAOA gene.

REFERENCES

The following references, to the extent that they provide exemplary procedural or other details supplementary to those set forth herein, are specifically incorporated herein by reference.

U.S. Pat. No. 5,143,854
U.S. Pat. No. 5,202,231
U.S. Pat. No. 5,242,974
U.S. Pat. No. 5,288,644
U.S. Pat. No. 5,324,633
U.S. Pat. No. 5,384,261
U.S. Pat. No. 5,405,783
U.S. Pat. No. 5,412,087
U.S. Pat. No. 5,424,186
U.S. Pat. No. 5,429,807
U.S. Pat. No. 5,432,049
U.S. Pat. No. 5,436,327
U.S. Pat. No. 5,445,934
U.S. Pat. No. 5,468,613
U.S. Pat. No. 5,470,710
U.S. Pat. No. 5,472,672
U.S. Pat. No. 5,492,806
U.S. Pat. No. 5,503,980
U.S. Pat. No. 5,510,270
U.S. Pat. No. 5,525,464
U.S. Pat. No. 5,525,464
U.S. Pat. No. 5,527,681
U.S. Pat. No. 5,529,756
U.S. Pat. No. 5,532,128
U.S. Pat. No. 5,545,531
U.S. Pat. No. 5,547,839
U.S. Pat. No. 5,554,501
U.S. Pat. No. 5,556,752
U.S. Pat. No. 5,561,071
U.S. Pat. No. 5,571,639
U.S. Pat. No. 5,580,726
U.S. Pat. No. 5,580,732
U.S. Pat. No. 5,593,839
U.S. Pat. No. 5,599,672
U.S. Pat. No. 5,599,695
U.S. Pat. No. 5,610,287
U.S. Pat. No. 5,624,711
U.S. Pat. No. 5,631,134
U.S. Pat. No. 5,639,603
U.S. Pat. No. 5,654,413
U.S. Pat. No. 5,658,734
U.S. Pat. No. 5,661,028
U.S. Pat. No. 5,665,547
U.S. Pat. No. 5,667,972
U.S. Pat. No. 5,695,940
U.S. Pat. No. 5,700,637
U.S. Pat. No. 5,744,305
U.S. Pat. No. 5,800,992
U.S. Pat. No. 5,807,522
U.S. Pat. No. 5,830,645
U.S. Pat. No. 5,837,196
U.S. Pat. No. 5,847,219
U.S. Pat. No. 5,871,928
U.S. Pat. No. 5,876,932
U.S. Pat. No. 5,919,626
U.S. Pat. No. 6,004,755
U.S. Pat. No. 6,087,102
U.S. Pat. No. 6,368,799
U.S. Pat. No. 6,383,749
U.S. Pat. No. 6,617,112
U.S. Pat. No. 6,638,717
U.S. Pat. No. 6,720,138
U.S. Patent Publn. 2010/0135956
Belanoff et al., *Eur. J. Pharmacol.*, 655(1-3):117-20, 2011.
Cho et al. *Biochemistry*, 44(9):3547-61, 2005.
Clark, *Curr. Top. Med. Chem.* 8(9):813-838, 2008.
Colleoni et al., *Annals of Oncology*, 11(8):1057, 2000.
Euopean Appln. EP 373 203
Euopean Appln. EP 785 280
Euopean Appln. EP 799 897
Evans, *Science*, 240:889, 1988.
Fodor et al., *Science*, 251:767-777, 1991.
Grover and Martin, *Carcinogenesis*, 23(7):1095-102, 2002.
Hacia et al., *Nature Genet.*, 14:441-449, 1996.
Harrison's Principles of Internal Medicine, Kasper et al. (Eds.), 16th Ed., Chapter 70, 2005.
Henderson et al. *Cancer Res.*, 48:246-253, 1988.
Keen and Davidson, *Cancer*, 97(3 Suppl):825-33, 2003.
Ma et al., *J. Immunol.*, 171(2):608-615, 2003.
MacBeath and Schreiber, *Science*, 289(5485):1760-3, 2000.
Melhem et al, *Clin. Cancer Res.*, 15(9):3196-204, 2009.
Mikosz et al., *J. Biol. Chem.*, 276:16649-54, 2001.
Moran et al., *Cancer Res.*, 60:867-872, 2000.
Pandey and Mann, *Nature*, 405(6788):837-46, 2000.
Pang and Conzen, *Cancer Biol. Ther. Cancer Biol. Ther.*, 5(8):933-40, 2006.
PCT Appln. WO 01/68255
PCT Appln. WO 03/020898
PCT Appln. WO 03/022421
PCT Appln. WO 03/023058
PCT Appln. WO 03/029485
PCT Appln. WO 03/040410
PCT Appln. WO 03/053586
PCT Appln. WO 03/066906
PCT Appln. WO 03/067217
PCT Appln. WO 03/076928
PCT Appln. WO 03/087297
PCT Appln. WO 03/091426
PCT Appln. WO 03/093810
PCT Appln. WO 03/100448A1
PCT Appln. WO 04/020085
PCT Appln. WO 04/027093
PCT Appln. WO 09/923256
PCT Appln. WO 09/936760
PCT Appln. WO 93/17126
PCT Appln. WO 95/11995
PCT Appln. WO 95/21265
PCT Appln. WO 95/21944
PCT Appln. WO 95/35505
PCT Appln. WO 96/30347
PCT Appln. WO 96/31622
PCT Appln. WO 96/33980
PCT Appln. WO 97/10365
PCT Appln. WO 97/27317
PCT Appln. WO 9743450
PCT Appln. WO 99/35505
PCT Appln. WO 01/38580
PCT Appln. WO 03/100012
Pease et al., *Proc. Natl. Acad. Sci. USA*, 91:5022-5026, 1994.
Peeters et al., *Ann. NY Acad. Sci.*, 1148:536-41, 2008.
Pike et al., *Epidemiologic Revi.*, 15(1):17-35, 1993.
Shoemaker et al., *Nature Genetics*, 14:450-456, 1996.
Sims et al. *BMC Medical Genomics*, 1(42):1-14, 2008.
Sorlie et al., *Proc. Natl. Acad. Sci. USA*, 98:10869-10874., 2001.
Srinivas et al., *Clin. Chem.*, 48(8):1160-9, 2002.
UK Appln. 8 803 000
Wu et al., *Cancer Res.*, 64:1757-64, 2004.
Wu et al., *J. Clin. Invest.*, 114:560-568, 2004.
Wu et al., *Mol Endocrinol.*, 2006

What is claimed is:

1. A method of killing breast cancer cells comprising administering to a breast cancer patient an effective amount of a combination of anti-cancer compounds, wherein the anticancer compounds comprise a glucocorticoid receptor antagonist selected from beclometasone, betamethasone, budesonide, ciclesonide, flunisolide, fluticasone, mometasone, triamcinolone, mifepristone (RU-486), RU-43044, 10β-substituted steroids, 11β-aryl conjugates of mifepristone, phosphorous-containing mifepristone analogs, 11-monoaryl and 11,21 bisaryl steroids (including 11 (3-substituted steroids), octahydrophenanthrenes, spirocyclic dihydropyridines, triphenylmethanes and diaryl ethers, chromenes, dibenzyl anilines, dihyrdroquinolines, pyrimidinediones, azadecalins, aryl pyrazolo azadecalins (including 8a-benzyl isoquinolones, N-substituted derivatives, bridgehead alcohol and ethers, bridgehead amines, ORG-34517 (Merck), dexamethasone mesylate (Dex-Mes), dexamethasone oxetanone (Dex-Ox), deoxycorticosterone (DOC), CORT 0113083 and CORT 00112716,
and a chemotherapeutic agent.

2. A method of treating breast cancer in a patient comprising administering to the patient an effective amount of glucocorticoid receptor antagonist selected from beclometasone, betamethasone, budesonide, ciclesonide, flunisolide, fluticasone, mometasone, triamcinolone, mifepristone (RU-486), RU-43044, 10β-substituted steroids, 11β-aryl conjugates of mifepristone, phosphorous-containing mifepristone analogs, 11-monoaryl and 11,21 bisaryl steroids (including 11 (3-substituted steroids), octahydrophenanthrenes, spirocyclic dihydropyridines, triphenylmethanes and diaryl ethers, chromenes, dibenzyl anilines, dihyrdroquinolines, pyrimidinediones, azadecalins, aryl pyrazolo azadecalins (including 8a-benzyl isoquinolones, N-substituted derivatives, bridgehead alcohol and ethers, bridgehead amines, ORG-34517 (Merck), dexamethasone mesylate (Dex-Mes), dexamethasone oxetanone (Dex-Ox), deoxycorticosterone (DOC), CORT 0113083 and CORT 00112716,
and a chemotherapeutic agent.

3. The method of treating breast cancer in a patient of claim 2, wherein said breast cancer comprises chemotherapy-insensitive breast cancer cells, the method comprising administering to a breast cancer patient an effective amount of said glucocorticoid receptor antagonist followed by chemotherapy agent.

4. The method of treating breast cancer in a patient of claim 2, comprising administering to said breast cancer patient an effective amount of said glucocorticoid receptor antagonist followed by at least one apoptosis-inducing agent.

5. The method for treating breast cancer in a patient of claim 2, further comprising:
    a) administering radiation or at least a first chemotherapeutic to the patient;
    b) subsequently administering an effective amount of said glucocorticoid receptor antagonist to the patient;
    c) administering radiation again or at least a second chemotherapeutic to the patient after the glucocorticoid receptor antagonist is administered to the patient.

6. The method for treating breast cancer in a patient of claim 2, further comprising:
    a) administering an effective amount of said glucocorticoid receptor antagonist to the patient, wherein the patient expresses a detectable level of glucocorticoid receptor prior to administration of the GR antagonist;
    b) then administering an effective amount of radiation or at least one chemotherapeutic.

7. A method for evaluating a patient with breast cancer comprising:
    a) measuring the activity level of glucocorticoid receptor (GR) from a biological sample from the patient containing breast cancer cells;
    b) measuring the expression level of estrogen receptor (ER) in breast cancer cells from the patient;
    c) identifying the patient as having or not having a risk factor for cancer recurrence based on measurements in a) and b).

8. The method for evaluating a patient with breast cancer of claim 7, further comprising
    calculating a prognosis score for the patient based on the measurements in a) and b).

9. The method for evaluating a patient with breast cancer of claim 7, further comprising:
    identifying the patient as having a poor prognosis if the patient is determined to have i) an activity level of glucocorticoid receptor that is higher than the activity level of glucocorticoid receptor in normalized control sample and ii) a expression level of estrogen receptor expression that is lower than the expression level of estrogen receptor in a normalized control sample.

10. The method for evaluating a patient with breast cancer of claim 7, further comprising:
    categorizing the patient as i) GR+ or GR− based on the level of glucocorticoid activity assayed in the biological sample and compared to a predetermined threshold value for GR activity; and ii) ER+ or ER− based on the level of estrogen receptor expression assayed in the biological sample and compared to a predetermined threshold value for ER expression.

11. The method for evaluating a patient with breast cancer of claim 7, further comprising:
    prognosing the patient based on the measurements in a) after obtaining information about the level of estrogen receptor expression in breast cancer cells of the patient.

12. The method for evaluating a patient with breast cancer of claim 7, further comprising
    identifying the patient as having a poor prognosis if the patient is determined to have a glucocorticoid receptor activity level in the 65th percentile or above based on breast cancer patients whose levels of estrogen receptor are in the 35th percentile or below.

* * * * *

SEQUENCE LISTING

```
Sequence total quantity: 46
SEQ ID NO: 1            moltype = DNA   length = 4794
FEATURE                 Location/Qualifiers
source                  1..4794
                        mol_type = other DNA
                        organism = Homo sapiens
SEQUENCE: 1
tttttagaaa aaaaaaatat atttccctcc tgctccttct gcgttcacaa gctaagttgt    60
ttatctcggc tgcggcggga actgcggacg gtggcgggcg agcggctcct ctgccagagt   120
tgatattcac tgatggactc caaagaatca ttaactcctg gtagagaaga aaaccccagc   180
agtgtgcttg ctcaggagag gggagatgtg atggacttct ataaaaccct aagaggagga   240
gctactgtga aggtttctgc gtcttcaccc tcactggctg tcgcttctca atcagactcc   300
aagcagcgaa gacttttggt tgattttcca aaaggctcag taagcaatgc gcagcagcca   360
gatctgtcca aagcagtttc actctcaatg ggactgtata tgggagagac agaaacaaaa   420
gtgatgggaa atgacctggg attcccacag cagggccaaa tcagcctttc ctcgggggaa   480
acagacttaa agcttttgga agaaagcatt gcaaacctca ataggtcgac cagtgttcca   540
gagaacccca agagttcagc atccactgct gtgtctgctg cccccacaga aaggagttt    600
ccaaaaactc actctgatgt atcttcagaa cagcaacatt tgaagggcca gactggcacc   660
aacggtggca atgtgaaatt gtataccaca gaccaaagca cctttgacat tttgcaggat   720
ttggagtttt cttctgggtc cccaggtaaa gagacgaatg agagtccttg gagatcagac   780
ctgttgatag atgaaaactg tttgctttct cctctggcgg gagaagacga ttcattcctt   840
ttggaaggaa actcgaatga ggactgcaag cctctcattt taccggacac taaacccaaa   900
attaaggata atggagatct ggttttgtca agcccagta atgtaacact gccccaagtg   960
aaaacagaaa aagaagattt catcgaactc tgcaccccctg ggtaattaa gcaagagaaa  1020
ctgggcacag tttactgtca ggcaagcttt cctggagcaa atataattgg taataaaatg  1080
tctgccattt ctgttcatgg tgtgagtacc tctggaggac agatgtacca ctatgacatg  1140
aatacagcat ccctttctca acagcaggat cagaagccta ttttttaatgt cattccacca  1200
attcccgttg gttccgaaaa ttggaatagg tgccaaggat ctggagatga caacttgact  1260
tctctgggga ctctgaactt ccctggtcga acagttttt ctaatggcta ttcaagcccc  1320
agcatgagac cagatgtaag ctctcctcca tccagctcct caacagcaac aacaggacca  1380
cctcccaaac tctgcctggt gtgctctgat gaagcttcag gatgtcatta tggagtctta  1440
acttgtggga gctgtaaagt tttcttcaaa agagcagtgg aaggacagca caattaccta  1500
tgtgctggaa ggaatgattg catcatcgat aaaattcgaa gaaaaaactg cccagcatgc  1560
cgctatcgaa aatgtcttca ggctggaatg aacctggaag ctcgaaaaac aaagaaaaaa  1620
ataaaaggaa ttcagcaggc cactacagga gtctcacaag aaacctctga aatcctggt   1680
aacaaaacaa tagttcctgc aacgttacca caactcaccc ctaccctggt gtcactgttg  1740
gaggttattg aacctgaagt gttatatgca ggatatgata gctctgttcc agactcaact  1800
tggaggatca tgactacgct caacatgtta ggagggcggc aagtgattgc agcagtgaaa  1860
tgggcaaagg caataccagg tttcaggaac ttacacctgg atgaccaaat gaccctactg  1920
cagtactcct ggatgtttct tatggcattt gctctgggt ggagatcata tagacaatca  1980
agtgcaaacc tgctgtgttt tgctcctgat ctgattatta atgagcagag aatgactcta  2040
ccctgcatgt acgaccaatg taaacacatg ctgtatgttt cctctgagtt acacaggctt  2100
caggtatctt atgaagagta tctctgtatg aaaaccttac tgcttctctc ttcagttcct  2160
aaggacggtc tgaagagcca agagctattt gatgaaatta gatgaccta catcaaagag  2220
ctaggaaaag ccattgtcaa gagggaagga aactccagcc agaactggca gcggttttat  2280
caactgacaa aactcttgga ttctatgcat gaagtggttg aaaatctcct taactattgc  2340
ttccaaacat ttttggataa gaccatgagt attgaattcc ccgagatgtt agctgaaatc  2400
atcaccaatc agataccaaa atattcaaat ggaaatatca aaaaacttct gtttcatcaa  2460
aagtgactgc cttaataaga atggttgcct taaagaaagt cgaattaata gcttttattg  2520
tataaactat cagtttgtcc tgtagaggtt tgttgttttt atttttttatt gttttcatct  2580
gttgttttgt tttaaatacg cactacatgt ggtttataga gggccaagac ttggcaacag  2640
aagcagttga gtcgtcatca cttttcagtg atgggagagt agatggtgaa attattagt   2700
taatatatcc cagaaattag aaaccttaat atgtggacgt aatctccaca gtcaaagaag  2760
gatggcacct aaaccaccag tgcccaaagt ctgtgtgatg aactttctct tcatactttt  2820
tttcacagtt ggctggatga aattttctag actttctgtt ggtgtatccc cccccctgta  2880
tagttaggat agcattttg atttatgcat ggaaacctga aaaaaagttt acaagtgtat  2940
atcagaaaag ggaagttgtg cctttttatag ctattactgt ctggttttaa caatttcctt  3000
tatatttagt gaactacgct tgctcatttt ttcttacata attttttatt caagttattg  3060
tacagctgtt taagatgggc agctagttcg tagctttccc aaataaactc taaacattaa  3120
tcaatcatct gtgtgaaaat gggttggtgc ttctaacctg atggcactta gctatcagaa  3180
gaccacaaaa attgactcaa atctccagta ttcttgtcaa aaaaaaaaaa aaaaaagctc  3240
atattttgta tatatctgct tcagtggaga attatatagg ttgtgcaaat taacagtcct  3300
aactggtata gagcacctag tccagtgacc tgctgggtaa actgtggatg atggttgcaa  3360
aagactaatt taaaaaataa ctaccaagag gccctgtctg tacctaacgc ctatttttg   3420
caatggctat tggcaagaa agctggtaaa ctatttgtct ttcaggacct tttgaagtag  3480
tttgtataac ttcttaaaag ttgtgattcc agataaccag ctgtaacaca gctgagagac  3540
ttttaatcag acaaagtaat tcctctcact aaacttacc caaaaactaa atctctaata   3600
tggcaaaaat ggctagacac ccatttttcac attcccatct gtcaccaatt ggttaatctt  3660
tcctgatggt acaggaaagc tcagctactg attttttgtga tttagaactg tatgtatgtc  3720
agacatccat gtttgtaaaa ctacacatcc ctaatgtgtg ccatagagtt taacacaagt  3780
cctgtgaatt tcttcactgt tgaaaattat tttaaacaaa atagaagctg tagtagccct  3840
ttctgtgtgc accttaccaa cttctgtaa actcaaaact taacatattt actaagccac  3900
aagaaattg atttcatttc aaggtggcca aattatttgt gtaatagaaa actgaaaatc  3960
taatattaaa aatattggaac ttctaatata tttttatatt tagttatagt ttcagatata  4020
tatcatattg gtattcacta atctgggaag ggaagggcta ctgcagcttt acatgcaatt  4080
tattaaaatg attgtaaaat agcttgtata gtgtaaaata agaatgattt ttagatgaga  4140
ttgttttatc atgacatgtt atatattttt tgtagggtc aaagaaatgc tgatggataa  4200
cctatatgat ttatagtttg tacatgcatt catacaggca gcgatggtct cagaaaccaa  4260
```

```
acagtttgct ctaggggaag agggagatgg agactggtcc tgtgtgcagt gaaggttgct   4320
gaggctctga cccagtgaga ttacagagga agttatcctc tgcctcccat tctgaccacc   4380
cttctcattc aacagtgag tctgtcagcg caggtttagt ttactcaatc tcccctttgca   4440
ctaaagtatg taaagtatgt aaacaggaga caggaaggtg gtgcttacat ccttaaaggc   4500
accatctaat agcgggttac tttcacatac agccctcctc cagcagttga atgacaacag   4560
aagcttcaga agtttggcaa tagtttgcat agaggtacca gcaatatgta aatagtgcag   4620
aatctcatag gttgccaata atacactaat tcctttctat cctacaacaa gagtttattt   4680
ccaaataaaa tgaggacatg ttttttgtttt ctttgaatgc ttttttgaatg ttatttgtta   4740
ttttcagtat tttggagaaa ttatttaata aaaaaaacaa tcatttgctt tttg          4794

SEQ ID NO: 2            moltype = DNA   length = 6330
FEATURE                 Location/Qualifiers
source                  1..6330
                        mol_type = other DNA
                        organism = Homo sapiens
SEQUENCE: 2
aggagctggc ggagggcgtt cgtcctggga ctgcacttgc tcccgtcggg tcgcccggct   60
tcaccggacc cgcaggctcc cggggcaggg ccggggccag agctcgcgtg tcggcgggac   120
atgcgctgcg tcgcctctaa cctcgggctg tgctcttttt ccaggtggcc cgccggtttc   180
tgagccttct gccctgcggg gacacggtct gcacccgtgcc cgcggccacg gaccatgacc   240
atgaccctc acaccaaagc atctgggatg cccctactgc atcagatcca agggaacgag   300
ctggagcccc tgaaccgtcc gcagctcaag atcccccctg agcggccccct gggcgaggtg   360
tacctggaca gcagcaagcc cgccgtgtac aactacccccg agggcgccgc ctacgagttc   420
aacgccgcgg ccgccgccaa cgcgcaggtc tacggtcaga ccggcctccc ctacggcccc   480
gggtctgagg ctgcggcgtt cggctccaac ggcctggggg gtttccccccc actcaacagc   540
gtgtctccga gcccgctgat gctactgcac ccgccgccgc agctgtccgc tttcctgcag   600
ccccacggcc agcaggtgcc ctactacctg gagaacgagc ccagcggcta cacggtgcgc   660
gaggccggcc cgccggcatt ctacaggcca aattcagata atcgacgcca gggtggcaga   720
gaaagattgg ccagtaccaa tgacaaggga agtatggcta tggaatctgc caaggagact   780
cgctactgtg cagtgtgcaa tgactatgct tcaggctacc attatggagt ctggtcctgt   840
gagggctgca aggccttctt caagagaagt attcaaggac ataacgacta tatgtgtcca   900
gccaccaacc agtgcaccat tgataaaaac aggaggaaga gctgccaggc ctgccggctc   960
cgcaaatgct acgaagtggg aatgatgaaa ggtgggatac gaaaagaccg aagaggaggg   1020
agaatgttga aacacaagcg ccagagagat gatgggggag gcagggggtga agtgggtct   1080
gctggagaca tgagagctgc caacctttgg ccaagcccgtc tcatgatcaa acgctctaag   1140
aagaacagcc tggccttgtc cctgacggcc gaccagatgg tcagtgcctt gttggatgct   1200
gagcccccca tactctattc cgagtatgat cctaccagac ccttcagtga agcttcgatg   1260
atgggcttac tgaccaaacct ggcagacagg gagctggttc acatgatcaa ctgggcgaag   1320
agggtgccag gcttctgtgga tttgacccctc catgatcagg tccaccttct agaatgtgcc   1380
tggctagaga tcctgatgat tggtctcgtc tggcgctcca tggagcaccc agggaagcta   1440
ctgtttgctc ctaacttgct cttggacagg aaccagggaa aatgtgtaga gggcatggtg   1500
gagatcttcg acatgctgct ggctacatca tctcggttcc gcatgatgaa tctgcaggga   1560
gaggagtttg tgtgcctcaa atcttattatt ttgcttaatt ctggagtgta cacatttctg   1620
tccagcaccc tgaagtctct ggaagagaag gaccatatcc accgagtcct ggacaagatc   1680
acagacactt tgatccacct gatggccaag gcaggcctga ccctgcagca gcagcaccag   1740
cggctggccc agctcctcct catcctctcc cacatcaggc acatgagtaa caaaggcatg   1800
gagcatctgt acagcatgaa gtgcaagaac gtggtgcccc tctatgacct gctgctggag   1860
atgctggacg cccaccgcct acatgcgccc actagccgtg gaggggcatc cgtggaggag   1920
acggaccaaa gccactggc cactgcgggc tctacttcat cgcattcctt gcaaaagtat   1980
tacatcacgg gggaggcaga gggtttccct gccacggtct gagagctccc tggctcccac   2040
acggttcaga taatccctgc tgcatttttac cctcatcatg caccacttta gccaaattgt   2100
gtctcctgca tacactccgg catgcatcca acaccaatgg cttttctagat gagtggccat   2160
tcatttgctt gctcagttct tagtggcaca tcttctgtct tctgtttggga acagccaaag   2220
ggattccaag gctaaatctt tgtaacagct ctcttttcccc cttgctatgt tactaagcgt   2280
gaggattccc gtagctcttc acagctgaac tcagtctatg ggtggggct cagataactc   2340
tgtgcattta agctacttgt agagacccag gcctggagag tagacatttt gcctctgata   2400
agcactttt aaatggctct aagaataagc cacagcaaag aatttaaagt ggctccttta   2460
attggtgact tggagaaagc taggtcaagg gtttattata gcaccctctt gtattcctat   2520
ggcaatgcat ccttttatga aagtggtaca ccttaaagct tttatatgac tgtagcagag   2580
tatctggtga ttgtcaattc attccccta taggaataca aggggcacac agggaaggca   2640
gatcccctag ttggcaagac tatttttaact tgatacactg cagattcaga tgtgctgaaa   2700
gctctgcctc tggctttccg gtcatggggtt ccagttaatt catgcctccc atggacctat   2760
ggagagcagc aagttgatct tagttaagtc tccctatatg agggataagt tcctgatttt   2820
tgtttttatt tttgtgttac aaaagaaagc cctccctccc tgaacttgca gtaaggtcag   2880
cttcaggacc tgttccagtg ggcactgtac ttggatcttc ccggcgtgtg tgtgccttac   2940
acaggggtga actgttcact gtggtgatgc atgatgaggg taaatggtag ttgaaaggag   3000
caggggccct ggtgttgcat ttagccctgg ggcatggagc tgaacagtac ttgtgcagga   3060
ttgttgtggc tactagagaa caagagggaa agtagggcag aaactggata cagttctgag   3120
gcacagccag acttgctcag ggtggccctg ccacaggctag cagctaccta ggaacattcc   3180
ttgcagaccc cgcattgccc tttgggggtg ccctgggatc cctggggtag tccagctctt   3240
cttcatttcc cagcgtggcc ctggttgaa gaagcagctg tcacagctgc tgtagacagc   3300
tgtgttccta caattggccc agcaccctgg ggcacggaga aagggtgggg accgttgctg   3360
tcactactca ggctgactgg ggcctggtca gattacgtat gcccttggtg gtttagagat   3420
aatccaaaat caggttttgg tttggggaag aaaaatcctc ccgcccccgt                     3480
tccctaccgc ctccactcct gccagctcat ttccttcaat ttcctttgac ctataggcta   3540
aaaaagaaag gctcattcca gccacagggc agccttccct gggcctttgc ttctctagca   3600
caattatggg ttacttcctt tttcttaaca aaaaagaatg tttgatttcc tctgggtgac   3660
cttattgtct gtaattgaaa ccctattgag aggtgatgtc tgtgttagcc aatgacccag   3720
gtgagctgct cgggcttctc ttggtatgtc ttgtttggaa aagtggattt cattcatttc   3780
```

```
tgattgtcca gttaagtgat caccaaagga ctgagaatct gggagggcaa aaaaaaaaaa    3840
aaagttttta tgtgcactta aatttgggga caatttatg tatctgtgtt aaggatatgt    3900
ttaagaacat aattcttttg ttgctgtttg tttaagaagc accttagttt gtttaagaag    3960
cacctttat agtataatat atattttttt gaaattacat tgcttgttta tcagacaatt    4020
gaatgtagta attctgttct ggatttaatt tgactgggtt aacatgcaaa aaccaaggaa    4080
aaatatttag tttttttttt tttttttgta tactttcaa gctaccttgt catgtataca    4140
gtcatttatg cctaaagcct ggtgattatt catttaaatg aagatcacat ttcatatcaa    4200
cttttgtatc cacagtagac aaaatagcac taatccagat gcctattgtt ggatactgaa    4260
tgacagacaa tcttatgtag caaagattat gcctgaaaag gaaaattatt cagggcagct    4320
aattttgctt ttaccaaaat atcagtagta atattttgg acagtagcta atgggtcagt    4380
gggttctttt taatgtttat acttagattt tcttttaaaa aaattaaaat aaaacaaaaa    4440
aaaatttcta ggactagacg atgtaatacc agctaaagcc aaacaattat acagtggaag    4500
gttttacatt attcatccaa tgtgtttcta ttcatgttaa gatactacta catttgaagt    4560
gggcagagaa catcagatga ttgaaatgtt cgcccagggg tctccagcaa ctttggaagt    4620
ctctttgtat ttttacttga agtgccacta atggacagca gatattttct ggctgatgtt    4680
ggtattgggt gtaggaacat gatttaaaaa aaaactcttg cctctgcttt cccccactct    4740
gaggcaagtt aaaatgtaaa agatgtgatt tatctggggg gctcaggtat ggtggggaag    4800
tggattcagg aatctgggga atggcaaata tattaagaag agtattgaaa gtatttggag    4860
gaaaatggtt aattctgggt gtgcaccagg gttcagtaga gtccacttct gccctggaga    4920
ccacaaatca actagctcca tttacagcca tttctaaaat ggcagcttca gttctagaga    4980
agaaagaaca acatcagcag taaagtccat ggaatagcta gtggtctgtg tttcttttcg    5040
ccattgccta gcttgccgta atgattctat aatgccatca tgcagcaatt atgagaggct    5100
aggtcatcca aagagaagac cctatcaatg taggttgcaa aatctaaccc ctaaggaagt    5160
gcagtctttg atttgatttc cctagtaacc ttgcagatat gtttaaccaa gccatagccc    5220
atgcctttg agggctgaac aaataaggga cttactgata atttacttt gatcacatta    5280
aggtgttctc accttgaaat cttatacact gaaatggcca ttgatttagg ccactggctt    5340
agagtactcc ttcccctgca tgacactgat tacaaatact ttcctattca tactttccaa    5400
ttatgagatg gactgtgggt actgggagtg atcactaaca ccatagtaat gtctaatatt    5460
cacaggcaga tctgcttggg gaagctagtt atgtgaaagg caaatagagt catacagtag    5520
ctcaaaaggc aaccataatt ctctttggtg caggtcttgg gagcgtgatc tagattacac    5580
tgcaccattc ccaagttaat cccctgaaaa cttactctca actggagcaa atgaactttg    5640
gtcccaaata tccatctttt cagtagcgtt aattatgctc tgtttccaac tgcatttcct    5700
ttccaattga attaaagtgt ggcctcgttt ttagtcattt aaaattgttt tctaagtaat    5760
tgctgcctct attatggcac ttcaattttg cactgtcttt tgagattcaa gaaaaatttc    5820
tattcttttt tttgcatcca attgtgcctg aacttttaaa atatgtaaat gctgccatgt    5880
tccaaaccca tcgtcagtgt gtgtgtttag agctgtgcac cctagaaaca acatattgtc    5940
ccatgagcag gtgcctgaga cacagacccc tttgcattca cagagaggtc attggttata    6000
gagacttgaa ttaataagtg acattatgcc agtttctgtt ctctcacagg tgataaacaa    6060
tgctttttgt gcactacata ctcttcagtg tagagctctt gttttatggg aaaaggctca    6120
aatgccaaat tgtgtttgat ggattaatat gcccttttgc cgatgcatac tattactgat    6180
gtgactcggt tttgtcgcag ctttgctttg tttaatgaaa cacacttgta aacctctttt    6240
gcactttgaa aaagaatcca gcgggatgct cgagcacctg taaacaattt tctcaaccta    6300
tttgatgttc aaataaagaa ttaaactaaa                                     6330
```

SEQ ID NO: 3          moltype = DNA   length = 4107
FEATURE               Location/Qualifiers
source                1..4107
                      mol_type = other DNA
                      organism = Homo sapiens
SEQUENCE: 3
```
gcgcaaccct ccggaagctg ccgccccttt ccccttttat gggaatactt ttttaaaaa      60
aaaagagttc gctggcgcca ccccgtagga ctggccgccc taaaaccgtg ataaaggagc    120
tgctcgccac ttctcacttc cgcttccttc cagtaaggag tcgggtctt ccccagtttt    180
ctcagccagg cggcggcggc gactggcaat gtttggcctc aaaagaaacg cggtaatcgg    240
actcaacctc tactgtgggg gggccggctt gggggccggc aggcgcggcg ccacccgccc    300
gggagggcga cttttggcta cggagaagga ggcctcggcc cggcgagaga taggggagg    360
ggaggccggc gcggtgattg gcggaagcgc cggcgcaagc ccccgtcca ccctcacgcc    420
agactcccgg agggtcgcgc ggccgccgcc cattggcgcc gaggtccccg acgtcaccgc    480
gaccccgcg aggctgctt tcttcgcgcc caccgccgc gcggcgccgc ttgaggagat    540
ggaagccccg gccgctgacg ccatcatgtc gcccgaagag gagctggacg ggtacgagcc    600
ggagcctctc gggaagcggc cggctgtcct gccgctgctg gagttggtcg ggaatctgg    660
taataacacc agtacggacg ggtcactacc ctcgacgccg ccgccagcag aggaggagga    720
ggacgagttg taccggcagt cgctggagat tatctctcgg taccttcggg agcaggccac    780
cggcgccaag gacacaaagc caatggcgag gtctgggcg aggcgctgga    840
gaccttacga cgggttgggg atggcgtgca gcgcaaccac gagacggcct tccaaggcat    900
gcttcggaaa ctgacatca aaacgaaga cgatgtgaaa tcgttgtctc gagtgatgat    960
ccatgttttc agcgacggcg taacaaactg gggcaggatt gtgactctca ttttcttttgg   1020
tgccttttgtg gctaaacact tgaagaccat aaaccaagaa agctgcatcg aaccattage   1080
agaaagtatc acagacgttc tcgtaaggac aaaacgaggc tggctagtta aacaagagg   1140
ctgggatggg tttgtggagt tcttccatgt agaggaccta gaaggtggca tcaggaatgt   1200
gctgctggct tttgcaggtg ttgctggagt aggagctggt ttggcatatc taataagata   1260
gccttactgt aagtgcaata gttgactttt aaccaaccac caccaccacc aaaaccagtt   1320
tatgcagttg gactccaagc tgtaacttcc tagagttgca cccagcaac ctagccagaa    1380
aagcaggca caagaggatt atggctaaca agaataaata catgggaaga gtgctcccca   1440
ttgattgaag agtcactgtc tgaaagaagc aaagttcagt ttcagcaaca aacaaacttt   1500
gtttgggaag ctatggagga ggactttag atttagtgaa gatggtaggg tggaaagact   1560
taatttcctt gttgagaaca ggaaagtggc cagtagccag gcaagtcata gaattgatta   1620
cccgccgaat tcattaattt actgtagtgt taagagaagc actaagaatg ccagtgacct   1680
gtgtaaaagt tacaagtaat agaactatga ctgtaagcct cagtactgta caaggagag    1740
```

```
ttttcctctc tctaattagc tttcccagta tacttcttag aaagtccaag tgttcaggac   1800
ttttatacct gttatacttt ggcttggttt ccatgattct tacttгатта gcctagttta   1860
tcaccaataa tacttgacgg aaggctcagt aattagttat gaatatggat atcctcaatt   1920
cttaagacag cttgtaaatg tatttgtaaa aattgtatat attttтасад aaagtctatt   1980
tctttgaaac gaaggaagta tcgaatttac attagttttc ttcataccct tttgaacttt   2040
gcaacttccg taattaggaa cctgtttctt acagcttttc tatgctaaac tttgttctgt   2100
tcagttctag agtgtataca gaacgaattg atgtgtaact gtatgcagac tggttgtagt   2160
ggaacaaatc tgataactat gcaggtttaa attttcttat ctgattttgg taagtattcc   2220
ttagataggt ttttctttga aaacctggga ttgagaggtt gatgaatgga aattctttca   2280
cttcattata tgcaagttttt caataattag gtctaagtgg agttttaagg ttactgatga   2340
cttacaaata atgggctctg attgggcaat actcatttga gttccttcca tttgacctaa   2400
tttaactggt gaaatttaaa gtgaattcat gggctcatct ttaaagcttt tactaaaaga   2460
ttttcagctg aatggaactc attagctgtg tgcatataaa aagatcacat caggtggatg   2520
gagagacatt tgatcccctтg tttgcttaat aaattataaa atgatggctt ggaaaagcag   2580
gctagtctaa ccatggtgct attattaggc ttgcttgtta cacacacagg tctaagccta   2640
gtatgtcaat aaagcaaata cttactgttt tgtttctatt aatgattccc aaaccttgtt   2700
gcaagttttt gcattggcat ctttggattt cagtcttgat gtttgttcta tcagacttaa   2760
ccttttattt cctgtccttc cttgaaattg ctgattgttc tgctccctct acagatattt   2820
atatcaattc ctacagctttt cccctgccat ccctgaactc tttctagccc ttttagattt   2880
tggcactgtg aaacccctgc tggaaacctg agtgaccctc cctccccacc aagagtccac   2940
agacctttca tctттсасда acttgatcct gттадсадgt ggtaatacca tgggtgctgt   3000
gacactaaca gtcattgaga ggtgggagga agtccctttt cctggactg gtatcttttc   3060
aactattgtt ttatcctgtc tttgggggca atgtgtcaaa agtcccctca ggaattttca   3120
gaggaaagaa catтттатда ggctttctct aaagtttcct ttgtatagga gtatgctcac   3180
ttaaatttac agaagaggt gagctgtgtt aaacctcaga gтттаааадс tactgataaa   3240
ctgaagaaag tgtctatatt ggaactaggg tcatttgaaa gcttcagtct cggaacatga   3300
ccтттадтct gtggactcca tttaaaaata ggtatgaata agatgactaa gaatgtaatg   3360
gggaagaact gcсстдсстg сссатстсад agccataagg tcatcтттдс tagagctatt   3420
tttacctatg tатттатсдt tсттдатсат aagccgctta tttatatcat gtatctctaa   3480
ggacctaaaa gcactttatg tagттттттаа ttaatcttaa gatctggtta cggtaactaa   3540
aaaagcctgt ctgccaaatc cagtggaaac aagtgcatag atgtgaattg gтттттаддд   3600
gcccacttc ccaattcatt aggtatgact gtggaaatac agacaaggat cttagttgat   3660
attttgggct tggggcagtg agggcttagg асасссcаад tggтттgдда aaggaggagg   3720
ggagtggtgg gтттатаддд ggaggaggag gcaggtggtc taagtgctga ctggctacgt   3780
agttcgggca aatcctccaa aagggaaagg gaggatttgc ttagaaggat ggcgctccca   3840
gtgactactt tttgacttct gtttgtctta cgcttctctc agggaaaaac atgcagtcct   3900
ctagtgtttc atgtacattc tgtgggggt gaacaccttg gttctggtta aacagctgta   3960
ctttt gatag ctgtgccagg aagggттадg accaactaca aattaatgtt ggttgtcaaa   4020
tgтадтgтgт ттсссстаасt ттсtgтттттт cctgagaaaa aaaaataaat cttttattca   4080
aatacaggga aaaaaaaaa aaaaaa                                        4107

SEQ ID NO: 4        moltype = DNA  length = 1126
FEATURE             Location/Qualifiers
source              1..1126
                    mol_type = other DNA
                    organism = Homo sapiens
SEQUENCE: 4
tccccatgtg acagtgagcg gggtccccgc tccaggagac gctcgagtct gcgtcccggc   60
cctcagcact gtccactgtt tcggtgccac cagagaccag caggcccggg acagttggtg   120
tттgсссдтt ccgctgtcta acttggtgtg cagagtgaat tgccgctgcc ggagcggaga   180
gaggcggagc ggccaggaga gaggggattt ctgtcagcgc ggcccctcgg agctcggaga   240
catgaacggc ttcacgcctg acgagatgag ccgcggcggg gatgcggccg ccgcagtggc   300
cgcagtggtc gctgccgcgg ccgccgccgc ctcggcgggg aacgggaccg gcgcgggcac   360
cggggctgag gtgccgggcg cggggcggt tcagcggct gggccccgg gggcggccgg   420
gccgggcccc gggcaactgt gctgcctgcg ggaggatggt gagcggtgcg gccgggcggc   480
aggcaacgcc agcttcagca agaggatcca gaagagcatc tcccagaaga aggtgaagat   540
cgagctggat aagagcgcaa ggcatcttta catatgtgat tatcataaaa acttaattca   600
gagtgttcda aacagaagaa agagaaaagg gagtgatgat gatggaggtg attcacctgt   660
tcaagatatt gatacccсад aaggттдаттт ataccaatta caagtaaata cacттаддад   720
atacaaaaga cacttcaagc taccaaccag accaggactt aataaagcac aacttgttga   780
gatagttggt tgccacttta ggtctattcc agтдаатдаа aaagcaccct taacatattt   840
catctactca gtgaagaatg acaagaacaa atcagatctc aaggttgata gtggtgttca   900
ctaggagacg tggaattgag actaataact tggatgttaa cactgtttac tgтттттттса   960
catgtagaaa tgttctttgt gтатттттттс tacagaggat tttctctgat tttattttct   1020
ttgtttctga ctctaataat tagttggaaa ctcatataaa atgagctttc ctaaattaaa   1080
tctатттттаа ataaaggtta ttactattaa aaaaaaaaaa aaaaaa             1126

SEQ ID NO: 5        moltype = DNA  length = 2040
FEATURE             Location/Qualifiers
source              1..2040
                    mol_type = other DNA
                    organism = Homo sapiens
SEQUENCE: 5
tcgctgcgaa ggacatttgg gctgtgtgtg cgacgcgggt cggaggggca gtcgggggaa   60
ccgcgaagaa gccgaggagc ccggagcccc gcgtgacgct cctctctcag tccaaaagcg   120
gcтттттggтт cggcgcagag agacccgggg gtctagcttt cctcgaaaa gcgccgccct   180
gcccтттддсс ccgagaacag acaaagagca ccgcagggcc gatcacgctg ggggcgctga   240
ggccggccat ggtcatggaa gtgggcaccc tggacgctgg aggcctgcgg gcgctgctgg   300
gggagcgagc ggcgcaatgc ctgctgctgg actgccgctc cттстт cgct ттсаасдссд   360
```

```
gccacatcgc cggctctgtc aacgtgcgct tcagcaccat cgtgcggcgc cgggccaagg   420
gcgccatggg cctggagcac atcgtgccca acgccgagct ccgcggccgc ctgctggccg   480
gcgcctacca cgccgtggtg ttgctggacg agccagcgc cgccctggac ggcgccaagc   540
gcgacggcac cctggccctg gcggccggcg cgctctgccg cgaggcgcgc gccgcgcaag   600
tcttcttcct caaaggagga tacgaagcgt tttcggcttc ctgcccggag ctgtgcagca   660
aacagtcgac ccccatgggg ctcagccttc ccctgagtac tagcgtccct gacagcgcgg   720
aatctgggtg cagttcctgc agtaccccac tctacgatca gggtggcccg gtggaaatcc   780
tgcccttcct gtacctgggc agtgcgtatc acgcttcccg caaggacatg ctggatgcct   840
tgggcatcac tgccttgatc aacgtctcag ccaattgtcc caaccatttt gagggtcact   900
accagtacaa gagcatccct gtggaggaca accacaaggc agacatcagc tcctggttca   960
acgaggccat tgacttcata gactccatca agaatgctgg aggaagggtg tttgtccact  1020
gccaggcagg catttcccgg tcagccacca tctgccttgc ttaccttatg aggactaatc  1080
gagtcaagct ggacgaggcc tttgagtttg tgaagcagag gcgaagcatc atctctccca  1140
acttcagctt catgggccag ctgctgcagt ttgagtccca ggtgctggct cgcactgtt   1200
cggcagaggc tgggagcccc gccatggctg tgctcgaccg aggcacctcc accaccaccg  1260
tgttcaactt ccccgtctcc atccctgtcc actccacgaa cagtgcgctg agctaccttc  1320
agagccccat tacgacctct cccagctgct gaaaggccac gggaggtgag gctcttcaca  1380
tcccattggg actccatgct ccttgagagg agaaatgcaa taactctgag aggggctcga  1440
gagggctggt ccttatttat ttaacttcac ccgagttcct ctgggtttct aagcagttat  1500
ggtgatgact tagcgtcaag acatttgctg aactcagcac attcgggacc aatatatagt  1560
gggtacatca agtccatctg acaaaatggg gcagaagaga aaggactcag tgtgtgatcc  1620
ggtttctttt tgctcgcccc tgttttttgt agaatctctt catgcttgac ataccacca   1680
gtattattcc cgacgacaca tatacatatg agaatatacc ttatttattt ttgtgtaggt  1740
gtctgccttc acaaatgtca ttgtctactc ctagaagaac caaatacctc aattttttgtt  1800
tttgagtact gtactatcct gtaaatatat cttaagcagg tttgttttca gcactgatgg  1860
aaaataccag tgttgggttt ttttttagtt gccaacagtc gtatgtttgc tgattattta  1920
tgacctgaaa taatatattt cttcttctaa gaagacattt tgttacataa ggatgacttt  1980
tttatacaat ggaataaaatt atgcgcattc tattgaaatt tcaaaaaaaa aaaaaaaaaa  2040
```

SEQ ID NO: 6          moltype = DNA   length = 3208
FEATURE               Location/Qualifiers
source                1..3208
                      mol_type = other DNA
                      organism = Homo sapiens
SEQUENCE: 6

```
agatattcat gaaccgttgc ttcttccagc ctcgccttct cgctccctct gcctttctgg     60
cgctgttctc cctccctccc tctggcttct gctctttctt actccttctc tcagctgctt    120
aactacagct cccactggaa cttgcacaat caaaaacaac tctcctctct caagccgcct    180
ccaggacgcg atcacctgga gaagagcgac tcgctccccg cgccggccgc ggaagagcga    240
ccaggtagct gggggcgggg aggcgtaccc ttctcccgct cggtaagagc cacagcatct    300
ccccggagat tggccgtatc ccaccgtccg gcccccaggg tcctgcagcg gtgatgcata    360
tgtttcggag caatgatgga aggagaaaag ccgctgtcgg tggcaactga agtggggag    420
aggttgctgc agtagctggt gctgcagaat gcgcgagtga agaactggag ccgctagat    480
tctccatccc gctcagtctt cattaactgt ctgcaggagg taaaccgggg aaacagatat    540
gcactaacca ggcgggtgcc aacctggatc tataactgtg aattccccac ggtgaaaat    600
ggtaaacaaa gacatgaatg gattcccagt caagaaatgc tcagccttcc aattttttaa    660
gaagcgggta cgaaggtgga tcaagagccc aatggtcagt gtggacaagc atcagagtcc    720
cagcctgaag tacaccggct cctccatggt gcacatccct ccaggggagc cagacttcga    780
gtcttccttg tgtcaaacat gcctgggtga acatgctttc caaagagggg ttctcctca    840
ggagaacgag tcatgttcat gggaaactca atctgggtgt gaagtgagag agccatgaa    900
tcatgccaac atcctgacca agcccgatcc aagaaccttc tggactaatg atgatccgaa    960
tttcatgaag cagaggagga tgggtctgaa cgactttatt cagaagattg ccaataactc   1020
ctatgcatgc aaacaccctg aagttcagtc catcttgaag atctcccaac tcaggagcc   1080
tgagcttatg aatgccaacc cttctcctcc accaagtcct tctcagcaaa tcaaccttgg   1140
cccgtcgtcc aatcctcatg ctaaaccatc tgactttcac ttcttgaaag tgatcggaaa   1200
gggcagttttt ggaaaggttc ttctagcaag acacaaggca gaagaagtgt tctatgcagt   1260
caaagtttta cagaagaaag caatcctgaa aaagaaagag gagaagcata tatgtcgga    1320
gcggaatgtt ctgttgaaga atgtgaagca cccttcctg gtgggccttc acttctcttt    1380
ccagactgct gacaaattgt actttgtcct agactacatt aatggtggag agttgttcta   1440
ccatctccag agggaacgct gcttcctgga accacgggct cgtttctatg ctgctgaaat   1500
agccagtgcc ttgggctacc tgcattcact gaacatcgtt tatagagact aaaaccaga   1560
gaatattttg ctagattcac agggacacat tgtccttact gacttcggac tctgcaagga   1620
gaacattgaa cacaacagca caacatccac cttctgtggc acgccggagt atctcgcacc   1680
tgaggtgctt cataagcagc cttatgacag gactgtgac tggtggtgcc tgggagctcc   1740
cttgtatgag atgctgtatg gcctgccgcc tttttatagc cgaaacacag ctgaaatgta   1800
cgacaacatt ctgaacaagc ctccagct gaaaccaaat attacaaatt ccgcaagaca    1860
cctcctggag ggcctcctgc agaaggacag acaaagcgg ctcggggcca aggatgactt   1920
catggagatt aagagtcatg tcttcttctc cttaattaac tgggatgatc tcattaataa   1980
gaagattact ccccctttta gagtgggccc aacgacctac ggcactttga              2040
ccccgagttt accgaagagc ctgtcccaa ctccattggc aagtccctg acagcgtcct   2100
cgtcacagcc agcgtcaagg aagctgccga ggctttccta ggcttttcct atgcgcctcc   2160
cacggactct ttcctctgaa ccctgttagg gcttggtttt aaaggattt atgtgtgttt   2220
ccgaatgttt tagttagcct tttggtggag ccgccagctg acaggacatc ttacaagaga   2280
atttgcacat cttctcggaagc ttagcaatct tattgacaac ttcgctggg aagctttttg   2340
aagagccact tctcctcagt gagctcatga ggttttcatt tttattcttc cttccaacgt   2400
ggtgctatct ctgaaacgag cgttagagtg ccgccttaga cggaggcagg agtttcgtta   2460
gaaagcggac gctgttctaa aaaaggtctc ctgcagatct gtctgggctg tgatgacgaa   2520
tattatgaaa tgtgcctttt ctgaagagat tgtgttagct ccaaagctt tcctatcgca   2580
gtgtttcagt tctttatttt cccttgtgga tatgctgtgt gaaccgtcgt gtgagtgtgg   2640
```

-continued

```
tatgcctgat cacagatgga ttttgttata agcatcaatg tgacacttgc aggacactac 2700
aacgtgggac attgtttgtt tcttccatat ttggaagata aatttatgtg tagacttttt 2760
tgtaagatac ggttaataac taaaatttat tgaaatggtc ttgcaatgac tcgtattcag 2820
atgcttaaag aaagcattgc tgctacaaat atttctatttt ttagaaaggg tttttatgga 2880
ccaatgcccc agttgtcagt cagagccgtt ggtgtttttc attgtttaaa atgtcacctg 2940
taaaatgggc attatttatg tttttttttt tgcattcctg ataattgtat gtattgtata 3000
aagaacgtct gtacattggg ttataacact agtatattta aacttacagg cttatttgta 3060
atgtaaacca ccatttttaat gtactgtaat taacatggtt ataatacgta caatccttcc 3120
ctcatcccat cacacaactt tttttgtgtg tgataaactg attttggttt gcaataaaac 3180
cttgaaaaat atttacatat aaaaaaaa                                   3208
```

SEQ ID NO: 7            moltype = DNA   length = 5758
FEATURE                 Location/Qualifiers
source                  1..5758
                        mol_type = other DNA
                        organism = Homo sapiens
SEQUENCE: 7

```
tttctgtact ctgggtgact cagagaggga agagattcag ccagcacact cctcgcgagc 60
aagcattact ctactgactg gcagagacag gagaggtaga tgtccacgcc cacagaccct 120
ggtgcgatgc cccacccagg gccttcgccg gggcctgggc cttcccctgg gccaattctt 180
gggcctagtc caggaccagg accatcccca ggttccgtcc acagcatgat ggggccaagt 240
cctggacctc caagtgtctc ccatcctatg ccgacgatgg ggtccacaga cttcccacag 300
gaaggcatgc atcaaatgca taagcccatc gatggtatac atgacaaggg gattgtagaa 360
gacatccatt gtggatccat gaagggcact ggtatgcgac cacctcaccc aggcatgggc 420
cctccccaga gtccaatgga tcaacacagc caaggttata tgtcaccaca cccatctcca 480
ttaggagccc cagagcacgt ctccagccct atgtctgagg gagcccaac tccacctcag 540
atgccaccaa gccagccggg ggccctcatc ccaggtgatc cgcaggcat gagccagccc 600
aacagaggtc cctcaccttt cagtcctgtc cagctgcatc agcttcgagc tcagatttta 660
gcttataaaa tgctggcccg aggccagccc ctccccgaaa cgctgcagct tgcagtccag 720
gggaaaagga cgttgcctgg cttgcagcaa caacagcagc agcaacagca gcagcagcag 780
cagcagcagc agcagcagca gcagcaacag cagccgcagc agcagccgcc gcaaccacag 840
acgcagcaac aacagcagcc ggccttgtt aactacaaca gaccatctgg cccggggccg 900
gagctgagcg gcccgagcac cccgcagaag ctgccggtgc ccgcgcccgg cggccggccc 960
tcgcccgcgc cccccgcagc cgcgcagccg cccgcggccg cagtgcccgg gccctcagtg 1020
ccgcagccgg cccccggggca gccctcgccc gtcctccagc tgcagcagaa gcagagccgc 1080
atcagcccca tccagaaacc gcaaggcctg gaccccgtgg aaattctgca agagcgggaa 1140
tacagacttc aggcccgcat agctcatagg atacaagaac tggaaaatct gcctggctct 1200
ttgccaccag atttaagaac caaagcaacc gtggaactaa aagcacttcg gttactcaat 1260
ttccagcgtc agctgagaca ggaggtggtg gcctgcatgc gcagggacac gaccctggaa 1320
acggctctca actccaaagc atacaaacgg agcaagcgcc agactctgag agaagctcgc 1380
atgaccgaga agctggagaa gcagcagaag attgagcagg agaggaaacg ccgtcagaaa 1440
caccaggaat acctgaacag tatttttgca atgcaaaag attttaagga atatcatcgg 1500
tctgtggccg gaaagatcca gaagctctcc aaagcagtgg caacttggca tgccaacact 1560
gaaagagagc agaagaagga gacagagcgg attgaaaagg agagaatgcg gcgactgatg 1620
gctgaagatg aggagggtta tagaaaactg attgatcaaa agaaagacag gcgtttagct 1680
tacctttgc agcagaccga tgagtatgta gccaatctga ccaatctggt ttgggagcac 1740
aagcagcccc aggcagccaa agagaagaag aagaggagga gaaggaagaa gaaggctgag 1800
gagaatgcag agggtgggga gtctgccctg ggaccggatg gagagcccat agatgagagc 1860
agccagatga gtgacctccc tgtcaaagtg actcacacag aaaccggcaa ggttctgttc 1920
ggaccagaag caccccaaagc aagtcagctg gacgcctggc tggaaatgaa tcctggttat 1980
gaagttgccc ctagatctga cagtgaagag agtgattctg attatgagga agaggatgag 2040
gaagaagagt ccagtaggca ggaaaccgaa gagaaaatac tcctggatcc aaatagcgaa 2100
gaagtttctg agaaggatgc taagcagatc attgagacag ctaagcaaga cgtggatgat 2160
gaatacagca tgcagtacag tgccagggggc tcccagtcct actacaccgt ggctcatgcc 2220
atctcggaga gggtggagaa acagtctgcc ctcctaatta atgggaccct aaagcattac 2280
cagctccagg gcctgaatg gatggtttcc ctgtataata caacttgaa cggaatctta 2340
gccgatgaaa tggggcttgg aaagaccata cagaccattg cactcatcac ttatctgatg 2400
gagcacaaaa gactcaatgg cccctatctc atcattgttc cctttcgac tctatctaac 2460
tggacatatg aattttgacaa atgggctcct tctgtggtga agatttctta caagggtact 2520
cctgccatgc gtcgctccct tgtccccag ctacgggagtg gcaaattcaa tgtcctcttg 2580
actacttatg agtatattat aaaagacaag cacattcttg caaagattcg gtggaaatac 2640
atgatagtgt acgaaggcca ccgaatgaag aataccact gcaagctgac tcaggtcttg 2700
aacactcact atgtggcccc cagaaggatc ctcttgactg gaccccgct gcagaataag 2760
ctccctgaac tctgggcccct cctcaactc ctcctcccaa caatttttaa gagctgcagc 2820
acatttgaac aatggttcaa tgctccattt gccatgactg tgaaagggt ggacttaaat 2880
gaagaagaaa ctatattgat catcaggcgt ctacataagg tgttaagacc atttttacta 2940
aggagactga agaaggaagt tgaatcccag cttcccgaaa aagtggaata tgtgatcaag 3000
tgtgacatgt cagctctgca gaagattctg tatcgccata tgcaagccaa gggatcctt 3060
ctcacagatg gttctgagaa agataagaag gggaaaggag gtgctaagac acttatgaac 3120
actattatgc agttgagaaa aatctgcaac cacccatata tgtttcagca cattgaggaa 3180
tccttttgctg aacacctagg ctattcaaat gggtcatca atgggctga actgtatcgg 3240
gcctcaggga agtttgagct gcttgatcgt attctgccaa aattgagagc gactaatcac 3300
cgagtgctgc ttttctgcca gatgacatct ctcatgacca tcatggagga ttattttgct 3360
tttcggaact tcctttacct acgccttgat ggcaccacca gtcgaagac tcgtgctgct 3420
ttgctgaaga aattcaatga acctggatcc cagtatttca ttttcttgct gagcacaaga 3480
gctggtggcc tgggcttaaa tcttcaggca gctgatacag tggtcatctt tgacagcgac 3540
tggaatcctc atcaggatct gcaggcccaa gaccgagctc accgcatcgg gcagcagaac 3600
gaggtccggg tactgaggct ctgtaccgtg aacagcgtgg aggaaagat cctgcgggcc 3660
gcaaaataca agctgaacgt ggatcagaaa gtgatccagg cgggcatgtt tgaccaaaag 3720
```

```
tcttcaagcc acgagcggag ggcattcctg caggccatct tggagcatga ggaggaaaat   3780
gaggaagaag atgaagtacc ggacgatgag actctgaacc aaatgattgc tcgacgagaa   3840
gaagaatttg acctttttat gcggatggac atggaccggc ggagggaaga tgcccggaac   3900
ccgaaacgga agcccgttt aatggaggag gatgagctgc cctcctggat cattaaggat   3960
gacgctgaag tagaaaggct cacctgtgaa gaagaggagg agaaaatatt tgggaggggg   4020
tcccgccagc gccgtgacgt ggactacagt gacgccctca cggagaagca gtggctaagg   4080
gccatcgaag acggcaattt ggaggaaatg gaagaggaag tacggcttaa gaagcgaaaa   4140
agacgaagaa atgtggataa agatcctgca aagaagatg tggaaaaagc taagaagaga   4200
agaggccgcc ctcccgctga gaaactgtca ccaaatcccc ccaaactgcc aaagcagatg   4260
aacgctatca tcgatactgt gataaactac aaagataggt gtaacgtgga gaaggtgccc   4320
agtaattctc agttgaaat agaaggaaac agttcagggc gacagctcag tgaagtcttc   4380
attcagttac cttcaaggaa agaattacca gaatactatg aattaattag gaagccagtg   4440
gatttcaaaa aaataaagga aaggattcgt aatcataagt accggagcct aggcgacctg   4500
gagaaggatg tcatgcttct ctgtcacaac gctcagacgt tcaacctgag gggatcctag   4560
atctatgaag actccatcgt cttacagtca gtgtttaaga gtgcccggca gaaaattgcc   4620
aaagaggaag agagtgagga tgaaagcaat gaagaggagg aagaggaaga tgaagaagag   4680
tcagagtccg aggcaaaatc agtcaaggtg aaaattaagc tcaataaaaa agatgacaaa   4740
ggccgggaca aagggaaagg caagaaaagg ccaaatcgga gaaaagccaa acctgtagtg   4800
agcgattttg acagcgatga ggagcaggat gaacgtgaac agtcagaagg aagtgggacg   4860
gatgatgagt gatcagtatg gaccttttc cttggtagaa ctgaattcct tcctcccctg   4920
tctcatttct acccagtgag ttcatttgtc atataggcac tgggttgttt ctatatcatc   4980
atcgtctata aactagcttt aggatagtgc cagacaaaa tatgatatca tggtgtaaaa   5040
aacacacaca tacacaaata tttgtaacat attgtgacca aatgggcctc aaagattcag   5100
attgaaacaa acaaaaagct tttgatggaa aatatgtggg tggatagtat atttctatgg   5160
gtgggtctaa tttggtaacg gtttgattgt gcctggtttt atcacctgtt cagatgagaa   5220
gattttttgtc tttgtagca ctgataacca ggagaagcca ttaaaagcca ctggttattt   5280
tatttttcat caggcaattt tcgaggtttt tatttgttcg gtattgtttt tttacactgtt   5340
ggtacatata agcaacttta ataggtgata aatgtacagt agttagattt cacctgcata   5400
tacatttttc catttatgc tctatgatct gaacaaaagc ttttgaatt gtataagatt   5460
tatgtctact gtaaacattg cttaatttt ttgctcttga tttaaaaaaa agttttgttg   5520
aaagcgctat tgaatattgc aatctatata gtgtattgga tggcttcttt tgtcaccctg   5580
atctcctatg ttaccaatgt gtatcgtctc cttctcccta aagtgtactt aatctttgct   5640
ttctttgcac aatgtctttg gttgcaagtc ataagcctga ggcaaataaa attccagtaa   5700
tttcgaagaa tgtggtgttg gtgctttcct aataaagaaa taatttagct tgacaaaa    5758

SEQ ID NO: 8           moltype = DNA   length = 837
FEATURE                Location/Qualifiers
source                 1..837
                       mol_type = other DNA
                       organism = Homo sapiens
SEQUENCE: 8
gctcctcctg cacacctccc tcgctctccc acaccactgg caccaggccc cggacacccg     60
ctctgctgca ggagaatggc tactcatcac acgctgtgga tgggactggc cctgctgggg    120
gtgctgggcg acctgcaggc agcaccggag gccaggtcct ccgtgcagcc caacttccag    180
caggacaagt tcctggggcg ctggttcagc gcgggcctcg cctccaactc gagctggctc    240
cgggagaaga aggcggcgtt gtccatgtgc aagtctgtgt ggccctgc cacggatggt    300
ggcctcaacc tgacctccac cttcctcagg aaaaaccagt gtgagacccg aaccatgctg    360
ctgcagcccg cggggtccct cggctcctac agctaccgg gtcccactg ggcagcacc    420
tactccgtgt cagtggtgga gaccgactac gaccagtacg cgctgctgta cagccagggc    480
agcaaggggc ctggcgagga cttccgcatg gccaccctct acagccgaac ccagacccc    540
agggctaagt taaggagaa attcaccgcc ttctgcaagg cccagggctt cacagaggat    600
accattgtct tcctgcccca aaccgataag tgcatgacgg aacaatagga ctccccaggg    660
ctgaagctgg gatcccggcc agcaggtga cccccacgct ctggatgtct ctgctctgtt    720
ccttccccga gccctgccc cggctccccg ccaaagcaac cctgcccact caggcttcat    780
cctgcacaat aaactccgga agcaagtcag taaaaaaaa aaaaaaaaaa aaaaaa       837

SEQ ID NO: 9           moltype = DNA   length = 6001
FEATURE                Location/Qualifiers
source                 1..6001
                       mol_type = other DNA
                       organism = Homo sapiens
SEQUENCE: 9
caaggaggga tcccacagat gtcacagggc tgtcacagag ctgtggtggg aatttcccat     60
gagaccccgc ccctggctga gtcaccgcac tcctgtgttt gacctgaagt cctctcgagc    120
tgcagaagcc tgaagaccaa ggagtggaaa gttctccggc agccctgaga tctcaagagt    180
gacatttgtg agaccagcta atttgattaa aattctcttg gaatcagctt tgctagtatc    240
atacctgtgc cagatttcat catgggaaac agctgttaca acatagtagc cactctgttg    300
ctggtcctca actttgagag gacaagtaca ttgcaggatc cttgtagtaa ctgcccagct    360
ggtacattct gtgataataa caggaatcag ccctgtcctc ccaaatagttc    420
tccagcgcag gtggacaaag gacctgtgac atatgcaggc agtgtcaaagg tgttttcagg    480
accaggaagg agtgttcctc caccagcaat gcagagtgtg actgcactcc agggtttcac    540
tgcctggggg caggatgcag catgtgtgaa caggattgta acaaggtca agaactgaca    600
aaaaaggtt gtaagactg ttgctttggg acatttaacg atcagaaacg tggcatcgt    660
cgaccctgca caactgttc tttggatgga aagtctgtgc ttgtgaatgg gacgaaggag    720
agggacgtgt tctgtggacc atctccagcc gacctctctc gggagcatc ctctgtgacc    780
ccgcctgccc ctgcgagaga gccaggacac tctccgcaga tcatctcctt cttttcttgcg    840
ctgacgtcga ctgcgttgct cttcctgctg ttcttcctca cgctccgttt ctctgttgtt    900
aaacggggca gaaagaaact cctgtatata ttcaaacaac catttatgag accagtacaa    960
actactcaag aggaagatgg ctgtagctgc cgatttccag aagaagaaga aggaggatgt   1020
```

```
gaactgtgaa atggaagtca atagggctgt tgggactttc ttgaaaagaa gcaaggaaat   1080
atgagtcatc cgctatcaca gctttcaaaa gcaagaacac catcctacat aatacccagg   1140
attcccccaa cacacgttct tttctaaatg ccaatgagtt ggcctttaaa aatgcaccac   1200
tttttttttt tttttgacag ggtctcactc tgtcacccag gctggagtgc agtggcacca   1260
ccatggctct ctgcagcctt gacctctggg agctcaagtg atcctcctgc ctcagtctcc   1320
tgagtagctg gaactacaag gaagggccac cacacctgac taacttttt gttttttgtt   1380
tggtaaagat ggcatttcac catgttgtac aggctggtct caaactccta ggttcacttt   1440
ggcctcccaa agtgctggga ttacagacat gaactgccag gcccggccaa aataatgcac   1500
cacttttaac agaacagaca gatgaggaca gagctggtga taaaaaaaaa aaaaaaaaag   1560
cattttctag ataccactta acaggtttga gctagttttt ttgaaatcca agaaaattta   1620
tagtttaaat tcaattacat agtccagtgg tccaactata attataatca aaatcaatgc   1680
aggtttgttt tttggtgcta atatgacata tgacaataag ccacgaggtg cagtaagtac   1740
ccgactaaag tttccgtggg ttctgtcatg taacacgaca tgctccaccg tcagggggga   1800
gtatgagcag agtgcctgag tttagggtca aggacaaaaa acctcaggcc tggaggaagt   1860
tttggaaaga gttcaagtgt ctgtatatcc tatggtcttc tccatcctca caccttctgc   1920
ctttgtcctg ctcccttta agccaggtta cattctaaaa attcttaact tttaacataa   1980
tattttatac caaagccaat aaatgaactg catatgatag gtatgaagta cagtgagaaa   2040
attaacacct gtgagctcat tgtcctacca cagcactaga gtggggggccg ccaaactccc   2100
atggccaaac ctggtgcacc atttgccttt gtttgtctgt tggtttgctt gagacagtct   2160
tgctctgttg cccaggctgg aatggagtgg ctattcacag gcacaatcat agcacacttt   2220
agccttaaac tcctgggctc aagtgatcca cccgcctcag tctcccaagt agctgggatt   2280
acaggtgcaa acctggcatg cctgccattg tttggcttat gatctaagga tagcttttta   2340
aatttattc attttatttt tttttgagac agtgtctcac tctgtctccc aggctggagt   2400
acagtggtac aatcttggat caccgcctcc cagtttcaag tgatcccct gcctcagcct   2460
cctaagtagc tgggactaca ggtatgtgcc accacgcctg gctaatttt atattttag   2520
tagagacggg gtttcaccat gttgtccagg ctggtctcaa actcctgacc tcaggtgatc   2580
tgcccacctc tgcctccaa agtgctggga ttacaggcat gagccaccat gcctggccat   2640
ttcttacact tttgtatgac atgcctattg caagcttgcg tgcctctgtc ccatgttatt   2700
ttactctggg atttaggtgg agggagcagc ttctatttgg aacattggcc atcgcatggc   2760
aaatgggtat ctgtccacttc tgctcctatt tagttggttc tactataacc tttagagcaa   2820
atcctgcagc caagccaggc atcaataggg cagaaaagta tattctgtaa ataggggtga   2880
ggagaagata tttctgaaca atagtctact gcagtaccaa attgcttttc aaagtggctg   2940
ttctaatgta ctcccgtcag tcatataagt gtcatgtaag tatcccattg atccacatcc   3000
ttgctaccct ctggtactat caggtgccct taattttgcc aagccagtgg gtatagaatg   3060
agatctcact gtggtcttag tttgcatttg cttggttact gatgagcacc ttgtcaaata   3120
tttatatacc atttgtgttt atttttttaa ataaaatgct tgctcatgct ttttgccca   3180
tttgcaaaaa aacttgggc cgggtgcagt ggctcatgcc tgtagtccca gctctttggg   3240
aggccaaggt gggcagatcg cttgagccca ggagttcgag accagcctttg caacatggc   3300
gaaaccctgt ctttacaaaa aatacaaaaa ttagccggcgt gtggtggtgt gcacctgaag   3360
tcccagctac tcagtaggtt cgctttgagc ctgggaggca gaggttgcag tgagctggga   3420
ccgcatcact acacttcagc ctgggcaaca gagaaaaacc ttttctcaga acaaacaaa   3480
cccaaatgtg gttgtttgtc ctgattccta aaaggtcttt atgtattcta gataataatc   3540
tttggtcagt tatatgtgtt aaaaaatatc ttctttgtg ccaggcacgg tagctcacac   3600
ctgtaatccc agcactttgc ggggctgagg tgggtggatc atctgaggtc aagagttcaa   3660
gatcagcctg gccaacacag tgaaacccca tctctactaa acatgtacaa aacttagctg   3720
ggtatggtgg cgggtgcctg taaccccagc tgctccagag gctgtggcag aagaatcgct   3780
tgaacccagg aggcagaggt tgcagcgaga caagattgtg ccattgcact ccagactggg   3840
tgacaagagt gaaattctgc ctatctatct atctatctat ctatatctat atatatatat   3900
atatatatcc tttgtaattt attttccct ttttaaaatt tttataaaa ttctttttta   3960
tttttatttt tagcagaggt gaggtttctg aggtttcatt atgttgccca ggctggtctt   4020
gaactcctga gctcaagtga tcctcccacc tcagccttcc aaagtgctgg aattgcaac   4080
atgagccacc gcgcccctcc tgtttttctc taattaatgg tgtctttctt tgtctttctg   4140
gtaataagca aaaagttctt catttgattt ggttaaattt ataactgttt tctcatatgg   4200
ttaacatttt tccttgcctg gctaaagaaa tccttttctg cccaatacta taagagggtt   4260
tgcccacatt ttattccaaa agttttaagt tttgtcttc atcttgaagt ctaatgtatc   4320
aggaactggc ttttgtgcct gttgggaggt agtgatccaa ttccatgtct tgcatgtagg   4380
taaccactgg tccctgcgcc atgtattcaa tacgtcgtct ttctcctgcg ggtctgcaat   4440
ctcacctacc atccatcaag tttccatagg gccatgggtc tgcttctggg ctccctgttc   4500
tgttccattg tcaatttgtc tatcctgtgc cagtatcaca ctgtgttttat tacaatagct   4560
ttgtaacagc tctcgatatc cggtaggaca tctccctcca ccttctttt ctacttcaga   4620
agtgtcttag ctaggtcagg cacggtggct cacgcctgta atcccagcac tttgggaggc   4680
cgacgcggat ggatcacctg aggtcaggag ttttgagaca gcctggccaa catggtgaaa   4740
ccccatctct actaaaaaat acaaaaatta gtcaggcatg gtggcatgtg cctgtaatcc   4800
cagctatttg ggaggctgag gccggagaat tgcttgaacc cgggggggagg aggttgcagt   4860
gagccgagat cgtaccattg cactccagcc tgggtgacag agcgaaactc tgtctcagga   4920
aaaaaagaa aagagatgtc ttggttattc ttggttcttt attattcaat ataaatttta   4980
gaagctgaat ttgaaaagat ttggattgga atttcattaa atctacaggt caatttaggg   5040
agagttgata atttacaga attgagtcat ctggtgttcc aataagaaca agagaacaat   5100
tattggctgt acaattcttg ccaaatagta ggcaaagcaa agcttaggaa gtatactggt   5160
gccatttcag gaacaaagct aggtgcgaat attttttgtct ttctgaatca tgatgctgta   5220
agttctaaag tgatttctcc tcttggcttt ggacacatgg tgtttaatta cctactgctg   5280
actatccaca aacagaaaga gactggtcat gccccacagg gttgggggtat ccaagataat   5340
ggagcgaggc tctcatgtgt cctaggttac acaccgaaaa tccacagttt attctgtgaa   5400
gaaaggagtc tatgttttatg atacagactg tgatatttat actatagcct atttctggtat   5460
catgtgcaaa agctataaat gaaaacacac ggaacttggc atgtgagtca ttgctccccc   5520
taaatgacaa ttaataagga aggaacattg agacagaata aaatgatccc cttctggggtt   5580
taatttagaa agttccataa ttaggttaa tagaaataaa tgtaaatttc tatgattaaa   5640
aataaattag cacatttagg gatacacaaa ttataaatca ttttctaaat gctaaaaaca   5700
agctcaggtt ttttcagaa gaaagtttta atttttttc tttagtggaa gatatcactc   5760
```

```
tgacggaaag ttttgatgtg aggggcggat gactataaag tgggcatctt cccccacagg   5820
aagatgtttc catctgtggg tgagaggtgc ccaccgcagc tagggcaggt tacatgtgcc   5880
ctgtgtgtgg taggacttgg agagtgatct ttatcaacgt ttttatttaa aagactatct   5940
aataaaacac aaaactatga tgttcacagg aaaaaaagaa taagaaaaaa agaaaaaaaa   6000
a                                                                  6001

SEQ ID NO: 10           moltype = DNA  length = 1336
FEATURE                 Location/Qualifiers
source                  1..1336
                        mol_type = other DNA
                        organism = Homo sapiens
SEQUENCE: 10
gagagacaca gagtccggca ttggtcccag gcagcagtta gcccgccgcc cgcctgtgtg   60
tccccagagc catggagaga gccagtctga tccagaaggc caagctggca gagcaggccg   120
aacgctatga ggacatggca gccttcatga aaggcgccgt ggagaagggc gaggagctct   180
cctgcgaaga gcgaaacctg ctctcagtag cctataagaa cgtggtgggc ggccagaggg   240
ctgcctggag ggtgctgtcc agtattgagc agaaaagcaa cgaggagggc tcggaggaga   300
aggggcccga ggtgcgtgag taccgggaga aggtggagac tgagctccag ggctgtgcg   360
acaccgtgct gggcctgctg gacagccacc tcatcaagga ggccggggac gccgagagcc   420
gggtcttcta cctgaagatg aagggtgact actaccgcta cctggccgag gtggccaccg   480
gtgacgacaa gaagcgcatc attgactcag cccggtcagc ctaccaggag gccatggaca   540
tcagcaagaa ggagatgccg cccaccaacc ccatccgcct gggcctggcc ctgaacttt   600
ccgtcttcca ctacgagatc gccaacagcc ccgaggaggc catctctctg gccaagacca   660
ctttcgacga ggccatggct gatctgcaca ccctcagcga ggactcctac aaagacagca   720
ccctcatcat gcagctgctg cgagacaacc tgacactgtg gacggccgac aacgccgggg   780
aagagggggg cgaggctccc caggagcccc agagctgggt gttgcccgcc accgccgc    840
cctgcccct ccagtcccc accctgccga gaggactagt atgggggtggg aggccccacc   900
cttctcccct aggcgctgtt cttgctccaa agggctccgt ggagagggac tggcagagct   960
gaggccacct ggggctgggg atcccactct tcttgcagct gttgagcgca cctaaccact   1020
ggtcatgccc ccaccctgc tctccgcacc cgcttcctcc cccccagg accaggctac   1080
ttctccctcc ctcttgcctc cctcctgccc ctgctgcctc tgatcgtagg aattgaggag   1140
tgtcccgcct tgtggctgag aactggacag tggcaggggc tggagatggg tgtgtgtgtg   1200
tgtgtgtgtg tgtgtgtgtg tgtgcgcgcg cgccagtgca agaccgagat tgagggaaag   1260
catgtctgct gggtgtgacc atgtttcctc tcaataaagt tccctgtgaa cactcaaaaa   1320
aaaaaaaaaa aaaaaa                                                  1336

SEQ ID NO: 11           moltype = DNA  length = 2240
FEATURE                 Location/Qualifiers
source                  1..2240
                        mol_type = other DNA
                        organism = Homo sapiens
SEQUENCE: 11
ggagggcagc cagcagcttc cccttctctg ccctgctcca ggcaccaggc tctttccct   60
tcagtgtctc agaggagggg acggcagcac catggacccc gcttgtcca ctgtccgcca   120
gacctgctgc tgcttcaatg tccgcatcgc aaccaccgcc ctggccatct accatgtgat   180
catgagcgtc ttgttgttca tcgagcactc agtagaggtg gccatggca aggcgtcctg   240
caagctctcc cagatgggct acctcaggat cgctgacctg atctccagct tcctgctcat   300
caccatgctc ttcatcatca gcctgagcct actgatcggc gtagtcaaga accgggagaa   360
gtacctgctg cccttcctgt ccctgcaaat catggactat ctcctgtgcc tgctcaccct   420
gctgggctcc tacattgagc tgcccgccta cctcaagttg gcctcccgga gccgtgctag   480
ctcctccaag ttccccctga tgacgctgca gctgctgaga ttctgcctga gcatcctgac   540
cctctgcagc tcctcatgg aagtgccac ctatctcaac ttcaagtcca tgaaccacat   600
gaattacctc cccagccagg aggatatgcc tcataaccag ttcatcaaga tgatgatcat   660
cttttccatc gccttcatca ctgtccttat cttcaaggtc tacatgttca agtgcgtgtg   720
gcggtgctac agattgatca agtgcatgaa atcggtggga gagaagagaa actccaagat   780
gctccagaag gtggtcctgc cgtcctacga ggaagccctg tctttgccat cgaagaccc    840
agaggggggc ccagcaccac cccatactc agaggtgtga ccctgccag gcccagccc    900
cagtgctggg aggggtggag ctgcctcata atctgcttt ttgctttggt ggcccctgtg    960
gcctgggtgg gccctcccgc ccctccctgg caggacaatc tgcttgtgtc tccctgcctg  1020
gcctgctcct cctgcaggcg cctgtgagctg ctcacaactg ggtcaacgct ttaggctgag  1080
tcactcctcg ggtctctcca taattcagcc caacaatgct tggtttattt caatcagctc  1140
tgacacttgt ttagacgatt ggccattcta agttggtga gtttgtcaag caactatcga  1200
cttgatcagt tcagccaagc aactgacaaa tcaaaaaccc acttgtcagt tcagtaaaat  1260
aatttggtca aacaacagtc tattgcattg attataaat agttgtcagt tcacatagca  1320
atttaatcaa gtaatcatta attagttacc ccctatatat aaatatatgt aatcaattc   1380
ttcaaataqc ttqcttacat qataatcaat taqccaacca tqaqtcattt aqaataqtqa  1440
taaataqaat acacaqaata gtqatqaaat tcaatttaaa aaatcacqtt aqcctccaaa  1500
ccatttaatt caaatgaacc catcaactgg atgccaactc tggcgaatgt aggacctctg  1560
agtggctgta taattgttaa ttcaaatgaa attcatttaa acagttgaca aactgtcatt  1620
caacaattag ctccaggaaa taacagttat ttcatcataa aacagtccct tcaaacacac  1680
aattgttctg ctgaagagtt gtcatcaaca atccaatgct cacctattca gttgctctgt  1740
ggtcagtgtg gctgcataac agtggattcc atgaaaggag tcatttagt gatgagctgc   1800
cagtccattc ccaggccagg ctgtcgctgg ccatccattc agtcgattca gtcataggcg  1860
aatctgttct gcccgaggct tgtggtcaag caaaaattca gccctgaaat caggcacatc  1920
tgttcgttgg actaaaccca caggttagtt cagtcaaagc aggcaacccc cttgtgggca  1980
ctgaccctgc cactgggtc atggcggttg tggcagctgg ggaggtttgg ccccaacagc   2040
cctcctgtgc ctgcttccct gtgtgtcggg gtcctccagg gagctgaccc agaggtggag  2100
gccacggagg cagggtctct ggggactgtc gggggtaca gagggagaag gctctgcaag   2160
agctccctgg caatacccc ttgtgtaatt gctttgtgtg cgacagggag gaagtttcaa   2220
```

```
taaagcagca acaagcttct                                                    2240
```

SEQ ID NO: 12              moltype = DNA  length = 3039
FEATURE                    Location/Qualifiers
source                     1..3039
                           mol_type = other DNA
                           organism = Homo sapiens SEQUENCE: 12
```
aggcgcagag gagggcggtg ttgagaccgg cggagcggcg ggaccccag gtggcggagg    60
gacgctccgg gaaagcgagg ggcgctacga gctctggccc acgtgacctg ccggggcgg   120
gagcaggggg cgcgccggcc tcctgcggtg ccctgcctt ggggaggggc cgtgaccacc   180
cgtctgtcgc ccgaggcggc cgccgctgca ccttcaccgc gtaccgggga cccgccgcc   240
cgcgggagaa atgttgctga agtgctgctg aaagggccag agatgcaagg atttgggata   300
cattttgaac ctttaagctg tctgacattg acctcctttc attattaata aagaagaatc   360
aggagcttag gatgtattaa caccaactca ttaatatact aaccggacaa tgttctacaa   420
acaattctac attgtaaagg actggattgg cacaaaataa aataatttta ttttattcag   480
cttataatat gactcgatgg aggaaattt gataagcatg agagaagacc attcttttca   540
tgttcgttac agaatggaag cttcttgcct agagctggcc ttggaagggg aacgtctatg   600
taaatcagga gactgccgcg ctggcgtgtc attctttgaa gctgcagttc aagttggaac   660
tgaagaccta aaaacactta gcgctattta cagccagttg ggcaatgctt atttctattt   720
gcatgattat gccaaagcat tagaatatca ccatcatgat ttaaccctg caaggactat   780
tggagaccag ctgggggcag cgaaagctag tggtaatctg ggaaacacct taaaagttct   840
tgggaatttt gacgaagcca tagtttgttg tcagcgacac ctagatattt ccagagagct   900
taatgacaag gtgggagaag caagagcact ttacaatctt gggaatgtgt atcatgccaa   960
agggaaaagt tttggttgcc ctggtcccca ggatgtagga gaattccag aagaagtgag  1020
agatgctctg caggcagccg tggattttta tgaggaaaac ctatcattag tgactgcttt  1080
gggtgaccga gcggcacaag gacgtgcctt tggaaatctt ggaaacacac attacctcct  1140
tggcaacttc agggatgcag ttatagctca tgagcagcgt ctccttattg caaaagaatt  1200
tggagataaa gcagctgaaa gaagagcata tagcaacctt ggaaatgcat atatatttct  1260
tggtgaattt gaaactgcct cggaatacta caagaagaca ctactgttgg cccgacagt  1320
taaagaccga gctgtagaag cacagtcttg ttacagtctt ggaaatacat atactttact  1380
tcaagactat gaaaaggcca ttgattatca tctgaagcac ttagcaattg ctcaagagct  1440
gaatgataga attggtgaag gaagagcatg ttggagctta ggaaatgcat acacagcact  1500
aggaaatcat gatcaagcaa tgcattttgc tgaaaagcac ttggaatttt caagagaggt  1560
tggggataaa agtggtgaac taacagcaca acttaatctc tcagaccttc aaatggttct  1620
tggtctgagc tacagcacaa ataactccat aatgtctgaa aatactgaaa ttgatagcag  1680
tttgaatggt gtacgcccca agttgggacg ccggcatagt atggaaaata tggaacttat  1740
gaagttaaca ccagaaaagg tacagaactg gaacagtgaa attcttgcta agcaaaaacc  1800
tcttattgcc aaaccttctg caaagctact ctttgtcaac agactgaagg ggaaaaaata  1860
caaaacgaat tcctccacta aagttctcca agatgccagt aattctattg accaccgaat  1920
tccaaattct cagaggaaaa tcagtgcaga tactattgga gatgaagggt ctttgactt  1980
attaagccga tttcaaagca ataggatgga tgatcagaga tgttgcttac aagaaaagaa  2040
ctgccataca gcttcaacaa caacttcttc cactcccccat aaaatgatgc taaaaacatc  2100
atctgttcct gtggtatccc ccaacacgga tgagttttta gatcttcttg ccagctcaca  2160
gagtcgccgt ctgatgacc agaggggctag tttcagtaat ttgccagggc ttcgtctaac  2220
acaaaacagc cagtcggtac ttagccacct gatgactaat gacaacaaag aggctgatga  2280
agatttcttt gacatccttg taaaatgtca aggatccaga ttagatgatc aaagatgtgc  2340
tccaccacct gctaccacaa agggtccgac agtaccagat gaagacttt tcagcctat  2400
tttacggtcc cagggaaaga gaatggatga acagagagtt cttttacaaa gagatcaaaa  2460
cagagacact gactttgggc taaaggactt tttgcaaaat aatgctttgt tggagtttaa  2520
aaattcaggg aaaaaatcgg cagaccatta gttactatg atttatttt tttccttca  2580
aacacggtaa ggaaacaatc tattacttt tccttaaaa ggagaattta tagcactgta  2640
atacagctta aaatattttt agaatgatgt aaatagttaa cctcagtag tctattaagg  2700
cattaatact tctctggaca tgcgcgtttg agggtggagg ggtcctgtaa ggtgcttcat  2760
cgtctgtgat tactgcttgg gatgtgttct ttggcagctt gtgagattac tttacctagt  2820
gtttataaag taggaagtta agtgaatcat agattagaat ttaatactct tatggaaata  2880
atttttaac atcttaattg acaatggcgt tttttatac ataaccatgg atgtagtggg  2940
aaacaatgtt gtttggtaaa aataatgtac ttgatcaatg taaaaagta tataaatag  3000
tcttactaaa aatctaggtt tttttttcct ccaaaaaaa                         3039
```

SEQ ID NO: 13              moltype = DNA  length = 7018
FEATURE                    Location/Qualifiers
source                     1..7018
                           mol_type = other DNA
                           organism = Homo sapiens SEQUENCE: 13
```
ggcgggcgcg ccgggcggca ggtgtcgcg tcggcggcat tcggcggcga tggagcggcc    60
ctggggagct gcggacggcc tctcgcgctg gccccatggc ctcggcctcc tcctcctcct   120
gcagctgctg ccgccgtcga ccctcagcca ggacccgtcg gacgcgcgc cgccgccgcc   180
tgcgccgctg ccgcgctggt ctggccccat cggggtgagc tggggctgc gggcggccgc   240
agccgggggc gcgtttcccc gcggcggccg ttggcgtcgc agcgcgccgg gcgaggacga   300
ggagtgcggc cgggtccggg acttcgtcgc caagctggcc aacaacacgc accagcatgt   360
gtttgatgat ctcagaggct cagtatcctt gtcctgggtt ggagatagca ctgggggtcat   420
tctagtcttg actaccttcc atgtaccact gtaattatg acttttggac agtccaagct   480
atatcgaagt gaggattatg ggaagaactt taaggatatt acagatctca tcaataaac   540
ctttattcgg actgaatttg gcatggctat tggtcctgag aactctggaa aggtggtgtt   600
aacagcagag gtgtctggag gaagtcgtgg aggaagaatc ttcagatcat cagatttgtg   660
gaagaatttt gtgcaaacag atcteccttt tcatcctctc actcagatga tgtatagccc   720
tcagaattct gattatctt tagctctcag cactgaaaat ggcctgtggg tgtccaagaa   780
```

```
ttttggggga aaatgggaag aaatccacaa agcagtatgt ttggccaaat ggggatcaga   840
caacaccatc ttctttacaa cctatgcaaa tggctcctgc aaagctgacc ttggggctct   900
ggaattatgg agaacttcag acttgggaaa aagcttcaaa actattggtg tgaaaatcta   960
ctcatttggt cttggggggac gtttcctttt tgcctctgtg atggctgata aggataccac  1020
aagaaggatc cacgtttcaa cagatcaagg ggacacatgg acatggccc agctcccctc   1080
cgtgggacag gaacagttct attctattcc ggcagcaaat gatgacatgg tattcatgca  1140
tgtagatgaa cctggagaca ctgggtttgg cacaatcttt acctcagatg atcgaggcat  1200
tgtctattcc aagtctttgg accgacatct ctacactacc acaggcggag agacggactt  1260
taccaacgtg acctccctcc gcggcgtcta cataacaagc gtgctctccg aagataattc  1320
tatccagacc atgatcactt ttgaccaagg aggaaggtgg acgcacctga ggaagcctga  1380
aaacagtgaa tgtgatgcta cagcaaaaaa caagaatgag tgcagccttc atattcatgc  1440
ttcctacagc atctcccaga aactgaatgt tccaatggcc ccactctcag agccgaatgc  1500
cgtaggcatt gtcattgctc atggtagcgt gggggatgcc atctcagtga tggttccaga  1560
tgtgtacatc tcagatgatg gggttactc ctggacaaaa atgctggaag gaccccacta  1620
ttacaccatc ctggattctg gaggcatcat tgtggccatt gagcacagca gccgtcctat  1680
caatgtgatt aagttctcca cagacgaagg tcaatgctgg caaacctaca cgttcaccag  1740
ggaccccatc tatttcactg gcctagcttc agaacctgga gctaggtcca tgaatatcag  1800
catttgggc ttcacagaat cttttcctgac cagccagttg gtctcctaca ccattgattt  1860
taaagatatc cttgaaagga actgtgaaga gaaggactat accatatggc tggcacactc  1920
cacagaccct gaagattatg aagatggctg catttttggc tacaaagaac agtttctgcg  1980
gctacgcaag tcatccgtgt gtcagaatgg tcgagactat gttgtgacca agcagccctc  2040
catctgcctc tgttccctgg aggactttct ctgtgatttt ggctactacc gtccagaaaa  2100
tgactccaag tgtgtggaac agccagaact gaagggccac gacctggagt tttgtctgta  2160
cggaagagaa gaacacctaa caacaaatgg gtaccggaaa attccagggg acaaatgcca  2220
gggtggggta aatccagttc gagaagtaaa agacttgaaa aagaaatgca caagcaactt  2280
tttgagtccg gaaaaacaga attccaagtc aaattctgtt ccaattatcc tggccatcgt  2340
gggattgatg ctggtcacag tcgtagcagg agtgctcatt gtgaagaaat atgtctgtgg  2400
gggaaggttc ctggtgcatc gatactctgt gctgcagcag catgcagagg ccaatggtgt  2460
ggatggtgtg gatgctttgg acacagcctc ccacactaat aaaagtggtt atcatgatga  2520
ctcagatgag gacctcttgg aatagtctct cagaggagct ggacccagca tggatggtgg  2580
aaccacagta cctcttacac tccctgtggc tccaacttca ggaaataaat ttcccattgc  2640
gagggaccca gctctgtttc tgctgcttcc atcaaagcca aaaggaccta cactaaagaa  2700
atgcagggtg ggggtgggga accctgagca cttttttaca attggctctg agaaaaaggg  2760
agacattta aattcttaa cttcttattt ctcgtcctgt ctctttgcaa agtatgggct  2820
tttttgtttt tgtttttaa gggaaacgaa atggaattcg aagggacctt ttcactaacc  2880
ccacttctgt gtgttctgca tggcgcctgc cccagggcat ctgccaactc cagtatcagc  2940
tctcacagtg tacttggtac catccctggg ctctgctggc gagacgaaac agctgtagag  3000
atgaaaacag gctgcagagg ctggcacagc ctggccggct tttctccatc tggggacagt  3060
cctactccaa gaacactgca caccagctcc tcacacagct ccacttact ctttttttt   3120
ttttcagaga ccacagacca cagtgatttt tctttccct tgtttaatta ggcaatacc   3180
ttgttaattg cccttttggca actaacttaa ccatgtgctt cccacacagt acatcaggaa  3240
aacttacagg gcaatatttt taacttgggg caggaagaag ggagcagcag agaattgact  3300
agatatagca tctattaaaa gagaacttct gcttcttctg agattttca agctgtgctt  3360
tgtgtgtgtg ccagtagact tacgcaagga cagggtacaa acttagctgg aagtctgccc  3420
aggctgaatg atctcttccc tagagttgat tgtcgggtac acagtgtgaa cccccgaaga  3480
cggaacctca cagtcttcca tgttcccttc ttaactgtcg tgtggctcgt tgctaaatca  3540
tgacaatggc tgcctatctg ctgcttctta ggttgctgtt gtacatggaa ccaggactag  3600
agatttttc agatttatag acttaaaaaa ttagaatttt attaccagcc ttccttctc   3660
accccttttt tctgactttg ccaagtaatt tgttgacacg aaaatttgg aggaaccaat   3720
tgaaaacaca cttccagtct agatgatgct ttgtgtgata cattaagttc ttattttgga  3780
ttaaaagaag ttttccattt gatacttctc taaattaaat aaattataga atgtagttgg  3840
gtggattttg gggtggccat atagtaatgg aaagctgcaa taattagttt taatacagct  3900
tgaatatttg ctatatagaa atatagtatg gaaagttttt ggtcttaatg tagctactgt  3960
gcgggtcaca gtttctccca atgattatga ctgggacatt cttttggtaga taccatttgc  4020
tactagttta ttttgtggct agaaagtcag tttttgtgt ttttttttt ttttatttga   4080
agtgccaaat taactttagt cagaatgtga tgcagatggc aagttctctc ctccccagaa  4140
tggattaaca gctgcgtgga aagtggggga gagtggat ggagacttt agagatgtta   4200
aaactgcagt agaatgaaat gagtcaggga gcttcagtta gaaaataaag ttgaggcagt  4260
ttttgtgaag ataatatggt tagggctgga gtgcactagt cttttttgctt attcattttg  4320
catgctttta aaattaaaaaa taattccgaa gatacaccag ctcacaaatg aaaacgtcag  4380
cctctgcccc accctccctc ctgcccaaag tgaattgggt actcagaaaa gaactgttta  4440
taccactcac cttttctccca gcatgtactc actgtgggca gatgcaccaa tacatggtaa  4500
tcctcttact cattttaaga cgtaggaaac tcaaatattc tctctaacca tatacgatag  4560
ggctcttcgc ttttaatgat atctgggatt tctgtggaac ttcagaaaatt tcagagcac  4620
cttcactcac ataatgtcat ttgaacctca caatgttctt gggatggagt cagttgttca  4680
gggtccccgt gtgtgtgata agcagtgctg gctggctgtc ttcagaactc ttggaaatct  4740
ttacacatgc gagtgctaac cactttgagc aaggctgcct tcttgtagat gacttgctgt  4800
tctttatgac agggatcagt ggcatttgtt tcctagcagt atttagcacc tttttgccac  4860
cttggtgaac agaaaattgt attttcctgt ctttcatggc tgaaaacaaa agtaatggga  4920
attttaaata cgtttgcaga aactgcccct ccctcattg agggtcactg ctcaagagtg  4980
caggagtgga ctctccactg atgggtctcc ctccccatcc tggtttccac cccgggctgg  5040
ctagctctgt tggtttgaag actgacagcc agcctggctc attctcatta ttggctagtt  5100
agctttcttt atcaacctgc tcactcacaa atgtgtgccc tcagccagag agtaagaaag  5160
cccaaatctg ttacagcttc taaaaaaata gatttctaat ttgtcctact catgttagga  5220
gcattatctt tgaaggtaaa acatagtgta tcattgtgta aactcccagg cttgatgtag  5280
cagaagagat catttctgga ggcttcagca atggaattta gcattataag agagattgga  5340
caaccagtc caaagtggtc cgagttctta aatccaggta gggaactcac tcttcttct   5400
tctctggacc taattgggca ttgggctta gtgagaccac agaccaggcc cgtctctcct   5460
gtaggctttt aattcaatgg caactctatt tcaaagaata aaagctttg gagagttgcg  5520
```

-continued

```
gcagttctgg gggcgggctc aggagagtcc atagatcagc cgtaactgga acgtagaatc   5580
tacgtctgcc tctgaatgga cttcccacct cctctctctt gctctgatgc ttgcctctgg   5640
gcctctccat gcccaaggtg gtctttcatc cttgacaggc tggtaatgtg ctggccacct   5700
ccagctcctg catcgagtct gtaaaccaga gctggttctc atggccttcg tcacgatacc   5760
aggatacgga ggggagccca gggccatcca tacccaccca agggtaacgg agctggcctg   5820
gcattagtca ttatttagtt tccaggccaa ccatccagat agagattccc tctttccttt   5880
gagcagtgct ctcaagagct ccgtgcctgt ccacaatgac ctagagtgca tcctgctcat   5940
tgtcagtgta gcccctcgcc cctatattca tccaggatac ttggaagtgc taaaatagga   6000
agggattcgg ctttcaactt tgctaccatc ttccctgaag caggaaaatg aacatggact   6060
taaatgttct ttgaaaaaac caaagtttta agatttgctg tgtgatgaag tgacagggag   6120
ggccggagtc agcaggtgcc agactttctg ttctgtctgc catggggttg tccagctcag   6180
gtagctctag gagcaccatc ctgccctagc agagcccagg ccttgccctc atgaagcatc   6240
attgaaatag caggagcatg ttgatttctt ggttaggttg cattataata acaagagtca   6300
aacattaat tcgaaacaac ttgcatatg catttcttca caccagtaca ttcttaagtg    6360
tacttgttta taaggaataa cataaactaa tctgtacctt tatatatatg tgtgtgtaca   6420
tatatacata tataaactgt atagtgtaca tggtaatgat ttattgctat gccccagatc   6480
cttaatgtag ttctcatcct ccgcatgccc tcagccacaa gcgggtgact gactgttccc   6540
tgatgatttg gcccacctcc tgtgtttgga cctctaggga ggagggtttt ggtcatactc   6600
tccttatcct cgtgcacaga aatgctcagg gtcccccatgt gcctgttgtt cagccctctc   6660
tcttgttccc tttctgagca tgtggtcctt cccaggctg tgggacagct gccttccac    6720
gaaagtgtaa agcagtatta agatcattac tgcatgtgcc ctaaaaccc aagttttcta    6780
ttcccttagg acagaaaatt gcatgtgagg tgggataatt gcgtttcagt gacccacgtc   6840
agttacacat taaagccaga ccccatgata aaattccaca aaatgaaat aaaactcaaa    6900
tttctttagc attgtgtaaa taaatctgaa tgtgtttaac tttgtactgg taattttctg   6960
tatatttgga atatttgggt taaaaataaa acagactgga ctttgttacc tgacctac     7018
```

```
SEQ ID NO: 14          moltype = DNA  length = 1749
FEATURE                Location/Qualifiers
source                 1..1749
                       mol_type = other DNA
                       organism = Homo sapiens
SEQUENCE: 14
gtgacattgt ttgccaaaat cccaggcagc atggacctca gtcttctctg ggtacttctg   60
ccctagtca ccatggcctg gggccagtat ggcgattatg gatacccata ccagcagtat   120
catgactaca gcgatgatgg gtgggtgaat ttgaaccggc aaggcttcag ctaccagtgt   180
ccccaggggc aggtgatagt ggccgtgagg agcatcttca gcaagaagga aggttctgac   240
agacaatgga actacgcctg catgcccacg ccacagagcc tcggggaacc cacggagtgc   300
tggtgggagg agatcaacag ggctggcatg gaatggtacc agacgtgctc caacaatggg   360
ctggtggcag gattccagag ccgctacttc gagtcagtgc tggatcggga gtggcagttt   420
tactgttgtc gctacagcaa gaggtgccca tattcctgct ggctaacaac agaatatcca   480
ggtcactatg tgaggaaat ggacatgatt cctacaatt atgattacta tatccgagga    540
gcaacaacca ctttctctgc agtggaaagg gatcgccagt ggaagttcat aatgtgccgg   600
atgactgaat acgactgtga atttgcaaat gtttagattt gccacatacc aaatctgagg   660
gaaaggaaag gggccgggga caggagggtg tccacatatg ttaacatcag ttggatctcc   720
tatagaagtt tctgctgctc tcttttccttc tccctgagct ggtaactgca atgccaactt   780
cctgggcctt tctgactagt atcacactc taataaaatc cacaattaaa ccatgtttct    840
cactttcac atgttcata caactgctt tatatgactg atgatggctt ccttgcacac     900
cacatataca gtgcgcatgc ttacagccgg gcttctggag caccagctgc agcctggcta   960
ctgcttttta ctgcagaatg aactgcaagt tcagcatagt ggagggagaa ggcagaactg   1020
gaggagaggt gcagtgaagg ttctctacag ctaagcctgt ttgaatgata cgtaggttcc   1080
ccaccaaaag caggctttct gccctgaggg acatcttccc actcccctgc tccacatgag   1140
ccatgcatgc ttagcaatcc aagtgcagag ctctttgctc caggagtgag gagactggga   1200
ggtgaaatgg ggaaatggaa gggttttgag gcagagctga aaacagggtt ggaaggattt   1260
cctgaattag aagacaaacg ttagcatacc cagtaaggaa aatgagtgca ggggccaggg   1320
gaaccgtga ggatcactct caaatgagat taaaaacaag gaagcagaga atggtcagag    1380
aatgggattc agattgggaa cttgtgggga tgagagtgac caggttgaac tgggaagtga   1440
aaaaaggagt ttgagtcact ggcacctaga agcctgccca cgattcctag gaaggctggc   1500
agacaccctg gaaccctggg gagctactgg caaactctcc tggattgggc ctgatttttt   1560
tggtgggaaa ggctgccctg gggatcaact ttccttctgt gtgtggctca ggagttcttc   1620
tgcagagatg gcgctatctt tcctcctcct gtgatgtcct gctcccaacc atttgtactc   1680
ttcattacaa aagaaataaa aatattaacg ttcactatgc tgaaaataaa aaaaaaaaa    1740
aaaaaaaa                                                           1749
```

```
SEQ ID NO: 15          moltype = DNA  length = 2478
FEATURE                Location/Qualifiers
source                 1..2478
                       mol_type = other DNA
                       organism = Homo sapiens
SEQUENCE: 15
gcagttggtg aaactcctct gtctcccgct catcttttca ttgctcgttc ccctccttcc   60
cgcagacacc cggacctccc ctgggcgcca gctccgcggc tccaacgggt ccagaaacaa   120
gccgattttt ttttttttct tcctggaaat tggctttggt gtgtgttgcc ctacctcct    180
cctcccctc ccacccacag ccccccccg gccttttttt tttttttttt ttttttgag     240
acatgggccg ggcagtggct cctggaagag gaacaagtgg gggaaaaggg agaggaagcc   300
ggagctaaat gacaggatgc aggcgacttg agacacaaaa agagaagcgt tcctctcgga   360
tccaggcatt gcctcgctgc ttctttttct ccaagacggg ctgaggattg tacagctcta   420
ggcggagttg gggctcttcg gatcgcttag attctcctct ttgctgcatt tccccccacg   480
tcctcgttct cccgcgtctg cctgcggacc cggagagg agaatggaga ggggggctgcc    540
gctcctctgc gccgtgctcg ccctcgtcct cgccccggcc ggcgcttttc gcaacgataa   600
```

```
atgtggcgat actataaaaa ttgaaagccc cgggtacctt acatctcctg gttatcctca   660
ttcttatcac ccaagtgaaa aatgcgaatg gctgattcag gctccggacc cataccagag   720
aattatgatc aacttcaacc ctcacttcga tttggaggac agagactgca agtatgacta   780
cgtgaagtc ttcgatggag aaaatgaaaa tggacatttt aggggaaagt tctgtggaaa   840
gatgcccct cctcctgttg tgtcttcagg gccatttctt tttatcaaat ttgtctctga   900
ctacgaaaca catggtgcag gatttttccat acgttatgaa attttcaaga gaggtcctga   960
atgttcccag aactacacaa cacctagtgg agtgataaag tcccccggat tccctgaaaa  1020
atatcccaac agccttgaat gcacttatat tgtctttgcg ccaaagatgt cagagattat  1080
cctggaattt gaaagctttg acctggagcc tgactcaaat cctccagggg ggatgttctg  1140
tcgctacgac cggctagaaa tctgggatgg attccctgat gttggccctc acattgggcg  1200
ttactgtgga cagaaaacac caggtcgaat ccgatcctca tcgggcattc tctccatggt  1260
tttttacacc gacagcgcga tagcaaaaga aggtttctca gcaaactaca gtgtcttgca  1320
gagcagtgtc tcagaagatt tcaaatgtat ggaagctctg gcatggaat caggagaaat  1380
tcattctgac cagatcacag cttcttccca gtatagcaca aactggtctg cagagcgctc  1440
ccgcctgaac taccctgaga atgggtggac tcccggagag gattcctacc gagagtggat  1500
acaggtagac ttgggccttc tgcgctttgt cacggcgtc gggacacagg gcgccatttc  1560
aaaagaaacc aagaagaaat attatgtcaa gacttacaag atcgacgtta gctccaacgg  1620
ggaagactgg atcaccataa aagaaggaaa caaacctgtt ctcttcagg gaaacaccaa  1680
ccccacagat gttgtggttg cagtattccc caaaccactg ataactcgat tgtccgaat  1740
caagcctgca acttgggaaa ctggcatatc tatgagattt gaagtatacg gttgcaagat  1800
aacagattat ccttgctctg gaatgttggg tatggtgtct ggacttattt ctgactccca  1860
gatcatca tccaaccaag gggacagaaa ctggatgcct gaaaacatcc gcctggtaac  1920
cagtcgctct ggctgggcac ttccaccgc acctcattcc tacatcaatg agtggctcca  1980
aatagacctg gggaggaga agatcgtgag gggcatcatc attcaggtg ggaagcaccg  2040
agagaacaag gtgttcatga ggaagttcaa gatcgggtac agcaacaacg gctcggactg  2100
gaagatgatc atggatgaca gcaaacgcaa ggcgaagtct tttgagggca acaacaacta  2160
tgatacacct gagctgcgga cttttccagc tctctccacg cgattcatca ggatctaccc  2220
cgagagagcc actcatggcg gactgggggct cagaatggag ctgctgggct gtgaagtgga  2280
agcccctaca gctggaccga ccactcccaa cgggaacttg gtggatgaat gtgatgacga  2340
ccaggccaac tgccacagtg aacaggtga tgacttccag ctcacaggtg gcaccactgt  2400
gctggccaca gaaaagccca cggtcataga cagcaccata caatcaggta tcaaataaaa  2460
tacgaaatgt gacagatt                                                2478

SEQ ID NO: 16           moltype = DNA  length = 3372
FEATURE                 Location/Qualifiers
source                  1..3372
                        mol_type = other DNA
                        organism = Homo sapiens
SEQUENCE: 16
taaaaccagg aagtgaagtc cccgagcacg ttagaaagcc tgacatggcc tgactcggga    60
cagctcagag caggggcagaa ctggggacac tctgggccgg ccttctgcct gcatggacgc   120
tctgaagcca ccctgtctct ggaggaacca cgagcgaggg aagaaggaca gggactcgtg   180
tggcaggaag aatcagagc cgggaagccc ccattcacta gaagcactga gagatgcgac   240
cccctcgcag ggtctgaatt tcctgctgct gttcacaaag atgctttta tctttaactt   300
tttgtttcc ccacttccga cccccggcgtt gatctcatc ctgacatttg gagctgccat   360
cttcttgtgg ctgatcacca gacctcaacc cgtcttacct cttcttgacc tgaacaatca   420
gtctgtggga attgagggag gagcacggaa gggggtttcc cagaagaaca atgacctaac   480
aagttgctgc ttctcagatg ccaagactat gtatgaggtt ttccaaagag gactcgctgt   540
gtctgacaat gggccctgct gggatatag aaaaccaaac cagccctaca gatggctatc   600
ttacaaacag gtgtctgata gagcagagta cctgggttcc tgtctcttgc ataaaggtta   660
taaatcatca ccagaccagt ttgtcggcat ctttgctcag aataggccag agtggatcat   720
ctccgaattg gcttgttaca cgtactctat ggtagctgta cctctgtatg acaccttggg   780
accagaagcc atcgtacata ttgtcaacaa ggctgatatc gccatggtga tctgtgacac   840
accccaaaag gcattggtgc tgataggaa tgtagagaaa ggcttcaccc cgagcctgaa   900
ggtgatcatc cttatggacc cctttgatga tgacctgaag caaagagggg agaagagtga   960
aattgagatc ttatccctat atgatgctga gaacctaggc aaagagcact tcagaaaacc  1020
tgtgcctcct agcccagaag acctgagcgt catctgcttc accagtggga ccacaggtga  1080
ccccaaagga gccatgataa cccatcaaaa tattgtttca aatgctgctg cctttctcaa  1140
atgtgtggag catgcttatg agcccactcc tgatgatgtg gccatatcct acctccctct  1200
ggctcatatg tttgagaggt tgtacaggc tgttgtgtac agctgtggag ccagagttgg  1260
attcttccaa ggggatattc ggttgctggc tgacgacatg aagactttga agcccacatt  1320
gtttcccgcg gtgcctcgac tccttaacag gatctacgat aaggtacaaa atgaggccaa  1380
gacacccttg aagaagttct tgttgaagct ggctgtttcc agtaaattca aagagcttca  1440
aaagggtatc atcaggcatg atagtttctg ggacaaggtc atctttgcaa agatccagga  1500
cagcctgggc ggaagggttc gtgtaattgt cactggagct gccccccatgt ccacttcagt  1560
catgacattc ttccgggcag caatgggatg tcaggtgtat gaagcttatg gtcaaacaga  1620
atgcacaggt ggctgtacat ttacattacc tgggactgg acatcaggtc acgttggggt  1680
gcccctggct tgcaattacg tgaagctgga agatgtggct gacatgaact actttacagt  1740
gaataatgaa ggagaggtct gcatcaaggg tacaaacgtg ttcaaaggat acctgaagga  1800
ccctgagaag acacaggaag ccctggacag tgatggctgg cttcacacag agacattgg  1860
tcgctgctc ccgaatggaa ctctgaagat catcgaccgt aaaagaaca ttttcaagct  1920
ggcccaagga gaatacattg caccagagaa gatagaaaat atctacaaca ggagtcaacc  1980
agtgttacaa atttttgtac acgggaggag cttacggtca tccttagtag gagtggtggt  2040
tcctgacaca gatgtacttc cctcatttgc agccaagtgt ggtgagaag gctccttga  2100
ggaactgtgc caaaaccaag ttgtaaggga agccattta gaagacttgc agaaaattgg  2160
gaaagaaagt ggccttaaaa cttttgaaca ggtcaaagcc attttcttc atccagagcc  2220
atttttccatt gaaaatgggc tcttgacacc aacattgaaa gcaaagcgag gagagctttc  2280
caaatacttt cggaccaaa ttgacagcct gtatgagcac atccaggatt aggataaggt  2340
acttaagtac ctgccggccc actgtgcact gcttgtgaga aaatggatta aaactattc  2400
```

```
ttacatttgt tttgcctttc ctcctatttt tttttaacct gttaaactct aaagccatag  2460
cttttgtttt atattgagac atataatgtg taaacttagt tcccaaataa atcaatcctg  2520
tctttcccat cttcgatgtt gctaatatta aggcttcagg gctacttta tcaacatgcc  2580
tgtcttcaag atcccagttt atgttctgtg tccttcctca tgatttccaa ccttaatact  2640
attagtaacc acaagttcaa gggtcaaagg gaccctcctg gccttcttct ttgttttgtg  2700
ataaacataa cttgccaaca gtctctatgc ttatttacat cttctactgt tcaaactaag  2760
agatttttaa attctgaaaa actgcttaca attcatgttt tctagccact ccacaaacca  2820
ctaaaatttt agtttagcc tatcactcat gtcaatcata tctatgagac aaatgtctcc  2880
gatgctcttc tgcgtaaatt aaattgtgta ctgaagggaa aagtttgatc ataccaaaca  2940
tttcctaaac tctctagtta gatatctgac ttgggagtat taaaaattgg gtctatgaca  3000
tattgtccaa aaggaatgct gttcttaaag cattatttac agtaggaact ggggagtaaa  3060
tctgttccct acagtttgct gctgagctgg aagctgtggg ggaaggagtt gacaggtggg  3120
cccagtgaac ttttccagta aatgaagcaa gcactgaata aaaacctcct gaactgggaa  3180
caaagatcta caggcaagca agatgcccac acaacagctt tattttctgt gaaggaacca  3240
actgatctcc cccaccccttg gattagagtt cctgctctac cttacccaca gataacacat  3300
gttgtttcta cttgtaaatg taaagtcttt aaaataaaact attacagata cttaaaaaaa  3360
aaaaaaaaaa aa                                                    3372

SEQ ID NO: 17         moltype = DNA   length = 5243
FEATURE               Location/Qualifiers
source                1..5243
                      mol_type = other DNA
                      organism = Homo sapiens
SEQUENCE: 17
agcgtgagac tcgcgccctc cggcacggaa aaggccaggc gacaggtgtc gcttgaaaag   60
actgggcttg tccttgctgg tgcatgcgtc gtcggcctct gggcagcagg tttacaaagg  120
aggaaaacga cttcttctag atttttttt cagtttcttc tataaatcaa aacatctcaa  180
aatggagacc taaaatcctt aaagggactt agtctaatct cgggaggtag ttttgtgcat  240
gggtaaacaa attaagtatt aactggtgtt ttactatcca aagaatgcta atttataaa  300
catgatcgag ttatataagg tataccataa tgagttgact tttgaatttg atttgtggaa  360
ataaaggaaa agtgattcta gctggggcat attgttaaag cattttttc agagttggcc  420
aggcagtctc ctactggcac attctcccat tatgtagaat agaaatagta cctgtgtttg  480
ggaaagattt taaatgagt gacagttatt ggaacaaag agctaataat caatccactg  540
caaattaaag aaacatgcag atgaaagttt tgacacatta aaatacttct acagtgacaa  600
agaaaaatca agaacaaagc tttttgatat gtgcaacaaa tttagaggaa gtaaaaagat  660
aaatgtgatg attggtcaag aaattatcca gttatttaca aggccactga tattttaaac  720
gtccaaaagt ttgtttaaat gggctgttac cgctgagaat gatgaggatg agaatgatgg  780
ttgaaggtta cattttagga aatgaagaaa cttagaaat taatataag acagtgatga  840
atacaaagaa gattttata acaatgtgta gaatttttgg ccagggaaag gagaattgaa  900
gttagataca attcttacc tttgagggaa ataattgttg gtaatgagat gtgatgtttc  960
tcctgccacc tggaaacaaa gcattgaagt ctgcagttga aaagcccaac gtctgtgaga  1020
tccaggaaac catgcttgca aaccactggt aaaaaaaaaa aaaaaaaaa aaaaaagcca  1080
cagtgacttg cttattggtc attgctagta ttatcgactc agaacctctt tactaatggc  1140
tagtaaatca taattgagaa attctgaatt ttgacaaggt ctctgctgtt gaatgtgtaa  1200
attttattatt ttttttgtca tgataaaattc tggttcaagg tatgctatcc atgaaataat  1260
ttctgaccaa aactaaattg atgcaatttg attatccatc ttagcctaca gatggcatct  1320
ggtaacttt gactgtttta aaaaataaat ccactatcag agtagatttg atgttggctt  1380
cagaaacatt tagaaaaaca aaagttcaaa aatgttttca ggaggtgata agttgaataa  1440
ctctacaatg ttagttctt gaggggggaca aaaaatttaa aatctttgaa aggtcttatt  1500
ttacagccat atctaaatta tcttaagaaa attttttaaca aagggaatga aatatatatc  1560
atgattctgt tttttccaaaa gtaacctgaa tatagcaatg aagttcagtt ttgttattgg  1620
tagtttgggc agagtctctt tttgcagcac ctgttgtcta ccataattac agaggacatt  1680
tccatgttct agccaagtat actattagaa taaaaaaact taacattgag ttgcttcaac  1740
agcatgaaac tgagtccaaa agaccaaatg aacaaacaca ttaatctctg attatttatt  1800
ttaaatagaa tatttaattg tgtaagatct aatagtatca ttatacttaa gcaatcatat  1860
tcctgatgat ctatgggaaa taactattat ttaattaata ttgaaaccag gttttaagat  1920
gtgttagcca gtcctgttac tagtaaatct ctttatttgg agagaaattt tagattgttt  1980
tgttctcctt attagaagga ttgtagaaag aaaaaaatga ctaattggag aaaaattggg  2040
gatatatcat atttcactga attcaaaatg tcttcagttg taaatcttac cattattta  2100
cgtacctcta agaaataaaa gtgcttctaa ttaaaatatg atgtcattaa ttatgaaata  2160
cttcttgata acagaagttt taaaatagcc atcttagaat cagtgaaata tggtaatgta  2220
ttattttcct cctttgagtt aggtcttgtg cttttttttc ctggccacta aatttccaca  2280
tttccaaaaa gcaaataaa catattctga atatttttgc tgtgaaacac ttgacagcag  2340
agcttccac catgaaaaga gcttcatga gtcacacatt acatcttttgg gttgattgaa  2400
tgccactgaa acattctagt agcctggaga agttgaccta cctgtggaga tgcctgccat  2460
taaatggcat cctgatggct taatacacat cactcttctg tgaagggttt taattttcaa  2520
cacagcttac tctgtagcat catgttaaca ttgtatgtat aaagattata caaaggtgca  2580
attgtgtatt tcttccttaa aatgtatcag tataggatca agtctcca tgttgaaact  2640
ctaaatgcat agaaataaaa ataataaaaa atttttcatt ttggcttttc agcctagtat  2700
taaaactgat aaaagcaaag ccatgcacaa aactacctcc ctagagaaag gctagtccct  2760
tttcttcccc attcatttca ttatgaacat agtagaaaac agcatattct tatcaaattt  2820
gatgaaaagc gccaacacgt ttgaactgaa atacgacttg tcatgtgaac tgtaccgaat  2880
gtctacgtat tccacttttc ctgctggggt tcctgtctca gaaggagtc ttgctcgtgc  2940
tggttctat tacactggtg tgaatgacaa gtcaaatgc ttctgttgtg gcctgatgct  3000
ggataactgg aaaagaggag acagtcctac tgaaaagcat aaaaagttgt atcctagctg  3060
cagattcgtt cagagtctaa attccgttaa caacttggaa gctaccctc agcctacttt  3120
tccttcttca gtaacaaatt ccacacactc attacttccg ggtacagaaa acagtggata  3180
tttccgtggc tcttattcaa actctccatc aaatcctgta aactcagag caaatcaaga  3240
tttttctgcc ttgatgagaa gttcctacca ctgtgcaatg aataacgaaa atgccagatt  3300
```

-continued

```
acttactttt cagacatggc cattgacttt tctgtcgcca acagatctgg caaaagcagg    3360
cttttactac ataggacctg gagacagagt ggcttgcttt gcctgtggtg gaaaattgag    3420
caattgggaa ccgaaggata atgctatgtc agaacacctg agacattttc ccaaatgccc    3480
atttatagaa aatcagcttc aagacacttc aagatacaca gtttctaatc tgagcatgca    3540
gacacatgca gcccgcttta aaacattctt taactgcccc tctagtgttc tagttaatcc    3600
tgagcagctt gcaagtgcgg gtttttatta tgtgggtaac agtgatgatg tcaaatgctt    3660
ttgctgtgat ggtggactca ggtgttggga atctggagat gatccatggg ttcaacatgc    3720
caagtggttt ccaaggtgtg agtacttgat aagaattaaa ggacaggagt tcatccgtca    3780
agttcaagcc agttaccctc atctacttga acagctgtcc cacatcag acagcccagg     3840
agatgaaaat gcagagtcat caattatcca ttttgaacct ggagaagacc attcagaaga    3900
tgcaatcatg atgaatactc ctgtgattaa tgctgccgtg gaaatgggct ttagtagaag    3960
cctggtaaaa cagacagttc agagaaaaat cctagcaact ggagagaatt atagactagt    4020
caatgatctt gtgttagact tactcaatgc agaagatgaa ataagggaag aggagagaga    4080
aagagcaact gaggaaaaag aatcaaatga tttattatta atccggaaga atagaatggc    4140
acttttttcaa catttgactt gtgtaattcc aatcctggat agtctactaa ctgccggaat    4200
tattaatgaa caagaacatg atgttattaa acagaagaca cagacgtctt tacaagcaag    4260
agaactgatt gatacgattt tagtaaaagg aaatattgca gccactgtat tcagaaactc    4320
tctgcaagaa gctgaagctg tgttatatga gcatttattt gtgcaacagg acataaaata    4380
tattcccaca gaagatgttt cagatctacc agtggaagaa caattgcgga gactacaaga    4440
agaaagaaca tgtaaagtgt gtatggacaa agaagtgtcc atagtgttta ttccttgtgg    4500
tcatctagta gtatgcaaag attgtgctcc ttctttaaga aagtgtccta tttgtaggag    4560
tacaatcaag ggtacagttc gtacatttct ttcatgaaga agaaccaaaa catcgtctaa    4620
actttagaat taatttatta aatgtattat aactttaact tttatcctaa tttggttttcc   4680
ttaaaatttt tatttattta caactcaaaa aacattgttt tgtgtaacat atttatatat    4740
gtatctaaac catatgaaca tatatttttt agaaactaag agaatgatag cttttgttc    4800
ttatgaacga aaaagaggta gcactacaaa cacaatattc aatcaaaatt tcagcattat    4860
tgaaattgta agtgaagtaa aacttaagat atttgagtta acctttaaga atttttaaata    4920
ttttggcatt gtactaatac cgggaacatg aagccaggtg tggtggtatg tgcctgtagt    4980
cccaggctga ggcaagagaa ttacttgagc ccaggagttt gaatccatcc tgggcagcat    5040
actgagaccc tgcctttaaa aacaaacaga acaaaaacaa aacaccaggg acacatttct    5100
ctgtctttttt tgatcagtgt cctatacatc gaaggtgtgc atatatgttg aatgacattt    5160
tagggacatg gtgtttttat aaagaattct gtgagaaaaa atttaataaa gcaacaaaaa    5220
ttactcttaa aaaaaaaaaa aaa                                             5243

SEQ ID NO: 18         moltype = DNA   length = 1579
FEATURE               Location/Qualifiers
source                1..1579
                      mol_type = other DNA
                      organism = Homo sapiens
SEQUENCE: 18
gaggaggtgc ttgccagaca ctgggtcatg cagtggtcg gtgaagctgc agttgcctag     60
ggcagggatg gagagagagt ctgggcatga ggagagggtc tcgggatgtt tggctggact   120
agattttaca gaaagcctta tccaggcttt taaaattact ctttccagac ttcatctgag   180
actccttctt cagccaacat tccttagccc tgaatacatt tcctatcctc atctttccct   240
tctttttttt cctttctttt acatgtttaa atttaaacca ttcttcgtga ccccttttct   300
tgggagattc atgcaagaa cgagaagaat gatggtgctt gttaggggat gtcctgtctc    360
tctgaacttt ggggtcctat gcattaaata attttcctga cgagctcaag tgctccctct   420
ggtctacaat ccctggcggc tggccttcat cccttgggca agcattgcat acagctcatg   480
gccctccctc taccataccc tccacccccg ttcgcctaag ctcccttctc cgggaatttc   540
atcatttcct agaacagcca gaacattgt ggtctatttc tctgttagtg tttaaccaac    600
catctgttct aaaagaaggg ctgaactgat ggaaggaatg ctgttagcct gagactcagg   660
aagacaactt ctgcagggtc actccctggc ttctggagga aagagaagga gggcagtgct   720
ccagtggtac agaagtgaga cataatgaa tcaggcttca cctccaagga cacctatcta    780
agccatttta accctcggga ttaccctagaa aaatattaca agtttggttc taggcactct   840
gcagaaagcc agattcttaa gcaccttctg aaaaatcttt tcaagatatt ctgcctagac   900
ggtgtgaagg gagacctgct gattgacatc ggctctggcc ccactatcta tcagctcctc   960
tctgcttgtg aatccttaa ggagatcgtc gtcactgact actcagacca gaacctgcag    1020
gagctggaga agtggctgaa gaaagagcca gaggcctttg actggtcccc agtggtgacc   1080
tatgtgtgtg atcttgaagg gaacagtgc aagggtccag agaaggagga gaagttgaga    1140
caggcggtca agcaggtgct gaagtgtgat gtgactcaga gccagccact gggggccgtc   1200
cccttacccc cggctgactg cgtgctcagc acactgtgtc tggatgccgc ctgcccagac   1260
ctccccacct actgcaggc gctcaggaac ctcggcagcc tactgaagcc aggggggcttc    1320
ctggtgatca tggatgcgct caagagcagc tactacatga ttggtgagca gaagtctctc   1380
agcctcccccc tgggccggga gcagtagag gctgctgga aagagcctgg ctacacaatc    1440
gaatggtttg aggtgatctc gcaaagttat tcttccacca tggccaacaa cgaaggactt   1500
ttctcccctgg tggcgaggaa gctgagcaga ccctgtgat gcctgtgacc tcaattaag    1560
caattccttt gacctgtca                                                 1579

SEQ ID NO: 19         moltype = DNA   length = 980
FEATURE               Location/Qualifiers
source                1..980
                      mol_type = other DNA
                      organism = Homo sapiens
SEQUENCE: 19
gcggcggcgg gcagcagctg cgctgcgact gctctggaag gagaggacgg ggcacaaacc     60
ctgaccatga ccccccacag gctgctgcca ccgctgctgc tgctgctagc tctgctgctc    120
gctgccagcc caggaggcgc cttggcgcgg tgcccaggct gcgggcaagg ggtgcaggcg    180
ggttgtccag ggggctgcgt ggaggaggag gatgggggt cgccagccga gggctgcgcg    240
gaagctgagg gctgtctcag gagggagggg caggagtgcg gggtctacac ccctaactgc    300
```

```
gccccaggac tgcagtgcca tccgcccaag gacgacgagg cgcctttgcg ggcgctgctg    360
ctcggccgag gccgctgcct tccgcccgc gcgcctgctg ttgcagagga gaatcctaag    420
gagagtaaac cccaagcagg cactgcccgc ccacaggatg tgaaccgcag agaccaacag    480
aggaatccag gcacctctac cacgccctcc cagcccaatt ctgcgggtgt ccaagacact    540
gagatgggcc catgccgtag acatctggac tcagtgctgc agcaactcca gactgaggtc    600
taccgagggg ctcaaacact ctacgtgccc aattgtgacc atcgaggctt ctaccggaag    660
cggcagtgcc gctcctccca ggggcagcgc cgaggtccct gctggtgtgt ggatcggatg    720
ggcaagtccc tgccagggtc tccagatggc aatggaagct cctcctgccc cactgggagt    780
agcggctaaa gctgggggat agaggggctg cagggccact ggaaggaaca tggagctgtc    840
atcactcaac aaaaaaccga ggccctcaat ccaccttcag gcccgcccc atgggcccct    900
caccgctggt tggaaagagt gttggtgttg gctgggtgt caataaagct gtgcttgggg    960
tcgctgaaaa aaaaaaaaaa                                                980

SEQ ID NO: 20            moltype = DNA    length = 7346
FEATURE                  Location/Qualifiers
source                   1..7346
                         mol_type = other DNA
                         organism = Homo sapiens
SEQUENCE: 20
gcgaggagga aacggtgccg gagcgcgcag ggcttgctgc cgccaccgcc gctgcacagg     60
ctgccggagc gagcctgccg cgcgccgccc tcccgctct ccttcctggg cgagctgcgg    120
ggatgggcg gccgcgggag cccgagcgcg gcaggaacg gccgccgcg gccgccgcg     180
ctccgttgcc gcgcgcctga gccgccgtcg ccgccgcgcg ccctgcccgg ggcggcccc    240
cccagcccca tggaggtctc ccggaggaag gcgccgccgc gccccccgcg ccccgcagcg    300
ccactgcccc tgctcgccta tctgctggca ctggcggctc ccggccgggg cgcggacgag    360
cccgtgtggc ggtcggagca agccatcgga gccatcgcgg ccgcaggga gccggccgcg    420
tttgtggcga gcggcagctg cctgaccagg ctggactaca gcctggagca cagcctctcg    480
cgcctgtacc gggaccaagc gggcaactgc acagagccgg tctcgctggc gcccccgcg    540
cggccccggc ccgggagcag cttcagcaag ctgctgctgc cctaccgcga gggggcggcc    600
ggcctggggg ggctgctgct caccggctgg accttcgacc ggggccgctg gggtcgcacc    660
ccctgggca acctgagccg caactccctg cgcaacggca ccgaggtggt gtcgtgccac    720
ccgcagggct cgacggccgg cgtggtgtac cgcgcgggcc ggaacaaccg ctggtacctg    780
gcggtggccg ccacctacgt gctgcctgag ccggagacgg cgagccgctg caaccccgcg    840
gcatccgacc acgacacggc catcgcgctc aaggacagg aggggcgcag cctgccacg     900
caggagctgg ggcgcctcaa gctgtgcgag ggcgcgggca gcctgcactt cgtcgacgcc    960
tttctctgga acggcagcat ctacttcccc tactaccct acaactacac gagcggcgct   1020
gccaccggct ggcccagcat ggcgcgcatc gcgcagagca ccgaggtgct gttccagggc   1080
caggcatccc tcgactgcgg ccacggccac cccgacggcc gccgctgct cctctcctcc   1140
agcctagtgg aggcctgga cgtctggcg gagtgttca ggggccgc tggagggc   1200
caggagcggc gctccccac caccacggcg ctctgcctct tcagaatgag tgagatccag   1260
gcgcgcgcca agaggtcag ctgggacttc aagacggccg agagccactg caaagaaggg   1320
gatcaacctg aaagagtcca accaatcgca tcatctacct tgatccattc cgacctgaca   1380
tccgttatg gcaccgtggt aatgaacagg actgtttat tcttggggac tggagatgac   1440
cagttactta aggttattct tggtgagaat ttgacttcaa attgtccaga ggttatctat   1500
gaaattaaag aagagacacc tgttttctac aaactcgttc ctgatcctgt gaagaatatc   1560
tacatttatc taacagctgg gaagaggtg aggagaattc gtgttgcaaa ctgcaataaa   1620
cataaatcct gttcggagtg tttaacagcc acagaccctc atcgcggttg gtgccattcg   1680
ctacaaaggt gcactttca aggagattgt gtacattcag agaacttaga aaactggctg   1740
gatatttcgt ctggagcaaa aaagtgcccc aaaattcaga taattcgaag cagtaaagaa   1800
aagactacag tgactatggt gggaagcttc tctccaagac actcaaagtg catggtgaag   1860
aatgtggact ctagcaggga gctctgccag aataaaagtc agcccaaccg gacctgcacc   1920
tgtagcatcc caaccagagc aacctacaaa gatgtttcag ttgtcaacgt gatgttctcc   1980
ttcggttctt ggaatttatc agacagattc aactttacca actgctcatc attaaaagaa   2040
tgcccagcat gcgtagaaac tggctgcgcg tggtgtaaaa gtgcaagaag gtgtatccac   2100
ccccttcacag cttgcgaccc ttctgattat gagagaaaca ggaacagtg tccagtggct   2160
gtcgagaaga catcaggagg aggaagaccc aaggagaaca agggggaacag aaccaaccag   2220
gctttacagg tcttctacat taagtccatt gagccacaga agtatcgac attagggaaa   2280
agcaacgtga tagtaacggg agcaaactt accgggcat cgaacatcac aatgatcctg   2340
aaaggaacca gtaccgtga taaggatgtg atacaggtta gccatgtgct aaatgaccac   2400
cacatgaaat tctctcttcc atcaagccgg aagaaatga aggatgtgtg tatccagttt   2460
gatggtggga actgctcttc tgtgggatcc ttatcctaca ttgctctgcc acattgttcc   2520
cttatatttc ctgctaccac ctggatcagt ggtggtcaaa atataaccat gatgggcaga   2580
aattttgatg taattgacaa cttaatcatt tcacatgaat taaaggaaa cataaatgtc   2640
tctgaatatt gtgttggcgac ttactgcggg ttttagccc cagttttaaa gagttcaaaa   2700
gtcgcacga atgtcactgt gaagctgaga gtacaagaca cctacttgga ttgtggaacc   2760
ctgcagtatc gggaggaccc cagattcacg gggtatcggg tggaatccga ggtgacaca   2820
gaactggaag tgaaaattca aaagaaaat gacaacttca acatttccaa aaagacatt   2880
gaaattactc tcttccatgg ggaaaatggg caattaatt gcagtttga aaatattact   2940
agaaatcaag atcttaccac catccttgc aaaattaaag gcatcaagac tgcaagcacc   3000
attgccaact cttctaagaa agttcgggtc aagctgggaa acctggagct ctacgtcgag   3060
caggagtcag ttccttccac atggtatttt ctgattgtgc tccctgtctt gctagtgatt   3120
gtcatttttg cggccgtggg ggtgaccagg cacaaatcga aggagctgag tcgcaaacag   3180
agtcaacaac tagaattgct ggaaagcgag ctccggaaag agatacgtga cggctttgct   3240
gagctgcaga tggataaatt ggatgtggtt gatagtttga gaactgttcc cttccttgac   3300
tacaaacatt ttgctctgag aactttcttc cctgagtcag gtggcttcac ccacatcttc   3360
actgaagata tgcataacag agacgccaac gacaagaatg aaagtctcac agcttttgat   3420
gccctaatct gtaataaaag cttcttgtt actgtcatcc acaccttga aaagcagaag   3480
aactttcctg tgaaggacag gtgtctgttt gcctccttcc taaccattgc actgcaaacc   3540
aagctggtct acctgaccag catcctagag gtgctgacca gggacttgat ggaacagtgt   3600
```

```
agtaacatgc agccgaaact catgctgaga cgcacggagt ccgtcgtcga aaaactcctc  3660
acaaactgga tgtccgtctg cctttctgga tttctccggg agactgtcgg agagcccttc  3720
tatttgctgg tgacgactct gaaccagaaa attaacaagg gtcccgtgga tgtaatcact  3780
tgcaaagccc tgtacacact taatgaagac tggctgttgt ggcaggttcc ggaattcagt  3840
actgtggcat taaacgtcgt cttttgaaaaa atcccgaaa acgagagtgc agatgtctgt  3900
cggaatattt cagtcaatgt tctcgactgt gacaccattg gccaagccaa agaaaagatt  3960
ttccaagcat tcttaagcaa aaatggctct ccttatggac ttcagcttaa tgaaattggt  4020
cttgagcttc aaatgggcac acgacagaaa gaacttctgg acatcgacag ttcctccgtg  4080
attcttgaag atggaatcac caagctaaac accattggac actatgagat atcaaatgaa  4140
tccactataa aagtctttaa gaagatagca aatttttactt cagatgtgga gtactcggat  4200
gaccactgcc atttgatttt accagattcg gaagcattcc aagatgtgca aggaaagaga  4260
catcgaggga agcacaagtt caaagtaaaa gaaatgtatc tgacaaagct gctgtcgacc  4320
aaggtggcaa ttcattctgt gcttgaaaaa ctttttagaa gcatttggag tttacccaac  4380
agcagagctc catttgctat aaaatacttt tttgacttttt tggacgccca ggctgaaaac  4440
aaaaaaatca cagatcctga cgtcgtacat atttggaaaa caaacagcct tcctcttcgc  4500
ttctgggtaa acatcctgaa gaaccctcag tttgtctttg acattaagaa gacaccacat  4560
atagacggct gtttgtcagt gattgccagg cattcatgg atgcattttc tctcacagag  4620
cagcaactag ggaaggaagc accaactaat aagcttctct atgccaagga tatcccaacc  4680
tacaagaag aagtaaaatc ttattacaaa gcaatcaggg attttgcctcc attgtcatcc  4740
tcagaaatgg aagaattttt aactcaggaa tctaagaaac atgaaaatga attttaatgaa  4800
gaagtggcct tgacagaaat ttacaaatac atcgtaaaat attttgatga gattctaaat  4860
aaactagaaa gagaacgagg gctggaagaa gctcagaaac aactcttgca tgtaaaagtc  4920
ttatttgatg aaaagaagaa atgcaagtgg atgtaagcac tctgggcct ggcttaatct  4980
ggcaaagttc ttcagacgac ttgggagcaa aatggctgct tgagctactc tgtgtcgtta  5040
atttgttgtt tgcacatagg ttccactttg ggcactgtct ttttaagaga ccaaggcaca  5100
tgcacagctt ttagaaagca taccaaccct tgtgcctgtg tgtataccgt gggaaccctt  5160
ctgtaaatag agttgaagtg gttgttgcaa acagcctcct tgtttacaga gaatacaagg  5220
ccagtaagcg aatgtcagta ttgtaactac agtctccact taagcacaat gatataagtg  5280
gttttgtttg aaaactacag ctatgtagca cttgtgctac actgcacctc tgcattgtaa  5340
agggatactg ccagtgctca aaacaaaatg tgaaatgaat catttggaaa caaggtgggg  5400
gtgttagggc aacctcgagg atttgcagca ttgaaacttt ccccagtagt tcttggaaaa  5460
gctgaccgca gaatttggta gtgtacactt agcatttgtg agtgtgtgtg tgtgtttaaa  5520
ccaaaaacta acagtgttgc aacattgttg aagggctcg tgttttttcag tggtcatcaa  5580
ctgcactcca tcaaactcac ctccatttca ccaaggagct ctaaagtaag gagagtgggc  5640
tttatttaaa tgaacagcat tttaaccaga tactttgtcc taatgtatgt tcctttttctt  5700
catctgtttt ttcatactaa atgtatttga tagtggacat gttggatatt atacaaaaaa  5760
atcattaatt catttctgtt ccaaaacctt tgatcagaac gatctgtgga agagtaactc  5820
catttctata tgagtgagtg tctccttgct ttagatttct ggtgaaccct gtggttatga  5880
atacttgtgt gtgatttaaa aaaaaaaaga tacattttac atttcatcga attgctgttc  5940
acactggagt attatatata aatatatata tttgaggccc aaggcctgaa aaatattagt  6000
atacaacttg gtatccttagt cttactatgt acttttttgaa agtattcctc gcaggagaaa  6060
gaatttaaaa tacccatttt attcatgcct ttctttttaa agaattctct atccagttat  6120
actgtagtct ttttagtgct gatttttttaa ttcctgaatt tttgctgctc atgaccagtt  6180
ttaataccac tgtgttttcc ttctattaaa ccagaagaag taaacagcat aattggcaac  6240
tcttgagctt tcttgtggc aggcacctttt taccccttggt gctccaaatc ccccatctag  6300
gaaagaaaat ttttttcaagt caaataacat tgatcacata ttccttgaaa tcattttacca  6360
acactgtatg gagcattagg atttaaatat gaatttgtct taaaggcaat tccttttttgc  6420
ttctgtatta tctggaaaag catgagagag gtgacacctc aacaaactga tcagagaaaa  6480
taagcagtta ctaccctgat aggcaccttc ccaatcctgt tgctttttgac cattgtctgt  6540
ccaacgaca cacctcaaac aaacaaaact accaaataga tgacagatca gaataaaggt  6600
gagaggtctg gtcccccattg aaggctgcta cagtcttcaa agaggtgaag gagttcataa  6660
gagaacaaca gtaggaaagt tgagagccaa gggtaggaga gttgcccaaa agacttcccc  6720
tactacttta gggtactgaa aactcaaagg atcagctaca gctttatcta agtatttact  6780
aaatgctaca tgagggtgtc cctgtccagc tttctggcac atgagtcctg tgtggagagt  6840
tacctcctct tccagggact gtgctgttgg gaactttggc caagtcactt accctctttgt  6900
gcctcaattt ctgtataata tttctaagct acctcactga ggtggttgatga agattcacta  6960
atgtatgtag cgtgttttgtc aatcctccag tgaaaagcac tatctagatc acatttttgga  7020
tcacattagc caaatgcagt aaatggccaa attagatgtg tgctgaagac aatcagtcac  7080
tgggtctata ttaaacagca accagagcaa caaatggcaa acaatttcta ttttcaagtt  7140
tctttgcata ttttttttggt gcaaaaccat ttataaactt ttttttctaa cactagtgtc  7200
tacagcagca ttcaaaaaaa ttctgttacc ttttctgtat taggattaa agtctatttc  7260
ttattgtata cctgattgaa gctgttcttg gagatgaatg ttttaaatgt ctatatccaa  7320
aaaataaaca ttttgatgta actgtg                                       7346

SEQ ID NO: 21           moltype = DNA    length = 2828
FEATURE                 Location/Qualifiers
source                  1..2828
                        mol_type = other DNA
                        organism = Homo sapiens
SEQUENCE: 21
agaacagtga cagcgccgcg gcagccgacc ccgcctcctc ggcggacagc gatgctcagc    60
tggctgcggc cgagtcatcg cctagcgctg gcagggccgc tgaccgaccg acggaggcgc   120
cgattggccg attgtccact gcgcagaagg agcagctgct ccgcgccccg ccgcgccgcg   180
ctgagggcga ggtccgcagg gccgcgggga agccgagggc tgccgaggaa ccctgcaggt   240
gtcactcggg acgcggaagt gcgcttgccg aggtttgctt tacaatacgc ttgagactcc   300
ccgacaagcg taatttggtc gagttcgacg ggaaagtact ctcccacccc cagcgccggc   360
cgcgtagtcc gaggttactg tccccggcgc gtcctctgtt gccccagtcc agaggctgcc   420
cttgaacccg ggcgcgcacg agcgcagggc atccgaggcg acagccctg gcacggcccg   480
acctgtaccc agcctggcag gaagactgta atcgtgggaa tacagctacc tacccaggca   540
```

```
atatgaagat tttatttgta gaacctgcca ttttccttag tgcatttgct atgactttga    600
ccggtccact gacaacgcaa tatgtttatc ggagaatatg ggaagaaact ggcaactaca    660
cttttccatc tgatagcaat atttctgagt gtgaaaaaaa caaaagcagc ccaattttg    720
cattccagga ggaagttcag aaaaaagtgt cacgttttaa tctgcagatg gacataagtg    780
gattaattcc tggtctagtg tctacattca tacttttgtc tattagtgat cactacggac    840
gaaaattccc tatgattttg tcttccgttg gtgctcttgc aaccagcgtt tggctctgtt    900
tgctttgcta ttttgccttt ccattccagc ttttgattgc atctaccttc attggtgcat    960
tttgtgcaa ttataccaca ttttggggag cttgctttgc ctatatagtt gatcagtgta    1020
aagaacacaa acaaaaaaca attcgaatag ctatcattga cttctactt ggacttgtta    1080
ctggactaac aggactgtca tctggctatt ttattagaga gctaggtttt gagtggtcgt    1140
ttctaattat tgctgtgtct cttgctgtta atttgatcta tattttattt tttctcggag    1200
atccagtgaa agagtgttca tctcagaatg ttactatgtc atgtagtgaa ggcttcaaaa    1260
acctatttta ccgaacttac atgcttttta agaatgcttc tggtaagaga cgattttgc     1320
tctgtttgtt actttttaca gtaatcactt atttttttgt ggtaattggc attgcccaa     1380
tttttatcct ttatgaattg gattcaccac tctgctggaa tgaagttttt ataggttatg    1440
gatcagcttt gggtagtgcc tctttttga ctagttcct aggaatatgg ctttttttctt    1500
attgtatgga agatattcat atggccttca ttgggatttt taccacgatg acaggaatgg    1560
ctatgaccgc gtttgccagt acaacactga tgatgttttt agccaggggtg ccgttcctt     1620
tcactattgt gccattctct gttctacggt ccatgttgtc aaaagtggtt cgttcgactg    1680
aacaaggtac cctgtttgct tgtattgctt tcttagaaac acttggagga gtcactgcag    1740
tttctacttt taatggaatt tactcagcca ctgttgcttg gtaccctggc ttcacttttcc   1800
tgctgtctgc tggtctgtta tacttccag ccatcagtct atgtgttgtc aagtgtacca    1860
gctggaatga gggaagctat gaacttctta tacaagaaga atccagtgaa gatgcttcag    1920
acagagcctg ttaagctgct attgatagtc ggagcttata tactgtgact tctgaagact    1980
atacatgaat tccacaatca gtgctttgtt gatacaaaat ccttaaaagg gaggcacttt    2040
aaagaatatg tatttttcac ttttcttaat atgtttacat ggtgacaggc atgataaat     2100
ttctatatgt aatgggtaat tggaaaaaa tagatgataa ataaaattgc tctaaagaag     2160
ttaaaaaact gaatgaacag ctaatactgg tataaagtaa ctaatgtttg gagccaaacat   2220
ttgttccttg tgtcagcaaa aggatattca cattccatga tccctggctg agaattctgc    2280
ctctagtctt tcttacccag ctgttgtcta tccttgttca attataaata ctgctaaggg    2340
catttttaaa atacgatctt gtactcctta aatttgaatc cgtcagcacg gtcactcata    2400
ggaaaatgat caaacaagca agccagtcat gatttgactc cttcccatct catttcttac    2460
tgccttacgc tcatcctgag gtccaccttg gtctctaaaa acaccatgtg ttctcatgcc    2520
tccatgtctt ttcacacact gttccatttg ctcttcctcc cacattacat tgaaacttttc   2580
aagcctcagt cgaaacattg cttcttctgg atagcagcct tcttgacatc cctcctcact    2640
ccccagtccc tacagggctt ccatagctct ttgtgtgcac ttcgatccca gcattttcca    2700
tcgacttgta attgtttctg ctacctgaca atcatcgcct tgagtactgg gacaacctttc   2760
gattactcat tatatcctca ataaatattt gttgaactaa aaaaaaaaaa aaaaaaaaaa    2820
aaaaaaaa                                                              2828

SEQ ID NO: 22         moltype = DNA   length = 2840
FEATURE               Location/Qualifiers
source                1..2840
                      mol_type = other DNA
                      organism = Homo sapiens
SEQUENCE: 22
gttttgtgc aggaacagcc cctcccgtct ttgtcctggc ggtgagcacc cagggctaag      60
cttttgaaca ctttctttgt gtttggattc agcccaggca atgcatattt gctttcattt    120
cttcttgagc ttgaggagct cctgggtgca aatcttggaa aatgaggatc tctgagcctt    180
tccaggccag ctctttgttt tgtagcagac aattgaggct ttgaaaagga agtgggtgg     240
gggcaccca caggtggccc tcatcaccca attgccagtg cctgcaggct gcttcagcag    300
aggcccagag tcaaagagga cttaaaacca gctgtcgttt ctcccttagc ttctgtgtat    360
gagagaaacg acttctgttt ttcaaagtaa gaacaaggag gaatttgttt ctaaagaac     420
attaaaacac aggctcgtgg tctaaaagca aatggttcag caggatgttc agggccttaa    480
agcacagtca gcaggactca gcatctccca gcacctgctc tccggttgtc atggtaacat    540
catccccaac ccaaccacct tgtccagccg agagacagca atcataagga gggacctcgg    600
tttccccga ggatcctggg cttccttcct gaaacgcttg cttctgagct cagcaaccag    660
gaacaccagg ccagcccatc cccagcacct ctgtggagat gagggacaaa gtcctacagt    720
ccctcttcct gttctgatga gaaagggagg gaagaaaaca taccccgagc gcctgcaata    780
tggtcatgac acttttcaaa agcctgtgct atggagtcat gatcagaaac cagagtgtgg    840
agagggtcag cagcctgcct cagagcagcc agctaggcgg ggagtggtaa atttgggact    900
tgtacccagg catgactggc tccgagccca gtgctccact ctatgaaatg ttccctgggc    960
ctcagttgct ttccttttcct ttgcaggccg cgggctgctg ccactctggc agctggtgag   1020
ttagctggag ggcaacattc caaagcaggg gcagcatgct gcttcctcc tgtgctgaa     1080
cctgcgggga agtccgttga ctccaccgc tgaaggagc tggcaacacc aggatgaggt    1140
cccaggggac gggagcaggt acccactgtc tgtctacctt cccactggaa aagcacggac    1200
aggccagccc ttgcgggggc aggcagagga cagagttggc tttgcgcggt ctctgcctgc    1260
tgagcagttc caattcctct catggagaa acaaggaggc agtcgcttgt gcatgttcca    1320
gaagttttac tgggaggag gaagcggaca gaggaagctg tgtgtgcatg tgaagggtg     1380
ggcagggtgg gagggatgca cgcgtatgtg agcatagcat gtgtgagtac tacacacatc    1440
tccatgcaga agcacaactg ggcagccctg gcttccagct ctgggcttca gcacaacaga    1500
caccagcctg tggtctctca gaagccaggg agaccacatc gggctcagga cgttttaccc    1560
aaagtccaga gtttttatgc ctctccctgg cattctccat aaagaaggga aggtcagatg    1620
acccccttaga tctgtgtcat ctgggaattt ccttgggctg gtttagacac gatgccctct    1680
ttttctcagg atagcagata acctgctttg aaagaggggc taattctgtg ggtcctaaat    1740
tttctccttt ctctctctct ttctgtgtgt gtgtgttggg aaaatggcaa gtttccaata    1800
ccagctttgt aggaacgatt acgttttccc tccaatttca agtccgaaag accagagccc    1860
tcattccaaa gccccccacc cagatggatt ttttcgtttc atttgtcatc cgtcccatgg    1920
gagggcccca tgtctcctca gaacccatcc tggaggcagc aggtcgggta gagtgagttt    1980
```

```
ggcctgctca tgacctccac ccctgagatt gtgaacaagg atgtctgggg cgatgctgag   2040
aatgtttttg aagctgctcc cagatgacgc tgatgatcac accagattga gtgctgcgat   2100
cgccttgagt ccaacctctg cataaacgag gttctcataa acaagttcac tctaccctaa   2160
gctaagtcta tgtgagcaaa cccacttcat cctttgtacc tggagacctg gttacactaa   2220
cctgatactg acctgttcat gtagctggaa tggtgtgttt catgcagtgt ggaccaagca   2280
atggcatggg gtgtgtgtgt gtgtgtgtgt gtgtctgtgt gtgtgtgttt gtgtatgcgt   2340
tcacacttgt gtgtgtatat gtgcatgtag atgctgcata aatgattttt gatgtcaaag   2400
acaaacacat tccattgttt taaatattct attatgtaaa caatacgcag agggaccata   2460
tctactcttg tcatattatt tgtgatggta aaacatgcat ttgcaataaa ttaagctttc   2520
tgggaaggca agcagtattg gagccaaacg actgtctcgg aacatgtgtg tgttatctcg   2580
gttcatatca agtccaaagc taatggagcc ttccccgcca tccagggagg aacaccagga   2640
ccccggagtt tcttcttagt gctatatttt aagttgcat tgacgttttc ctccccttcc   2700
ttttgtgcaa gttggaagta gcagtgttct aaaagatggt ttgacgtttt tgctgttgtt   2760
ttatgttttt aaaaatgtat ctgctttgtg tttggaaata aaaatctcta ttttggtcta   2820
tgaaaaaaaa aaaaaaaaaa                                               2840

SEQ ID NO: 23        moltype = DNA  length = 2309
FEATURE              Location/Qualifiers
source               1..2309
                     mol_type = other DNA
                     organism = Homo sapiens
SEQUENCE: 23
gcggggcgg gccggggcgg ggccaggccg gctagagggg cgggtctagc ggcggccccc     60
ggcgaagttc actgcgcttg cgctgacaga cgcaagatgg cggacagtgc ggaactaaag   120
caaatggtta tgagccttag agtttctgaa ctccaagtac tgttgggcta cgccgggaga   180
aacaagcacg gacgcaaaca cgaacttctc acaaaagccc tgcatttgct aaaggctggc   240
tgtagtcctg ctgtgcaaat gaaaattaag gaactctata ggcggcggtt cccacagaaa   300
atcatgacgc ctgcagactt gtccatcccc aacgtacatt caagtcctat gccagcaact   360
ttgtctccat ctaccattcc acaactcact tacgatggtc accctgcatc atcgccatta   420
ctccctgttt ctcttctggg acctaaacat gaactgaaac tcccacatct tacatcagct   480
cttcacccag tccatccgga tataaaactt caaaaattac cattttatga tttactggat   540
gaactgataa aacccaccag tctagcatca gacaacagtc agcgcttctcg agaaacctgt   600
tttgcatttg ccttgacacc acaacaagtg cagcaaatca gtagttccat ggatatttct   660
gggaccaaat gtgacttcac agtacaggtc cagttaaggt tttgtttatc agaaaccagt   720
tgtccacaag aagatcactt cccacccaat ctttgtgtga agtgaatac aaaaccttgc   780
agccttccag gttaccttcc acctacaaaa aatggcgtgg aaccaaagcg acccagccga   840
ccaattaata tcacctcact tgtccgactg tccacaacag taccaaacac gattgttgtt   900
tcttggactg cagaaattgg aagaaactat tccatgcag tatatcttgt aaaacagttg   960
tcctcaacag ttcttcttca gaggttacga gcaaaggaga taaggaatcc ggatcattct  1020
agagctttaa ttaaagagaa gttgactgcg gatccagaca gtgaaatagc tacaaccagc  1080
ctaagggttt ctctactatg tccacttggt aaaatgcggc tgacaattcc gtgtcgggcc  1140
cttacatgtt ctcatctaca atgttttgac gcaactcttt acattcagat gaatgagaaa  1200
aaaccaacct gggtttgtcc tgtctgtgat aagaaggctc catatgaaca cctattatt   1260
gatggcttgt ttatggaaat cctaaagtac tgtacagact gtgatgaaat acaattttaag  1320
gaggatggca cttgggcacc gatgagatca aaaaaggaag tacgaagt ttctgcctct     1380
tacaatggag tcgatggatg cttgagctcc acattggagc atcaggtagc gtctcaccac  1440
cagtcctcaa ataaaaacaa gaaagtagaa gtgattgacc taaccataga cagttcatct  1500
gatgaagagg aagaagagcc atctgccaag aggacctgtc cttccctatc tcccacatca  1560
ccactaaata taaaggcat tttaagtctt ccacatcaag catctccagt atcccgcacc    1620
ccaagccttc ctgctgtaga cacaagctac attaatacct ccctcatcca agactatagg  1680
catcctttcc acatgacacc catgccttac gacttacaag gattagattt ctttccttt   1740
ttatcaggag acaatcagca ttacaacacc tccttgcttg ccgctgcagc agcagcagtt  1800
tcagatgatc aagaccttcc acactcgtct cggtttttcc cgtatacctc ctcacagatg  1860
tttcttgatc agttaagtgc aggaggcagt acttctctgc caaccaccaa tggaagcagt  1920
agtggcagta acagcagcct ggtttcttcc aacagcctaa gggaaagcca tagccacacc  1980
gtcacaaaca ggagcagcac ggacacggca tccatctttg gcatcatacc agacattatt  2040
tcattggact gattcccagg ccctgctgct cccatcccca cccagatcg aatgaacttg    2100
gcagaaagaa gagaactttg tgctctgttt taccttactc tgtttagaaa agtatacaag  2160
cgtgttttt ttcctttttt tagggaaaaa attaaaagaa atgtacagag aacaaaacta    2220
tattttcagt tttacttttg tatataaatc taagactgcc tgtgtgataa aacacttgtt  2280
taaaaaaaaa aaaaaaaaaa aaaaaaaa                                     2309

SEQ ID NO: 24        moltype = DNA  length = 1740
FEATURE              Location/Qualifiers
source               1..1740
                     mol_type = other DNA
                     organism = Homo sapiens
SEQUENCE: 24
ccagcgttag cccgcggcca ggcagccggg aggagcggcg cgcgctcgga cctctcccgc     60
cctgctcgtt cgctctccag cttgggatgg ccggctacct gcgggtcgtg cgctcgctct   120
gcagagcctc aggctcgcgg ccggcctggg cgccggcggc cctgacagcc cccacctcgc   180
aagagcagcc gcgcgccac tatgccgaca aaaggatcaa ggtggcgaag cccgtggtgg    240
agatggatgg tgatgagatg accccgtatta tctggcagtt catcaaggag aagctcatcc  300
tgcccacgt ggacatccag ctaaagtatt ttgacctcgg gctcccaaac cgtgaccaga   360
ctgatgacca ggtcaccatt gactctgcac tggccaccca gagtacagt gtggctgtca   420
agtgtgccac catcaccccct gatgaggccc gtgtggaaga gttcaagctg aagaagatgt  480
ggaaaagtcc caatgaact atccggaaca tcctgggggg gactgtcttc cgggagccca   540
tcatctgcaa aaacatccca cgcctagtcc ctggctggac caagcccatc accattggca   600
ggcacgccca tggcgaccag tacaaggcca cagactttgt ggcagaccgg gccggcactt   660
```

```
tcaaaatggt cttcacccca aaagatggca gtggtgtcaa ggagtgggaa gtgtacaact    720
tccccgcagg cggcgtgggc atgggcatgt acaacaccga cgagtccatc tcaggttttg    780
cgcacagctg cttccagtat gccatccaga agaaatggcc gctgtacatg agcaccaaga    840
acaccatact gaaagcctac gatgggcgtt tcaaggacat cttccaggag atctttgaca    900
agcactataa gaccgacttc gacaagaata agatctgtga tgagcaccgg ctcattgatg    960
acatggtggc tcaggtcctc aagtcttcgg gtgtgctttg tgtgggcctg caagaactat g   1020
acggagatgt gcagtcagac atcctggccc agggctttgg ctcccttggc ctgatgacgt   1080
ccgtcctggt ctgccctgat gggaagacga ttgaggctga ggccgctcat gggaccgtca   1140
cccgccacta tcgggagcac cagaagggcc ggcccaccag caccaacccc atcgccagca   1200
tctttgcctg gacacgtggc ctggagcacc ggggaagct ggatgggaac caagacctca   1260
tcaggtttgc ccagatgctg gagaaggtgt gcgtggagac ggtggagagt ggagccatga   1320
ccaaggacct ggcgggctgc attcacggcc tcagcaatgt gaagctgaac gagcacttcc   1380
tgaacaccac ggacttcctc gacaccatca agagcaacct ggacagagcc ctgggcaggc   1440
agtaggggga ggcgccaccc atggctgcag tggaggggcc agggctgagc cggcgggtcc   1500
tcctgagcgc ggcagagggt gagcctcaca gcccctctct ggaggccttt ctaggggatg   1560
ttttttttata agccagatgt ttttaaaagc atatgtgtgt ttcccctcat ggtgacgtga   1620
ggcaggagca gtgcgtttta cctcagccag tcagtatgtt ttgcatactg taatttatat   1680
tgcccttgga acacatggtg ccatatttag ctactaaaaa gctcttcaca aaaaaaaaaa   1740

SEQ ID NO: 25          moltype = DNA   length = 1552
FEATURE                Location/Qualifiers
source                 1..1552
                       mol_type = other DNA
                       organism = Homo sapiens
SEQUENCE: 25
ggtcgcttta agaaaggagt agctgtaatc tgaagcctgc tggacgctgg attagaaggc     60
agcaaaaaaa gctctgtgct ggctggagcc cctcagtgt gcaggcttag agggactagg    120
ctgggtgtgg agctgcagcg tatccacagg ccccaggatg caggccctgg tgctactcct    180
ctgcattgga gccctcctcg gcacagcag ctgccagaac cctgccagcc ccccggagga    240
gggctcccca gaccccgaca gcacaggggc gctggtgga gaggaggatc ctttcttcaa    300
agtcccccgtg aacaagctgg cagcggctgt ctccaacttc ggctatgacc tgtaccgggt    360
gcgatccagc acgagcccca cgaccaacgt gctcctgtct cctctcagtg tggccacggc    420
cctctcggcc ctctcgctgg gagcggagca gcgaacagaa tccatcattc accgggctct    480
ctactatgac ttgatcagca gcccagacat ccatgaagca tataaggagc tccttgacac    540
ggtcactgcc ccccagaaga acctcaagag tgcctccccgg atcgtcttttg agaagagct    600
gcgcataaaa tccagcttttg tggcacctct ggaaaagtca tatgggacca ggcccagagt    660
cctgacgggc aaccctcgct tggacctgca agagatcaac aactgggtgc aggcgcagat    720
gaaagggaag ctcgccaggt ccacaaagga aattcccgat gagatcagca ttctccttct    780
cggtgtgcga cacttcaagg ggcagtgggt aacaaagttt gactccagaa agacttccct    840
cgaggatttc tacttggatg aagagaggac cgtgagggtc cccatgatgt cggacccctaa   900
gctgttttta cgctatggct tggattcaga tctcagctgc aagattgccc agctgccctt    960
gaccggaagc atgagtatca tcttcttcct gccccctgaaa gtgacccaga atttgacctt   1020
gatagaggag agcctcacct ccgagttcat tcatgacaga gaccgagaac tgaagaccgt   1080
gcaggcggtc ctcactgtcc ccaagctgaa gctgagttat gaaggcgaag tcaccagtc   1140
cctgcaggag atgaagctgc aatccttgtt tgattcacca gactttagca agatcacagg   1200
caaacccatc aagctgactc aggtggaaca ccggggctgg ctttgagtgga acgaggatgg   1260
ggcgggaacc acccccagcc cagggctgcc gcctgcccac ctcaccttcc cgctggacta   1320
tcaccttaac cagcctttca tcttcgtact gagggacaca gacacagggg cccttctcttt   1380
cattggcaag attctggacc ccaggggccc ctaatatccc agtttaatat tccaatacccc   1440
tagaagaaaa cccgagggac agcagattcc acaggacacg aaggctgccc ctgtaaggtt   1500
tcaatgcata caataaaaga gctttatccc taaaaaaaaa aaaaaaaaaa aa            1552

SEQ ID NO: 26          moltype = DNA   length = 4816
FEATURE                Location/Qualifiers
source                 1..4816
                       mol_type = other DNA
                       organism = Homo sapiens
SEQUENCE: 26
gttcccggat ttttgtgggc gcctgccccg cccctcgtcc ccctgctgtg tccatatatc     60
gaggcgatag ggttaaggga aggcggacgc ctgatgggtt aatgagcaaa ctgaagtgtt    120
ttccatgatc ttttttgagt cgcaattgaa gtaccactc ccgagggtga ttgcttcccc    180
atgcggggta gaacctttgc tgtcctgttc accactctac ctccagcaca gaatttggct    240
tatgcctact caatgtgaag atgatgagga tgaaaacctt tgtgatgatc cactttccact    300
taatgaatgg tggcaaaagca aagctatatt caagaccaca tgcaaagcta ctccctgagc    360
aaagagtcac agataaaacg ggggcaccag tagaatggcc aggacaaacg cagtgcagca    420
cagagactca gaccctggca gccatgcctg cgcaggcagt gatgagagtg acatgtactg    480
ttgtggacat gcacaaaagt gagtgtgcac cggcacagac atgaagctgc ggctccctgc    540
cagtcccgag acccaccctgg acatgctccg ccacctctaca cagggctgcc aggtggtgca    600
gggaaacctg gaactcacct acctgcccac caatgccagc ctgtccttcc tgcaggatat    660
ccaggaggtg caggggctacg tgctcatcgc tcacaaccca gtgaggcagg tccactgca    720
gaggctgcgg attgtgcgag gcacccagct cttttgaggac aactatgccc tggccgtgct    780
agacaatgga gaccgctga caataccac ccctgtcaca ggggcctccc caggaggcct    840
gcgggagctg cagcttcgaa gcctcacaga gatcttgaaa ggaggggtct tgatccagcg    900
gaacccctcac tctgtctacc aggacacgat ttttgtggag gacatctttcc acaagaacaa    960
ccagctggct ctcacactga tagacaccaa ccgctctcgg gcctgccacc cctgttctcc   1020
gatgtgtaag ggctcccgct gctggggaga gagttctgag gattgtcaga gcctgacgcg   1080
cactgtctgt gccggtggct gtgccgctc aaggggcca ctgccactg actgctgcca   1140
tgagcagtgt gctgccggct gcacgggccc caagcactct gactgctggg cctgcctcca   1200
cttcaaccac agtggcatct gtgagctgca ctgcccagcc ctggtcacct acaacacaga   1260
```

```
cacgtttgag tccatgccca atcccgaggg ccggtataca ttcggcgcca gctgtgtgac   1320
tgcctgtccc tacaactacc tttctacgga cgtgggatcc tgcaccctcg tctgcccct    1380
gcacaaccaa gaggtgacag cagaggatgg aacacagcgg tgtgagaagt gcagcaagcc   1440
ctgtgcccga gtgtgctatg gtctgggcat ggagcacttg cgagaggtga gggcagttac   1500
cagtgccaat atccaggagt ttgctggctg caagaagatc tttgggagcc tggcatttct   1560
gccggagagc tttgatgggg acccagcctc caacactgcc ccgctccagc cagagcagct   1620
ccaagtgttt gagactctgg aagagatcac aggttaccta tacatctcag catggccgga   1680
cagcctgcct gacctcagcg tcttccagaa cctgcaagta atccgggac gaattctgca    1740
caatggcgcc tactcgctga ccctgcaagg gctgggcatc agctggctgg ggctgcgctc   1800
actgagggaa ctgggcagtg gactggccct catccaccat aacacccacc tctgcttcgt   1860
gcacacggtg ccctgggacc agctctttcg gaacccgcac caagctctgc tccacactgc   1920
caaccggcca gaggacgagt gtgtgggcga gggcctggcc tgccaccagc tgtgcgcccg   1980
agggcactgc tgggtccag ggcccaccca gtgtgtcaac tgcagccagt tccttcgggg    2040
ccaggagtgc gtggaggaat gccgagtact gcaggggctc cccagggagt atgtgaatgc   2100
caggcactgt ttgccgtgcc accctgagtg tcagcccag aatggctcag tgacctgttt    2160
tggaccggag gctgaccagt gtgtggcctg tgcccactat aaggaccctc ccttctgcgt   2220
ggcccgctgc cccagcggtg tgaaacctga cctctcctac atgcccatct ggaagtttcc   2280
agatgaggag ggcgcatgcc agccttgcc catcaactgc acccactcct gtgtggacct    2340
ggatgacaag ggctgccccg ccgagcagag agccagccct ctgacgtcca tcatctctgc   2400
ggtggttggc attctgctgg tcgtggtctt ggggtgtgtc tttgggatcc tcatcaagcg   2460
acggcagcag aagatccgga gtacacgat gcggagactg ctgcaggaaa cggagctggt    2520
ggagccgctg acacctagcg gagcgatgcc caaccaggca cagatgcgga tcctgaaaga   2580
gacggcgctg aggaaggtga aggtgcttgg atcggcgct tttggcacag tctacaaggg    2640
catctggatc cctgatgggg agaatgtgaa aattccagtg gccatcaaag tgttgaggga   2700
aaacacatcc cccaaagcca acaaagaaat cttagacgaa gcatacgtga tggctggtgt   2760
gggctcccca tatgtctccc gccttctggg catctgcctg acatccacgg tgcagctggt   2820
gacacagctt atgcctatg gctgcctctt agaccatgtc cgggaaaacc gcggacgcct    2880
gggctcccag gacctgctga actggtgtat gcagattgcc aaggggatga gctacctgga   2940
ggatgtgcgc ctcgtacaca gggacttggc cgctcggaac gtgctggtca agagtcccaa   3000
ccatgtcaaa attacagact tcgggctggc tcggctgctg gacattgacg agacagagta   3060
ccatgcagat gggggcaagg tgcccatcaa gtggatggcg ctggagtcca ttctccgccg   3120
gcggttcacc caccagagtg atgtgtggag ttatggtgtg actgtgtggg agctgatgac   3180
ttttggggc aaaccttacg atgggatccc agcccgggag atccctgacc tgctggaaaa   3240
gggggagcgg ctgccccagc cccccatctg caccattgat gtctacatga tcatggtcaa   3300
atgttggatg attgactctg aatgtcggcc aagattccgg gagttggtgt ctgaattctc   3360
ccgcatggcc agggaccccc agcgctttgt ggtcatccag aatgaggact gggcccagc    3420
cagtcccttg gacagcacct tctaccgctc actgctggag gacgatgaca tggggggacct   3480
ggtggatgct gaggagtatc tggtacccca gcagggcttc ttctgtccag accctgcccc   3540
gggcgctggg ggcatggtcc accacaggca ccgcagctca tctaccagga gtggcggtgg   3600
ggacctgaca ctagggctgg agccctctga gaggaggcc cccaggtctc cactgcacc    3660
ctccgaaggg gctggctccg atgtatttga tggtgacctg ggaatgggg cagccaaggg   3720
gctgcaaagc ctccccacac atgacccag ccctctacag cggtacagtg aggacccac    3780
agtaccccctg ccctctgaga ctgatgccta cgttgccccc ctgacctgca gtcccaggcc   3840
tgaatatgtg aaccagccag atgttcggcc ccagccccct tcgccccgag agggccctct   3900
gcctgctgcc cgacctgctg gtgccactct ggaaaggccc aagactctct ccccagggaa   3960
gaatgggtc gtcaaagacg tttttgcctt tggggtgcc gtgagaaacc ccgagtactt    4020
gacaccccag ggaggagctg cccctcagcc ccaccctca cctgccttca gcccagcctt   4080
cgacaacctc tattactggg accaggacc accagagcgg ggggctccac ccagcacctt    4140
caaagggaca cctacggcag agaacccaga gtacctgggt ctggacgtgc agtgtgaac   4200
cagaaggcca agtccgcaga agccctgatg tgtcctcagg gagcagggaa ggcctgactt   4260
ctgctggcat caagaggtgg gagggccctc cgaccacttc cagggggaacc tgccatgcca   4320
ggaacctgtc ctaaggaacc ttccttcctg cttgagttcc cagatggctg aaggggtcc    4380
agcctcgttg gaagaggaac agcactggga agtctttgtg gattctgagg ccctgcccaa   4440
tgagactcta gggtccagtg gatgccacag cccagcttgg ccctttcctt ccagatcctg   4500
ggtactgaaa gccttaggga agctggcctg agaggggaag cggccctaag gagtgtcta    4560
agaacaaaag cgaccccattc agagactgtc cctgaaacct agtactgccc cccatgagga   4620
aggaacagca atggtgtcag tatccaggct ttgtacagag tgcttttctg tttagttttt   4680
acttttttg ttttgttttt ttaaagatga aataaagacc caggggagaa atgggtgttg    4740
tatgggagg caagtgtggg gggtccttct ccacacccac tttgtccatt tgcaaatata   4800
ttttggaaaa cagcta                                                  4816
```

```
SEQ ID NO: 27             moltype = DNA  length = 6831
FEATURE                   Location/Qualifiers
source                    1..6831
                          mol_type = other DNA
                          organism = Homo sapiens
SEQUENCE: 27
ccaggcccca ttgttcccgg tttccagcca tggctgccat tacctgacca gcgccacagc   60
cggtctctct gcaggcgccg ggagaagtga ccagagcaat ttctgctttt cacagggcgg   120
gtttctcaac ggtgacttgt gggcagtgcc ttctgctgag cgagtcatgg cccgaaggca   180
gaactaactg tgcctgcagt cttcactctc aggatgcagc cgaggtgggc caagggggcc   240
acgatgtggc ttgagtcct gctgaccctt ctgctctgtt caagcttga gggtcaagaa     300
aactctttca caatcaacag tgttgacatg aagagcctgc cggactggac ggtgcaaaat   360
gggaagaacc tgacctgca gtgcttcgcg gatgcgaca ccactcctca cgtcaagcct    420
cagcaccaga tgctgttcta taggatgac gtgctgtttt acaacatctc ctccatgaag    480
agcacagaga gttatttttat tcctgaagtc cggatctatg actcagggac atataaatgt   540
actgtgattg tgaacaacaa agagaaaacc actgcagagt accaggtgtt ggtggaagga   600
gtgcccagtc ccagggtgac actggacaag aaagaggcca tccaaggtgg gatcgtgagg   660
gtcaactgtt ctgtcccaga ggaaaaggcc ccaatacact tcacaattga aaaacttgaa   720
```

```
ctaaatgaaa aaatggtcaa gctgaaaaga gagaagaatt ctcgagacca gaattttgtg   780
atactggaat tccccgttga ggaacaggac cgcgttttat ccttccgatg tcaagctagg   840
atcatttctg ggatccatat gcagacctca gaatctacca agagtgaact ggtcaccgtg   900
acggaatcct tctctacacc caagttccac atcagcccca ccggaatgat catggaagga   960
gctcagctcc acattaagtg caccattcaa gtgactcacc tgcccagga gtttccagaa   1020
atcataattc agaaggacaa ggcgattgtg gcccacaaca gacatggcaa caaggctgtg   1080
tactcagtca tggccatggt ggagcacagt ggcaactaca cgtgcaaagt ggagtccagc   1140
cgcatatcca aggtcagcag catcgtggtc aacataacag aactatttc caagcccgaa   1200
ctggaatctt ccttcacaca tctggaccaa ggtgaaagac tgaacctgtc ctgctcccat   1260
ccaggagcac ctccagccaa cttcaccatc cagaaggaag atacgattgt gtcacagact   1320
caagatttca ccaagatagc ctcaaagtcg acagtgggga cgtatatctg cactgcaggt   1380
attgacaaag tggtcaagaa aagcaacaca gtccagatag tcgtatgtga aatgctctcc   1440
cagcccagga tttcttatga tgcccagttt gaggtcataa aaggacagac catcgaagtc   1500
cgttgcgaat cgatcagtgg aactttgcct atttcttacc aacttttaaa aacaagtaaa   1560
gtttggaga atagtaccaa gaactcaaat gatcctgcgg tattcaaaga caacccccact   1620
gaagacgtcg aataccagtg tgttgcagat aattgccatt cccatgccaa aatgttaagt   1680
gaggttctga gggtgaaggt gatagccccg gtggatgagg tccagatttc tatcctgtca   1740
agtaaggtgg tggagtctgg agaggacatt gtgctgcaat gtgctgtgaa tgaaggatct   1800
ggtcccatca cctataagtt ttacagagaa aaagagggca aacccttcta tcaaatgacc   1860
tcaaatgcca cccaggcatt ttggaccaag cagaaggcta gcaaggaaca ggagggagag   1920
tattactgca cagccttcaa cagagccaac cacgcctcca gtgtccccag aagcaaaata   1980
ctgacagtca gagtcattct tgccccatgg aagaaaggac ttattgcagt ggttatcatc   2040
ggagtgatca ttgctctctt gatcattgcg gccaaatgtt attttctgag gaaagtcaag   2100
gccaagcaga tgccagtgga aatgtccagg ccagcagtac cacttctgaa ctccaacaac   2160
gagaaaatgt cagatcccaa tatggaagct aacagtcatt acggtcacaa tgacgatgtc   2220
agaaaccatg caatgaaacc aataaatgat aataaagagc ctctgaactc agacgtgcag   2280
tacacggaag ttcaagtgtc ctcagctgag tctcacaaag atctaggaaa gaaggacaca   2340
gagacagtgt acagtgaagt ccggaaagct gtccctgatg ccgtgaaag cagatactct   2400
agaacggaag gctcccttga tggaacttag acagcaaggc cagatgcaca tccctggaag   2460
gacatccatg ttccgagaag aacagataat ccctgtattt caagacctct gtgcacttat   2520
ttatgaacct gccctgctcc cacagaacac agcaattcct caggctaagc tgccggttct   2580
taaatccatc ctgctaagtt aatgttgggt agaaagagat acagagggc tgttgaattt   2640
cccacatacc ctccttccac caagttggaa catccttgga aattgaaga gcacaagagg   2700
agatccaggg caaggccatt gggatattct gaaacttgaa tattttgttt tgtgcagaga   2760
taaagacctt ttccatgcac cctcatacac agaaaccaat tttctttttt atactcaatc   2820
atttctagcg catggcctgg ttagaggctg gtttttctc ttttccttg gtccttcaaa   2880
ggcttgtagt tttggctagt ccttgttctt tggaaataca cagtgctgac cagacagcct   2940
cccctgtcc cctctatgac ctcgccctcc acaaatggga aaccagact acttgggagc   3000
accgcctgtg aaataccaac ctgaagcacc cgttcattca gcaacgcac aaaacagaaa   3060
atgaaggtgg aacaagcaca gatgttcttc aactgttttt gtctacactc tttctctttt   3120
cctctaccat gctgaaggct gaaagacagg aagatggtgc catcagcaaa tattattctt   3180
aattgaaaac ttgaaatgtg tatgtttctt actaattttt aaaaatgtat tccttgccag   3240
ggcaggcaag gtggctcacg cctgtaatcc cagcacttca ggaggctgag gtgggcggat   3300
cacctgaggt caggagtttg agaccagcct gatgaaaccc tgtctctact aaaaatacaa   3360
gaattagccg ggcgtggtgg cgcatgcctg tagtatcagc tactcaagag gctgaggtga   3420
gattatcgct tgaacccagg aaacggaggt tgtagtgagc cgagatcgcg ccactgcact   3480
ccagcctgag tgacagaaagt agaatccatc tcaaaaaaaa caaaaaacaa aattgcttgc   3540
taaagaagtg gtctcctgag gtcttaagac attcctgaca gtgtcttgag tgggtgggag   3600
agaggctgct gtcattgcgc tgtggaattt cacagatgag aaccacgcct agccaaaatc   3660
acttttcctg ttttgcctcag tgacacagct gcagggaccc tcgtggatgt tgtattaaat   3720
aaatttgaac tttgctcttt gcagatctgt gaaatgttgt cttctgaggg gccacatgca   3780
tctatagtgc tgaggactcc ttgggcctct gaagtcacag agagaaccga gcaggtctat   3840
gttttgttt tgttgttttg agacggagat tcgctcttgt tgcccgggct ggactgcagc   3900
ggcgcaacct ctgctcactg caacctccgc tcctgggtt caagcagttc tcctgtctca   3960
gcctcccgag tagctgggat tacaggcaca tgtcaccacg cctggctaat ttttgtattt   4020
ttagtagaga tgggggttca ccacgttggc caggctgatc tcgaatgcct gacctttggt   4080
gatctgcccg ccttgtcctc atgtgtgctc cacaggcctt tgggttggga ttgcaggcgt   4140
gagccaccat gcccagccta gactcttttg acaatatgat gaaagctgtt ggttcctttc   4200
cccaacacac acaccgag ttgtatcacg aaaatgtcat acaatttcca ggttttctga   4260
gtggtgggct cagattgagg tcaaaggatc agacgacctc taacgacctt catgtctctg   4320
ttgatgatct ggggacagcc agatccctg tgtccaggga gttccttagt cccttgccac   4380
caccagagaa gggcaattgc cacgggagct gcaaagaccc tattcctact cctggtgcct   4440
tacttatgca gcacgactga attttttgtt ttgttttgtt ttgttgagac aggggcttgc   4500
tctgttgccc aggctggagt gcagtggcac aacaatggct caccgcagcc tcgaacctcc   4560
gggctcaagc gatcctccca tctcagcttc ctgggtagct gggaccagag gcgtgagccg   4620
ccatagctgg ctaatttta atttttttt tgcagagatg aggtttcacc atggtgccca   4680
ggctggtctc gaacttctgg gctcaagtga tcctccctcc ttggcctcgc aaagtgctgg   4740
gattgcaggc atgagccacc gcccccggcc tgtgagcac acatgagttt aaaattactt   4800
tcccttctgc ctatatttcc gaggaggaaa cttcatgcgc agggatcttt cttagtggat   4860
ttaatggcta aaaggtctgt ctgaatccag gacgctggct ttagccttcc tcggcagctg   4920
ccgtaacccc ggtgtctaaa cctgaagcat cccaggagca cccactccag gagttttctc   4980
ggccgcggaa ctcattagtt agagcgccct cttgtgttct catgtggtaa tcggtcactg   5040
aaggacttaa aatggtcctt agccaacaca cagtaaaact tttcccttctt ctgacccaa   5100
gaggtcagcc accattttca tgagcatata ctgtcattac catcaggtct ctctgattgg   5160
ctaactgaac ccactccccg acctagactc aagacaggcg aagtgacgct taggtcaaca   5220
ttcactcact aaagcaacga ctgtcgggcg attttgtctc ccgctggttt tggaatggtg   5280
tctgagacaa tttttggttg tcacagctgg gtgggtgtgc tcccggcatc tggtgggtag   5340
aaaccaagca tgctcctaaa catcctacag gcacagaacc gtctcccacg accaagcatg   5400
atcaagtccc aaatgccaat aatggccagg ttgagaaact ctgcacagaa gcatccagtt   5460
```

```
atttgtctgt tgctcaaca agcttgtgct catcatgctc tgtgttcctg acgctgtgct   5520
gggtgttggc ggtgggaaga ttacaagagt cacatggcag ctgtcctcct ggaaggtaca   5580
acccagtaga gatgcagact aacagagagc caattacaaa gcagtgtgac aagcgtcatg   5640
gtggaaaatt aaaagctcaa acaagggcac atgggagggg cttccaacac agactttggg   5700
ggatccagga aggtctaaga ggaaagtggg tctcaccaaa gccttgacca taggcagagg   5760
gtaccagtgg aaaaggtggg gtgaagaaca ttgaggacaa aaggaagaag tgcaggaagg   5820
ccctgaggca agggagtggg gggtgccctg gagggatggc agcagggcag tctgtcagac   5880
ccaagtggcc tccagcccta gaagccaatt agtcctcctc aaaaagctgt cactgtcccc   5940
taagaattgc tgccaggctc ccactggcct gactcagtct ttgagagtct taaggaggag   6000
gtctctgaaa ggtacacacc aagaactctc cccagcacag ctgttttaa gactcctccac   6060
cagcgtcatt ggcgtgttgg gaagaaaccc tctgccacag aggccagctt cagcctttgc   6120
ctaacaccgc aagggcaaat ggaaaggtaa acgggaagga gatgtctccc cagcaggcta   6180
tttgaggaca gtcttccctg cagaagatct caacctgggg tccacagagt ggaaatgtta   6240
gagtagggag ctaggcaaac atgagcagga caggtgaggg ccccacagg aatgtcaggc   6300
taccatcagg tgatggtcag gtggttgtta aactgtctct gtaaaataat aattggttgc   6360
agccagctcc aagcaaggac agtctctcaa tagatacaaa acaccctgat ctggtgatca   6420
gccgcttccc gataagatct caggagctgg gcaagcagcc tggagcatgc gcaccaagag   6480
gcaaaatggc ggaatttaac cagtatatga cctaccttcc tctgggaacg cagcactggt   6540
aaggggaaaa atgcctcaag tgagcatgcg cgcaacttca gtaatcacac tgtgcatgcg   6600
accccttcca agtgctggca ggtcaccaca tacgcggaca gcctgctgca agggaagaat   6660
caggggagat gagacgtaaa tcccagaact atgccaaata cataaaaccc caagttaagg   6720
gtcaggcagg gcacttagat ctcttcaagtt gcctgcctga cccaagtgta gtgtacttcc   6780
ttttgttcct gctctaaaac ttttttaataa actctcactc ctgctctaaa a            6831
SEQ ID NO: 28          moltype = DNA   length = 2956
FEATURE                Location/Qualifiers
source                 1..2956
                       mol_type = other DNA
                       organism = Homo sapiens
SEQUENCE: 28
ggggctgagt gctcagtgga gagcggggag ttgtgtccac cttgccgacg tcgctagccg     60
tggggctgtc ctgggaaggc ggacggcgag cgccggtgt ccgcactcgg ccgcctgccg    120
tgcccgtctg cgcccgtgtc atcctcactc gggacgcagg gaccgttttt aaatcacagg    180
ggcgtgtgtc agcctgccct aggacttcat gtctatatat ttccccattc actgcccga    240
ctatctgaga tcggccaaga tgactgaggt gatgatgaac acccagccca tggaggagat    300
cggcctcagc ccccgcaagg atggcctttc ctaccagatc ttcccagacc cgtcagattt    360
tgaccgctgc tgcaaactga aggaccgtct gccctccata gtggtggaac ccacagaagg    420
ggaggtggag agcggggagc tccggtggcc ccctgaggag ttcctggtcc aggaggatga    480
gcaagataac tgcgaagaga cagcgaaaga aaataaagag cagtagagtc cctgtggact    540
cccatgggtc ataccagcca gcatctgttc ctgaactgtg ttttttcccat catgacggaa    600
gaagagagtg agccgcaatt gttctgaaaa tgtcaaacga ggcttctgtt ttgcacctgc    660
agatcaccga gttggttttc ttttcttttc ttgccttttt tttttttga aatttgccga    720
gcagtggagc cctctgacaa tttgcaaggc cctctgaaga aggaagctgc ttagagccag    780
ggggttagtg ggtgagggga gcgagtgctg tttttgagat cattatctga actcaggcag    840
cctagtagag gcagtggtgg gattccaatg ggtcttggtg ggtgggaggt ggggcatgtg    900
caaagcaagc aaggaacatt tggggtaaga aaacaaacat gaggcaaaag aaaaaataca    960
tgttttttaag aaaacattga gcagagaact gcagccagca tgcgctcagc agacattcac   1020
tctggctgct gggacatcag aaaacaaagt cttcatctct ctctccagtt tcacccaccc   1080
caccctttgc tttcatttca ggtgtgttgg tctatatgac agggaggaga gtaaaggaga   1140
gcaggagcaa ttggctgcct gcaaagccag ctggaggtga agtgcaggaa aggaaaggtc   1200
accccattct actccatggc ctctctgctc ccagctgtgg taggctcaca tagccagtgt   1260
gatcggtttt taagaggcag tgcttttcag cttttctccc tgatatatcc attttgcttc   1320
ccagcacttt ttaggagtag tgagagcact tcctgccctt gttggaagcc cagggtgga   1380
cactcagcac gaaggtctct cccttaactg ctgcccttcc aagacttgct cccgagatgg   1440
agtgggcgtg gtcttccagg ctggcccttc ctttctcctca ccgccaccctt ccctgcccca   1500
gccccagcag ccatgggtac atgggtcccc agctccaccta tggattcccg ccagtctgcc   1560
cagctgcagt actcacgccc catggggat cttggtctgt tttcttgtg ggagcctagt   1620
ggagagcaga cgtggctttt tatgtgtctt gttggggagg tgacttgcat ggtggggaca   1680
aggctgtcgt ggcaaccttg ggatcgagtt tgagactaaa ggatgtcatg agatccctgg   1740
cttctcccca tgttgttccc ggacaagggc agaagggagg catgcaagg gacctctgct   1800
gtccttactc aacagtggtc ctcatccctc cccacctccc actgcttcct gcaagggcac   1860
cagttgtatg agaaagttgg cctttggact taggatttct tattgtagct aagagccatc   1920
tgaagcagca ggttgcagga caaatgcttc agtccgccga gagcagtacc gtgtggccaa   1980
gaggtggact cagagccttc cttgagctaa actcggccaa ccaaggcagc catgtcc      2040
cctcaggtct ccagtcagtc caggttgacc ctcagttctg gacgtgtgta tatagctgta   2100
tttaatacct caaggtcatt gtggctctgg ggatgccggg gcaggaggac gagggtgcgc   2160
tgtggacaca gcagtccgcg gaattccgtt ctggaagcc aatggtcgcc ggcacccctt   2220
gcttcctccc tctgttgtct gcctgtgtga cacacatcaa tggcaataac ttcttccaac   2280
tcctcgcaga agtgggaagg gccggcagcc tgcaccgagg ggggcttttcc tctctctcaag   2340
tccccgcttc gttctgttttt ggctgcagag agtggttcat ccatactctc attccctcgc   2400
ctccccttgt ggacggggt cttgccttttt caattcctgt gttttggtgt cttccctat   2460
ctgctaccct gaatcacctg tcctggtctt gctgtgtgat gggaacatgc ttgtaaactg   2520
cgtaacaaat ctactttgtg tatgtgtctg tttatggggg tggtttatta ttttttgctgg   2580
tccctagacc actttgtatg accgtttgca gtctgagcag gccaggggct gacagctaat   2640
gtcaggaccc tcagcggtgg agcctgctgg ggggacccag ctgctcttgg acaagtggct   2700
gagctcctat ctggcctcct cttttttttt tttcaagta atttgtgtgt atttctaact   2760
gattgtattg aaaaaattcc tagtatttca gtaaaaatgc ctgttgtgag atgaacctcc   2820
tgtaacttct atctgttctt tttgaggct cagggagaaa ctagcatttt tttttttcca   2880
aactactttt tgtcactgtg acagttgtaa ataaagtttg aaaatgcttt ccactctgaa   2940
```

```
aaaaaaaaaa aaaaaa                                                                 2956

SEQ ID NO: 29           moltype = DNA   length = 2262
FEATURE                 Location/Qualifiers
source                  1..2262
                        mol_type = other DNA
                        organism = Homo sapiens
SEQUENCE: 29
ctggggagta atagcatggg caaccattat cctgtctcgc cgccacccag gacatggctt   60
ctgttccaat gccaagtgag tacacctatg tgaaactgag aagtgattgc tcgaggcctt  120
ccctgcaatg gtacacccga gctcaaagca agatgagaag gcccagcttg ttattaaaag  180
acatcctcaa atgtacattg cttgtgtttg gagtgtggat cctttatatc ctcaagttaa  240
attatactac tgaagaatgt gacatgaaaa aaatgcatta tgtggaccct gaccatgtaa  300
agagagctca gaaatatgct cagcaagtct tgcagaagga atgtcgtccc aagtttgcca  360
agacatcaat ggcgctgtta tttgagcaca ggtatagcgt ggacttactc ccttttgtgc  420
agaaggcccc caaagacagt gaagctgagt ccaagtacga tcctcctttt gggttccgga  480
agttctccag taaagtccag accctcttgg aactcttgcc agagcacgac ctccctgaac  540
acttgaaagc caagacctgt cggcgctgtg tggttattgg aagcggagga atactgcacg  600
gattagaact gggccacacc ctgaaccagt tcgatgttgt gataaggtta aacagtgcac  660
cagttgaggg atattcagaa catgttggaa ataaaactac tataaggatg acttatccag  720
agggcgcacc actgtctgac cttgaatatt attccaatga cttatttgtt gctgttttat  780
ttaagatgtg tgatttcaac tggcttcaag caatggtaaa aaaggaaacc ctgccattct  840
gggtacgact cttcttttgg aagcaggtgg cagaaaaaat cccactgcag ccaaaacatt  900
tcaggatttt gaatccagtt atcatcaaag agactgcctt tgacatcctt cagtactcag  960
agcctcagtc aaggttctgg ggccgagata gaaacgtccc cacaatcggt gtcattgccg 1020
ttgtcttagc cacacatctg tgcgatgaag tcagtttgag ggttttga tatgacctca 1080
atcaacccag aacaccttg cactacttcg acagtcaatg catggctgct atgaactttc 1140
agaccatgca taatgtgaca acggaaacca agttcctctt aaagctggtc aaagagggag 1200
tggtgaaaga tctcagtgga ggcattgatc gtgaattttg aacacagaaa acctcagttg 1260
aaaatgcaac tctaactctg agagctgttt ttgacagcct tcttgatgta tttctccatc 1320
ctgcagatac tttgaagtgc agctcatgtt tttaactttt aatttaaaaa cacaaaaaaa 1380
attttagctc ttcccacttt ttttttccta tttatttgag gtcagtgttt gttttttgcac 1440
accatttgt aaatgaaact taagaattga attggaaaga cttctcaaag agaattgtat 1500
gtaacgatgt tgtattgatt tttaagaaag taatttaatt tgtaaaactt ctgctcgtt  1560
acactgcaca ttgaatacag gtaactaatt ggaaggagag gggaggtcac tcttttgatg 1620
gtggccctga acctcattct ggttccctgc tgcgctgctt ggtgtgaccc acggaggatc 1680
cactcccagg atgacgtgct ccgtagctct gctgctgata ctgggtctgc gatgcagcgg 1740
cgtgaggcct gggctggttg gagaaggtca caaccccttct ctgttggtct gccttctgct 1800
gaaagactcg agaaccaacc agggaagctg tcctggaggt ccctggtcgg agagggacat 1860
agaatctgtg acctctgaca actgtgaagc caccctgggc tacagaaacc acagtcttcc 1920
cagcaattat tacaattctt gaattccttg gggatttttt actgcccttt caaagcactt 1980
aagtgttaga tctaacgtgt tccagtgtct gtctgaggtg acttaaaaaa tcagaacaaa 2040
acttctatta tccagagtca tgggagagta caccctttcc aggaataatg ttttgggaaa 2100
cactgaaatg aaatcttccc agtattataa attgtgtatt taaaaaaaag aaacttttct 2160
gaatgcctac ctgcggtgt ataccaggca gtgtgccagt ttaaaaagat gaaaaagaat 2220
aaaaactttt gaggaaaaaa aaaaaaaaaa aaaaaaaaa aa                    2262

SEQ ID NO: 30           moltype = DNA   length = 4909
FEATURE                 Location/Qualifiers
source                  1..4909
                        mol_type = other DNA
                        organism = Homo sapiens
SEQUENCE: 30
tagacgcacc ctctgaagat ggtgactccc tcctgagaag ctggaccect tggtaaaaga   60
caaggccttc tccaagaaga atatgaaagt gttactcaga cttatttgtt tcatagctct  120
actgatttct tctctggagg ctgataaatg tcaaggaacgt gaagaaaaaa taattttagt  180
gtcatctgca aatgaaattg atgttcgtcc ctgtcctctt aacccaaatg aacacaaagg  240
cactataact tggtataaag atgacagcaa gacacctgta tctacagaac aagcctccag  300
gattcatcaa cacaaagaga aactttggtt tgttcctgct aaggtggagg attcaggaca  360
ttactattgc gtggtaagaa attcatctta ctgcctcaga attaaaataa gtgcaaaatt  420
tgtggagaat gagcctaact tatgttataa tgcacaagcc atatttaagc agaaactacc  480
cgttgcagga gacggaggac ttgtgtgccc ttatatggag ttttttaaaa atgaaaataa  540
tgagttacct aaaattacagt ggtataagga ttgcaaacct ctacttcttg acaatataca  600
ctttagtgga gtcaaagata ggctcatcgt gatgaatgtg gtgaaagc ataganggaa   660
ctatacttgt catgcatcct acacatactg gcaagcaa tatcctatta cccgggtaat  720
agaatttatt actctagagg aaaacaaacc cacaaggcct gtgattgtga gcccagctaa  780
tgagacaatg gaagtagact gggatccca gatacaattg atctgtaatg tcaccggcca  840
gttgagtgac attgcttact ggaagtggaa tgggtcagta attgatgaag atgacccagt  900
gctaggggaa gactattaca gtgtggaaaa tcctgcaaac aaaagaaggg agtacctcat  960
cacagtgctt aatatatcgg aaattgaaag tagatttat aaacatccat ttacctgttt 1020
tgccaagaat acacatggta tagatgcagc atatatccag ttaatatatc cagtcactaa 1080
tttcagaag cacatgattg gtatatgtgt cacgttgaca gtcataattg tgtgttctgt 1140
tttcatctat aaaatcttca gattgacat tgtgcttttg gacagggatt cctgctatga 1200
ttttctccca ataaaagctt cagatgaaa gacctataga gcatatatac tgtatccaaa 1260
gactgtgggg gaaggtctca cctctgactg tgatattttt gtgtttaaag tcttgcctga 1320
ggtcttggaa aaacagtgtg gatataagct gttcattat ggaagggatg actacgttgg 1380
ggaagacatt gttgaggtca ttaatgaaaa cgtaaagaaa agcagaagac tgattatcat 1440
tttagtcaga gaaacatcag gcttcagctg gctgggtggt tcatctgaag agcaaatagc 1500
catgtataat gctcttgttc aggatggaat taaagttgtc ctgcttgagc tggagaaaat 1560
```

```
ccaagactat gagaaaatgc cagaatcgat taaattcatt aagcagaaac atggggctat    1620
ccgctggtca ggggacttta cacagggacc acagtctgca aagacaaggt tctggaagaa    1680
tgtcaggtac cacatgccag tccagcgacg gtcaccttca tctaaacacc agttactgtc    1740
accagccact aaggagaaac tgcaaagaga ggctcacgtg cctctcgggt agcatggaga    1800
agttgccaag agttctttag gtgcctcctg tcttatgcgg ttgcaggcca ggttatgcct    1860
catgctgact tgcagagttc atggaatgta actatatcat cctttatccc tgaggtcacc    1920
tggaatcaga ttattaaggg aataagccat gacgtcaata gcagcccagg gcacttcaga    1980
gtagagggct tgggaagatc ttttaaaaag gcagtaggcc cggtgtggtg gctcacgcct    2040
ataatcccag cactttggga ggctgaagtg ggtggatcac cagaggtcag gagttcgaga    2100
ccagcccagc caacatggca aaaccccatc tctactaaaa atacaaaaat gagctaggca    2160
tggtggcaca cgcctgtaat cccagctaca cctgaggctg aggcaggaga attgcttgaa    2220
ccggggagac ggaggttgca gtgagccgag tttgggccac tgcactctag cctggcaaca    2280
gagcaagact ccgtctcaaa aaaagggcaa taaatgccct ctctgaatgt ttgaactgcc    2340
aagaaaaggc atggagacag cgaactagaa gaaagggcaa gaaggaaata gccaccgtct    2400
acagatggct tagttaagtc atccacagcc caagggcggg gctatgcctt gtctggggac    2460
cctgtagagt cactgaccct ggagcggctc tcctgagagg tgctgcaggc aaagtgagac    2520
tgacacctca ctgaggaagg gagacatatt cttggagaac ttttccatctg cttgtatttt    2580
ccatacacat ccccagccag aagttagtgt ccgaagaccg aatttatttt tacagagctt    2640
gaaaactcac ttcaatgaac aaagggattc tccaggattc caaagttttg aagtcatctt    2700
agctttccac aggagggaga gaacttaaaa aagcaacagt agcagggaat tgatccactt    2760
cttaatgctt tcctccctgg catgaccatc ctgtcctttg ttattatcct gcattttacg    2820
tctttggagg aacagctccc tagtggcttc ctccgtctgc aatgtccctt gcacagccca    2880
cacatgaacc atccttccca tgatgccgct cttctgtcat cccgctcctg ctgaaacacc    2940
tcccagggc tccacctgtt caggagctga agcccatgct ttcccaccag catgtcactc    3000
ccagaccacc tccctgccct gtcctccagc ttcccctcgc tgtcctgctg tgtgaattcc    3060
caggttggcc tggtggccat gtcgcctgcc cccagcactc ctctgtctct gctcttgcct    3120
cgacccttcc tcctccttgg cctaggaggc cttctcgcat tttctctagc tgatcagaat    3180
tttaccaaaa ttcagaacat cctccaattc cacagtctct gggagacttt ccctaagagg    3240
cgacttcctc tccagccttc tctctctggt caggcccact gcagagatgg tggtgagcac    3300
atctgggagc ctggtctccc tccagctgga attgctgctc tctgagggag aggctgtggt    3360
ggctgtctct gtccctcact gccttccagg agcaatttgc acatgtaaca tagatttatg    3420
taatgcttta tgtttaaaaa cattccccaa ttatcttatt taattttgc aattattcta    3480
attttatata tagagaaagt gacctatttt ttaaaaaaat cacactctaa gttctattga    3540
acctaggact tgagcctcca tttctggctt ctagtctggt gttctgagta cttgatttca    3600
ggtcaataac ggtcccccct cactccacac tggcacgttt gtgagaagaa atgacatttt    3660
gctaggaagt gaccgagtct aggaatgctt ttattcaaga caccaaattc caaacttcta    3720
aatgttggaa ttttcaaaaa ttgtgtttag attttatgaa aaactcttct actttcatct    3780
attctttccc tagaggcaaa catttcttaa aatgtttcat tttcattaaa aatgaaagcc    3840
aaatttatat gccaccgatt gcaggacaca agcacagttt taagagttgt atgaactgtg    3900
agaggacttt tggttttat atttctcgta tttaatatgg gtgaacacca acttttattt    3960
ggaataataa ttttcctcct aaacaaaaac acattgagtt taagtctctg actcttgcct    4020
ttccacctgc tttctcctgg gcccgctttg cctgcttgaa ggaacagtgc tgttctggag    4080
ctgctgttcc aacagacagg gcctagcttt catttgacac acagactaca gccagaagcc    4140
catggagcag ggatgtcacg tcttgaaaag cctattagat gttttacaaa tttaattttg    4200
cagattattt tagtctgtca tccagaaaat gtgtcagcat gcatagtgct aagaaagcaa    4260
gccaatttgg aaacttaggt tagtgacaaa attggccaga gagtgggggt gatgatgacc    4320
aagaattaca agtagaatgg cagctggaat ttaaggaggg aacaagaatca atggataagc    4380
gtgggtggag gaagatccaa acagaaaagt gcaaagttat tccccatctt ccaagggttg    4440
aattctggag gaagaagaca cattcctagt tccccgtgaa cttcctttga cttattgtcc    4500
ccactaaaac aaaacaaaaa acttttaatg ccttccacat taattagatt ttcttgcagt    4560
ttttttatgg cattttttta aagatgccct aagtgttgaa gaagagtttg caaatgcaac    4620
aaaatattta attaccggtt gttaaaactg gtttagcaca atttatattt tccctctctt    4680
gccttcttca tttgcaataa aaggtattga gccattttt aaatgacatt tttgataaat    4740
tatgtttgta ctagttgatg aaggagtttt ttttaacctg tttatataat tttgcagcag    4800
aagccaaatt ttttgtatat taaagcacca aattcatgta cagcatgcat cacggatcaa    4860
tagactgtac ttattttcca ataaaatttt caaactttgt actgttaaa                4909

SEQ ID NO: 31           moltype = DNA   length = 2210
FEATURE                 Location/Qualifiers
source                  1..2210
                        mol_type = other DNA
                        organism = Homo sapiens
SEQUENCE: 31
cgcgcccctc cctcctcgcg gacctggcgg tgccggcgcc cggagtggcc ctttaaaagg      60
cagcttattg tccggagggg gcgggcgggg ggcgccgacc gcggcctgag gcccggcccc     120
tccccctctcc ctccctctgt ccccgcgtcg ctcgctggct agctcgctgg ctcgctcgcc    180
cgtccggcgc acgctccgcc tccgtcagtt ggctccgctg tcgggtgcgc ggcgtggagc     240
ggcagccggt ctggacgcgc ggccggggct gggggctggg agcgcggcgc gcaagatctc     300
cccgcgcgag agcggcccct gccaccgggc gaggcctgcc ccgcgatgcc agagatggcc    360
agtaaagggg tgacgcgggg aaagatcgcc agcaacgtgc agaagaagct cacccgcgcg    420
caggagaagg ttctccagaa gctggggaag gcagatgaga ccaaggatga gcagtttgag    480
cagtgcgtcc agaatttcaa caagcagctg acggagggca cccggctgca aaggatctc    540
cggacctacc tggcctccgt caaagccatg cacgaggctt ccaagaagct gaatgagtgt    600
ctgcaggagg tgtatgagcc cgattggcc gcagggatg aggcaaacaa gatcgcagag    660
aacaacgacc tgctgtggat ggattaccac cagaagctgg tggaccaggc gctgctgacc    720
atggacacgt acctgggcca gttccccgac atcaagtcac gcattgccaa gcgggggcgc    780
aagctggtgg actacgacag tgcccggcac cactacgagt cccttcaaac tgccaaaag    840
aaggatgaag ccaaaattgc caaggccgag gaggagctca tcaaagccca gaaggtgttt    900
gaggagatga atgtggatct gcaggaggag ctgccgtccc tgtggaacag ccgcgtaggt    960
```

```
ttctacgtca acacgttcca gagcatcgcg ggcctggagg aaaacttcca caaggagatg  1020
agcaagctca accagaacct caatgatgtg ctggtcggcc tggagaagca cacgggagc   1080
aacaccttca cggtcaaggc ccagcccaga aagaaaagta aactgttttc gcggctgcgc  1140
agaaagaaga acagtgacaa cgcgcctgca aagggaaca agagcccttc gcctccagat   1200
ggctcccctg ccgccacccc cgagatcaga gtcaaccacg agccagagcc ggccggcggg  1260
gccacgcccg gggccaccct ccccaagtcc ccatctcagc cagcagaggc ctcggaggtg  1320
gcgggtggga cccaacctgc ggctggagcc caggagccag gggagacggc ggcaagtgaa  1380
gcagcctcca gctctcttcc tgctgtcgtg gtggagacct tcccagcaac tgtgaatggc  1440
accgtggagg gcggcagtgg ggccgggcgc ttggacctgc ccccaggttt catgttcaag  1500
gtacaggccc agcacgacta cacggccact gacacagacg agctgcagct caaggctggc  1560
gatgtggtgc tggtgatccc cttccagaac cctgaagagc aggatgaagg ctggctcatg  1620
ggcgtgaagg agagcgactg gaaccagcac aaggagctgg agaagtgccg tggcgtcttc  1680
cccgagaact tcactgagag ggtcccatga cggcggggcc caggcagcct ccgggcgtgt  1740
gaagaacacc tcctcccgaa aaatgtgtgg ttcttttttt tgttttgttt tcgttttttca 1800
tcttttgaag agcaaaggga aatcaagagg agacccccag gcagaggggc gttctcccaa  1860
agattaggtc gttttccaaa gagccgcgtc ccggcaagtc cggcggaatt caccagtgtt  1920
cctgaagctg ctgtgtcctc tagttgagtt tctggcgccc ctgcctgtgc ccgcatgtgt  1980
gcctggccgc agggcggggc tgggggctgc cgagccaccca tgcttgcctg aagcttcggc  2040
cgcgccaccc gggcaagggt cctcttttcc tggcagctgc tgtgggtggg gcccagacac  2100
cagcctagcc tggctctgcc ccgcagacgt tctgtgtgct gtttgaaaat aaatcttagt  2160
gttcaaaaca aaatgaaaca aaaaaaaaat gataaaaact ctcaaaaaaa              2210

SEQ ID NO: 32        moltype = DNA   length = 4664
FEATURE              Location/Qualifiers
source               1..4664
                     mol_type = other DNA
                     organism = Homo sapiens
SEQUENCE: 32
gcagcctccc ggcgctgagc gcttttcctg cccgcccggc tcagccctgc ggaccccggg  60
agaagtttcc cagaaaaaat gcccagcgcg cgcggggcgt gcggagtcgt ccggagccgc  120
tgcgcgattt atcagcaaga ctgttgaacg cataactgcc caagatgcct gtccctcccc  180
ctccagcacc cccgccgccc ccgacgtttt cactggccaa tacagagaag cctaccttga  240
ataagacaga gcaggctggg agaaatgctc tcctttctga tatcagcaaa gggaagaaac  300
taaagaagac ggtcaccaat gacagaagtg caccaatact ggacaaacct aaaggagctg  360
gtgctggagg cggtggtggt ggcttttggtg gaggcggcgg atttggcgga ggaggtggtg  420
gcggaggcgg tggaagtttt ggaggggcg gacctccagg tctggaggga ttgttccagg  480
ctggaatgcc gaagctgaga tccacggcca acagggataa tgattctgga ggaagccgac  540
caccattgtt gccaccggga ggaagatcca catctgcgaa acccttttca cccccaagtg  600
gcccagggag gtttcctgtg ccttctccag gccacagaag tggtccccca gagcctcaga  660
ggaaccgaat gccgccccca aggcccgacg tgggctcaaa gctgatagc attcctcctc   720
cagtacctag tactccaaga cccattcaat caagtccgca caaccgggg tccccaccag    780
tgcccggagg ccccaggcag cccagccccg ggccactcc tcccccttc cctggaaacc    840
gcggcactgc tttgggagga ggctcaatac gtcagtcccc cttgagctcc tcctcgcccc   900
tctccaaccg gcctcccctg ccgcctaccc ccagcagggc cttggatgac aaacccctc    960
caccacctcc tccagtgggc aacaggcctt ccatccacag ggaagcggtt cccctcctc   1020
ctcctcagaa caacaagcct ccagtgcctt ccactccgcg gccttcggcc tcctcacagg  1080
ccccactctc gccgccacct cccagcaggc ccgggccgcc tcctctgcct ccaagttcca  1140
gcggcaatga cgaaacccca agactccac agcggaatct gtccctcagt tcgtccacgc   1200
ccccgttacc ttcgccagga cgttcaggtc ctcttcctcc cccgcccagt gagagacccc   1260
cacctccagt gagggacccg ccaggccgat caggcccccct ccaccacct cctcagtaa   1320
gcagaaacgg cagcacatct cgggcctgc ctgctaccc tcagttgcca tccaggagtg   1380
gagtagacag tcccaggagt ggacccaggc ctccccttcc tcctgatagg cccagtgctg  1440
gggcacctcc cccacctcca ccatcaacat ctattagaaa tggcttccaa gactctccat  1500
gtgaagatga gtgggaaagc agattctact tccatccgat ttccgatttg ccacctccag   1560
agccatatgt acaaacgacc aaaagttatc ccagcaaact ggcaagaaac gaaagccgaa   1620
gtggatccaa ccgaagagaa aggggtgctc caccactccc tcccatccg aggtgatctt   1680
tgcctgctct tctctaccca agctcaagag ctgcttctgt tgctatctaa gaactgcata  1740
ccctcctccc tgcttcttcc cttgtgcctc atgtatgggc aggaggaaag gtgggagggg   1800
gagtgggaat atgcgtgtgt gggtgggaat cggtaagaaa tgcacctagc ttttcatatt   1860
gtgtttattc tccaggctat tgcttcttc agctgcagcc tgcctgtgct ggctgctggg   1920
gtcgataggc ttttgtcgta ataggcagag atgacttgca tcccagcttt ccaccaacca   1980
aattcaaaca ttcactgctt atttgttaca gactgtaatt attaaagtcc ctgagagctg   2040
ttttctcccg ttccttttc gcatgcttgg cctcctctct gtttctatga accacagacc    2100
acctaagcaa gctgctgagt aagggctcac tggaaacttg cagtcacagg atgtccaatc   2160
tttggcagtc cgagcttggc tctaggacag agctgtccaa tagaaatata atgtgagccc   2220
catatacaat ttttacattt ctaatatatt ttaaacaagt gaagttaata tgcatccaaa   2280
atatttcaac ctgtaatcaa cataaaattt taatgagata ttttatatta ttttttggta   2340
ctgaatcttc aaaatccaga gtgtatttta cacttaccgc acatctccat tcagactagt   2400
cacattttta agtgctcagt agccacatgt ggctggtggc tactggatta gacagcacga   2460
gtctggaaga tggaagctag tgcagaaacc tcttgtttaa aaaacaaaaa aggcaagatg   2520
ggcttgagcg attcaagagg caactaaaaa taaaattagg acccagcacc ttgtttgaca   2580
cacagtttga ccttcgattt tcctccctta acttccctct tcccttaata tctgtataca   2640
agtgttgctt caaagtacca aggtcagaaa ttgattcagt acggtttact aaagtcatgt   2700
ggaataaagc cattggaaac aaatggaaag cctgtcggga cttctgggct cagaaccagc   2760
tggctcacgc actccacttg tcagctggac ttctgccttg tgaaatggaa gcagccttg    2820
ttcctttctg gctgagcaag ctcctgaggc tgggagagac taggaaggct tggtaggagg   2880
ggaaaaaagt caggaaaaga tatcaaatca gaaacatgga agaagaaggg aaccgatttg   2940
agttggtggg caaaactcta aaaatctaaa tctgatgctt atgtaagggt tgagcgaatt   3000
agggagattg ctagtggaaa ttggagggaa tttgttttgc atcatttgtc taggatctat   3060
```

```
gcaaatatag ctccactaaa ggaccatagg gaagagccag ccttgccttt tcttatatga   3120
ttttgtttac aaaattttac tgggactttt aaatctagct atagagttgg gaaaaaatat   3180
ttccacttag atattttaca tggttttgtt taaaattacc attacttgtt ttttaaaaac   3240
acatgaccac atatgtatat gtatatctac ctaaacattg tatcatggtt tcagtatgtt   3300
attcatgtat tactgggaga tgctaccaag aaaccaaccc aaagaaaatt ctgaaaaata   3360
catttctatt tatagaataa atgtttcatt tatataaaag caaaagaact tagagttcta   3420
ataaatggga tgtctaataa attatgaagt tactgatttg aatatattat attttttataa  3480
cttccttgcc aaagtcctga tttagtacat tagagaacct gtgtttcctc tctcctctac   3540
cattcatctc tcttccatac agtcatttgg gcttttttact caaagagaat caagaaataa   3600
taaggtataa caagcttggc aaagtgttgg ctttttaaaa aaaaattttt ttaatctcta   3660
gcagtttggt aatttagcag catcatttat ttgggattct tttatctgat ttcaacagtg   3720
aaaaacatcc ctatgataaa gcctaatgac ccatttcaca aaagatggaa tttgcccttc   3780
ctagaaaata tgacggagaa aagtctgact cagagaaagt gagtctgaat tttataaggg   3840
gtagtaagaa ttggacaatt cctttgcata tctgaacttg gcaggtaccg ttctaaatct   3900
gaaacagggt gatagctcaa agttgccatt catccagaat agattgtttt agaatgtagt   3960
gtttaagtga ctgtttcatt aatacaccta cacccttct ttgaaagttt gcaacctaat    4020
tgcatctaaa actatgaata agtctgtgg taaaatctta aactatggaa aattacaaaa    4080
atgaatttt cttccctgaa atcagagctt acatgtgtgt tttttataa cattttcaga     4140
taaatgtatt caacatgtaa tacagtatttt taacattcac ctcttatttt atattgaaat  4200
gtattacagt attaaaactc agtgttcagt atttatttca ctatgcattt tatttagtaa   4260
aagccaggag aaatgtttaa tccaatggtg ccttactttg tgatttaaaa gaaatcaact   4320
ttttttatg tctaagtagt agattatttg catattgta aaaactgtta ggtctttata     4380
ttttaaagtg taataccagt tttgttattt tagtagcaga aatgggatga ttgttaaagt   4440
tccccaaaaa tgtggcatg aaattaattt ttccctcctt atagtcaagg accgtagagg    4500
aagaaaaact ttttttttcat accatgcact atgtaaacag acacattttg ctatctgtgt  4560
catcaggata gtgtaagtgg tagggtagag actaccctag acatctgcat ctttgtaagt   4620
tagccagaca ataaagaaaa gcagaatgaa aaaaaaaaaa aaaa                    4664

SEQ ID NO: 33           moltype = DNA   length = 1166
FEATURE                 Location/Qualifiers
source                  1..1166
                        mol_type = other DNA
                        organism = Homo sapiens
SEQUENCE: 33
attcccaact gccagtgatc tctgaagccg actctgaggc tccctctttg ctctaacaga    60
cagcagcgac tttaggctgg ataatagtca aattcttacc tcgctctttc actgctagta   120
agatcagatt gcgtttcttt cagttactct tcaatcgcca gtttcttgat ctgcttctaa   180
aagaagaagt agagaagata aatcctgtct tcaataacctg gaaggaaaaa caaaataacc  240
tcaactccgt tttgaaaaaa acattccaag aactttcatc agagatttta cttagatgat   300
ttacacaatg aagaaagtac atgcactttg ggcttctgta tgcctgctgc ttaatcttgc   360
ccctgcccct cttaatgctg attctgagga agatgaagaa cacacaatta tcacagatac   420
ggagttgcca ccactgaaac ttatgcattc attttgtgca ttcaaggcgg atgatggccc   480
atgtaaagca atcatgaaaa gattttttctt caatattttc actcgacagt gcgaagaatt   540
tatatatggg ggatgtgaag gaaatcagaa tcgatttgaa agtctggaag agtgcaaaaa   600
aatgtgtaca agagataatg caaacaggat tataaagaca acattgcaac aagaaaagcc   660
agatttctgt ttttttggaag aagatcctgg aatatgtcga ggttatatta ccaggtatt    720
ttataacaat cagacaaaac agtgtgaacg tttcaagtat ggtggatgcc tgggcaatat   780
gaacaattt gagacactgg aagaatgcaa gaacatttgt gaagatggtc cgaatgggttt  840
ccaggtggat aattatggaa cccagctcaa tgctgtgaat aactccctga ctccgcaatc   900
aaccaaggtt cccagccttt tgttacaaa agaaggaaca aatgatggtt ggaagaatgc    960
ggctcatatt taccaagtct ttctgaacgc ctttctgcatt catgcatcca tgttcttct   1020
aggattggat agcatttcat gcctatgtta atatttgtgc ttttggcatt tccttaatat  1080
ttatatgtat acgtgatgcc tttgatagca tactgctaat aaagttttaa tatttacatg  1140
catagtaaaa aaaaaaaaa aaaaaa                                       1166

SEQ ID NO: 34           moltype = DNA   length = 8449
FEATURE                 Location/Qualifiers
source                  1..8449
                        mol_type = other DNA
                        organism = Homo sapiens
SEQUENCE: 34
gcccgcgccg gctgtgctgc acaggggag gagagggaac cccaggcgcg agcgggaaga      60
ggggacctgc agccacaact tctctggtcc tctgcatccc ttctgtccct ccacccgtcc    120
ccttcccccac cctctggccc ccaccttctt ggaggcgaca accccggga ggcattagaa    180
gggatttttc ccgcaggttg cgaagggaag caaacttggt ggcaacttgc ctcccggtgt    240
gggcgtctct cccccaccgt ctcaacatgc ttaggggtcc ggggcccggg ctgctgctgc    300
tggccgtcca gtgcctgggg acagcggtgc cctccacggg agcctcgaag agcaagaggc   360
aggctcagca aatggttcag ccccagtccc cggtggctgt cagtcaaagg aagcccggtt    420
gttatgacaa tggaaaacac tatcagataa atcaacagtg gagcggacc taccctaggca   480
atgcgttggt ttgtacttgt tatggaggaa gccgagggtt taactgcgag agtaaacctg    540
aagctgaaga gacttgcttt gacaagtaca ctggaaacac ttaccgagtg ggtgacactt    600
atgagcgtcc taaagactcc atgatctggg actgtacctg catcgggct gggcgaggga   660
gaataagctg taccatcgca aaccgctgcc atgaagggg tcagtcctac aagattggtg    720
acacctggag gagaccacat gagctggtg gttacatgt agtgtgtggt gtcttggta     780
atggaaaagg agaatggacc tgcaagccca tagctgagaa gtgttttgat catgctgctg    840
ggacttccta tgtggtcgga gaaacgtggg agaagccta ccaaggctgg atgatggtag   900
attgtacttg cctgggagaa ggcagcggac gcatcacttg cacttctaga aatagatgca   960
acgatcagga cacaaggaca tcctatagaa ttggagacac ctggagcaag aaggataatc   1020
gaggaaacct gctccagtgc atctgcacag gcaacggccg aggagagtgg aagtgtgaga   1080
```

```
ggcacacctc tgtgcagacc acatcgagcg gatctggccc cttcaccgat gttcgtgcag   1140
ctgtttacca accgcagcct caccccagc ctcctccta tggccactgt gtcacagaca    1200
gtggtgtggt ctactctgtg gggatgcagt ggctgaagac acaaggaaat aagcaaatgc  1260
tttgcacgtg cctgggcaac ggagtcagct gccaagagac agctgtaacc cagacttacg  1320
gtggcaactc aaatggagag ccatgtgtct taccattcac ctacaatggc aggacgttct   1380
actcctgcac cacagaaggg cgacaggacg gacatctttg gtgcagcaca acttcgaatt   1440
atgagcagga ccagaaatac tctttctgca cagaccacac tgttttggtt cagactcgag   1500
gaggaaattc caatggtgcc ttgtgccact tccccttcct atacaacaac cacaattaca   1560
ctgattgcac ttctgagggc agaagagaca acatgaagtg gtgtgggacc acacagaact   1620
atgatgccga ccagaaagttt gggttctgcc ccatggctgc ccacgaggaa atctgcacaa  1680
ccaatgaagg ggtcatgtac cgcattgag atcagtggga taagcagcat gacatgggtc    1740
acatgatgag gtgcacgtgt gttgggaatg gtcgtgggga atggacatgc attgcctact   1800
cgcagcttcg agatcagtgc attgttgatg acatcactta caatgtgaac gacacattcc   1860
acaagcgtca tgaagagggg cacatgctga actgtacaga cttcggtcag ggtcggggca   1920
ggtggaagtg tgatcccgtc gaccaatgcc aggattcaga gactgggacg ttttatcaaa   1980
ttggagattc atgggagaag tatgtgcatg gtgtcagata ccagtgctac tgctatggcc   2040
gtggcattgg ggagtggcat tgccaacctt tacagaccta tccaagctca agtggtcctg   2100
tcgaagtatt tatcactgag actccgagtc agcccaactc ccacccccatc cagtggaatg  2160
caccacagcc atctcacatt tccaagtaca ttctcaggtg gagacctaaa aattctgtag   2220
gccgttggaa ggaagctacc ataccaggcc acttaaactc ctacaccatc aaaggcctga   2280
agcctggtgt ggtatacgag ggccagctca tcagcatcca gcagtacggc caccaagaag   2340
tgactgcgtt tgacttcacc accaccagca ccagcacacc tgtgaccagc aacaccgtga   2400
caggagagac gactcccttt tctcctcttg tggccacttc tgaatctgtg accgaaatca   2460
cagccagtag ctttgtggtc tcctgggtct cagcttccga caccgtgtcg ggattccggg   2520
tggaatatga gctgagtgag gaggggagatg agccacagta cctggatctt ccaagcacag   2580
ccacttctgt gaacatccct gacctgcttc ctggccgaaa atacattgta aatgtctatc   2640
agatatctga ggatggggag cagagtttga tcctgtctac ttcacaaaaca acagcgcctg   2700
atgcccctcc tgacccgact gtggaccaag ttgatgacac ctcaattgtt gttcgctgga   2760
gcagacccca ggctcccatc acagggtaca gaatagtcta ttcgccatca gtagaaggta   2820
gcagcacaga actcaacctt cctgaaactg caaactccgt caccctcagt gacttgcaac   2880
ctggtgttca gtataacatc actatctatg ctgtggaaga aaatcaagaa agtacacctg   2940
ttgtcattca acaagaaacc actggcaccc cacgctcaga tacagtgccc tctcccaggg   3000
acctgcagtt tgtggaagtg acagacgtga aggtcaccat catgtggaca ccgcctgaga   3060
gtgcagtgac cggctaccgt gtggatgtga tcccccgtcaa cctgcctggc gagcacgggc   3120
agaggctgcc catcagcagg aacacctttg cagaagtcac cgggctgtcc cctgggggtca   3180
cctattactt caaagtcttt gcagtgagcc atgggagggag gagcaagcct ctgactgctc   3240
aacagacaac caaactggat gctcccacta acctccagtt tgtcaatgaa actgattcta   3300
ctgtcctggt gagatggact ccacctcggg cccagataac aggataccga ctgaccgtgg   3360
gccttacccg aagaggacag cccaggcagt acaatgtggg tccctctgtc tccaagtacc   3420
cactgaggaa tctgcagcct gcatctgagt acaccgtatc cctcgtggcc ataaagggca   3480
accaagagag ccccaaagcc actggagtct taccacact gcagcctggg agctctattc   3540
caccttacaa caccgaggtg actgagacca ccattgtgat cacatggacg cctgctccaa   3600
gaattggttt taagctgggt gtacgaccaa gccagggagg agaggcacca cgagaagtga   3660
cttcagactc aggaagcatc gttgtgtccg gcttgactcc aggagtagaa tacgtctaca   3720
ccatccaagt cctgagagat ggacaggaaa gagatgcgcc aattgtaaac aaagtggtga   3780
caccattgtc tccaccaaca aacttgcatc tggaggcaaa ccctgacact ggagtgctca   3840
cagtcctctg ggagaggagc actaccccag acattactgg ttatagaatt accacaaccc   3900
ctacaaacgg ccagcaggga aattctttgg aagaagtggt ccatgctgat cagagctcct   3960
gcactttga taacctgagt cccggcctgg agtacaatgt cagtgtttac actgtcaagg   4020
atgacaagga aagtgtccct atctctgata ccatcatccc agctgttcct cctcccactg   4080
acctgcgatt caccaacatt ggtccagaca ccatgcgcat cacctgggct ccacccccat   4140
ccattgattt aaccaacttc ctggtgcgtt actcacctgt gaaaaatgag gaagatgttg   4200
cagagttgtc aattttctcct tcagacaatg cagtggtctt aacaaatctc ctgcctggta   4260
cagaatatgt agtgagtgtc tccagtgtct acgaacaaca tgagagcaca cctcttagag   4320
gaagacagaa aacaggtctt gattcccaa ctggccattga cttttctgat attactgcca   4380
actcttttac tgtgcactgg attgctcctc gagccaccat cactggctac aggatccgcc   4440
atcatcccga gcacttcagt gggagacctc gagaagatcg ggtgccccac tctcggaatt   4500
ccatcaccct caccaacctc actccaggca cagagtatgt ggtcagcatc gttgctctta   4560
atggcagaga ggaaagtccc ttattgattg gccaacaatc aacagtttct gatgttccga   4620
gggacctgga gttgttgct gcgaccccca ccagcctact gatcagctgg gatgctcctg   4680
ctgtcacagt gagatattac aggatcactt acggagagac aggaggaaat agccctgtcc   4740
aggagttcac tgtgcctggg agcaagtcta cagctaccat cagcggcctt aaacctggag   4800
ttgattatac catcactgtg tatgctgtca ctggccgtgg agacagcccc gcaagcagca   4860
agccaatttc cattaattac cgaacagaaa ttgcaaacc atcccagatg caagtgaccg   4920
atgttcagga caacagcatt agtgtcaagt ggctgcctttc aagttcccct gttactggtt   4980
acagagtaac caccactccc aaaaatggac caggaccaac aaaaactaaa actgcaggtc   5040
cagatcaaac agaaatgact attgaaggct tgcagcccac agtggagtat gtggttagtg   5100
tctatgctca gaatccaagc ggagagagtc agcctctggt tcagactgga gtaaccaaca   5160
ttgatcgccc taaaggactg gcattcactg atgtggatgt cgattccatc aaaattgctt   5220
gggaaagccc acaggggcaa gtttccaggt acaggggcaga ctactcgagc cctgaggatg   5280
gaatccatga gctattccct gcacctgatg gtgaagaaga cactgcagag ctgcaaggcc   5340
tcagaccggg ttctgagtac acagtcagtg tggttgcctt gcacgatgat atggagagcc   5400
agccctgat tggaacccag tccacagcta ttcctgcacc aactgacctg aagttcactc   5460
aggtcacacc cacaagcctg agcgcccagt caatgttcag ctcactggat   5520
atcgagtgcg ggtgacccc aaggagaaga ccgaccaat gaaagaaatc aaccttctc   5580
ctgcagactc atccgtggtt gtatcaggac ttatggtggc caccaaatat gaagtgagtg   5640
tctatgctct aaggacact tgacaagca gaccagctca gggagttgtc accactctgg   5700
agaatgtcag cccaccaaga agggctcgtg tgacagatgc tactgagacc accatcacca   5760
ttagctggag aaccaagact gagacgatca ctggcttcca agttgatgcc gttccagcca   5820
```

```
atggccagac tccaatccag agaaccatca agccagatgt cagaagctac accatcacag   5880
gtttacaacc aggcactgac tacaagatct acctgtacac cttgaatgac aatgctcgga   5940
gctcccctgt ggtcatcgac gcctccactg ccattgatgc accatccaac ctgcgtttcc   6000
tggccaccac acccaattcc ttgctggtat catggcagcc gccacgtgcc aggattaccg   6060
gctacatcat caagtatgag aagcctgggt ctcctccaca agaagtggtc cctcggcccc   6120
gccctggtgt cacagaggct actattactg gcctggaacc gggaaccgaa tatacaattt   6180
atgtcattgc cctgaagaat aatcagaaga gcgagcccct gattggaagg aaaaagacag   6240
acgagcttcc ccaactggta acccttccac accccaatct tcatggacca gagatcttgg   6300
atgttccttc cacagttcaa aagacccctt tcgtcaccca ccctgggtat gacactggaa   6360
atggtattca gcttcctggc acttctggtc agcaacccag tgttgggcaa caaatgatct   6420
ttgaggaaca tggttttagg cggaccacac cgcccacaac ggccaccccc ataaggcata   6480
ggccaagacc ataccgccg aatgtaggac aagaagctct ctctcagaca accatctcat   6540
gggccccatt ccaggacact tctgagtaca tcatttcatg tcatcctgtt ggcactgatg   6600
aagaacccti acagttcagg gttcctggaa cttctacctg tgccactctg acaggcctca   6660
ccagaggtgc cacctacaac atcatagtgg aggcactgaa agaccagcag aggcataagg   6720
ttcgggaaga ggttgttacc gtgggcaact ctgtcaacga aggcttgaac caacctacgg   6780
atgactcgtg cttttgacccc tacacagttt cccattatgc cgttggagat gagtgggaac   6840
gaatgtctga atcaggcttt aaactgttgt gccagtgctt aggcttttga agtggtcatt   6900
tcagatgtga ttcatctaga tggtgccatg acaatggtgt gaactacaag attggagaga   6960
agtgggaccg tcaggagaa aatgccaga tgatgagctg cacatgtctt gggaacggaa   7020
aaggagaatt caagtgtgac cctcatgagg caacgtgtta tgatgatggg aagacatacc   7080
acgtaggaga acagtggcag aaggaatatc tcggtgccat ttgctcctgc acatgcttg   7140
gaggccagcg gggctggcgc tgtgacaact gccgcagacc tgggggtgaa cccagtcccg   7200
aaggcactac tggccagtcc tacaaccagt attctcagag ataccatcag agaacaaaca   7260
ctaatgttaa ttgcccaatt gagtgcttca tgccttaga tgtacaggct gacagagaag   7320
attcccgaga gtaaatcatc tttccaatcc agaggaaca gcatgtctct ctgccaagat   7380
ccatctaaac tggagtgatg ttagcagacc cagcttagag ttcttctttc tttcttaagc   7440
cctttgctct ggaggaagtt ctccagcttc agctcaactc acagcttctc caagcatcac   7500
cctgggagtt tcctgagggt tttctcataa atgagggctg cacattgcct gttctgcttc   7560
gaagtattca ataccgctca gtatttaaa tgaagtgatt ctaagatttg gtttgggatc   7620
aataggaaag catatgcagc caaccaagat gcaaatgttt tgaaatgata tgaccaaaat   7680
tttaagtagg aaagtcaccc aaacacttct gctttcactt aagtgtctgg cccgcaatac   7740
tgtaggaaca agcatgatct tgttactgtg atattttaaa tatccacagt actcactttt   7800
tccaaatgat cctagtaatt gcctagaaat atctttctct tacctgttat ttatcaattt   7860
ttcccagtat ttttatacgg aaaaaattgt attgaaaaca cttagtatgc agttgataag   7920
aggaatttgg tataattatg gtgggtgatt attttttata ctgtatgtgc caaagcttta   7980
ctactgtgga aagacaactg ttttaataaa agatttacat tccacaactt gaagttcatc   8040
tatttgatat aagacacctt cggggggaaat aattcctgtg aatattcttt ttcaattcag   8100
caaacatttg aaaatctatg atgtgcaagt ctaattgttt atttcagtac aagattttct   8160
aaatcagttg ctacaaaaac tgattggttt ttgtcacttc atctcttcac taatgggagt   8220
agctttacac tttctgctttt aatagattta agtggacccc aatatttatt aaaattgcta   8280
gtttaccgtt cagaagtata atagaaataa tctttagttg ctcttttcta accattgtaa   8340
ttcttcccttt cttccctcca cctttccttc attgaataaa cctctgttca aagagattgc   8400
ctgcaaggga aataaaaatg actaagatat aaaaaaaaa aaaaaaaa                 8449
SEQ ID NO: 35              moltype = DNA   length = 4625
FEATURE                    Location/Qualifiers
source                     1..4625
                           mol_type = other DNA
                           organism = Homo sapiens
SEQUENCE: 35
agcgctccgc agtcacgtga cgctcgtccg caacctctgc tgtcctccgc ggcgcccct     60
tccgcctgac gcgcccccgg cggcggccgc gcagccctgg ctcctcgcgg gctcgggcgg   120
cggctgcggc ggggctatgg cgagcggcgg tgcggggt aacactggcg cgggtggggg     180
gccggggatg ggcctgagcc tgggcctggg tctgggtctg agcctaggca tgagtgaggc   240
caccagtgag gcagaggagg aggcggccac ggccggaggcg gtgggacgcc tggccacgac   300
gctgtggctg cggctccgcg gctgggaggc ggtgctggcg gcggcgcagc ggttgctggt   360
gtgggagaag ccgctgcaca gcctggtcac ggcggccgcg ctcaacgcc tcttctggtt   420
gctgtcttcc tcgtccctcc ggcccttctt cctactcagc gtctcacttt tggcctattt   480
tctgctggat ctctcggcag ctcgctttct ccctgacgtt tcagcatcat ccccagagga   540
gccacactct gacagtgagg gtgcgggctc aggcgcccgg ccgcacctgc tgagtgtgcc   600
cgagttgtgc agatacctgg ctgagagctg gctcaccttc cagattcacc tgcaggagct   660
gctgcagtac aagaggcaga atcagctca gttctgcgtt cgagtctgct ctggctgtgc   720
tgtgttgcct gtgttgggac atctatgttcc agggattatg atttcctaca ttgtcttgtt   780
gagtatcctg ctgtggcccc tggtggttta tcatgagctg atccagagga tgtacactcg   840
cctggagccc ctgctcatgc agctggacta cagcatgaag gcagaagcca atgccctgca   900
tcacaaacac gacaagagga agcgtcaggg gaagaatgca ccccaggag tgatgagcc    960
actggcagag acagagagtg aaagcgaggc agagctggct ggcttctccc cagtggtgga  1020
tgtgaagaaa acagcattgg ccttggccat tacagactca gagctgtcag atgaggagcc  1080
ttctatcttg gagagtggtg gcttctccgt atcccgggcc acaactccgc agctgactga  1140
tgtctccgag gatttggacc agcagaggcct gccaagtgaa ccagaggaga ccctaagccg  1200
ggacctaggg gagggagagg agggagagct ggcccctccc gaagacctac taggccgtcc  1260
tcaagctctg tcaaggcaag ccctggactc ggaggaagaa gaaggaggatg tggcagctaa  1320
ggaaacttg ttgcggctct catccccct ccacttttgg aacaccact tcaatgggcc     1380
agggtccccc ccagatggag tgaaatgctc ccctggagga ccagtcgaga cactgagccc  1440
cgagacagtg agtggtggcc tcactgctct gccccggcacc ctgtcacctc cactttgcct  1500
tgttggaagt gaccagcccc cctcccctcc cattctccca cctgttcccc aggactcacc  1560
ccagcccctg cctgccctg aggaagaaga ggcactcacc actgaggact tgagttgct    1620
ggatcagggg gagctggagc agctgaatgc agagctgggc ttggagccag agacaccgcc  1680
```

```
aaaaccccct gatgctccac ccctggggcc cgacatccat tctctggtac agtcagacca  1740
agaagctcag gccgtggcag agccatgagc cagccgttga ggaaggagct gcaggcacag  1800
tagggcttcc tggctaggag tgttgctgtt tcctcctttg cctaccactc tggggtgggg  1860
cagtgtgtgg ggaagctggc tgtcggatgg tagctattcc accctctgcc tgcctgcctg  1920
cctgctgtcc tgggcatggt gcagtacctg tgcctaggat tggttttaaa tttgtaaata  1980
attttccatt tgggttagtg gatgtgaaca gggctaggga agtccttccc acagcctgcg  2040
cttgcctccc tgcctcatct ctattctcat tccactatgc cccaagccct ggtggtctgg  2100
cccttctctt ttcctcctat cctcagggac ctgtgctgct ctgccctcat gtcccacttg  2160
gttgtttagt tgaggcactt tataattttt ctcttgtctt gtgttccttt ctgctttatt  2220
tccctgctgt gtcctgtcct tagcagctca acccccatcc ttgccagctc ctcctatccc  2280
gtgggcactg gccaagcttt agggaggctc ctggtctggg aagtaaagag taaacctggg  2340
gcagtgggtc aggccagtag ttacactctt aggtcactgt agtctgtgta accttcactg  2400
catccttgcc ccattcagcc cggcctttca tgatgcagga gagcagggat cccgcagtac  2460
atggcgccag cactggagtt ggtgagcatg tgctctctct tgagattagg agcttcctta  2520
ctgctcctct gggtgatcca agtgtagtgg gaccccctac tagggtcagg aagtggacac  2580
taacatctgt gcaggtgttg acttgaaaaa taaagtgttg attggctaga actgctgcct  2640
ccctgactgt gagctgcctt ccacaccctg cactgcactg tgttctctcc tcacccttaa  2700
cctgcttcac tccagtctgt tctggctgtt tattaccttg ttgcaaaaca gggccgaagc  2760
aaggattacc ttgacaaccc tagcttctcc ttagccatct tccttgacag tgtgatctgt  2820
ttagttgagat ttagcatgtg tgaataaagt atatgcagga ggaaattgct ttgtcttccc  2880
aatcggtaga aattcgggac cataaaaatt gtgttttacc atgtggccta caaccttaac  2940
actgctttct taagaagtct tcacccatct acatgctaac aactcactca gcctggattt  3000
atctttactg gggaagccaa acaagcaata gaggaccttt acctgtgtta gaaatgagtt  3060
ggagccaagg aacactgaag aaatagtatc ttaacagtta ctgagtccat tgtatgtgct  3120
tggctctgct ctgagtgatt tatatgtatt aagatttttc ctcacaggtc agatatatac  3180
tgttactaac ttcattttat agacaggtta agcttcctga agcttcctga tcccagtaaa  3240
ttgtggagcc agaacccaaa cccaagaagt tttggcttca gcaaatgcat cagacagccc  3300
ctgtccatta ataggacaca ggtaggaaga tgcacaagga tgtgggaact atagagaacc  3360
aatctgatgc cttggcttaa caaagagtgg acatggcaag ccttcctctt tggggaagaa  3420
aagcccagaa ctgagcagat ggcctccttt atgagttcat gtcctccgcc ttcagctgga  3480
ggtaccatat ggcgatgcta cctgtctttc tgctgaggt accatatgat aatgctgcct  3540
ggctgtctgc tggaggtacc atatggtaat gctgcctgtc tttctgaggt tgactttat  3600
gccatgtctt tcctaagtgt gtaagaattt ttctgtttgc ttcacatttg actgagaatc  3660
attctagggt ttgattgagc ccctgtcctg tgccactaaa ggaactcgaa cttttcatca  3720
cttagagatt tcagagggga atggaaaaac agttctaatc aataagcaag caattcaaga  3780
aaaatagaat taatcaggca atgactgcaa catgtcctat ctttaatcta tttttcttatt  3840
aagcttggac attgacaata gaaccagaag cttgtagctg gatcaaaata ttctccatag  3900
gcctggagtt tcatgagggt ctattctttt gttgttgttg ttttggtttt ttgtttttg  3960
tgggtttttt tttttttttt tttgagacgg agtcttgttc tgttgcccag gctggagtgc  4020
aatggtgcag tcttggttca ctgcaacctc tgcctcccag gttcaaacaa ttctcctgcc  4080
tcagccgtcc aagtagctgg gattacaggt gcatgccacg atgcctggct atttttgta  4140
ttttttagtag aggtgggggtt tcaccatgtt ggccaggctg gtctcgaact cctgacctca  4200
ggtgattcac ccacctcggc ctcccaaagt gctgggatta caggtgtgag ccacggcgcc  4260
cagcctcatg agggtctatt ctttacattc accatggtct gatggttgct acatgtttgt  4320
ctatgatttt ttttttctat tatcaggtgt cttggccggt tcatgcccca cgatgaaagg  4380
gccagaggtt tcatatgag taaaagaaaa agcagaaat gtgaaaccta caattaggct  4440
aaacaaaaat caactggaaa agtacaggct gaggggagaa gagttggcta catgttttatg  4500
ttaggggagg agggagtaca ttttagctat gtattcaaac agctaatagt ttaatgttgc  4560
tgcttataaa cttaattttta ggctgcatta ataaaagtgt agtctccaaa acaaaaaaaa  4620
aaaaa                                                              4625

SEQ ID NO: 36         moltype = DNA  length = 7556
FEATURE               Location/Qualifiers
source                1..7556
                      mol_type = other DNA
                      organism = Homo sapiens
SEQUENCE: 36
gcaggcgcct tcgcgaccg agcctgacgg agcggaggc tgggagccgc ggcggcctgg    60
ggaagtgttt ggattgtgag ctatttcaga actgttctca ggactcatta ttttaacatt   120
tgggagaaac acagccagaa gatgcacact tgactgaagg aggacaggga atctgaagac   180
tccggatgac atcagagcta cttttcaaca gccttctcaa ttttctttct cagaaagcag   240
aggctcagag cttggagaca gacgaacact gatatttgca tttaatgggg aacaaaagat   300
gaagaaggaa aaggaatata ttcactaagg attctatctg cttactgcta cagacctatg   360
tgttaaggaa ttcttctcct cctccttgcg tagaagttga tcagcactgt ggtcagactg   420
catttatctt gtcattgcca gaagaaatct tggacagaat gtaacagtac gtctctctct   480
gattgcgatg gaaggtgata aactgatact ccttttattaa agttacatcg cactcaccac   540
agaaaaccat tctttaaagt gaatagaaac caagcccttg tgaacacttc tattgaacat   600
gactcatgga gaagagcttg gctctgatgt gcaccaggat tctattgttt taacttacct   660
agaaggatta ctaatgcatc aggcagcagg gggatcaggt actgccgttg acaaaaagtc   720
tgctgggcat aatgaagagg atcagaactt taacattttct ggcagtgcat ttcccaccctg  780
tcaaagtaat ggtccagttc tcaatacaca tacatatcag gggtctggca tgctgcaccct  840
caaaaaagcc agactgttgc agtcttctga ggactggaat gcagcaaagc ggaagaggct   900
gtctgattct atcatgaatt taaacagtaa aaggaagct tgctagctg catggttga    960
cagtgtgcct aaaggcaaac aggatagcac attactgcc tcttttgcttc agtcattcag  1020
ctctaggctg cagactgttg ctctgtcaca acaaatcagg cagagcctca aggagcaagg  1080
atatgccctc agtcatgatt cttttaaagt ggagaaggat ttaaggtgct atggtgttgc  1140
atcaagtcac ttaaaaactt tgttgaagaa agtaaagtt aaagatcaaa agcctgatac  1200
gaatcttcct gatgtgacta aaaacctcat cagagatagg tttgcagagt ctcctcatca  1260
tgttggacaa agtggaacaa aggtcatgag tgaaccgttg tcatgtgctg caagattaca  1320
```

```
ggctgttgca agcatggtgg aaaaaagggc tagtcctgcc acctcaccta aacctagtgt   1380
tgcttgtagc cagttagcat tacttctgtc aagcgaagcc catttgcagc agtattctcg   1440
agaacacgct ttaaaaacgc aaaatgcaaa tcaagcagca agtgaaagac ttgctgctat   1500
ggccagattg caagaaaatg gccagaagga tgttggcagt taccagctcc caaaaggaat   1560
gtcaagccat cttaatggtc aggcaagaac atcatcaagc aaactgatgg ctagcaaaag   1620
tagtgctaca gtgtttcaaa atccaatggg tatcattcct tcttccccta aaaatgcagg   1680
ttataagaac tcactggaaa gaaacaatat aaaacaagct gctaacaata gtttgctttt   1740
acatcttctt aaaagccaga ctatacctaa gccaatgaat ggacacagtc acagtgagag   1800
aggaagcatt tttgaggaaa gtagtacacc tacaactatt gatgaatatt cagataacaa   1860
tcctagtttt acagatgaca gcagtggtga tgaaagttct tattccaact gtgttcccat   1920
agacttgtct tgcaaacacc gaactgaaaa atcagaatct gaccaacctg tttccctgga   1980
taacttcact caatccttgc taaacacttg ggatccaaaa gtcccagatg tagatatcaa   2040
agaagatcaa gatacctcaa agaattctaa gctaaactca caccgaaaag taacacttct   2100
tcaattgcta cttggccata agaatgaaga aaatgtagaa aaaacacca gccctcaggg   2160
agtacacaat gatgtgagca agttcaatac acaaaattat gcaaggactt ctgtgataga   2220
aagccccagt acaaatcgga ctactccagt gagcactcca cctttactta catcaagcaa   2280
agcagggtct cccatcaatc tctctcaaca ctctctggtc atcaaatgga attccccacc   2340
atatgtctgc agtactcagt ctgaaaagct aacaaatact gcatctaacc actcaatgga   2400
ccttacaaaa agcaaagacc caccaggaga gaaaccagca caaatgaag gtgcacagaa   2460
ctctgcaacg tttagtgcca gtaagctgtt acaaaattta gcacaatgtg gaatgcagtc   2520
atccatgtca gtggaagagc agagacccag caaacagctg ttaactggaa acacagataa   2580
accgataggt atgattgata gattaaatag cccttttgtc tcaaataaaa caaatgcagt   2640
tgaagaaaat aaagcatttta gtagtcaacc aacaggtcct gaaccagggc tttctggttc   2700
tgaaatagaa aatctgcttg aaagacgtac tgtcctccag ttgctcctgg ggaaccccaa   2760
caaagggaag agtgaaaaaa aagagaaaac tcccttaaga gatgaaagta ctcaggaaca   2820
ctcagaagga gctttaagtg aacaaatact gatggtaaaa ataaaatctg agccttgtga   2880
tgacttacaa attcctaaca caaatgtgca cttgagccat gatgctaaga gtgcccatt   2940
cttgggtatg gctcctgctg tgcagagaag cgcacctgcc ttaccagtgt ccgaagactt   3000
taaatcggag cctgtttcac ctcaggattt ttctttctcc aagaatggtc tgctaagtcg   3060
attgctaaga caaaatcaag atagttacct ggcagatgat tcagacagga gtcacagaa   3120
taatgaaatg gcacttctag aatcaaagaa tctttgcatg gtccctaaga aaaggaagct   3180
ttatactgag ccattagaaa atccatttaa aaagatgaaa aacaacattg ttgatgctgc   3240
aaacaatcac agtgccccag aagtactgta tgggtccttg cttaaccagg aagagctgaa   3300
atttagcaga aatgatcttg aatttaaata tcctgctggt catggctcag ccagcgaaag   3360
tgaacacaga agttgggcca gagagagcaa aagtctgaaac agctgcttct   3420
ctcagaaaac tgtgtgcgag atttgtcccc gcacagaagt aactctgtgg ctgacagtaa   3480
aaagaaagga cacaaaaata atgtgaccaa cagcaaacct gaatttagca ttctcttctt   3540
aaatggactg atgtacagtt ccactcagcc cagcagttgc atggataaca ggacattttc   3600
atacccaggt gtagtaaaaa ctcctgctgag tcctacttc cctgagcact tgggctgtgc   3660
agggtctaga ccagaatctg ggcttttgaa tgggtgttcc atgcccagtg agaaaggacc   3720
cattaagtgg gttatcactg atgcggagaa gaatgagtat gaaaaagact ctccaagatt   3780
gaccaaaacc aacccaatac tatattcat gcttcaaaaa ggaggcaatt ctgttaccag   3840
tcgagaaaca caagacaagg acatttggag ggaggcttca tctgctgaaa gtgtctcaca   3900
ggtcacagcc aaaagaagagt tacttcctac tgcagaaacg aaagcttctt tctttaattt   3960
aagaagccct tacaatagcc atatgggaaa taatgcttct cgcccacaca gcgcaaatgg   4020
agaagtttat ggacttctgg gaagcgtgct aacgataaag aaagaatcag aataaaatgt   4080
acctgccatc cagttttgga tcttttttaaa actaatgagt atgaacttga gatctgtata   4140
aataagagca tgatttgaaa aaaagcatgg tataattgaa acttttttca ttttgaaaag   4200
tattggttac tggtgatgtt gaaatatgca tactaatttt tgcttaacat tagatgtcat   4260
gaggaaacta ctgaactagc aattggttgt ttaacacttc tgtatgcatc agataacaac   4320
tgtgagtagc ctatgaatga aattctttta taaatattag gcataaatta aaatgtaaaa   4380
ctccattcat agtggattaa tgcatttgtc tgcctttatt agggtacttt attttgcttt   4440
tcagaagtca gcctacataa cacatttta aagtctaaac tgttaaacaa ctcttttaaag   4500
gataattatc caataaaaaa aaacctagtg ctgattcaca gctattatc caattcaaaa   4560
ataaattaga aaatatatg cttacatttt tcacttttgc taaaaagaaa aaaaaaaggt   4620
gtttattttt aactcttgga agaggttttg tggttcccaa tgtgtctgtc ccaccctgat   4680
ccttttcaat atatatttct ttaaaccttg tgctacttag taaaaattga ttacaattga   4740
gggaagtttg atagatcctt taaaaaaaag gcagatttcc attttttgta ttttaactac   4800
tttactaaat taatactcct ccttttacag aattagaaaa gttaacattt atctttaggt   4860
ggtttcctga aaagttgaat atttaagaaa ttgtttttaa cagaagcaaa atggcttttc   4920
tttgacagt tttcaccatc tcttgtaaaa gttaattctc accattcctg tggtacctgc   4980
gagtgttatg accaggattc cttaaacctg aactcagacc acttgcatta gaaccatctg   5040
gagcacttgt tttaaaatgc agattcatag gcagcatctc agatctacag aacaagaatc   5100
tctgctaagt ggacctggaa tcttccatct gcatcttaac atgctctcta ggtgttttctt   5160
gtgtttgaga accatgactt atgacttcc tcagaacatg agactgtaaa acaaaaacaa   5220
aaaactatgt gatgcctcta ttttccccaa tacagtcaca catcagctca aaatttgcaa   5280
tattgtagtt catatattac cgttatgtct ttggaaatcg ggttcagaac acttttatg   5340
acaaaaatttg ggtggagggg ataacttca tatctggctc aacatctcag gaaaatctgt   5400
gattatttgt gtgttctaat gagtaacatc tacttagtta gccttaggga tggaaaaaca   5460
gggccactta ccaaactcag gtgattccaa gatggtttgg aaacttctcc tgaatgcatc   5520
cttaacctttt attaaaacca ttgtcctaag aacaatgcca acaaagctta caacatttag   5580
tttaaaccca agagggcac taaactcaga ttgactaaat aaaaagtaca aagggcacat   5640
atacgtgaca gaattgtaca caatcactcc attggatctt ttactttaaa gtagtgatga   5700
aaagtacatg ttgatactgt cttagaagaa attaatatat tagtgaagcc acatggggtt   5760
tcagttgcga aacaggtctg tttttatgtt cagtttgtac aatccacaat tcattccaca   5820
gatattttgt tcttaattgt gaaccaggtt agcaaatgac ctatcaaaaa ttattctata   5880
atcactacta gttaggatat tgatttaaaa ttgttctact tgaagtggtt tctaagagtt   5940
ttatattaaa aataggtgtg atttcctaat atgatctaaa accctaaatg gttatttttc   6000
ctcagaatga tttgtaaata gctactggaa atattataca gtaataggag tgggtattat   6060
```

```
gcaacatcat ggagaagtga aggcataggc ttattctgac ataaaattcc actggccagt   6120
tgaatatatt ctattccatg tccatactat gacaatctta ttgtcaacac tatataaata   6180
agcttttaaa caagtcattt ttcttgatcg ttgtggaagg tttggagcct tagaggtatg   6240
tcagaaaaaa tatgttggta ttctcccttg ggtaggggga aatgaccttt ttacaagaga   6300
gtgaaattta ggtcagggaa aagaccaagg gccagcattg ctacttttgt gtgtgtgtgt   6360
gtgggttttg ttttgttttt ttggttggct ggttgttttc gttgttgtta acaaaggaat   6420
gagaatatgt aatacttaaa taaacatgac cacgaagaat gctgttctga tttactagag   6480
aatgttccca atttgaattt agggtgattt taaagaacag tgagaaaggg catacatcca   6540
cagattcact ttgtttatgc atatgtagat acaaggatgc acatatacac attttcaagg   6600
actattttag atatctagac aatttcttct aataaagtca tttgtgaaag ggtactacag   6660
cttattgaca tcagtaaggt agcattcatt acctgtttat tctctgctgc atcttacaga   6720
agagtaaact ggtgagagta tatattttat atatatatat atatatatat ataatatgt    6780
tatatatata tatattgact tgttacatga agatgttaaa atcggttttt aaaggtgatg   6840
taaatagtga tttccttaat gaaaaataca tattttgtat tgttctaatg caacagaaaa   6900
gccttttaat ctctttggtt cctgtatatt ccatgtataa gtgtaaatat aatcagacag   6960
gtttaaaagt tgtgcatgta tgtatacagt tgcaagtctg gacaaatgta tagaataaac   7020
cttttatttta agttgtgatt acctgctgca tgaaaagtgc atggggacc ctgtgcatct    7080
gtgcatttgg caaaatgtct taacaaatca gatcagatgt tcatcctaac atgacagtat   7140
tccatttctg gacatgacgt ctgtggttta agctttgtga aagaatgtgc tttgattcga   7200
agggtcttaa agaattttt taatcgtcaa ccacttttaa acataaagaa ttcacacaac    7260
tactttcatg aatttttaa tcccattgca aacattattc caagagtatc ccagtattag    7320
caatactgga atataaggcac attaccattc atagtaagaa ttctggtgtt tacacaacca  7380
aatttgatgc gatctgctca gtaatataat ttgccatttt tattagaaat ttaatttctt   7440
catgtgatgt catgaaactg tacatactgc agtgtgaatt tttttgtttt gttttttaat   7500
cttttagtgt ttacttcctg cagtgaattt gaataaatga gaaaaaatgc attgtc       7556

SEQ ID NO: 37          moltype = DNA  length = 1516
FEATURE                Location/Qualifiers
source                 1..1516
                       mol_type = other DNA
                       organism = Homo sapiens
SEQUENCE: 37
tgccccacca ccgctgctcc tcagcaggcg cctcaccagc ctccacaccc cttgcgcccg      60
cagaaacgcg cctggccctg agctgtcacc accgacactc tccaggctcc ggacacgatg    120
caggccatca agtgtgtggt ggtgggagat ggggccgtgg gcaagacctg ccttctcatc    180
agctacacca ccaacgcctt tcccggagag tacatcccca ccgtgtttga caactattca    240
gccaatgtga tggtggacag caagccagtg aacctgggc tgtgggacac tgctgggcag    300
gaggactacg accgtctccg gccgctctcc tatccacaca cggacgtctt cctccatctgc   360
ttctccctcg tcagcccagc ctcttatgag aacgtccgcg ccaagtggtt cccagaagtg    420
cggcaccact gccccagcac acccatcatc ctggtgggca ccaagtggac cctgcgggac    480
gacaaggaca ccatcgagaa actgaaggag aagaagctgg ctcccatcac ctacccgcag    540
ggcctggcac tggccaagga gattgactcg gtgaaatacc tggagtgctc agctctcacc    600
cagagaggcc tgaaaaccgt gttcgacgag gccatccggg ccgtgctgtg ccctcagccc    660
acgcggcagc agaagcgcgc ctgcagcctc ctctagggt tgcacccag cgctcccacc      720
tagatgggtc tgatcctcca ggatcccac ccaaagcctg atggcacccc ggctggccat     780
gctgtcccct ccctgtggcg tttcttagca gatggctgca gagcttcgtt gatggtcttt    840
tctgtactgg aggcctcctg aggccaggaa cgtgcaaatt tgcaggtgct gcatcccaag    900
cccctcatgc tcctgccttc ctgagggcca gaggggagcc ccaggaccca ttaagccacc    960
ccgtgttcc tgccgtcagt gccaactgcc gcatgtggaa gcatctaccc gttcactcca    1020
gtcccaccc acgcctgact cccctctgga aactgcaggc cagatggttg ctgccacaac    1080
ttgtgtacct tcagggatgg ggctcttact ccctcctgag gccagctgct ctaatatcga   1140
tggtcctgct tgccagagag ttcctctacc cagcaaaaat gagtgtctca gaagtgtgct   1200
cctctggcct cagttctcct cttttggaac aacataaaac aaatttaatt ttctacgcct   1260
ctggggatat ctgctcagcc aatggaaaat ctgggttcaa ccagcccctg ccatttctta   1320
agactttctg ctgcactcac aggatcctga gctgcactta cctgtgagg tcttcaaact   1380
tttaaacctt gccagtcagg acttttgcta ttgcaaatag aaaacccaac tcaacctgct   1440
taagcagaaa ataaatttat tgattcaaaa aaaaaaaaaa aaaaaaaaaa aaaaaaaaaa   1500
aaaaaaaaaa aaaaaa                                                   1516

SEQ ID NO: 38          moltype = DNA  length = 1641
FEATURE                Location/Qualifiers
source                 1..1641
                       mol_type = other DNA
                       organism = Homo sapiens
SEQUENCE: 38
ctccctgtgt tggtggagga tgtctgcagc agcatttaaa ttctgggagg gcttggttgt      60
cagcagcagc aggaggaggc agagcacagc atcgtcggga ccagactcgt ctcaggccag    120
ttgcagcctt ctcagccaaa cgccgaccaa ggaaaactca ctaccatgag aattgcagtg    180
atttgctttt gcctcctagg catcacctgt gccataccag ttaaacaggc tgattctgaa    240
agttctgagg aaaagcagct ttacaacaaa tacccagatg ctgtggccac atggctaaac    300
cctgacccat ctcagaagca gaatctccta gccccacaga atgctgtgtc ctctgaagaa    360
accaatgact ttaaacaaga gaccttcca agtaagtcca acgaaagcca tgaccacatg    420
gatgatatgg atgatgaaga tgatgatgac catgtgggaca gccaggactc cattgactcg    480
aacgactgta tggtagtaga tgcactgtgat gattctgatg atgtctccca tccaccatca    540
tctgatgaat ctgatgaact ggtcactgat tttcccacgg acctgccagc aaccgaagtt    600
ttcactccag ttgtccccac agtagacaca tatgatggcc gaggtgatag tgtggttat    660
ggactgaggt caaatcta gaagtttcgc agacctgaca tccagtaccc tgatgctaca   720
gacgaggaca tcacctcaca catggaaagc gaggagttga atggtgcata caaggccatc   780
cccgttgccc aggaccgtgaa cgcgccttct gattgggaca gccgtgggaa ggacagttat   840
```

```
gaaacgagtc agctggatga ccagagtgct gaaacccaca gccacaagca gtccagatta    900
tataagcgga aagccaatga tgagagcaat gagcattccg atgtgattga tagtcaggaa    960
cttttccaaag tcagccgtga attccacagc catgaatttc acagccatga agatatgctg  1020
gttgtagacc ccaaaagtaa ggaagaagat aaacacctga aatttcgtat ttctcatgaa   1080
ttagatagtg catcttctga ggtcaattaa aaggagaaaa aatacaattt ctcactttgc   1140
atttagtcaa aagaaaaaat gctttatagc aaaatgaaag agaacatgaa atgcttcttt   1200
ctcagtttat tggttgaatg tgtatctatt tgagtctgga aataactaat gtgtttgata   1260
attagtttag tttgtggctt catggaaact ccctgtaaac taaaagcttc agggttatgt   1320
ctatgttcat tctatagaag aaatgcaaac tatcactgta ttttaatatt tgttattctc   1380
tcatgaatag aaaatttatg agaagcaaac aaaatacttt tacccactta aaaagagaat   1440
ataacatttt atgtcactat aatcttttgt tttttaagtt agtgtatatt ttgttgtgat   1500
tatcttttg tggtgtgaat aaatctttta tcttgaatgt aataagaatt tggtggtgtc    1560
aattgcttat ttgttttccc acggttgtcc agcaattaat aaaacataac ctttttact   1620
gcctaaaaa aaaaaaaaa a                                               1641
```

```
SEQ ID NO: 39          moltype = DNA   length = 6463
FEATURE                Location/Qualifiers
source                 1..6463
                       mol_type = other DNA
                       organism = Homo sapiens
SEQUENCE: 39
ctctcttgct cgctcgctcc ctctctctcc tgctggctgc ctgttctagg aagccagcgc     60
ggagagggg gggatgcaca gcacagggga gagagattgc gcatgttggt cagtcgtgtt    120
ttaaagagta cagtgcgggg aggctgagag gggcgcatgc aacaacaact tttggaagga   180
tggaagagaa gaggcgaaaa tactccatca gcagtgacaa ctctgacacc actgacagtc   240
atgcgacatc tacatccgca tcaagatgct ccaaactgcc cagcagccac aagtcgggct   300
ggccccgaca gaacgaaaag aagccctccg aggttttccg gacagacttg atcacagcca   360
tgaagatccc ggactcatac cagctcagcc cggatgacta ctacatcctg gcagaccccat  420
ggcgacagga atgggagaaa ggtgtgcagg tgcctgccgg ggcagaggcc atcccagagc   480
ccgtggtgag gatcctccca ccactggaag gccccctgc ccaggcatcc ccgagcagca    540
ccatgcttgg tgagggctcc cagcctgatt ggccaggggg cagccgctat gacttggacg   600
agattgatgc ctactggctg gagctcatca actcggagct taaggagatg gagaggccgg   660
agctggacga gctgacatta gagcgtgtgc tggaggagct ggagaccctg tgccaccaga   720
atatggccag ggccattgag acgcaggagg ggctgggcat cgagtacgac gaggatgttg   780
tctgcgacgt gtgtcgctct cctgagggcg aggatggcaa cgagatggtc ttctgtgaca   840
agtgcaacgt ctgtgtgcat caggcatgct acgggatcct caaggtgccc acgggcagct   900
ggctgtgccg gacgtgtgcc ctgggtgtcc agccaaagtg cctgctctgc cccaagcgag   960
gaggagcctt gaagcccact agaagtggga ccaagtgggg catgtcagc tgtgccctat    1020
ggattcctga ggtcagcatc ggctgcccag agaagatgga gccatcacc aagatctcgc    1080
atatcccagc cagccgctgg gctctgtcct gcagcctctg caaggaatgc acaggcacct   1140
gcatccagtg ttccatgcct tcctgcgtca cagcgttcca tgtcacatgc gccttttgacc  1200
acggcctgga aatgcggact atattagcag acaacgatga ggtcaagttc aagtcattct   1260
gccaggagca cagtgacggg ggcccacgta atgagccc atctgagccc gacggaaccca    1320
gccaggctgg cgaggacctg gaaaaggtga ccctgcgcaa gcagcggctg cagcagctag   1380
aggaggactt ctacgagctg gtggagccgg ctgaggtggc tgagcggctg gacctggctg   1440
aggcactggt cgacttcatc taccagtact ggaagctgaa gaggaaagcc aatgccaacc   1500
agccgctgct gaccccccaag accgacgagg tggacaacct ggccagcag gagcaggacg   1560
tcctctaccg ccgcctgaag ctcttcaccc atctgcggca ggacctagag agggttagaa   1620
atctgtgcta catggtgaca aggcgcgaga aacgaaaca cgccatctgc aaactccagg   1680
agcagatatt ccacctgcag atgaaactta ttgaacagga tctgtgtcga ggcctgtcca   1740
cctcattccc catcgatggc accttcttca cagctggttca ggcacagtcg gtgcagatca   1800
cagcagagaa catggccatg agcgagtggc cactgaacaa tgggcaccgc gaggaccctg   1860
ctccagggct gctgtcagag gaactgctgc aggacgagga cactgctc agcttcatgc    1920
gggaccctc gctgcgacct ggtgaccctg ctaggaaggc ccgaggccgc accgctgc     1980
ctgccaagaa gaaaccacca ccaccaccac cgcaggacgg gcctggttca cggacgactc   2040
cagacaaagc ccccaagaag acctggggcc aggatgcagg cagtggcaag gggggtcaag   2100
ggccacctac caggaagcca ccacgtcgga catcttctca cttgccgtcc agccctgcag   2160
ccggggactg tcccatccta gccacccctg aaagcccccc gccactggcc cctgagaccc   2220
cggacgaggc agcctcagta gctgctgact cagatgtcca agtgcctgcc cctgcagcaa   2280
gccctggcc tttgggccgg ctccggccac ccgcgagag caaggtaacc cggagattgc    2340
cgggtgccag gcctgatgct gggatgggac caccttcagc tgtggctgag aggcccaagg   2400
tcagcctgca ttttgacact gagactgatg gctacttctc tgatggggag atgagcgact   2460
cagatgtaga ggccgaggac gtgggggtgc agcgggtcc ccgggaggca ggggcagagg    2520
aggtggctca gatgggcgta ctggcctcct aactcacccc cttccctgtc ccaggcctgg   2580
ccctggtccc cccacaaggc ctcagcccag tcacaactgc catttccagt ctctgctgag   2640
tgtcccagac cctcgaggct gccactccgt cgtggtttta tttttaatat agagagagtt   2700
ttgaattcta cactgttgtc tttcctctgt gctggcctag acattagga ttccttccac    2760
ggctccggcc gctaggaccc tgccaggtcc cgcgcaccat ccctgccctg cccacgtggt   2820
attgctgggc tcctggctag atgcaagcaa ggtggacaag agctcaggac tccagcccac   2880
tgccactggg tgacacagac tgtcgtttgg gcattatttc atggcagatg gccagtccca   2940
gggcctaccc cgccttgccc ccagatccca ctggggtcca tttggggggt cctgctacac   3000
tccaccgatc cccaaggaag tataataaac gatacccagc cagagtctac tcactgtcac   3060
aagcacaacg agtttatatg agaaagcact gaggggggtgc agagggcccg ctagttccag   3120
gggaactgaa agcttgttcct gatcagaccg tatcatctga ggcctgcctc cacccctga    3180
caccctcccc tcccttgctg ctctgcccct gccagtgccc agccagcgg ctctgggaag    3240
gggttcccag aatcccttcct gagctgtgcc atttactcag gggactccca aacagccagc   3300
tgccagtgca ggtggagggc tgtagggag gccagtgcc cagacaggggt catgggctc     3360
agaccagccc actgtagaga atcactctga ggctccaact tccttccttc cttcggggcc   3420
agtctcggcc gaagtctggt cacgtcaga cagagctgac cagaccagac cgtttgcctt    3480
```

```
ttcaagtttc ctagtcctgc tacaagatga gcttcttccg tggtttcctt ttggaaactc    3540
ctccttccaa caagcagtgg gatcccgggg cccagggcgg gccggtgttg gccgctgggg    3600
ctgttgtaag tcttgctgga tgttcccctg ttcctgagcc ttaacccctc gcacagccat    3660
ccccccccc gtcctgccat ccccccccgc cgtcctgcct tccccacccc acccttaggt    3720
cccaggtagt tgctctgaag agtttcagta gagtggcccc agggtgatag ctcagggaac    3780
aacaaaaaag gaattccgtg aaaacatttt tttttctttg atgaattact cctgggtcac    3840
ttccaccact ggtaaagcca gaacttctcc aaaaagaacc ttgcaaaaag tccagtgaat    3900
cagtcgaatc attctgtgga tgccaaagaa tattttgacc ataatacagc acagcctgga    3960
cctgacaact tgtcatttgg actttttttt aaatggagtt ctttagcaac aaagtataga    4020
aacatgttca ttgcacacac ccaaggagaa gagctcaagc gcttggaaga ggatgctttg    4080
ctgctgctga agtgtacctg ggtgttagat ttcagatcct gggctgagcc cactgtgagc    4140
tttcctaaac tgtgagactc acagagggga aagatactga cggtaaaacc agcatggaaa    4200
acgtctttac catgtggttc cctcctcccc aaatacataa agcaaataag caggatgggg    4260
aacagcttga ccttcatcca cccctaactc caaaactatc aaggtacgac agtggcattg    4320
tcatcgacac tcaatttcat gtgaattta gcaaacagg aaacaaagat aatgactcag    4380
ttcagaggat cggacaaatg tgtctagtcc gggtggactc ggagggagtg gggtgggctt    4440
caaggattct gggcgttggg atggcatgag ctaccctgta gagtttagtc tgcctgcccg    4500
ccttggtagt agtgaccagt cagtgtcagc atcagtgtcc caaccccagt ctctgtttac    4560
tgccttgaa cagaacttct tccttcccca tgctttgggt caccctcggc tgcaaccctg    4620
tctgtgccag attgcccggt ctgacccctgc aggaagcaaa gaggtgagct taaagaacaa    4680
ccaaactctg ccaggggtcc cagaaagccc agggtccagc agtctcagca cttggcccct    4740
tgccccttca caccatcctg gggcaggggc tgggcctcag tggtgcagg ggtgggtgga    4800
gaattaggga gagggtgcaa cgagtctggc cccttgcctc gggctggctg gtgttcttcc    4860
aagagcctct gctcacattg ttggcctctg gattctggcc cttcttcatt ggctgttgct    4920
ttggactgga ctgttgctga gcctgtgtcc tgcagaaccc agatgtctgt taggctggct    4980
ggctgctgca aggggagggg ggtggccttt catttgggtg gccctttcac tcccaggcca    5040
agccctggag caatcttctt caggcagctg tctccacctc caggatgtcc agcaggctgc    5100
aaggagaagg atgccagcca cccatcctcc cccagttccc agcctttccc ctgttggtca    5160
cagccgcttc tgtctttttc cggtctactg tcccagtgt agagggcttt gctgtccctg    5220
agactgaggc aggttccttt tccaggtcag aggtggaggt agatcttct ctcaaccaca    5280
tctgcctcca cacacagctc ctccgcaggg aaggagaagc tgctctgtaa ctcattctgg    5340
ctatcgtccc ccttctcact gacctgaccg cccaccacct ccttcccct catcacatga    5400
caaaggataa tgtgcaagaa aagtattttt atgtatcata aatgtatttt gaaacaaatg    5460
agaagaagaa aggtagaagg gttttatttta ttaaatgagc ctgacttagt gacagtgtgt    5520
gagcatttgc aatgtaaggg cctcagcttc cttggagaag ccaccccagg tttccagaca    5580
tagatgttga attgtttgtg gggggtgtgc caggccacgt ctcgtgtgtc cgtatgcagg    5640
catgcctgtg tatactgtgt atgggcacac tgggactagc tgggacaatt cctagagatt    5700
caactgccca attctaacca acattggcag cggctgaact tggcatttcc ttgctaactg    5760
ccagatgtgg ccaaccttg tccatatgca aaccactgaa aaatgatctg gatttctata    5820
gcaaggccct tggggagggc actctcccat gcccttggcc tcgctggcca cattggccaa    5880
tgagccaggg ctggagtctg agacctttgg ttgttcttta aggcacctcc tgccactttc    5940
tccctcagag gcacaaacac tttgtgttcc acgtcagttt gaggggacgg tgggggatg    6000
atatgaatgt cacaggagga gacaccttct gtctttgttt caaagaaagt gatgtgccat    6060
ttgttaatat acaagagaaa tattgaaaat atattgaaaa gagcaatttt aaattatttt    6120
tggcttatgt tgcaatattt attttcttgt attagaaaag attcctttgt agagaaaaa    6180
tgtatttttc attaacgcaa agacctattt ctccttttg tacattgtcc atgtgcgcaa    6240
cccttaacga gcaatagaat gtatggtcac ctgggtgtgg ccagtgcccg ctgtgccctg    6300
catgattctg tgttgccgct gctgcatagt tcccagcccc atcctgtcct gctcactcat    6360
gggggcttcc agaccccggc cccaccaggg cttgtgtcat agggagccct ttgcactcct    6420
cgtgtgttgg caaacgcagt taataaagca gtgttttctg tgc              6463

SEQ ID NO: 40          moltype = DNA   length = 2828
FEATURE                Location/Qualifiers
source                 1..2828
                       mol_type = other DNA
                       organism = Homo sapiens
SEQUENCE: 40
catagatgaa aatggcaagt tccctggctt tccttctgct caactttcat gtctccctcc     60
tcttggtcca gctgctcact ccttgctcag ctcagttttc tgtgcttgga ccctctgggc    120
ccatcctggc catggtgggt gaagacgctg atctgccctg tcacctgttc ccgaccatga    180
gtgcagagac catggagctg aagtgggtaa gttccagcct aaggcaggtg gtgaacgtgt    240
atgcagatgt aaaggaagtg gaagacaggc agagtcacc gtatcgaggg agaacttcga    300
ttctgcggga tggcatcact gcaggaaggg ctgctctccg aatacacaac gtcacagcct    360
ctgacagtga aaagtacttg tgttatttcc aagatgatga cttctatgaa acagcccttg    420
tggagctgaa ggttcagca ctgggttcta atcttcacgt cgaagtgaag ggttatgagg    480
atggagggat ccatcggag tgcaggtcca ccggctggta ccccaaccc caaatacagt    540
ggagcaacgc caagggagag aacatcccag ctgtggaagc acctgtggtt gcagatgag    600
tgggcctata tgaagtagca gcatctgtga tcatgagagg cggctccggg gagggtatat    660
cctgcatcat cagaaattcc ctcctcggcc tggaaaagac agcagcatt tccatcgcag    720
accccttctt caggagcgcc cagccctgga tcgcagccc ggcagggacc ctgcctatct    780
tgctgctgct tctcgccgga gccagttact tcttgtggag acaacagaag gaaataactg    840
ctctgtccag tgagatagaa agtgagcaag agatgaaaga aatgggata gctgaacag    900
agcgggaat aagcctaaga gagagcctcc aggaggaact caagaggaaa aaatccagt    960
acttgactcg tggagatgag tcttcgtccg ataccaataa gtcagcctga tgtctcaatg   1020
gaaaatgtgc cctctttcaag cctgaaaaa tggctgaccc catgacacc tcctcaaact   1080
ctctgcagca gatgtaattc tgtatccaga catggcaaat gccatcctcc ttgttctga   1140
ggaccagagg agtgtacagc gtgctgagga gccccatgac ctaccagaca accctgagag   1200
atttgaatgg cgttactgtg tgcttggctg tgaaagcttc atgtcagaga gacactactg   1260
ggaggtggaa gtgggggaca gaaaagagtg gcatattggg gtatgtagta agaacgtgga   1320
```

-continued

```
gaggaaaaaa gtttgggtca aaatgacacc ggagaacgga tactggacta tgggcctgac   1380
tgatgggaat aagtatcggg ctctcactga gcccagaacc aacctgaaac ttcctgagcc   1440
tcctaggaaa gtgggggtca tcctggacta tgagactgga catatctcgt tctacaatgc   1500
cacgggatgga tctcatatct acacatttct gcacgcctct tcctctgagc ctctgtatcc   1560
tgtattcaga attttgacct tggagcccac tgccctgacc gtttgcccaa taccaaaagt   1620
agagagttcc cccgatcccg acctagtgcc tgatcattcc ctggagatac cactgacccc   1680
aggcttagct aatgaaagtg gggagcctca ggctgaagta acatctctgc ttctccctgc   1740
ccagcctgga gctaagggtc tcaccctcca caacagccag tcagaaccat aaagctacag   1800
gcacacactg aagcacttta ctgatattca ttcaattatt ccataggaca gttgtttgga   1860
tttggtgcca ccttattggc ccctttatac agataaggaa actggggtgt agaaaagtgt   1920
attgacttta caaagcagac aggaatagtg aacaacagag ctgggatctg aacaacaatg   1980
actaacatta atgagaatt taaaacgttc tgagtgctgt gttatgagct ttggtgggtg   2040
tcactccttt aatcctcaca acaccctgtc aggtagtctc atttggcaag tatgtaagca   2100
gaggcagggc aacattaagt agcttacata actcacacgg taatttgtgc agttgggaga   2160
tgttcagctt cagtccctgg ccaattgccc gttcttttcc agcctgattt ttcctgcatg   2220
ggaagagccc acatgtagcc ctgaggttcc cttcccagga cagctccagg atcgagatca   2280
ctgtgagtgg ttgtggagtt aagaccccta tggactcctt cccagctgat tatcagagcc   2340
ttagacccag cactccttgg attggctctg cagagtgtct tggttgagag aataacgttg   2400
cagttcccac agggcatgtg actttgaaag agactagagg ccacactcag ttaataatgg   2460
ggcacagatg tgttcccacc caacaaatgt gataagtgat cgtgcagcca gagccagcct   2520
tccttcagtc aaggttttcca ggcagagcaa ataccctaga gattctctgt aatattggta   2580
atttggatga aggaagctag aagaattaca gggatgttt taatcccact attggactcag   2640
tctcctggaa aaggatctgt ccactcctgg tcattggtgg atgttaaacc catattcctt   2700
tcaactgctg cctgctaggg aaaactgctc ctcattatca tcactattat tgctcaccac   2760
tgtatcccct ctactgggca agtgcttgtc aagttctagt tgttcaataa atttgttaat   2820
aatgctga                                                            2828

SEQ ID NO: 41         moltype = DNA   length = 2698
FEATURE               Location/Qualifiers
source                1..2698
                      mol_type = other DNA
                      organism = Homo sapiens
SEQUENCE: 41
gccgtccgtg ctgactgagg cgctgcagcc aggagccgcg gccggctgcc cagcgctcgc     60
cgcctccgcg cgtccgcagc cgtccccgcg ccgacatgcg cttggccgcc gccgcgaacg    120
aggcgtacac ggccccttg gcggtctcgg ggctgctggg ctgcaagcag tgcggcgggg    180
gccgcgacca ggacgaggaa cttggcatta gaattcctcg accactagga cagggaccaa    240
gcagattcat cccagaaaag gagatcctcc aagtggggag tgaagacgca cagatgcatg    300
cttttattgc agattctttt gctgctttgg gccgtttgga taacattacg ttagtgatgg    360
ttttccaccc acaatattta gaaagtttct taaaaactca gcactatcta ctgcaaatgg    420
atgggccgtt acccctacat tatcgtcact acattggaat aatggctgcg gcaagacatc    480
agtgctccta cttagtgaac ctgcatgtaa atgatttcct tcatgttggt ggggacccca    540
agtggctcaa tggtttagag aatgtccctc aaaaactaca gaatttagga gaacttaaca    600
aagtgttagc ccatagacct tggcttatta ccaaagaaca cattgaggga cttttaaaag    660
ctgaagagca cagctggtcc cttgcggaat tggtacatgc agtagtttta ctcacacact    720
atcattctct tgcctcattc acattcggct gtggaatcag tccagaaatt cattgtgatg    780
gtggccacac attcagacct cctttctgtta gcaactactg catctgtgac attacaaatg    840
gcaatcacag tgtggatgag atgccggtca actcagcaga aaatgtttct gtaagtgatt    900
cttttctttga ggttgaagcc ctcatggaaa agatgaggca gttacaggaa tgtcgagatg    960
aagaagaggc aagtcaggaa gagatggctt cacgttttga aatagaaaaa agagagagta   1020
tgttttgtctt ctcttcagat gatgaagaag ttacaccagc aagagctgta tctcgtcatt   1080
ttgaggatac tagttatggc tataaagatt tctctagaca tgggatgcat gttccaacat   1140
ttcgtgtcca ggactattgc tgggaagatc atggttattc tttggtaaat cgcctttatc   1200
cagatgtggg acagttgatt gatgaaaaat ttcacattgc ttacaatctt acttataata   1260
caatgcaat gcacaaagat gttgatacct caatgcttag acgggcaatt tggaactata   1320
ttcactgcat gtttgaata agatatgatg attatgacta tggtgaaatt aaccagctat   1380
tggatcgtag ctttaaagtt tatatcaaaa ctgttgtttg cactcctgaa aaggttacca   1440
aaagaatgta tgatagcttc tggaggcagt tcaagcactc tgagaaggtt catgttaatc   1500
tgcttcttat agaagctagg atgcaagcag aactcctta tgctctgaga gccattaccc   1560
gctatatgac ctgatgcctt tccttcatta aagatgattc tggaatgatc agcagatata   1620
gtctacaagg gggaaggtac taagcccccag gaccaatggt agacaaaata attcagaaat   1680
ccattgtgcc atgattcctt tagtttctgc tatttttctg tggaaaacca ctgctggcac   1740
aagcagtgac tgtttggcag cttcaagttt agagctgtga agacaggctg ccattccagg   1800
tattttgctt tttgacagta caagatgctg tgtaactgtt ttaatacagc aaatagtaac   1860
tctccaaatc ctgttgcttt tatgttaaat aagataacaa gaattggagc atgcaaagaa   1920
tgggacttgg ataatgactt aagctttata tgtaaagaat tttagaagat cttggtgctg   1980
ctattcctgc tggaggaatg aatagatggc tgtttcagtt aagctattag taataaaaagt   2040
gaacattgct actatctgag cctacataca taacttgtgt gatttcaaat taaacttgca   2100
ttatgtgtta atttttcttgc atctaaaaaa gcatagaatt cctactcaca cagctcagca   2160
acaaccattt tgatggtaac agttaatttc tttcattagt ttttttaaat cagggttctg   2220
gatattaaat taaaatggca ttcctaaaga ttttcttcaa aaagcaatcc taaatgaaag   2280
tgtgtaaatt ataagaagct ggcgatcttt tgatatgctg tttcacagga tcctgacact   2340
ggagggcagc tgtcttgtgc attacttgtg tttccagcac caaagttgtg ggacatgttg   2400
ctgtagactg ctcgcagtc ctgggtgcat tcagtctctc tgcctctgcc tgcctcctga   2460
tccccacttt aaaggctgtg cagctcctta aataataaag ctggaaaata ttttagtcg   2520
ggttatcaaa tttgatttac aaaaacgcta actttgttg aaatgcaaac aggtttgaaa   2580
atatgtatta agtactttgt attctggaag cgtgaattgc ttttgaagtc tgtcagtatt   2640
actggtattt ttaaataaag aagaattttt ctccaatttt aaaaaaaaa aaaaaaaa     2698
```

| SEQ ID NO: 42 | moltype = DNA length = 5215 |
|---|---|
| FEATURE | Location/Qualifiers |
| source | 1..5215 |
| | mol_type = other DNA |
| | organism = Homo sapiens |

SEQUENCE: 42

```
cgagcgcggc gcccttgagc tgcaccgcgg cgcaggtttg cgagccgact tgtcagccgg    60
ccaagaaaag gaagctccgt cccttccgc tcacccggct tccccacccc ttgtactcta   120
aactctgcag agggcgagcg gcgcggccac ggaggcgccg aggaggagcg agccgccgcc   180
gggcagcggc gtgccctcgg gggagagggc gccggagagg aggcggcggc gcggcggcga   240
gggcgcggcg cgcgatggca gctgcttagc ccggcgggcg cggagcagcc ccgagctgtg   300
gctggccagg cggtgcggct gggcggggga cgccgccgcc gttgctgccc ggcccggaga   360
gatgagcacg gaggcggacg agggcatcac tttctctgtg ccaccttcg ccccctcggg   420
cttctgcacc atccccgagg gcggcatctg caggagggga ggacggcggg cggtgggcga   480
gggcgaggag caccagctgc caccgccgcc gccgggcagc ttctggaacg tggagagcgc   540
cgctgcccct ggcatcggtt gtccggcggc cacctcctcg agcagtgcca cccgaggccg   600
gggcagctct gttggcgggg gcagccgacg gaccacggtg gcatatgtga tcaacgaagc   660
gagccaaggg caactggtgg tggccgagag cgaggccctg cagagcttgc gggaggcggc   720
cgagacagtg ggcgccaccc tggaaaccct gcattttggg aaactcgact ttggagaaac   780
caccgtgctg gaccgctttt acaatgcaga tattgcggtg gtggagatga gcgatgcctt   840
ccggcagccg tccttgtttt accaccttgg ggtgagagaa agtttcagca tggccaacaa   900
catcatcctc tactgtgata ctaactcgga ctctctgcag tcctgaagg aaataatttg   960
ccagaagaat actatgtgca ctgggaacta cacctttgtt ccttacatga taactccaca  1020
taacaaagtc tactgctgtg acagcagctt catgaagggg ttgacagagc tcatgcaacc  1080
gaacttcgag ctgcttcttg gacccatctg cttacctctt gtggatcgtt ttattcaact  1140
tttgaaggtg gcacaagcaa gttctagcca gtacttccgg gaatctatac tcaatgacat  1200
caggaaagct cgtaatttat acactggtaa agaattggca gctgagttgg caagaattgc  1260
gcagcgagta gataatatcg aagtcttgac agcagatatt gtcataaatc tgttactttc  1320
ctacagagat atccaggact atgattctat tgtgaagctg gtagagactt tagaaaaact  1380
gccaaccttt gatttggcct cccatcacca tgtgaagttt cattatgcat ttgcactgaa  1440
taggagaaat ctccctggtg acagagcaaa agctcttgat attatgattc ccatggtgca  1500
aagcgaagga caagttgctt cagatatgta ttgcctagtt ggtcgaatct acaaagatat  1560
gttttttggac tctaatttca cggacactga agcagagac catggagctt cttggttcaa  1620
aaaggcattt gaatctgagc caacactaca gtcaggaatt aattatgcgg tcctcctcct  1680
ggcagctgga caccagtttg aatcttcctt tgagctccgg aaagttgggg tgaagctaag  1740
tagtcttctt ggtaaaaagg gaaacttgga aaaactccag agctactggg aagttggatt  1800
tttctggggg gccagcgtcc tagccaatga ccacatgaga gtcattcaag catctgaaaa  1860
gcttttaaa ctgaagacac cagcatggta cctcaagtct attgtagaga caattttaat  1920
atataagcat tttgtgaaac tgaccacaga acagcctgtg gccaagcaga aacttgtgga  1980
cttttggatg gatttcctgg tcgaggccac aaagacagat gttactgtgg ttaggttcc  2040
agtattaata ttagaaccaa ccaaaatcta tcaaccttct tatttgtcta tcaacaatga  2100
agttgaggaa aagacaatct ctatttgca cgtgcttcct gatgacaaga aggtataca  2160
tgagtggaat tttagtgcct cttctgtcag ggggagtgat atttctaat ttgaagaaag  2220
atgctgcttt ctttatgtgc ttcacaattc tgatgatttc caaatctatt tctgtacaga  2280
acttcattgt aaaagtttt ttgagatggt gaacaccatt accgaagaga aggggagaag  2340
cacagaggaa ggagactgtg aaagtgactt gctggagtat gactatgaat atgatgaaaa  2400
tggtgacaga gtcgttttag gaaaaggcac ttatggata gtctacgcg gtcgggactt  2460
gagcaaccaa gtcagaattg ctattaagga aatcccagag agagacagca gatactctca  2520
gcccctgcat gaagaaatag cattgcataa cacctgaag cacaaaaata ttgtccagta  2580
tctgggctct tcagtgaga atggtttcat taaatcttc atggagcagg tccctggagg  2640
aagtcttctt gctctccttc gttccaaatg gggtccatta aaagcaatg agcaaacaat  2700
tggcttttat acaaagcaaa tactggaagg attaaaatat ctccatgaca atcagatagt  2760
tcaccgggac ataaagggtg acaatgtgtt gattaatacc tacagtgtg ttctcaagat  2820
ctctgacttc ggaacatcaa agaggcttgc tggcataaac ccctgtactg aaacttttac  2880
tggtaccctc cagtatatgg caccagaaat aatagataaa ggaccaagag gctacggaaa  2940
agcagcagac atctggtctc tgggctgtac aatcattgaa atggccacag gaaaaccccc  3000
atttatgaa ctgggagaac acaagcagc tatgttcaag gtgggaatgt ttaaagtcca  3060
ccctgagatc ccagagtcca tgtctgcaga ggccaaggca ttcatactga aatgttga  3120
accagatcct gacaagagag cctgtgctaa cgacttgctt gttgatgagt tttaaaagt  3180
ttcaagcaaa aagaaaaaga cacaacctaa gcttcagct cttttgactg gatcaaatga  3240
atatctcagg agtatatcct tgccggtacc tgtgctggtg gaggcacca gcagcagcag  3300
tgagtacggc tcagtttcac ccgacacgga gttgaaagtg gacccttct cttcaaaac  3360
aagagccaag tcctgcggag aaagagatgt caagggaatt cggacactct ttttgggcat  3420
tccagatgag aattttgaag atcagtgtc tcctcctcc cctgaagaaa aagattctga  3480
attcttcatg ctgaggaagg acagtgagag gcgagctacc cttcacagga tcctgacgga  3540
agaccaagac aaaattgtga gaacctaat ggaatcttta gctcagggg ctgaagaacc  3600
gaaactaaaa tggaacaca tcacaaccct cattgcaagc ctcagagaat tgtgagatc  3660
cactgaccga aaaatcatag ccaccacact gtcaaagctg aaactggagc tggacttctg  3720
cagccatgcg attagccaag tccaggtggt actcttttgt tttcaagatg ctgtcaataa  3780
agttcttcgg aatcataaca tcaagccgca ctgatgtttt gccttagaca gtatcattcg  3840
gaaggcggta cagacagcca ttaccatcct ggttccagaa ctaaggccac atttcagcct  3900
tgcatctgag agtgatactg ctgatcaaga agacttggat gtagaagatg accatgagga  3960
acagccttca aatcaaactg tccgaagacc tcaggctgtc attgaagatg ctgtggctac  4020
ctcaggcgtg agcacgctca gttctactgt gtctcatgat tcccagagtg ctcaccggtc  4080
actgaatgta cagcttggaa ggatgaaaat agaaaccaat agattactgg aagaattggt  4140
tcggaaagag aaagaattac aagcactcct tcatcgagct attgaagaaa agaccaaga  4200
aattaaaacac ctgaagctta gtcccaaacc catagaaatt cctgaattgc ctgtatttca  4260
tctaaattct tctggcacaa atactgaaga ttctgaactt accgactggc tgagagtgaa  4320
tggagctgat gaagacacta taagccggtt tttggctgaa gattatacac tattggatgt  4380
```

```
tctctactat gttacacgtg atgacttaaa atgcttgaga ctaaggggag ggatgctgtg   4440
cacactgtgg aaggctatca ttgactttcg aaacaaacag acttgactgt tgctcaatct   4500
aatcttcgat ggaaattcta aaaattaata cagagctgat cttcttgggg gtgggaaaat   4560
cgaagggaga ggagaaaggc gctgcacttt aaatccagta tttgtttact catgttaaaa   4620
aaaaaaaaaa cagacaaaac acactgaaat ttcctaacta catctatttc tataattttt   4680
aaggactctt cataaggact cttaaaataa tcctgaacat tagaacccta atgttcagga   4740
agattttaat ctaagcattt ttatggaaat attttttaatg cagcagctat tgcacttcag   4800
ccaaatgttt atttcacaca aaacggatgt aacatttcat gtgatcgtgc accactggaa   4860
caaaaccaaa atgtgaccat aactgtttag gcttctgtgt gtttgtaata tgctctaata   4920
atctgagtag aaatgcgtaa tttcaattac tgtataaagt ttatgttttt ttaagtgtgc   4980
agaatctgag agcaatggtt tttacttctc tgtgttaatt gtaatattga ctctattttg   5040
taacttaagt ttctgacctg tcgtacattt gtttgagtcg tttatgtact actgaactgt   5100
accagttgca catgcttgaa ctgtagtaat gttagcttgt tctaaagcta tccattgtgt   5160
catatttact ctaaaaatta aagagactct caacaaaaaa aaaaaaaaaa aaaaa        5215

SEQ ID NO: 43          moltype = DNA   length = 4655
FEATURE                Location/Qualifiers
source                 1..4655
                       mol_type = other DNA
                       organism = Homo sapiens
SEQUENCE: 43
tctgtgcacc ttgcggtggg cggcgaacgg cagccgcggc agcagctagg gggcttgtgc     60
acacagcgag ggagacttag ggactggcag acgacggac  ggacggcgag gaccctaccc    120
gagcccccga gccatggccg agagaaagca atccggaaag gcggcagagg acgaagaggt    180
ccctgctttt tttaaaaacc tgggctccgg cagcccaag  ccccggcaga aattctgtgg    240
catgttctgc ccggtggaag ggtcctcgga gaacaagacc atcgacttcg actcgctgtc    300
ggtgggccgg ggctcggggc aggtggtggc tcagcagcgg gacgtcgccc acttgggccc    360
ggacccgcag ccgccgtact cgcggcaggg ccggcgcgcc ggcggagagc catctgttga    420
atcgggccgg aaggtggaga tccggagggc ctcgggcaaa aagcctgc   agaacatcaa    480
cgaccagage gatcgtcttc tgatcaaagg aggtaaaatt gttaatgatg accagtcgtt    540
ctatgcagac atatacatgg aagatgggtt gatcaagcaa ataggagaaa atctcgattgt   600
gccaggagga gtgaaggacca tcgaggccca ctcccggatg gtgatccccg gaggaattga   660
cgtccacact cgtttccaga tgcctgatca gggaatgacg tctgctgatg atttcttcca   720
aggaaccaag gcggcctggg ctggggggaac cactatgatc attgaccacg ttgttcctga   780
gcctgggaca agcctgctcg ctgcctttga ccagtggagg gaatgggccg acagcaagtc   840
ctgctgtgac tactctctgc atgtggacat cagcgagtgg cataagggca tccaggagga   900
gatgaagcgc cttgtgaagg atcacggggt aaattcctc  ctcgtgtaca tggctttcaa    960
agatcgcttc cagctaacgg attgccagat ttatgaagta ctgagtgtga tccgggatat   1020
tggcgccata gcccaagtcc acgcagaaaa tggcgacatc attgcagagg agcagcagag   1080
gatcctggat ctgggcatca cgggccccga gggacatgtg ctgagccgac ctgaggaggt   1140
cgaggccgaa gccgtgaatc gtgccatcac catcgccaac cagaccaact gcccgctgta   1200
tatcaccaag gtgatgagca aaagctctgc tgaggtcatc gcccaggcac ggaagaaggg   1260
aactggtgtg tatgcgagc  ccatcactgc cagcttggga acggacggcct cccattactg   1320
gagcaagaac tgggccaagg ctgctgcctt tgtcacctcc ccaccttga  gccctgatcc   1380
aaccactcca gactttctca actccttgct gtcctgtgga gacctccagg tcacgggcag   1440
tgcccattgc acgtttaaca ctgccagaa  ggctgtagga aaggacaact tcaccctgat    1500
tccggagggc accaatggca ctgaggagcg gatgtccgtc atctgggaca aggctgtggt   1560
cactgggaag atgatgagaa accagtttgt ggctgtgacc agcaccaatg cagccaaagt   1620
cttcaacctt taccccggaa aaggccgcat tgctgtggga tccgatgccg acctggtcat   1680
ctgggacccc gacagcgtta aaaccatctc tgccaagaca cacaacagct ctctcgagta   1740
caacatcttt gaaggcatgg agtgccgcgg ctcccccactg gtggtcatca gccagggggaa   1800
gattgtcctg gaggacggca ccctgcatgt caccgaaggc tctggacgct acattccccg   1860
gaagcccttc cctgatttttg tttacaagcg tatcaaggca aggagcaggc tggctgagct   1920
gagaggggtt cctcgtggcc tgtatgacgg acctgtgtgt gaagtgtctg tgacgcccaa   1980
gacagtcact ccagcctcct cggccaagac gtctcctgcc aagcagcagg ccccacctgt   2040
ccggaacctg caccagtctg gattcagttt gtctggtgct cagattgatg acaacattcc   2100
ccgccgcacc acccagcgta tcgtggcgcc ccccggtggc cgtgccaaca tcaccagcct   2160
gggctagagc tcctgggctg tgccgtccac tggggactgg ggatgggaca cctgaggaca   2220
ttctgagact tcttttcttcc ttcctttttt tttttttgtt ttttttttttt agagcctgtg   2280
atagttactg tggagcagcc agttcatggg gtccccccttg ggcccccaca ccccgtctct   2340
caccaagagt tactgatttt gctcatccac ttccctacac atctatgggt atcacaccca   2400
agactaccca ccaagctcat acagggaacc acacccaaca cttagacatg cgaacaagca   2460
gcccccagcg agggtctcct tcgccttcaa cctcctagtg tctgttagca tcttccttttt   2520
catggggga  gggaagataa agtgaattgc ccagagctgc cttttttcttt tcttttttaa    2580
aatttttaaga agtttttcttt gtggggctgg ggaggggccg gggtcaggga gagtcttttt   2640
tttttttttt tttaaatact aaaattggaac atttaattcc atattaatac aaggggttttg   2700
aactggacat cctaatgatg caattacgtc atcacccagc tgattccggg tggttggcaa   2760
actcatcgtg tctgtcctga gaggctccac aatgcccacc cgcatcgcca ttctgtagtc   2820
ttcagggctca gctgttgata aaggggcagg cttgcgttat tggcctagat tttgctgcag   2880
attaaatcct ttgaggattc tcttctcttt taccattttt ctgcgtgctc tcactctctc   2940
tttctctctc tagcttttta attcatgaat attttcgtgt ctgtctctct ctctctctgt   3000
gtttcctcca gcccttgtct cggagacggt gtttcctcc  cttgccccat tatcttttca    3060
cctcccaggt ctaccatttc atggtggtcg ttgggtccgc ctaaaggatt tgagcgtttg   3120
ccattgcaag cataactgtg tgtcatcctg gtccatgtcg gactgggtgct aaccacctgc   3180
catcatgagg atgtgtgcta gagtgtggga ccctggccaa gtgcaggaat gggccatgcc   3240
gtctcaccca cagtatcaca cgtggaaccg cagacagggc ccagaagctt tagaggtatg   3300
aggctgcaga accggagaga ttttcctctg tgcagtgctc tctggctaaa gtcacggtca   3360
aacctaaaca ccgagcctca ttaacccaag tgaaccaacc aaagtcacca gttcagaagt   3420
gctaagctaa taggagtctg acccgagggc ctgctgcttc ctggttaagt atcttttgag   3480
```

```
attctagaac acatgggagc tttttatttt cggggaaaaa ccgtattttt ttcttgtcca  3540
attatttcta aagacacact acatagaaag aggccctata aactcaaaaa gtcattggga  3600
aacttaaagt ctattctact ttgcaagagg agaaatgtgt tttatgaacg atagatcaca  3660
tcagaactcc tgtggggagg aaaccttata aattaaacac atggcccct tagagaccac  3720
aggtgatgtc tgtctccatc cttccctctc cttttcgtc ctagctggct  3780
cctttggacc taccctgtc cttgctgact tgtgttgcat tgtattccaa acgtgtttac  3840
aggttctctt aagcaatgtt gtatttgcag gcttttctga ataccaaatc tgctttttgt  3900
aaagcgtaaa aacatcacaa agtaggtcat tccatcacca cccttgtctc tctacacatt  3960
ttgcctttgg ggatctggtt ggggttttgg gttttttgtt gttgttgttt atttgttatt  4020
ttaaaggtaa attgcacttt taaaaaata attggttgac ttaatatatt tgctttttt  4080
ctcacctgca cttagaggaa atttgaacaa gttggaaaaa aacatttttt gtttcaattc  4140
taagaaaacac ttgcagctct agtattcact tgagtcttcc tgtttttcct gtaccgggtc  4200
atggtaattt ttggttgtt tggttgtttt cttaaaaaac aagttaaaac ctgacgattt  4260
ctgcaggctg tgtaagcatg tttacctgtt ggcttgcttt gtgtgtctgt taaatgaatg  4320
tcatatgtaa atgctaaaat aaatcgacag tgtctcagaa ctgaataact gcagtgactt  4380
gatgctctaa aacagtgtag gatttaagaa tagatggttt ttaatcctgg aaattgtgat  4440
tgtgaccat gagtggagga actttcagtt ctaaagctga taagtgtgt agccagaaga  4500
gtactttttt ttttgtaacc actgtcttga tggcaaaata attatggtaa aaaacaagtc  4560
tcgtgtttat tattccttaa gaactctgtg ttatattacc atggaacgcc taataaagca  4620
aaatgtggtt gtttcaggaa aaaaaaaaaa aaaaa                              4655

SEQ ID NO: 44          moltype = DNA   length = 4417
FEATURE                Location/Qualifiers
source                 1..4417
                       mol_type = other DNA
                       organism = Homo sapiens
SEQUENCE: 44
gctgtaacac tcaccgtgaa ggtctgcagc ttcactcccg agccagcgag accacgaacc   60
caccagaagg aagaaactct gaacacatct gaacatcaga agggacagac tccagacgcg  120
ccaccactct gctaaccaca gatagtggaa agaaaccatg tgctgaaatg tttgacgaca  180
ctgatggttt gactctgcta actggaatgg cttattgtgc aagaaagtac acctggtcgg  240
gtcctggggc tcatctctag caccagcaaa gatttctgaa gacgtctttc tagaaatgac  300
tggaaagttt caagaggcat aagatacagc atttcttctg aggccctgaa gaagtatcaa  360
gtgggctttg acattgcggt ggtgagagcg accctcctc acctggagaa ctgggaaatg  420
tggattctca gggaccgcgc tgttcacgag ctccaggctg tgctgctggc cctggttcctg  480
gggcgctgag ccgcatctgc aatagcacac ttgcccggcc acctgctgcc gtgagccttt  540
gctgctgaag cccctggggt cgcctctacc tgatgaggat gtgcacccc attgggggc  600
tgctcatggc ccttgcagtg atgtttggga cagcgatggc atttgcaccc ataccccgga  660
tcacctggga gcacagagag gtgcacctgg tgcagtttca tgagccagac atctacaact  720
actcagcctt gctgctgagc gaggacaagg acaccttgta catggtgcc cgggaggcgg  780
tcttcgctgt gaacgcactc aacatctccg agaagcagca tgaggtgtat tggaaggtct  840
cagaagacaa aaaagcaaaa tgtgcagaaa aggggaaatc aaaacagaca gagtgcctca  900
actacatccg ggtgctgcag ccactcagcg ccacttccct ttacgtgtgt gggaccaacg  960
cattccagcc ggcctgtgac cacctgaact taacatcctt taagtttctg ggaaaaatg  1020
aagatggcaa aggaagatgt cccttgacc cagcacacag ctacacatcc gtcatggttg  1080
atggagaact ttattcgggg acgtcgtata atttttggg aagtgaaccc atcatctccc  1140
gaaattcttc ccacagtcct ctgaggacag aatatgcaat cccttggctg aacgagccta  1200
gtttcgtgtt tgctgacgtg atccgaaaaa gcccagacag ccccgacggc gaggatgaca  1260
gggtctactt cttcttcacg gaggtgtctg tggagtatga gtttgtgttc agggtgctga  1320
tcccacggat agcaagagtg tgcaagggg accagggcgg cctgaggacc ttgcagaaga  1380
aatggacctc cttcctgaaa gcccgactca tctgctcccg gacagacagc ggcttggtct  1440
tcaatgtgct gcgggatgtc ttcgtgctca ggtccccggg cctgaaggtg cctgtgttct  1500
atgcactctt caccccacag ctgaacaacg tgggctgtc ggcagtgtgc gcctacaacc  1560
tgtccacagc cgaggaggtc ttctcccacg ggaagtacat gcagagcacc acagtggagc  1620
agtccaacac caagtgggtg cgctataatg gcccggtacc caagccgcgg cctggagcgt  1680
gcatcgacag cgaggcacgg gccgccaact acaccagctc cttgaatttg ccagacaaga  1740
cgctgcagtt cgttaaagac caccctttga tggatgactc ggtaaccca atagacaaca  1800
ggcccaggtt aatcaagaaa gatgtgaact acacccgat cgtggtggac cggacccagg  1860
ccctggatgg gactgtctat gatgtcatgt ttgtcagcac agaccggggga gctctgcaca  1920
aagccatcag cctcgagcac gctgttcaca tcatcgagga gacccagctc ttccaggact  1980
ttgagccagt ccagaccctg ctgctgtctt caaagaaggg caacaggttt gtctatgctg  2040
gctctaactc gggcgtggtc caggcccgc tggcttctg tgggaagcac ggcacctgcg  2100
aggactgtg gctggcgcgg gacccctact gcgcctggag cccgcccaca gcgacctgcg  2160
tggctctgca ccagaccgag agccccagca gggtttgat tcaggagatg agcggcgatg  2220
cttctgtgtg cccggcctcg tctcctaagc ccctcctcc tcctggctcc tcttccctgt  2280
cctgtctggg ccatgtgggg gacaggaggc tttcctctcc ctgaccccc tggccagcct  2340
cgggtgcggg gcccgacagc agctcgaggg tctccttgct gccgcccttc ctgagtgacc  2400
aggcacagca cgtgcacgcc ctggggaact tctacctctt ctgccaggcc acaggtgtga  2460
cagacattcg cctttgtctgg gagaagaatg ggcgagctgc ttggaccctgt gtcctgtgc  2520
agacccatgc actgcccgat ggcagggcc atgcactcag ctggctgcag gacgccatca  2580
gggaaagcgc tgagtatcgc tgctctgtcc tctcctcagc agggaacaag acttcgaagg  2640
tgcaggttgc tgtgatgaga cctgaagtga cccaccagga gaggtgacc agagagctct  2700
ctgcctggag ggctgtggct ggggagcacg accggatgat gcagagctgg aggaaggcgt  2760
gggaaagctg tagcaaggac acccctgtagc caccaggaag gagtccctga caccgacctc  2820
aaccccaaca agaccctgct gccactgacc acagccaccc ccggagaagg cctggtcccc  2880
cacaactgtg aactgtcttg cccagcctgc tctctgaacac agcattggg ccaccacctg  2940
atgggcagag cgggacagt ggagaagcct ggaacccaag tgggcctgtg acaggaacta  3000
agacttaaaa aattaggtgc ttaccttgga cagtaagttc tgtctggcac aagcaggtaa  3060
ccaggatggc taacaggctt tgatagctgc tcgtgaacta aaacagcagg gtgtgtgcag  3120
```

```
gttcctcctc tacggtcagg cagcaggctc tgaaggctga tcctacaccg tcccagtgac  3180
tcccccttgac agagtgcccc caccccctaa tagccaacag ggttagcatg gccagcacag  3240
atcgctgctt ttattgatgc aaatcaagcc tgctgcttct cctccctgca gacttagcca  3300
aggaactcca agatgcatga ctgggacaag aaaaggtgag actccacatg gaaatgcctt  3360
gccctaaacc ttgaatgact gtgagatgcg atctgggagt gcatctgtca agtctttgtg  3420
ttttcttcac taacctcaga atactgggct ctattttatc aagcgctgca gtttatgcct  3480
ctgtcccgtc aatgctcagc ttctgcaaca ggacaccaaa cttgatgcag aaagccaaat  3540
aggtcaatta tgcaaatctc ctggtgccat attaaatttc ttgacgatgg aatgagtctc  3600
atgagtgttt tgttctacct gctttcaagt ctctaattat taaagctgta tctctgaaga  3660
ctgtgtcact gtgtgtgtga acttgtccta aagctactca gcctttaatc ttacacacac  3720
gtctcttctt gtctgttgaa tgacagtttt catgtctatc ataaaccaa agcctctgtt  3780
aaaagtcaag ccgcacccct ctggtgatcc tagcaaatac tgagtgtctt cccagcagtg  3840
tgacaatgac ctgttttgca tcccctcttt ctggagctgg acaaattctc taccagcctt  3900
tgtgtgggat cagcatacat cgcctgctaa ttccttcagg atccatccac acaggtgtcc  3960
tgaagatgct ggagacaccc tggttgtctc cacacgttcc ccctccgcac cccaagtcga  4020
gaggcccagc tgcctgtgag gtgtgtgctt gcccatccag ccaaggatgc cagtcttgct  4080
cacggaacca tcacatactc ataacctgaa gttttcctgt aaaatatcca tcagctcact  4140
gtggttcttg ctttgggtgt ggcttcaacc actacaaact gatgagtgaa atgctatggg  4200
ctttaggctt atattcttgg tgctgttttc tgtctcttct cctgaagtct ggatttcaag  4260
cactttcaca cttaacaaaa taattacata cttgaagttt tcgtaatgtg gagtgttcta  4320
ctgggaaatg gagttatgag gatgaatttc tgagtctttc tttgctctgc tggaaaaaat  4380
aaaaatagag ttgtacattg aaaaaaaaaa aaaaaaa                            4417

SEQ ID NO: 45          moltype = DNA   length = 3108
FEATURE                Location/Qualifiers
source                 1..3108
                       mol_type = other DNA
                       organism = Homo sapiens
SEQUENCE: 45
gcctctggct cctcagggca ttcccggcgg ctccgggttt ggcaacgagg acggggagt    60
gcgactgcgt ctcgggcagc atggccgaga gcggcacac acgggactcc gaagcccagc   120
ggctccccga ctccttcaag gacagcccca gtaaggggcct tggaccttgc ggatggattt   180
tggtggcgtt ctcattctta ttcaccgtta taactttccc aatctcaata tggatgtgca   240
taaagattat aaaagagtat gaaagagcca tcatctttag attgggtcgc attttacaag   300
gaggagccaa aggacctggt tgttttttta ttctgccatg cactgacagc ttcatcaaag   360
tggacatgag aactatttca tttgatattc ctcctcagga gatcctcaca aaggattcag   420
tgacaattag cgtggatggt gtggtctatt accgcgttca gaatgcaacc ctggctgtgg   480
caaatatcac caacgctgac tcagcaaccc gtcttttggc acaaactact ctgaggaatg   540
ttctgggcac caagaatctt tctcagatcc tctctgacag agaagaaatt gcacacaaca   600
tgcagtctac tctggatgat gccactgatg cctggggaat aaaggtggag cgtgtggaaa   660
ttaaggatgt gaaactacct gtgcagctcc agagagctat ggctgcagaa gcagaagcgt   720
cccgcgaggc ccgcgccaag gttattgcag ccgaaggaga atgaatgca tccagggctc   780
tgaaagaagc ctccatggtc atcactgaat ctcctgcagc ccttcagctc cgatacctgc   840
agacactgac caccattgct gctgagaaaa actcaacaat tgtcttccct ctgcccatag   900
atatgctgca aggaatcata gggcaaaaac acagccatct aggctagtgt agagatgagc   960
gctagccttc caagcatgaa gtcggggacc aaattagcct ttaactcata aagagaggt   1020
agggcttttc ttttttccata tgtcaattgt ggtgttccca gaatgtatag cagttataaa  1080
aataggtgaa agaattgtta gcttgtaaat actgagagat tggtgattta tataaggtaa  1140
tctgttagtc ttaaaatagt taaaagtttg tattttaga ttattatgta gtaggttaga   1200
tccctcttgt tttgacttcc actgactcat tctgaacccc ctaagcaccc aggccagagg  1260
caagaacctg ggctgtaact gccacctgac accgctgact ggctaaatgc tttgcagaaa  1320
gtgatgacct tacaccacaa ccagcttctc caggtcatat gtgccttacc tccagagagt  1380
cttttttttt tttttttctga gatggagttt cactcttgtt gcccaggctg gagtgcaata  1440
gcatgatctc ggctcactgc aacctccgcc tcctgggttc aagagattct cctgcctcag  1500
cctcccagt agctgggatt acaggcgcat gccaccatgc ccagctaatt tttgtattat   1560
tattattgtt ttttagtaga cacggggttt caccatgttg gccaggctag tcacgaactc  1620
ctaacctcag gtgatccacc cacctctgcc tcccaaagtg ctgggattac aggcatgagc  1680
taccacacct ggtttggaga gtcttaatta aggaaatttc cctaatgttc atttattttc   1740
taaatccaga ccgtgtttca gaataatcct tacttgagag tagccatttt cttgcctgta  1800
cttgtcagaa ctagaggaaa tagccaagac taatgaaaaa gattactcta acccttaaaa  1860
gactttttaaa ttcactacta gagtggtcat tttaaaaata catccatgtt ttaacttatt  1920
tgagccttct ttatgagtaa atgattcctc cttgttctgt ctttcaaacc agctaaatat  1980
ttgtcacaaa agtgctttt tctcactgtt gcctatttc atatatcagg ttttaaatag    2040
ttttaatttt ttaataaaat ttttctctacg ttctatatgc aattgttata tatctatttg  2100
aatagctgaa ggactaaaat acttttttaa gagataactt caggaaacca ttatattta   2160
ctatctgcat gctgttaact gtggtacact gtgaaatatg ttgattacaa acccattcat  2220
tacatagtat aaggaattca cagtatattg actatatagt gtctaatgat cttgggcaga  2280
tactgtcaaa cttacaatat ctatatagat gtaggtcttt ttaaatttac ctagtcattc   2340
ttctatcatg tatattgatg ctgaaagagg aactggtcag ctcctctgga caacaaattc  2400
ttagtctata atattaggag acatcttctg ttttgcaaat gtctgtgaat ctgagcaacc  2460
tggcattctg cttactggcc agaaagctgg cgggtgacat ttgtaacatt tcctctttga  2520
gactctgagt tcacctagag aagtctaagc ataacagctt ctttcccag cacgagcctt   2580
tatagctctc tttagctcaa ccactctgtc catccagcca atggatgtcc cttcccctgt   2640
accccaattt caagctctt ttaggaagcc tggatatcctg gctcctagct                2700
gagtttatta gaggtatgga gcagtgcaac ttaaactcaa gttgcactta catttttgaat   2760
tttaaaatga tggttttatc tgttgtgtga agtggttcac ccttgaggac caggagcctc  2820
catatcctga ctgaaaacct tttctgagac ttagagtaac agtgcttttg gttccttgag   2880
ttctcctgtc tccagatacc aaatgacctt gacttttctg ccttgtgaat tcgtagtcca   2940
atcagctgaa attaaatcac ttgggaggga cgcatagaag gagctctagg aacacagtgc   3000
```

-continued

```
cagtgcagaa gtttctccag gtggcctccc tttccaacaa tgtacataat aaagtgtatg    3060
cactttcact aataaaaaaa aaaaaaaaaa aaaaaaaaaa aaaaaaa                  3108

SEQ ID NO: 46          moltype = DNA   length = 4090
FEATURE                Location/Qualifiers
source                 1..4090
                       mol_type = other DNA
                       organism = Homo sapiens
SEQUENCE: 46
gggcgctccc ggagtatcag caaaagggtt cgcccgccc acagtgcccg gctcccccg       60
ggtatcaaaa gaaggatcgg ctccgccccc gggctcccg ggggagttga tagaagggtc    120
cttcccaccc tttgccgtcc ccactcctgt gcctacgacc caggagcgtg tcagccaaag   180
catggagaat caagagaagg cgagtatcgc gggccacatg ttcgacgtag tcgtgatcgg   240
aggtggcatt tcaggactat ctgctgccaa actcttgact gaatatgcg ttagtgtttt    300
ggttttagaa gctcgggaca gggttggagg aagaacatat actataagga atgagcatgt   360
tgattacgta gatgttggtg gagcttatgt gggaccaacc caaaacagaa tcttacgctt   420
gtctaaggag ctgggcatag agacttacaa agtgaatgtc agtgagcgtc tcgttcaata   480
tgtcaagggg aaaacatatc catttcgggg cgcctttcca ccagtatgaa atcccattgc   540
atatttggat tacaataatc tgtggaggac aatagataac atggggaagg agattccaac   600
tgatgcaccc tgggaggctc aacatgctga caaatgggac aaaatgacca tgaaagagct   660
cattgacaaa atctgctgga caaagactgc taggcggttt gcttatcttt ttgtgaatat   720
caatgtgacc tctgagcctc acgaagtgtc tgccctgtgg ttcttgtggt atgtgaagca   780
gtgcgggggc accactcgga tattctctgt caccaatggt ggccaggaac ggaagtttgt   840
aggtggatct ggtcaagtga gcgaacggat aatggacctc ctcggagacc aagtgaagct   900
gaaccatcct gtcactcacg ttgaccagtc aagtgacaac atcatcatag agacgctgaa   960
ccatgaacat tatgagtgca aatacgtaat cctccgacct tgactgccaa                1020
gattcacttc agaccagagc ttccagcaga gagaaaccag ttaattcagc ggcttccaat     1080
gggagctgtc attaagtgca tgatgtatta caaggaggcc ttctggaaga agaaggatta    1140
ctgtggctgc atgatcattg aagatgaaga tgctccaatt tcaataacct tggatgacac   1200
caagccagat gggtcactgc ctgccatcat gggcttcatt cttgcccgga aagctgatcg   1260
acttgctaag ctacataagg aaataaggaa gaagaaaatc tgtgagctct atgccaaagt   1320
gctgggatcc caagaagctt tacatccagt gcattatgaa gagaagaact ggtgtgagga   1380
gcagtactct gggggctgct acacggccta cttccctcct gggatcatga ctcaatatgg   1440
aagggtgatt cgtcaacccg tgggcaggat tttctttgcg ggcacagaga ctgccacaaa   1500
gtggagcggc tacatggaag gggcagttga cgctgggaga cgagcagcta gggaggtctt   1560
aaatggtctc gggaaggtga ccgagaaaga tatctgggta caagaacctg aatcaaagga   1620
cgttccagcg gtagaaatca cccacacctt ctgggaaagg aacctgccct ctgtttctgg   1680
cctgctgaag atcattggat tttccacatc agtaactgcc ctggggtttg tgctgtacaa   1740
atacaagctc ctgccacggt cttgaagttc tgttcttatg ctctctgctc actggttttc   1800
aataccacca agaggaaaat attgacaagt ttaaaggctg tgtcattggg ccatgtttaa   1860
gtgtactgga tttaactacc tttggcttaa ttccaatcat tgttaaagta aaaacaattc   1920
aaagaatcac ctaattaatt tcagtaagat caagctccat cttatttgtc agtgtagatc   1980
aactcatgtt aattgataga ataaagcctt gtgatcactt tctgaaattc acaaagttaa   2040
acgtgatgtg ctcatcagaa acaatttctg tgtcctgttt ttattccctt caatgcaaaa   2100
tacatgatga tttcagaaac aaagcatttg acttctgtc tgtggaggtg gagtaggtga    2160
aggcccagcc tgtaactgtc ctttttcttc ccttaggcaa tggtgaactg tcattacaga   2220
gcctagagtc tcacagcctc ctggaggaag cagcctccac tttggatcag gaaatagtaa   2280
aggaaagcag tgttgggggt agcggcatgc agacccctcag accagaatgg ggacatcttg   2340
tggtctgctg cctcaggaat ctcctgacca cttgtagtcc ctccgacttc tctagacatc   2400
tagtctcagt gctagcttat ttgtatttttt cctctttcac ttcttatgga ggagagtgtt   2460
taactgagtt agaatgttga aactgacttg ctgtgactta tgtgcagctt tccagttgag   2520
cagaggaaaa tagtggcagg actgtccccc aggaggactc cctgcttagc tctgtgggag   2580
accaactacg actggcatct tctcttcccc ctggaaggca gctagacacc aatggatcct   2640
tgtcagttgt aacattctat ttcaacttca ggaaagcagc agttttcttt taattttttcc   2700
tatgaccata caaattagaca tacctctcaa cttacatatg tcttcaacat ggttacctct   2760
gcataaatat tagcaaagca tgccaatttc tcttaagtac tgaaatacat atgataaatt   2820
tgactgttat ttgttgagac tatcaaacag aaaagaaatt agggctctaa tttccttaaa   2880
gcaagctcac ttgctttagt tgttaagttt tataaaagac atgaaattga gtcatttat     2940
atatgaaaac taagttctct atcttaggag taatgtcggc ccacaagggt gcccacctgt   3000
tgttttcccc tttaaaaac tcagattttt aaaagccctt tccaaaggtt tcaactgtaa    3060
aatacttctt tttacaatgt atcaacatat ttttatttaa ggggaattaa caattgccag   3120
ggaaccagcc caaccaagt ttattatatc attaacctta tcataaattc aaacctaagt     3180
tgctggaccc tggtgtgagg acataaatct tccaaagttt tgcctatcct aagagctgca   3240
tttttctact gctcttttacc ttgcatttta gctaatttag gagttttgag aatgtatttga   3300
atacgctcca gtacaaggg agttgccgca tattatca gactgctttg agaaatctca   3360
tccctagtct attgcagttg tttctattag cttactgatt aactcagtcc tgacacacct   3420
tttgggaaat gctgatttaa acttcttaac tggcaacagt tggaacagta atcagtttgc   3480
taacatattt aaagtcttga atgttgaaga actcatgtga tttacccttt tcaacttttt   3540
ggaaaacgat ttaatttatt ctaattagat taacccctatt aatctatga ttgggtcatca   3600
aaatgaatgc cagtccagat gtgcctagac acgaaattgg agctgaggac tctcacgata   3660
tgcaagttca tccaacgtga agataccata agcttttttct ctgaaccaga gaatgaaag   3720
tcagtttaag aggctgatag atcttggcc tgttaaggca tccacttcac agttctgaag   3780
gctgagtcag ccccactcca cagttaggcc aagaattaga ttttaaaact tcatctgtct   3840
gtcccagtta actgttaaat aaggcctcat cctccactga agagtatgga ttgaaggatt   3900
gtgaactatg tttagtgtga ttgtgaactt ggtgcctaat gttccatgtc tgaagtttgc   3960
cccagtgcta cacgttggag tataacctatg tgtgtgcttt gccactgaag taagattttg   4020
cctgtatggt actgttttgt ttgttaataa agtgcactgc caccccccaat gcaaaaaaa   4080
aaaaaaaaaa                                                         4090
```